US012620092B2

(12) United States Patent
Min et al.

(10) Patent No.: US 12,620,092 B2
(45) Date of Patent: May 5, 2026

(54) SYSTEMS, DEVICES, AND METHODS FOR NON-INVASIVE IMAGE-BASED PLAQUE ANALYSIS AND RISK DETERMINATION

(71) Applicant: Cleerly, Inc., Denver, CO (US)

(72) Inventors: James K. Min, Durham, NC (US);
James P. Earls, Alexandria, VA (US);
Shant Malkasian, Pasadena, CA (US);
Hugo Miguel Rodrigues Marques,
Lisbon (PT); Chung Chan, Northbrook,
IL (US); Shai Ronen, Westminster, CO
(US)

(73) Assignee: Cleerly, Inc., Denver, CO (US)

( * ) Notice: Subject to any disclaimer, the term of this patent is extended or adjusted under 35 U.S.C. 154(b) by 350 days.

(21) Appl. No.: 18/456,329

(22) Filed: Aug. 25, 2023

(65) Prior Publication Data

US 2023/0401710 A1 Dec. 14, 2023

Related U.S. Application Data

(63) Continuation of application No. 18/179,921, filed on Mar. 7, 2023, now Pat. No. 12,406,365.

(Continued)

(51) Int. Cl.
| | |
|---|---|
| G06T 7/62 | (2017.01) |
| A61B 5/00 | (2006.01) |
| G06T 7/00 | (2017.01) |

(52) U.S. Cl.
CPC .......... G06T 7/0012 (2013.01); A61B 5/7275 (2013.01); G06T 7/62 (2017.01);
(Continued)

(58) Field of Classification Search
CPC .................... G06T 7/0012; G06T 7/62; G06T 2207/30101; G06T 2207/10048;
(Continued)

(56) References Cited

U.S. PATENT DOCUMENTS

| | | | |
|---|---|---|---|
| 4,296,901 | A | 10/1981 | Perrott |
| 4,945,478 | A | 7/1990 | Merickel et al. |
| | | (Continued) | |

FOREIGN PATENT DOCUMENTS

| | | |
|---|---|---|
| AU | 2023200986 A1 | 3/2023 |
| CA | 2368390 C | 7/2010 |
| | (Continued) | |

OTHER PUBLICATIONS

US 11,791,027 B2, 10/2023, Buckler et al. (withdrawn)
(Continued)

*Primary Examiner* — Ming Y Hon
*Assistant Examiner* — Amanda H Pearson
(74) *Attorney, Agent, or Firm* — Perkins Coie LLP

(57) ABSTRACT

Systems and methods of facilitating determination of risk of coronary artery disease (CAD) based at least in part on one or more measurements derived from non-invasive medical image analysis. The methods can include accessing a non-invasive generated medical image, identifying one or more arteries, identifying, regions of plaque within an artery, analyzing the regions of plaque to identify low density non-calcified plaque, non-calcified plaque, or calcified plaque based at least in part on density, determining a distance from identified regions of low density non-calcified plaque to one or more of a lumen wall or vessel wall, determining embeddedness of the regions of low density non-calcified plaque by one or more of non-calcified plaque or calcified plaque, determining a shape of the more regions of low density non-calcified plaque, and generating a display of the analysis to facilitate determination of one or more of a risk of CAD of the subject.

20 Claims, 68 Drawing Sheets

Related U.S. Application Data

(60) Provisional application No. 63/381,210, filed on Oct. 27, 2022, provisional application No. 63/368,293, filed on Jul. 13, 2022, provisional application No. 63/365,381, filed on May 26, 2022, provisional application No. 63/364,084, filed on May 3, 2022, provisional application No. 63/364,078, filed on May 3, 2022, provisional application No. 63/362,856, filed on Apr. 12, 2022, provisional application No. 63/362,108, filed on Mar. 29, 2022, provisional application No. 63/269,136, filed on Mar. 10, 2022.

(52) U.S. Cl.
CPC .............. *G06T 2207/10048* (2013.01); *G06T 2207/10081* (2013.01); *G06T 2207/10101* (2013.01); *G06T 2207/10104* (2013.01); *G06T 2207/10108* (2013.01); *G06T 2207/10116* (2013.01); *G06T 2207/10132* (2013.01); *G06T 2207/20081* (2013.01); *G06T 2207/30101* (2013.01)

(58) Field of Classification Search
CPC . G06T 2207/10081; G06T 2207/10101; G06T 2207/10104; G06T 2207/10108; G06T 2207/10116; G06T 2207/10132; G06T 2207/20081; G06T 2207/10072; G06T 2207/20084; A61B 5/7275; A61B 5/02007; A61B 5/055; G06V 10/255; G06V 10/26; G06V 2201/03; G06V 10/82
See application file for complete search history.

(56) References Cited

U.S. PATENT DOCUMENTS

| | | | |
|---|---|---|---|
| 5,056,130 A | 10/1991 | Engel | |
| 5,722,408 A | 3/1998 | Dehner et al. | |
| 5,891,030 A | 4/1999 | Johnson et al. | |
| 5,944,689 A | 8/1999 | Houser et al. | |
| 6,047,080 A | 4/2000 | Chen et al. | |
| 6,320,931 B1 | 11/2001 | Arnold | |
| 6,591,004 B1 | 7/2003 | VanEssen et al. | |
| 6,993,382 B2 | 1/2006 | Casscells et al. | |
| 7,008,401 B2 | 3/2006 | Thompson et al. | |
| 7,011,655 B2 | 3/2006 | Thompson et al. | |
| 7,045,238 B2 | 5/2006 | Gottmann et al. | |
| 7,191,110 B1 | 3/2007 | Charbel et al. | |
| 7,276,044 B2 | 10/2007 | Ferry et al. | |
| 7,351,214 B2 | 4/2008 | Burgermeister | |
| 7,371,248 B2 | 5/2008 | Dapolito et al. | |
| 7,535,986 B2 | 5/2009 | Hempel | |
| 7,558,611 B2 | 7/2009 | Arnold et al. | |
| 7,570,983 B2 | 8/2009 | Becker et al. | |
| 7,705,490 B2 | 4/2010 | Srinivasan et al. | |
| 7,711,165 B2 | 5/2010 | Lesage et al. | |
| 7,715,626 B2 | 5/2010 | Florin et al. | |
| 7,766,856 B2 | 8/2010 | Ferry et al. | |
| 7,803,130 B2 | 9/2010 | Ryan et al. | |
| 7,805,385 B2 | 9/2010 | Steck et al. | |
| 7,813,549 B2 | 10/2010 | Buelow et al. | |
| 7,840,062 B2 | 11/2010 | Boroczky et al. | |
| 7,860,283 B2 | 12/2010 | Begelman et al. | |
| 7,876,939 B2 | 1/2011 | Yankelevitz et al. | |
| 7,899,764 B2 | 3/2011 | Martin et al. | |
| 7,904,977 B1 | 3/2011 | Singh | |
| 7,907,766 B2 | 3/2011 | Haas et al. | |
| 7,912,528 B2 | 3/2011 | Krishnan et al. | |
| 7,940,974 B2 | 5/2011 | Skinner et al. | |
| 7,940,977 B2 | 5/2011 | Begelman et al. | |
| 7,953,266 B2 | 5/2011 | Gulsun et al. | |
| 7,974,681 B2 | 7/2011 | Wallace et al. | |
| 7,993,274 B2 | 8/2011 | Pruvot et al. | |
| 7,998,020 B2 | 8/2011 | Kidd et al. | |
| 8,009,793 B2 | 8/2011 | Langheinrich et al. | |
| 8,021,326 B2 | 9/2011 | Moll et al. | |
| 8,046,488 B2 | 10/2011 | Cherukuri et al. | |
| 8,068,894 B2 * | 11/2011 | Huizenga | A61B 5/055 |
| | | | 600/410 |
| 8,107,695 B2 | 1/2012 | Wollenweber | |
| 8,108,069 B2 | 1/2012 | Stahler et al. | |
| 8,114,097 B2 | 2/2012 | Brock et al. | |
| 8,139,836 B2 | 3/2012 | Arnold et al. | |
| 8,144,949 B2 | 3/2012 | Simon et al. | |
| 8,186,880 B1 | 5/2012 | Arnold | |
| 8,200,466 B2 | 6/2012 | Spiker et al. | |
| 8,211,084 B2 | 7/2012 | Kassab et al. | |
| 8,257,302 B2 | 9/2012 | Beyar et al. | |
| 8,317,744 B2 | 11/2012 | Kirschenman | |
| 8,386,188 B2 | 2/2013 | Taylor et al. | |
| 8,390,438 B2 | 3/2013 | Olson et al. | |
| 8,460,236 B2 | 6/2013 | Roelle et al. | |
| 8,494,244 B2 | 7/2013 | Dutta et al. | |
| 8,526,699 B2 | 9/2013 | Mittal et al. | |
| 8,551,084 B2 | 10/2013 | Hauck et al. | |
| 8,582,854 B2 | 11/2013 | Zhang et al. | |
| 8,603,068 B2 | 12/2013 | Weitzner et al. | |
| 8,605,979 B2 | 12/2013 | Arnold et al. | |
| 8,615,288 B2 | 12/2013 | Govari et al. | |
| 8,660,326 B2 | 2/2014 | Ohayon et al. | |
| 8,684,953 B2 | 4/2014 | Cabiri | |
| 8,740,840 B2 | 6/2014 | Foley et al. | |
| 8,774,479 B2 | 7/2014 | Madabhushi et al. | |
| 8,777,854 B2 | 7/2014 | Patwardhan et al. | |
| 8,790,297 B2 | 7/2014 | Bromander et al. | |
| 8,867,822 B2 | 10/2014 | Oh et al. | |
| 8,885,905 B2 | 11/2014 | Dey et al. | |
| 8,938,106 B2 | 1/2015 | Aulbach et al. | |
| 9,005,217 B2 | 4/2015 | Govari et al. | |
| 9,008,392 B1 | 4/2015 | Bai et al. | |
| 9,058,692 B1 | 6/2015 | Grady et al. | |
| 9,066,740 B2 | 6/2015 | Carlson et al. | |
| 9,070,214 B1 | 6/2015 | Grady et al. | |
| 9,081,721 B1 | 7/2015 | Grady et al. | |
| 9,129,417 B2 | 9/2015 | Zheng et al. | |
| 9,138,566 B2 | 9/2015 | Cabiri | |
| 9,155,512 B2 | 10/2015 | Choi et al. | |
| 9,159,159 B2 | 10/2015 | Bai et al. | |
| 9,195,801 B1 | 11/2015 | Sankaran et al. | |
| 9,220,418 B2 | 12/2015 | Choi et al. | |
| 9,220,419 B2 | 12/2015 | Choi et al. | |
| 9,220,568 B2 | 12/2015 | Bromander et al. | |
| 9,235,887 B2 | 1/2016 | Bucker et al. | |
| 9,239,905 B1 | 1/2016 | Sankaran et al. | |
| 9,280,639 B2 | 3/2016 | Sankaran et al. | |
| 9,295,397 B2 | 3/2016 | Liu et al. | |
| 9,295,429 B2 | 3/2016 | Ong et al. | |
| 9,295,527 B2 | 3/2016 | Kirschenman et al. | |
| 9,320,573 B2 | 4/2016 | Sandhu et al. | |
| 9,333,324 B2 | 5/2016 | Cohen et al. | |
| 9,378,580 B2 | 6/2016 | Grady et al. | |
| 9,430,827 B2 | 8/2016 | Kelm et al. | |
| 9,538,925 B2 | 1/2017 | Sharma et al. | |
| 9,545,246 B2 | 1/2017 | Lavender | |
| 9,586,029 B2 | 3/2017 | Shekalim et al. | |
| 9,610,272 B2 | 4/2017 | Soni | |
| 9,633,277 B2 | 4/2017 | Feldman et al. | |
| 9,642,586 B2 | 5/2017 | Kelm et al. | |
| 9,649,171 B2 | 5/2017 | Sankaran et al. | |
| 9,655,563 B2 | 5/2017 | Liu et al. | |
| 9,679,374 B2 | 6/2017 | Choi et al. | |
| 9,700,219 B2 | 7/2017 | Sharma et al. | |
| 9,715,562 B2 | 7/2017 | Goldstein | |
| 9,721,340 B2 | 8/2017 | Gillies et al. | |
| 9,761,004 B2 | 9/2017 | Mittal et al. | |
| 9,763,650 B2 | 9/2017 | Chen et al. | |
| 9,767,557 B1 | 9/2017 | Gulsun et al. | |
| 9,770,303 B2 | 9/2017 | Choi et al. | |
| 9,785,748 B2 | 10/2017 | Koo et al. | |
| 9,805,463 B2 | 10/2017 | Choi et al. | |
| 9,805,470 B2 | 10/2017 | Bhatia et al. | |
| 9,814,490 B2 | 11/2017 | Neoh et al. | |
| 9,836,653 B2 | 12/2017 | Schnittman | |

(56)　　　　　References Cited

U.S. PATENT DOCUMENTS

| | | | |
|---|---|---|---|
| 9,839,399 | B2 | 12/2017 | Fonte et al. |
| 9,839,484 | B2 | 12/2017 | Taylor |
| 9,881,372 | B2 | 1/2018 | Gulsun et al. |
| 9,965,891 | B2 | 5/2018 | Grady et al. |
| 9,980,960 | B2 | 5/2018 | Chance |
| 10,010,255 | B2 | 7/2018 | Fonte et al. |
| 10,010,700 | B2 | 7/2018 | Romoscanu |
| 10,052,031 | B2 | 8/2018 | Sharma et al. |
| 10,078,124 | B2 | 9/2018 | Horkay et al. |
| 10,082,553 | B2 | 9/2018 | Boss |
| 10,082,793 | B1 | 9/2018 | Glaser |
| 10,130,242 | B2 | 11/2018 | Ostrovsky et al. |
| 10,149,728 | B2 | 12/2018 | Bencteux et al. |
| 10,170,206 | B2 | 1/2019 | Koo et al. |
| 10,176,408 | B2 | 1/2019 | Paik et al. |
| 10,307,131 | B2 | 6/2019 | Taylor et al. |
| 10,352,411 | B2 | 7/2019 | Fojtik |
| 10,354,360 | B2 | 7/2019 | Sakamoto |
| 10,357,230 | B2 | 7/2019 | Bolduc |
| 10,359,783 | B2 | 7/2019 | Williams et al. |
| 10,398,331 | B2 | 9/2019 | Relan |
| 10,433,740 | B2 | 10/2019 | Fonte et al. |
| 10,448,811 | B2 | 10/2019 | London et al. |
| 10,451,409 | B2 | 10/2019 | Tojo et al. |
| 10,453,191 | B2 | 10/2019 | Shalev et al. |
| 10,456,094 | B2 | 10/2019 | Fonte et al. |
| 10,456,556 | B2 | 10/2019 | Cabiri |
| 10,463,835 | B2 | 11/2019 | Jungles |
| 10,470,793 | B2 | 11/2019 | McArthur et al. |
| 10,478,130 | B2 | 11/2019 | Sharma et al. |
| 10,478,595 | B2 | 11/2019 | Kokish |
| 10,483,006 | B2 | 11/2019 | Itu et al. |
| 10,492,755 | B2 | 12/2019 | Lin |
| 10,498,755 | B2 | 12/2019 | Harris |
| 10,500,373 | B2 | 12/2019 | Barrish et al. |
| 10,507,037 | B2 | 12/2019 | Doud et al. |
| 10,517,677 | B2 | 12/2019 | Sankaran et al. |
| 10,542,878 | B2 | 1/2020 | Dewaele et al. |
| 10,549,071 | B2 | 2/2020 | Falb et al. |
| 10,610,203 | B2 | 4/2020 | Liang et al. |
| 10,632,287 | B2 | 4/2020 | Romoscanu et al. |
| 10,667,673 | B2 | 6/2020 | Su et al. |
| 10,695,023 | B2 | 6/2020 | Antoniades et al. |
| 10,695,533 | B2 | 6/2020 | Deboeuf et al. |
| 10,695,536 | B2 | 6/2020 | Weitzner et al. |
| 10,709,510 | B2 | 7/2020 | Kottenstette |
| 10,740,880 | B2 | 8/2020 | Paik et al. |
| 10,744,301 | B2 | 8/2020 | Pacheco et al. |
| 10,755,810 | B2 | 8/2020 | Buckler et al. |
| 10,762,624 | B2 | 9/2020 | Daughton et al. |
| 10,776,988 | B2 | 9/2020 | Grady et al. |
| 10,799,305 | B2 | 10/2020 | Murphy et al. |
| 10,799,677 | B2 | 10/2020 | Khuu et al. |
| 10,806,897 | B2 | 10/2020 | Furnish |
| 10,813,612 | B2 | 10/2020 | Min |
| 10,813,708 | B2 | 10/2020 | Reinstein et al. |
| 10,828,468 | B2 | 11/2020 | Selkee |
| 10,835,716 | B2 | 11/2020 | Kim et al. |
| 10,871,536 | B2 | 12/2020 | Golden et al. |
| 10,888,234 | B2 | 1/2021 | Sharma et al. |
| 10,929,828 | B2 | 2/2021 | Matsukura |
| 10,933,221 | B2 | 3/2021 | Lepak et al. |
| 10,939,828 | B2 | 3/2021 | Fonte et al. |
| 10,939,960 | B2 | 3/2021 | Choi et al. |
| 10,943,142 | B2 | 3/2021 | Daughton et al. |
| 10,945,606 | B2 | 3/2021 | Sanders et al. |
| 10,951,715 | B2 | 3/2021 | Hart et al. |
| 10,959,789 | B2 | 3/2021 | Yi et al. |
| 10,964,071 | B2 | 3/2021 | Grady et al. |
| 10,966,619 | B2 | 4/2021 | Fonte et al. |
| 10,973,469 | B2 | 4/2021 | Karimabadi |
| 10,973,583 | B2 | 4/2021 | Taylor et al. |
| 10,978,210 | B2 | 4/2021 | Grady et al. |
| 10,984,535 | B2 | 4/2021 | Grady et al. |
| 10,987,010 | B2 | 4/2021 | Grady et al. |
| 10,990,652 | B2 | 4/2021 | Tayler et al. |
| 10,991,465 | B2 | 4/2021 | Grady |
| 10,994,097 | B2 | 5/2021 | Ludwin et al. |
| 11,013,425 | B2 | 5/2021 | Fonte et al. |
| 11,017,904 | B2 | 5/2021 | Sankaran et al. |
| 11,033,332 | B2 | 6/2021 | Taylor |
| 11,042,822 | B2 | 6/2021 | Sankaran et al. |
| 11,071,501 | B2 | 7/2021 | Buckler et al. |
| 11,076,924 | B2 | 8/2021 | Kim et al. |
| 11,083,524 | B2 | 8/2021 | Taylor |
| 11,087,459 | B2 | 8/2021 | Buckler et al. |
| 11,087,460 | B2 | 8/2021 | Buckler et al. |
| 11,087,884 | B2 | 8/2021 | Sankaran et al. |
| 11,090,118 | B2 | 8/2021 | Taylor |
| 11,094,058 | B2 | 8/2021 | Buclker et al. |
| 11,094,060 | B1 | 8/2021 | Min et al. |
| 11,094,061 | B1 | 8/2021 | Min et al. |
| 11,113,811 | B2 | 9/2021 | Min et al. |
| 11,113,812 | B2 | 9/2021 | Buckler et al. |
| 11,116,575 | B2 | 9/2021 | Taylor |
| 11,120,312 | B2 | 9/2021 | Buckler et al. |
| 11,120,549 | B2 | 9/2021 | Min et al. |
| 11,120,550 | B2 | 9/2021 | Min et al. |
| 11,120,893 | B2 | 9/2021 | Choi et al. |
| 11,127,503 | B2 | 9/2021 | Rabbat et al. |
| 11,132,796 | B2 | 9/2021 | Min et al. |
| 11,135,012 | B2 | 10/2021 | Taylor |
| 11,138,337 | B2 | 10/2021 | Yousfi et al. |
| 11,141,566 | B2 | 10/2021 | Cabiri |
| 11,147,950 | B2 | 10/2021 | Destrebecq et al. |
| 11,154,361 | B2 | 10/2021 | Taylor |
| 11,169,538 | B2 | 11/2021 | Williams et al. |
| 11,185,368 | B2 | 11/2021 | Spilker et al. |
| 11,185,666 | B2 | 11/2021 | Choi et al. |
| 11,187,307 | B2 | 11/2021 | Asselin et al. |
| 11,196,068 | B2 | 12/2021 | Weingaertner et al. |
| 11,210,786 | B2 | 12/2021 | Min et al. |
| 11,213,356 | B2 | 1/2022 | Tanner et al. |
| 11,229,775 | B2 | 1/2022 | Kim et al. |
| 11,232,564 | B2 | 1/2022 | Min et al. |
| 11,234,767 | B2 | 2/2022 | Viswanathan et al. |
| 11,238,587 | B2 | 2/2022 | Min et al. |
| 11,244,451 | B1 | 2/2022 | Min et al. |
| 11,257,584 | B2 | 2/2022 | Buckler et al. |
| 11,257,585 | B2 | 2/2022 | Bhatia et al. |
| 11,266,424 | B2 | 3/2022 | Hofmann et al. |
| 11,272,995 | B2 | 3/2022 | Landey et al. |
| 11,273,038 | B2 | 3/2022 | Tang et al. |
| 11,276,170 | B2 | 3/2022 | Min et al. |
| 11,278,703 | B2 | 3/2022 | Kokish et al. |
| 11,288,799 | B2 | 3/2022 | Min et al. |
| 11,288,813 | B2 | 3/2022 | Grady et al. |
| 11,291,515 | B2 | 4/2022 | Sharon et al. |
| 11,295,865 | B2 | 4/2022 | Rabbat et al. |
| 11,298,187 | B2 | 4/2022 | Taylor |
| 11,298,198 | B2 | 4/2022 | Fournier et al. |
| 11,298,505 | B2 | 4/2022 | Bailey et al. |
| 11,302,001 | B2 | 4/2022 | Min et al. |
| 11,302,002 | B2 | 4/2022 | Min et al. |
| 11,308,617 | B2 | 4/2022 | Min et al. |
| 11,311,699 | B2 | 4/2022 | Weisz et al. |
| 11,315,247 | B2 | 4/2022 | Min et al. |
| 11,317,883 | B2 | 5/2022 | Min et al. |
| 11,318,302 | B2 | 5/2022 | Asleson et al. |
| 11,321,840 | B2 | 5/2022 | Min et al. |
| 11,328,824 | B2 | 5/2022 | Fonte |
| 11,337,764 | B2 | 5/2022 | Deboeuf et al. |
| 11,341,644 | B2 | 5/2022 | Min et al. |
| 11,350,899 | B2 | 6/2022 | Min |
| 11,357,469 | B2 | 6/2022 | Taylor et al. |
| 11,367,190 | B2 | 6/2022 | Min et al. |
| 11,382,569 | B2 | 7/2022 | Grady et al. |
| 11,386,563 | B2 | 7/2022 | Figueroa-Alvarez et al. |
| 11,398,029 | B2 | 7/2022 | Grady et al. |
| 11,399,729 | B2 | 8/2022 | Fonte et al. |
| 11,423,805 | B2 | 8/2022 | Sankaran et al. |
| 11,424,036 | B2 | 8/2022 | Fonte et al. |
| 11,424,038 | B2 | 8/2022 | Grady et al. |
| 11,430,113 | B2 | 8/2022 | Daughton et al. |

(56) References Cited

U.S. PATENT DOCUMENTS

| | | |
|---|---|---|
| 11,462,329 B2 | 10/2022 | Rabbat et al. |
| 11,482,339 B2 | 10/2022 | Koo et al. |
| 11,494,904 B2 | 11/2022 | Fonte et al. |
| 11,501,436 B2 | 11/2022 | Min et al. |
| 11,501,485 B2 | 11/2022 | Grady et al. |
| 11,504,019 B2 | 11/2022 | Fonte et al. |
| 11,508,063 B2 | 11/2022 | Buckler |
| 11,521,755 B2 | 12/2022 | Taylor et al. |
| 11,540,931 B2 | 1/2023 | Grady et al. |
| 11,547,367 B2 | 1/2023 | Taylor |
| 11,564,746 B2 | 1/2023 | Spilker et al. |
| 11,576,626 B2 | 2/2023 | Fonte et al. |
| 11,583,340 B2 | 2/2023 | Taylor |
| 11,589,924 B2 | 2/2023 | Passerini et al. |
| 11,592,836 B2 | 2/2023 | Williams et al. |
| 11,593,926 B2 | 2/2023 | Buckler et al. |
| 11,594,319 B2 | 2/2023 | Yousfi et al. |
| 11,599,996 B2 | 3/2023 | Isgum et al. |
| 11,605,466 B2 | 3/2023 | Grady et al. |
| 11,607,179 B2 | 3/2023 | Buckler et al. |
| 11,610,318 B2 | 3/2023 | Grady et al. |
| 11,617,620 B2 | 4/2023 | Tran et al. |
| 11,622,812 B2 | 4/2023 | Grady et al. |
| 11,638,609 B2 | 5/2023 | Sankaran et al. |
| 11,642,092 B1 | 5/2023 | Min |
| 11,642,171 B2 | 5/2023 | Jaquet et al. |
| 11,644,849 B2 | 5/2023 | Williams et al. |
| 11,646,118 B2 | 5/2023 | Grady et al. |
| 11,653,833 B2 | 5/2023 | Sanders et al. |
| 11,657,486 B2 | 5/2023 | Buckler et al. |
| 11,660,058 B2 | 5/2023 | Min |
| 11,660,143 B2 | 5/2023 | Taylor et al. |
| 11,663,715 B2 | 5/2023 | Choi et al. |
| 11,672,497 B2 | 6/2023 | Min |
| 11,676,359 B2 | 6/2023 | Buckler et al. |
| 11,678,937 B2 | 6/2023 | Choi et al. |
| 11,690,586 B2 | 7/2023 | Min |
| 11,696,735 B2 | 7/2023 | Buckler et al. |
| 11,701,175 B2 | 7/2023 | Bai et al. |
| 11,707,325 B2 | 7/2023 | Sankaran et al. |
| 11,715,187 B2 | 8/2023 | Buckler et al. |
| 11,715,198 B2 | 8/2023 | Kim et al. |
| 11,730,437 B2 | 8/2023 | Min |
| 11,737,718 B2 | 8/2023 | Min |
| 11,742,070 B2 | 8/2023 | Grady et al. |
| 11,751,826 B2 | 9/2023 | Min |
| 11,751,829 B2 | 9/2023 | Min |
| 11,751,830 B2 | 9/2023 | Min |
| 11,751,831 B2 | 9/2023 | Min |
| 11,756,690 B2 | 9/2023 | Koo et al. |
| 11,759,161 B2 | 9/2023 | Min |
| 11,766,229 B2 | 9/2023 | Min |
| 11,766,230 B2 | 9/2023 | Min |
| 11,779,292 B2 | 10/2023 | Min |
| 11,784,329 B1 | 10/2023 | Basu et al. |
| 11,803,965 B2 | 10/2023 | Fonte et al. |
| 11,817,219 B2 | 11/2023 | Rabbat et al. |
| 11,826,106 B2 | 11/2023 | Hart et al. |
| 11,832,982 B2 | 12/2023 | Min et al. |
| 11,837,353 B2 | 12/2023 | Bhatia et al. |
| 11,847,781 B2 | 12/2023 | Grady et al. |
| 11,854,704 B2 | 12/2023 | Grady et al. |
| 11,861,831 B2 | 1/2024 | Choi et al. |
| 11,861,833 B2 | 1/2024 | Min et al. |
| 11,862,342 B2 | 1/2024 | Grady et al. |
| 11,865,195 B2 | 1/2024 | Sinusas et al. |
| 11,869,186 B2 | 1/2024 | Buckler et al. |
| 11,869,669 B2 | 1/2024 | Spilker et al. |
| 11,883,225 B2 | 1/2024 | Sankaran et al. |
| 11,887,305 B1 | 1/2024 | Grady et al. |
| 11,887,701 B2 | 1/2024 | Buckler et al. |
| 11,887,713 B2 | 1/2024 | Buckler et al. |
| 11,887,734 B2 | 1/2024 | Buckler et al. |
| 11,896,415 B2 | 2/2024 | Min et al. |
| 11,901,076 B1 | 2/2024 | Daughton et al. |
| 11,915,822 B2 | 2/2024 | Yi et al. |
| 11,918,293 B2 | 3/2024 | Grady et al. |
| 11,941,152 B2 | 3/2024 | Yousfi et al. |
| 11,967,078 B2 | 4/2024 | Min et al. |
| 11,986,280 B2 | 5/2024 | Grady et al. |
| 11,992,293 B2 | 5/2024 | Fonte et al. |
| 11,996,182 B2 | 5/2024 | Lee et al. |
| 12,004,841 B2 | 6/2024 | Sanders et al. |
| 12,008,751 B2 | 6/2024 | Buckler et al. |
| 12,016,635 B2 | 6/2024 | Taylor |
| 12,020,432 B2 | 6/2024 | Ross et al. |
| 12,026,868 B2 | 7/2024 | Buckler et al. |
| 12,027,275 B2 | 7/2024 | Koo et al. |
| 12,029,494 B2 | 7/2024 | Taylor |
| 12,035,976 B2 | 7/2024 | Choi et al. |
| 12,039,765 B2 | 7/2024 | Buckler et al. |
| 12,045,983 B2 | 7/2024 | Buckler et al. |
| 12,046,367 B2 | 7/2024 | Yi et al. |
| 12,048,490 B2 | 7/2024 | Grady et al. |
| 12,051,497 B2 | 7/2024 | Grady et al. |
| 12,059,288 B2 | 8/2024 | Taylor et al. |
| 12,068,079 B2 | 8/2024 | Sankaran et al. |
| 12,073,561 B2 | 8/2024 | Buckler et al. |
| 12,073,943 B2 | 8/2024 | Yu et al. |
| 12,079,921 B2 | 9/2024 | Grady et al. |
| 12,079,988 B2 | 9/2024 | Yi et al. |
| 12,096,990 B2 | 9/2024 | Sankaran et al. |
| 12,100,149 B2 | 9/2024 | Buckler et al. |
| 12,106,477 B2 | 10/2024 | Buckler et al. |
| 12,112,483 B2 | 10/2024 | Grady et al. |
| 12,114,933 B2 | 10/2024 | Seo et al. |
| 12,118,694 B2 | 10/2024 | Buckler et al. |
| 12,125,261 B2 | 10/2024 | Petersen et al. |
| 12,125,571 B2 | 10/2024 | Buckler et al. |
| 12,125,572 B2 | 10/2024 | Buckler et al. |
| 12,131,147 B2 | 10/2024 | Reasor |
| 12,131,471 B2 | 10/2024 | Buckler et al. |
| 12,131,472 B2 | 10/2024 | Buckler et al. |
| 12,136,214 B2 | 11/2024 | Buckler et al. |
| 2001/0047137 A1 | 11/2001 | Moreno et al. |
| 2002/0172663 A1 | 11/2002 | Palasis |
| 2003/0152519 A1 | 8/2003 | Koenig et al. |
| 2003/0176780 A1 | 9/2003 | Arnold et al. |
| 2004/0017936 A1 | 1/2004 | Gopinath et al. |
| 2004/0059260 A1 | 3/2004 | Truwit |
| 2004/0101181 A1 | 5/2004 | Giger et al. |
| 2004/0133094 A1 | 7/2004 | Becker et al. |
| 2004/0133100 A1 | 7/2004 | Naghavi et al. |
| 2004/0135031 A1 | 7/2004 | Stupakis |
| 2004/0136491 A1 | 7/2004 | Iatrou et al. |
| 2004/0147838 A1 | 7/2004 | Londt et al. |
| 2004/0254566 A1 | 12/2004 | Plicchi et al. |
| 2005/0020998 A1 | 1/2005 | Bonnette et al. |
| 2005/0038575 A1 | 2/2005 | Wu |
| 2005/0043614 A1 | 2/2005 | Huizenga et al. |
| 2005/0110791 A1 | 5/2005 | Krishnamoorthy et al. |
| 2005/0118632 A1 | 6/2005 | Chen et al. |
| 2005/0171508 A1 | 8/2005 | Gilboa |
| 2005/0245862 A1 | 11/2005 | Seward et al. |
| 2006/0013460 A1 | 1/2006 | Dehmeshki |
| 2006/0036167 A1 | 2/2006 | Shina |
| 2006/0101075 A1 | 5/2006 | Lehel et al. |
| 2006/0146010 A1 | 7/2006 | Schneider |
| 2007/0018558 A1 | 1/2007 | Chua et al. |
| 2007/0019778 A1 | 1/2007 | Clouse et al. |
| 2007/0172447 A1 | 7/2007 | Sakurada et al. |
| 2007/0239140 A1 | 10/2007 | Chechelski et al. |
| 2007/0248250 A1 | 10/2007 | Gulsun et al. |
| 2007/0260141 A1 | 11/2007 | Margolis et al. |
| 2008/0058642 A1 | 3/2008 | Gould |
| 2008/0100621 A1 | 5/2008 | Aharon et al. |
| 2008/0103389 A1 | 5/2008 | Begelman et al. |
| 2008/0118131 A1 | 5/2008 | Skinner et al. |
| 2008/0119713 A1 | 5/2008 | Le et al. |
| 2008/0119734 A1 | 5/2008 | Pruvot et al. |
| 2008/0187199 A1 | 8/2008 | Gulsun et al. |
| 2008/0188962 A1 | 8/2008 | Suryanarayanan et al. |
| 2008/0226017 A1 | 9/2008 | Altman et al. |
| 2009/0012382 A1 | 1/2009 | Dutta et al. |

(56) References Cited

U.S. PATENT DOCUMENTS

| | | |
|---|---|---|
| 2009/0012533 A1 | 1/2009 | Barbagli et al. |
| 2009/0016588 A1 | 1/2009 | Slabaugh et al. |
| 2009/0082722 A1 | 3/2009 | Munger et al. |
| 2009/0129673 A1 | 5/2009 | Simon et al. |
| 2009/0264771 A1 | 10/2009 | Houben et al. |
| 2009/0276161 A1 | 11/2009 | Cobain |
| 2009/0278846 A1 | 11/2009 | Gulsun et al. |
| 2009/0299645 A1 | 12/2009 | Colby et al. |
| 2009/0307179 A1 | 12/2009 | Colby et al. |
| 2010/0030035 A1 | 2/2010 | Chan et al. |
| 2010/0137711 A1 | 6/2010 | Hamilton et al. |
| 2010/0156898 A1 | 6/2010 | Voros et al. |
| 2010/0177945 A1 | 7/2010 | Moriya |
| 2010/0201786 A1 | 8/2010 | Schaefer et al. |
| 2010/0204646 A1 | 8/2010 | Plicchi et al. |
| 2010/0215225 A1 | 8/2010 | Kadomura et al. |
| 2010/0278405 A1 | 11/2010 | Kakadiaris et al. |
| 2010/0316274 A1 | 12/2010 | Langheinrich et al. |
| 2011/0026798 A1 | 2/2011 | Madabhushi et al. |
| 2011/0077591 A1 | 3/2011 | Plicchi et al. |
| 2011/0116697 A1 | 5/2011 | Dafni et al. |
| 2011/0144576 A1 | 6/2011 | Rothe et al. |
| 2011/0144658 A1 | 6/2011 | Wenderow et al. |
| 2011/0206247 A1 | 8/2011 | Dachille et al. |
| 2011/0218427 A1 | 9/2011 | Kitamura |
| 2011/0229002 A1 | 9/2011 | Arnold et al. |
| 2011/0238010 A1 | 9/2011 | Kirschenman et al. |
| 2011/0243412 A1 | 10/2011 | Grass |
| 2011/0245650 A1 | 10/2011 | Kerwin et al. |
| 2011/0282182 A1 | 11/2011 | Ohayon et al. |
| 2012/0041323 A1 | 2/2012 | Taylor et al. |
| 2012/0075638 A1 | 3/2012 | Rollins et al. |
| 2012/0076377 A1 | 3/2012 | Dutta et al. |
| 2012/0128132 A1 | 5/2012 | Coolens et al. |
| 2012/0158011 A1 | 6/2012 | Sandhu et al. |
| 2012/0158432 A1 | 6/2012 | Jain |
| 2012/0219198 A1 | 8/2012 | Mohr |
| 2012/0226227 A1 | 9/2012 | Weitzner et al. |
| 2012/0232005 A1 | 9/2012 | Dasseux et al. |
| 2012/0243764 A1 | 9/2012 | Dey et al. |
| 2012/0245595 A1 | 9/2012 | Kesavadas et al. |
| 2012/0263368 A1 | 10/2012 | Nakano et al. |
| 2012/0330335 A1 | 12/2012 | Shekalim et al. |
| 2013/0046168 A1 | 2/2013 | Sui |
| 2013/0066188 A1 | 3/2013 | Taerum et al. |
| 2013/0094749 A1 | 4/2013 | Oh et al. |
| 2013/0101187 A1 | 4/2013 | Sundar et al. |
| 2013/0190592 A1 | 7/2013 | Coppini et al. |
| 2013/0190595 A1 | 7/2013 | Oraevsky et al. |
| 2013/0202173 A1 | 8/2013 | Buckler et al. |
| 2013/0246034 A1 | 9/2013 | Sharma et al. |
| 2013/0304034 A1 | 11/2013 | Cabiri |
| 2013/0304035 A1 | 11/2013 | Cabiri |
| 2014/0058715 A1 | 2/2014 | Sharma et al. |
| 2014/0073976 A1 | 3/2014 | Fonte et al. |
| 2014/0114176 A1 | 4/2014 | Hirschenbain et al. |
| 2014/0276392 A1 | 9/2014 | Wong et al. |
| 2014/0276647 A1 | 9/2014 | Yu |
| 2014/0277333 A1 | 9/2014 | Lewis et al. |
| 2014/0306961 A1 | 10/2014 | Nagata |
| 2014/0343457 A1 | 11/2014 | Shekalim et al. |
| 2014/0350568 A1 | 11/2014 | Shekalim et al. |
| 2015/0009465 A1 | 1/2015 | Park et al. |
| 2015/0015702 A1 | 1/2015 | Yamaguchi et al. |
| 2015/0016702 A1 | 1/2015 | Huizenga et al. |
| 2015/0045287 A1 | 2/2015 | Chen et al. |
| 2015/0065846 A1 | 3/2015 | Choi |
| 2015/0066818 A1* | 3/2015 | Choi ..................... G16H 50/20 |
| | | 706/12 |
| 2015/0073340 A1 | 3/2015 | Pacheco et al. |
| 2015/0073342 A1 | 3/2015 | Pacheco et al. |
| 2015/0080907 A1 | 3/2015 | Herrell et al. |
| 2015/0090057 A1 | 4/2015 | Pacheco et al. |
| 2015/0099997 A1 | 4/2015 | Cabiri |
| 2015/0164342 A1 | 6/2015 | Choi et al. |
| 2015/0187025 A1 | 7/2015 | Wasserkrug et al. |
| 2015/0193944 A1 | 7/2015 | Lang et al. |
| 2015/0220240 A1 | 8/2015 | Tsukijishin et al. |
| 2015/0223832 A1 | 8/2015 | Swaney et al. |
| 2015/0265359 A1 | 9/2015 | Camarillo |
| 2015/0313677 A1 | 11/2015 | Kidd et al. |
| 2015/0314107 A1 | 11/2015 | Rothe et al. |
| 2015/0356734 A1 | 12/2015 | Ooga et al. |
| 2016/0012614 A1 | 1/2016 | Goto |
| 2016/0038002 A1 | 2/2016 | Peters et al. |
| 2016/0058303 A1 | 3/2016 | Grady et al. |
| 2016/0066861 A1 | 3/2016 | Taylor |
| 2016/0078309 A1 | 3/2016 | Feldman |
| 2016/0103816 A1 | 4/2016 | Grady et al. |
| 2016/0104281 A1 | 4/2016 | Grady et al. |
| 2016/0203263 A1 | 7/2016 | Maier et al. |
| 2016/0210428 A1 | 7/2016 | Spilker et al. |
| 2016/0239564 A1 | 8/2016 | Sohma |
| 2016/0271368 A1 | 9/2016 | Falb et al. |
| 2016/0291110 A1 | 10/2016 | Balu et al. |
| 2016/0292372 A1 | 10/2016 | Kamen et al. |
| 2016/0296288 A1 | 10/2016 | Sankaran et al. |
| 2016/0300350 A1 | 10/2016 | Choi et al. |
| 2016/0306944 A1 | 10/2016 | Grady et al. |
| 2016/0310702 A1 | 10/2016 | Cabiri |
| 2016/0342765 A1 | 11/2016 | Sankaran et al. |
| 2016/0346043 A1 | 12/2016 | Jaquet et al. |
| 2016/0358333 A1 | 12/2016 | Lee et al. |
| 2017/0014034 A1 | 1/2017 | Koo et al. |
| 2017/0018081 A1 | 1/2017 | Taylor et al. |
| 2017/0046484 A1 | 2/2017 | Buckler et al. |
| 2017/0046839 A1 | 2/2017 | Paik et al. |
| 2017/0103525 A1 | 4/2017 | Hu et al. |
| 2017/0119333 A1 | 5/2017 | Zebaze et al. |
| 2017/0161455 A1 | 6/2017 | Grady et al. |
| 2017/0199654 A1 | 7/2017 | Wu et al. |
| 2017/0202621 A1 | 7/2017 | Taylor |
| 2017/0245821 A1 | 8/2017 | Itu et al. |
| 2017/0252025 A1 | 9/2017 | Cabiri et al. |
| 2017/0258433 A1 | 9/2017 | Gulsun et al. |
| 2017/0265831 A1 | 9/2017 | Sankaran et al. |
| 2017/0265832 A1 | 9/2017 | Antodiades |
| 2017/0337343 A1 | 11/2017 | Kakadiaris et al. |
| 2017/0340393 A1 | 11/2017 | Choi et al. |
| 2017/0348060 A1 | 12/2017 | Blacker |
| 2017/0360372 A1 | 12/2017 | Hauck et al. |
| 2017/0367776 A1 | 12/2017 | Kwok et al. |
| 2018/0050626 A1 | 2/2018 | Delp et al. |
| 2018/0064910 A1 | 3/2018 | Tegg |
| 2018/0078139 A1 | 3/2018 | Sanders et al. |
| 2018/0125596 A1 | 5/2018 | He et al. |
| 2018/0126122 A1 | 5/2018 | Cabiri |
| 2018/0165811 A1 | 6/2018 | Flohr et al. |
| 2018/0179189 A1 | 6/2018 | MacPhee et al. |
| 2018/0185104 A1 | 7/2018 | Olson et al. |
| 2018/0214675 A1 | 8/2018 | Shekalim et al. |
| 2018/0225847 A1 | 8/2018 | Grady et al. |
| 2018/0242944 A1 | 8/2018 | Uber et al. |
| 2018/0243033 A1 | 8/2018 | Tran et al. |
| 2018/0259976 A1 | 9/2018 | Williams et al. |
| 2018/0330477 A1 | 11/2018 | Paik et al. |
| 2018/0336319 A1 | 11/2018 | Itu et al. |
| 2018/0364738 A1 | 12/2018 | Bridges |
| 2019/0021608 A1 | 1/2019 | Cope et al. |
| 2019/0029519 A1 | 1/2019 | Itu et al. |
| 2019/0050807 A1 | 2/2019 | Ferguson et al. |
| 2019/0074082 A1 | 3/2019 | Buckler et al. |
| 2019/0076092 A1 | 3/2019 | Saroha et al. |
| 2019/0105112 A1 | 4/2019 | Popovic et al. |
| 2019/0110776 A1 | 4/2019 | Yu et al. |
| 2019/0111237 A1 | 4/2019 | Cabiri |
| 2019/0133456 A1 | 5/2019 | Grady et al. |
| 2019/0159737 A1 | 5/2019 | Buckler et al. |
| 2019/0167077 A1 | 6/2019 | Hancock et al. |
| 2019/0172197 A1 | 6/2019 | Buckler et al. |
| 2019/0174082 A1 | 6/2019 | Taruki et al. |
| 2019/0175130 A1 | 6/2019 | Raman et al. |
| 2019/0180153 A1 | 6/2019 | Buckler et al. |
| 2019/0180438 A1 | 6/2019 | Buckler et al. |

(56) References Cited

U.S. PATENT DOCUMENTS

| | | | |
|---|---|---|---|
| 2019/0200881 A1 | 7/2019 | Grady et al. | |
| 2019/0244347 A1 | 8/2019 | Buckler et al. | |
| 2019/0244348 A1 | 8/2019 | Buckler et al. | |
| 2019/0251713 A1 | 8/2019 | Chen et al. | |
| 2019/0254690 A1 | 8/2019 | Cabiri et al. | |
| 2019/0255289 A1 | 8/2019 | Cabiri | |
| 2019/0282211 A1 | 9/2019 | Merritt et al. | |
| 2019/0307987 A1 | 10/2019 | Yu | |
| 2019/0318476 A1 | 10/2019 | Isgum et al. | |
| 2019/0339712 A1 | 11/2019 | Williams et al. | |
| 2019/0343404 A1 | 11/2019 | Shekalim et al. | |
| 2019/0350538 A1 | 11/2019 | Wilson et al. | |
| 2019/0388164 A1 | 12/2019 | Gruionu et al. | |
| 2020/0000539 A1 | 1/2020 | Sholev et al. | |
| 2020/0060820 A1 | 2/2020 | Ben-Zvi et al. | |
| 2020/0069262 A1 | 3/2020 | Fonte et al. | |
| 2020/0085501 A1 | 3/2020 | Sankaran et al. | |
| 2020/0117851 A1 | 4/2020 | Grady et al. | |
| 2020/0129252 A1 | 4/2020 | Kokish et al. | |
| 2020/0129740 A1 | 4/2020 | Kottenstette et al. | |
| 2020/0134897 A1 | 4/2020 | Grady et al. | |
| 2020/0165309 A1 | 5/2020 | Yount et al. | |
| 2020/0178815 A1 | 6/2020 | Choi et al. | |
| 2020/0178990 A1 | 6/2020 | Chu | |
| 2020/0179649 A1 | 6/2020 | Kern et al. | |
| 2020/0188635 A1 | 6/2020 | Barrish et al. | |
| 2020/0197111 A1 | 6/2020 | Kim et al. | |
| 2020/0237329 A1 | 7/2020 | Min | |
| 2020/0237440 A1 | 7/2020 | Zabar et al. | |
| 2020/0243076 A1 | 7/2020 | Kim | |
| 2020/0243885 A1 | 7/2020 | Weingaertner et al. | |
| 2020/0246089 A1 | 8/2020 | Schlenk et al. | |
| 2020/0273579 A1 | 8/2020 | Wright | |
| 2020/0282181 A1 | 9/2020 | Cabiri | |
| 2020/0294659 A1 | 9/2020 | Gopinath et al. | |
| 2020/0297442 A1 | 9/2020 | Adebar et al. | |
| 2020/0297971 A1 | 9/2020 | Beeckler et al. | |
| 2020/0320775 A1 | 10/2020 | Holladay et al. | |
| 2020/0337585 A1 | 10/2020 | Shochat et al. | |
| 2020/0360659 A1 | 11/2020 | Wong et al. | |
| 2020/0372701 A1 | 11/2020 | Grady et al. | |
| 2020/0388391 A1 | 12/2020 | Upton et al. | |
| 2020/0402234 A1 | 12/2020 | Daughton et al. | |
| 2020/0405182 A1 | 12/2020 | Hoitink et al. | |
| 2020/0405413 A1 | 12/2020 | Kokish et al. | |
| 2021/0007807 A1 | 1/2021 | Sankaran et al. | |
| 2021/0023337 A1 | 1/2021 | Debuys et al. | |
| 2021/0030478 A1 | 2/2021 | Hart et al. | |
| 2021/0035287 A1 | 2/2021 | Kim et al. | |
| 2021/0035687 A1 | 2/2021 | Yi et al. | |
| 2021/0042918 A1 | 2/2021 | Bucker | |
| 2021/0042927 A1 | 2/2021 | Amis et al. | |
| 2021/0045764 A1 | 2/2021 | Sholev et al. | |
| 2021/0060310 A1 | 3/2021 | Kim et al. | |
| 2021/0074435 A1 | 3/2021 | Taylor et al. | |
| 2021/0077196 A1 | 3/2021 | Jaquet et al. | |
| 2021/0077209 A1 | 3/2021 | Yu | |
| 2021/0082579 A1 | 3/2021 | Grady et al. | |
| 2021/0085397 A1 | 3/2021 | Passerini et al. | |
| 2021/0090694 A1 | 3/2021 | Colley et al. | |
| 2021/0093384 A1 | 4/2021 | Grady et al. | |
| 2021/0151171 A1 | 5/2021 | Lee et al. | |
| 2021/0153749 A1 | 5/2021 | Fonte et al. | |
| 2021/0153945 A1 | 5/2021 | Choi et al. | |
| 2021/0161384 A1 | 6/2021 | Sanders et al. | |
| 2021/0177375 A1 | 6/2021 | Upton et al. | |
| 2021/0185131 A1 | 6/2021 | Hart et al. | |
| 2021/0186448 A1 | 6/2021 | Min | |
| 2021/0196387 A1 | 7/2021 | Seo et al. | |
| 2021/0196391 A1 | 7/2021 | Taylor et al. | |
| 2021/0201495 A1 | 7/2021 | Yu et al. | |
| 2021/0202110 A1 | 7/2021 | Grady et al. | |
| 2021/0209757 A1 | 7/2021 | Min et al. | |
| 2021/0210209 A1 | 7/2021 | Taylor et al. | |
| 2021/0212565 A1 | 7/2021 | Gardner et al. | |
| 2021/0217165 A1 | 7/2021 | Min et al. | |
| 2021/0217534 A1 | 7/2021 | Rabbat et al. | |
| 2021/0225006 A1 | 7/2021 | Grady et al. | |
| 2021/0228094 A1 | 7/2021 | Grady et al. | |
| 2021/0236105 A1 | 8/2021 | Hansen et al. | |
| 2021/0236775 A1 | 8/2021 | Schultz | |
| 2021/0236778 A1 | 8/2021 | Kim et al. | |
| 2021/0241455 A1 | 8/2021 | Min et al. | |
| 2021/0241920 A1 | 8/2021 | Sankaran et al. | |
| 2021/0244475 A1 | 8/2021 | Taylor | |
| 2021/0267690 A1 | 9/2021 | Taylor | |
| 2021/0272030 A1 | 9/2021 | Sankaran et al. | |
| 2021/0282719 A1 | 9/2021 | Buckler et al. | |
| 2021/0282860 A1 | 9/2021 | Taylor | |
| 2021/0312622 A1 | 10/2021 | Buckler et al. | |
| 2021/0319558 A1 | 10/2021 | Min et al. | |
| 2021/0322102 A1 | 10/2021 | Sankaran et al. | |
| 2021/0334961 A1 | 10/2021 | Min et al. | |
| 2021/0334962 A1 | 10/2021 | Min et al. | |
| 2021/0334964 A1 | 10/2021 | Min et al. | |
| 2021/0334965 A1 | 10/2021 | Min et al. | |
| 2021/0334966 A1 | 10/2021 | Min et al. | |
| 2021/0335497 A1 | 10/2021 | Sankaran et al. | |
| 2021/0338333 A1 | 11/2021 | Sankaran et al. | |
| 2021/0343010 A1 | 11/2021 | Min et al. | |
| 2021/0358634 A1 | 11/2021 | Sankaran et al. | |
| 2021/0358635 A1 | 11/2021 | Sankaran et al. | |
| 2021/0361366 A1 | 11/2021 | Murphy et al. | |
| 2021/0366111 A1 | 11/2021 | Min et al. | |
| 2021/0366112 A1 | 11/2021 | Min et al. | |
| 2021/0366113 A1 | 11/2021 | Min et al. | |
| 2021/0366114 A1 | 11/2021 | Min et al. | |
| 2021/0366115 A1 | 11/2021 | Min et al. | |
| 2021/0366116 A1 | 11/2021 | Min et al. | |
| 2021/0374969 A1 | 12/2021 | Grady et al. | |
| 2021/0375401 A1 | 12/2021 | Choi et al. | |
| 2021/0375476 A1 | 12/2021 | Rabbat et al. | |
| 2021/0386390 A1 | 12/2021 | Min | |
| 2021/0390689 A1 | 12/2021 | Buckler et al. | |
| 2021/0397746 A1 | 12/2021 | Yousfi et al. | |
| 2022/0012865 A1 | 1/2022 | Buckler et al. | |
| 2022/0012877 A1 | 1/2022 | Buckler et al. | |
| 2022/0012878 A1 | 1/2022 | Aoyama | |
| 2022/0026924 A1 | 1/2022 | Williams et al. | |
| 2022/0028070 A1* | 1/2022 | Min | A61B 6/504 |
| 2022/0059856 A1 | 2/2022 | Weingaertner et al. | |
| 2022/0079540 A1 | 3/2022 | Sankaran et al. | |
| 2022/0079681 A1 | 3/2022 | Grady et al. | |
| 2022/0084198 A1 | 3/2022 | Viti | |
| 2022/0097817 A1 | 3/2022 | Perry et al. | |
| 2022/0098249 A1 | 3/2022 | Shah et al. | |
| 2022/0110687 A1 | 4/2022 | Spilker et al. | |
| 2022/0110690 A1 | 4/2022 | Sankaran et al. | |
| 2022/0111176 A1 | 4/2022 | Dale et al. | |
| 2022/0114388 A1 | 4/2022 | Li et al. | |
| 2022/0117683 A1 | 4/2022 | Schnur et al. | |
| 2022/0122251 A1 | 4/2022 | Min et al. | |
| 2022/0139529 A1 | 5/2022 | Bhatia et al. | |
| 2022/0172353 A1 | 6/2022 | Yi et al. | |
| 2022/0202857 A1 | 6/2022 | Brewer et al. | |
| 2022/0211439 A1 | 7/2022 | Sankaran et al. | |
| 2022/0211452 A1 | 7/2022 | Clark et al. | |
| 2022/0216489 A1 | 7/2022 | Perry | |
| 2022/0221861 A1 | 7/2022 | McVeen | |
| 2022/0222825 A1 | 7/2022 | Yaacobi | |
| 2022/0230312 A1 | 7/2022 | Choi et al. | |
| 2022/0241019 A1 | 8/2022 | Taylor | |
| 2022/0253074 A1 | 8/2022 | Williams et al. | |
| 2022/0253992 A1 | 8/2022 | Buckler et al. | |
| 2022/0265239 A1 | 8/2022 | Taylor et al. | |
| 2022/0277443 A1 | 9/2022 | Min et al. | |
| 2022/0284572 A1 | 9/2022 | Min et al. | |
| 2022/0322953 A1 | 10/2022 | Fonte et al. | |
| 2022/0327695 A1 | 10/2022 | Min | |
| 2022/0327701 A1 | 10/2022 | Grady et al. | |
| 2022/0330902 A1 | 10/2022 | Forneris et al. | |
| 2022/0335603 A1 | 10/2022 | Min | |
| 2022/0335859 A1 | 10/2022 | Sankaran et al. | |
| 2022/0359063 A1 | 11/2022 | Tombropoulos et al. | |

(56) References Cited

U.S. PATENT DOCUMENTS

| | | |
|---|---|---|
| 2022/0366562 A1 | 11/2022 | Yu et al. |
| 2022/0367066 A1 | 11/2022 | Grady et al. |
| 2022/0375072 A1 | 11/2022 | Min et al. |
| 2022/0383464 A1 | 12/2022 | Buckler et al. |
| 2022/0383495 A1 | 12/2022 | Peterson et al. |
| 2022/0386979 A1 | 12/2022 | Min et al. |
| 2022/0392065 A1 | 12/2022 | Min |
| 2022/0392070 A1 | 12/2022 | Buckler et al. |
| 2022/0398706 A1 | 12/2022 | Buckler et al. |
| 2022/0400963 A1 | 12/2022 | Buckler et al. |
| 2022/0401050 A1 | 12/2022 | Min |
| 2022/0406459 A1 | 12/2022 | Buckler et al. |
| 2022/0406470 A1 | 12/2022 | Fonte et al. |
| 2022/0409160 A1 | 12/2022 | Buckler et al. |
| 2022/0415519 A1 | 12/2022 | Buckler et al. |
| 2023/0005582 A1 | 1/2023 | Buckler et al. |
| 2023/0005583 A1 | 1/2023 | Buckler et al. |
| 2023/0005622 A1 | 1/2023 | Rabbat et al. |
| 2023/0016104 A1 | 1/2023 | Koo et al. |
| 2023/0033594 A1 | 2/2023 | Grade et al. |
| 2023/0055828 A1 | 2/2023 | Fonte et al. |
| 2023/0113005 A1 | 4/2023 | Antoniades et al. |
| 2023/0117134 A1 | 4/2023 | Clifton et al. |
| 2023/0124826 A1 | 4/2023 | Spilker et al. |
| 2023/0130265 A1 | 4/2023 | Kodali et al. |
| 2023/0132940 A1 | 5/2023 | Min et al. |
| 2023/0137093 A1 | 5/2023 | Min |
| 2023/0137934 A1 | 5/2023 | Min et al. |
| 2023/0138144 A1 | 5/2023 | Min |
| 2023/0138468 A1 | 5/2023 | Martinovski |
| 2023/0138889 A1 | 5/2023 | Min |
| 2023/0139102 A1 | 5/2023 | Taylor |
| 2023/0142747 A1 | 5/2023 | Min et al. |
| 2023/0144293 A1 | 5/2023 | Min et al. |
| 2023/0144338 A1 | 5/2023 | Min et al. |
| 2023/0145596 A1 | 5/2023 | Min |
| 2023/0147336 A1 | 5/2023 | Min et al. |
| 2023/0147995 A1 | 5/2023 | Min |
| 2023/0148977 A1 | 5/2023 | Fonte et al. |
| 2023/0148981 A1 | 5/2023 | Min et al. |
| 2023/0154000 A1 | 5/2023 | Min |
| 2023/0154620 A1 | 5/2023 | Yi et al. |
| 2023/0162603 A1 | 5/2023 | Martin |
| 2023/0165544 A1 | 6/2023 | Hahn, III et al. |
| 2023/0169702 A1 | 6/2023 | Hahn et al. |
| 2023/0172451 A1 | 6/2023 | Seo et al. |
| 2023/0196582 A1 | 6/2023 | Grady et al. |
| 2023/0197286 A1 | 6/2023 | Grady et al. |
| 2023/0205227 A1 | 6/2023 | Williams et al. |
| 2023/0207137 A1 | 6/2023 | Buckler et al. |
| 2023/0210602 A1 | 7/2023 | Sankaran et al. |
| 2023/0218346 A1 | 7/2023 | Tran et al. |
| 2023/0218347 A1 | 7/2023 | Taylor |
| 2023/0223148 A1 | 7/2023 | Grady et al. |
| 2023/0233261 A1 | 7/2023 | Jaquet et al. |
| 2023/0237654 A1 | 7/2023 | Min |
| 2023/0237759 A1 | 7/2023 | Buckler et al. |
| 2023/0240619 A1 | 8/2023 | Daughton et al. |
| 2023/0245775 A1 | 8/2023 | Buckler et al. |
| 2023/0248242 A1 | 8/2023 | Sanders et al. |
| 2023/0277247 A1 | 9/2023 | Taylor et al. |
| 2023/0289939 A1 | 9/2023 | Buckler et al. |
| 2023/0289963 A1 | 9/2023 | Min et al. |
| 2023/0290433 A1 | 9/2023 | Buckler et al. |
| 2023/0290524 A1 | 9/2023 | Taylor et al. |
| 2023/0298168 A1 | 9/2023 | Lee et al. |
| 2023/0298176 A1 | 9/2023 | Choi et al. |
| 2023/0301720 A1 | 9/2023 | Grady et al. |
| 2023/0301722 A1 | 9/2023 | Choi et al. |
| 2023/0310085 A1 | 10/2023 | Sankaran et al. |
| 2023/0326166 A1 | 10/2023 | Buckler et al. |
| 2023/0342923 A1 | 10/2023 | Lee et al. |
| 2023/0342929 A1 | 10/2023 | Kim et al. |
| 2023/0343455 A1 | 10/2023 | Kwon et al. |
| 2023/0352152 A1 | 11/2023 | Grady et al. |
| 2023/0360803 A1 | 11/2023 | Sankaran et al. |
| 2023/0360804 A1 | 11/2023 | Koo et al. |
| 2023/0368365 A9 | 11/2023 | Buckler et al. |
| 2023/0386026 A1 | 11/2023 | Buckler |
| 2023/0386633 A1 | 11/2023 | Buckler et al. |
| 2023/0386634 A1 | 11/2023 | Buckler et al. |
| 2023/0397816 A1 | 12/2023 | Forneris et al. |
| 2023/0420130 A1 | 12/2023 | Buckler et al. |
| 2023/0420131 A1 | 12/2023 | Buckler et al. |
| 2023/0420143 A1 | 12/2023 | Buckler et al. |
| 2023/0420144 A1 | 12/2023 | Buckler et al. |
| 2024/0000414 A1 | 1/2024 | Abdolmanafi et al. |
| 2024/0006066 A1 | 1/2024 | Buckler et al. |
| 2024/0013388 A1 | 1/2024 | Fonte et al. |
| 2024/0021306 A1 | 1/2024 | Buckler et al. |
| 2024/0023918 A1 | 1/2024 | Min |
| 2024/0038398 A1 | 2/2024 | Rabbat et al. |
| 2024/0046457 A1 | 2/2024 | Buckler et al. |
| 2024/0047045 A1 | 2/2024 | Bhatia et al. |
| 2024/0050159 A1 | 2/2024 | Hart et al. |
| 2024/0057960 A1 | 2/2024 | Min et al. |
| 2024/0062901 A1 | 2/2024 | Buckler et al. |
| 2024/0070863 A1 | 2/2024 | Grady et al. |
| 2024/0078671 A1 | 3/2024 | Buckler et al. |
| 2024/0078672 A1 | 3/2024 | Buckler et al. |
| 2024/0078673 A1 | 3/2024 | Buckler et al. |
| 2024/0087742 A1 | 3/2024 | Buckler et al. |
| 2024/0130702 A1 | 4/2024 | Flack et al. |
| 2024/0153229 A1 | 5/2024 | Buckler et al. |
| 2024/0153252 A1 | 5/2024 | Phillips et al. |
| 2024/0161295 A1 | 5/2024 | Buckler et al. |
| 2024/0161296 A1 | 5/2024 | Buckler et al. |
| 2024/0161297 A1 | 5/2024 | Buckler et al. |
| 2024/0202915 A1 | 6/2024 | Buckler et al. |
| 2024/0212143 A1 | 6/2024 | Buckler et al. |
| 2024/0232433 A1 | 7/2024 | Yousfi et al. |
| 2024/0259352 A1 | 8/2024 | Yousfi et al. |
| 2024/0274276 A1 | 8/2024 | Lee et al. |
| 2024/0298894 A1 | 9/2024 | Sanders et al. |
| 2024/0315777 A1 | 9/2024 | Choi et al. |
| 2024/0331151 A1 | 10/2024 | Seo et al. |
| 2024/0331848 A1 | 10/2024 | Seo et al. |

FOREIGN PATENT DOCUMENTS

| | | |
|---|---|---|
| CA | 3017610 A1 | 9/2017 |
| CA | 3238598 A1 | 5/2023 |
| CA | 3240201 A1 | 6/2023 |
| CN | 1556688 A | 12/2004 |
| CN | 102415894 A | 4/2012 |
| CN | 106999122 A | 8/2017 |
| CN | 107530041 A | 1/2018 |
| CN | 110914866 A | 3/2020 |
| CN | 112288731 A | 1/2021 |
| CN | 112336365 A | 2/2021 |
| CN | 112567378 A | 3/2021 |
| CN | 113439287 A | 9/2021 |
| CN | 115511995 A | 12/2022 |
| CN | 117501379 A | 2/2024 |
| CN | 117918872 A | 4/2024 |
| CN | 118077008 A | 5/2024 |
| CN | 118334070 A | 7/2024 |
| EP | 3185762 A1 | 7/2017 |
| EP | 3278254 A1 | 2/2018 |
| EP | 3326092 A1 | 5/2018 |
| EP | 3355762 A1 | 8/2018 |
| EP | 3384413 A1 | 10/2018 |
| EP | 3 431 005 A1 | 1/2019 |
| EP | 3457959 A1 | 3/2019 |
| EP | 3516561 A1 | 7/2019 |
| EP | 3533410 A1 | 9/2019 |
| EP | 3569150 A2 | 11/2019 |
| EP | 3585253 A1 | 1/2020 |
| EP | 3665702 A2 | 6/2020 |
| EP | 3803687 A1 | 4/2021 |
| EP | 3846176 A1 | 7/2021 |
| EP | 3899864 A1 | 10/2021 |
| EP | 3912550 A1 | 11/2021 |
| EP | 4147632 A1 | 3/2023 |

(56) References Cited

FOREIGN PATENT DOCUMENTS

| | | |
|---|---|---|
| EP | 4183344 A1 | 5/2023 |
| EP | 4252186 A1 | 10/2023 |
| EP | 4292098 A1 | 12/2023 |
| EP | 4312776 A1 | 2/2024 |
| EP | 4334941 A1 | 3/2024 |
| EP | 4377885 A1 | 6/2024 |
| EP | 4404141 A2 | 7/2024 |
| EP | 4418280 A2 | 8/2024 |
| EP | 4430534 A1 | 9/2024 |
| EP | 4445835 A2 | 10/2024 |
| EP | 4447838 A1 | 10/2024 |
| FR | 2908976 A1 | 5/2008 |
| GB | 2557263 A | 6/2018 |
| GB | 2618468 A | 11/2023 |
| IN | 202317079967 | 9/2024 |
| JP | 2003-150703 | 5/2003 |
| JP | 2005-519657 A | 7/2005 |
| JP | 2007-029129 A | 2/2007 |
| JP | 2009-506854 A | 2/2009 |
| JP | 2011-115481 | 6/2011 |
| JP | 2011-135938 | 7/2011 |
| JP | 2012-509122 A | 4/2012 |
| JP | 2012-179360 A | 9/2012 |
| JP | 2012-196436 A | 10/2012 |
| JP | 5305821 B2 | 10/2013 |
| JP | 2014-534822 A | 12/2014 |
| JP | 2016-529037 A | 9/2016 |
| JP | 6203410 B2 | 9/2017 |
| JP | 2018-511791 A | 4/2018 |
| JP | 2021-525929 A | 9/2021 |
| JP | 2022-123103 A | 8/2022 |
| JP | 7113916 B2 | 8/2022 |
| JP | 2022-543330 A | 10/2022 |
| JP | 2023-054309 A | 4/2023 |
| JP | 2023-093605 A | 7/2023 |
| JP | 2023-118960 A | 8/2023 |
| JP | 2024-506605 A | 2/2024 |
| JP | 2024-069343 A | 5/2024 |
| JP | 7483079 B2 | 5/2024 |
| JP | 7505093 B2 | 6/2024 |
| JP | 2024-528679 A | 7/2024 |
| JP | 2024-113185 A | 8/2024 |
| JP | 2024-529232 A | 8/2024 |
| JP | 7542578 B2 | 8/2024 |
| KR | 10-2017-0120154 A | 10/2017 |
| KR | 10-2020-0115489 A | 10/2020 |
| KR | 10-2021-0042267 A | 4/2021 |
| KR | 10-2021-0096942 A | 8/2021 |
| KR | 10-2021-0121062 A | 10/2021 |
| KR | 10-2022-0155828 A | 11/2022 |
| KR | 10-2491988 B1 | 1/2023 |
| KR | 10-2023-0069884 A | 5/2023 |
| KR | 10-2023-0146038 A | 10/2023 |
| KR | 10-2024-0054248 A | 4/2024 |
| KR | 10-2024-0064617 A | 5/2024 |
| KR | 10-2690881 B1 | 8/2024 |
| KR | 10-2024-0133667 A | 9/2024 |
| KR | 10-2024-0147616 A | 10/2024 |
| KR | 10-2024-0147617 A | 10/2024 |
| WO | 03/39601 A1 | 5/2003 |
| WO | 2004/019256 A2 | 3/2004 |
| WO | WO 07/029129 | 3/2007 |
| WO | WO 09/105530 | 8/2009 |
| WO | WO 10/067276 | 6/2010 |
| WO | 2013/054947 A1 | 4/2013 |
| WO | WO 14/107402 | 7/2014 |
| WO | WO 14/132829 | 9/2014 |
| WO | WO 15/095282 | 6/2015 |
| WO | 2015/168682 A1 | 11/2015 |
| WO | WO 16/022533 | 2/2016 |
| WO | WO 16 /024128 | 2/2016 |
| WO | 2016/138449 A1 | 9/2016 |
| WO | 2016/165432 A1 | 10/2016 |
| WO | 2016/168292 A1 | 10/2016 |
| WO | WO 17/011555 | 1/2017 |
| WO | WO 17/096407 | 6/2017 |
| WO | WO 17/106819 | 6/2017 |
| WO | WO 18/078395 | 5/2018 |
| WO | 2018/156961 A1 | 8/2018 |
| WO | WO 19/033098 | 2/2019 |
| WO | WO 19/165432 | 8/2019 |
| WO | 2019/200108 A1 | 10/2019 |
| WO | 2019/231844 A1 | 12/2019 |
| WO | WO 19/242227 | 12/2019 |
| WO | 2020/146360 A1 | 7/2020 |
| WO | 2021/011518 A1 | 1/2021 |
| WO | 2021/011533 A1 | 1/2021 |
| WO | 2021/011551 A1 | 1/2021 |
| WO | 2021/011554 A1 | 1/2021 |
| WO | 2021/026125 A1 | 2/2021 |
| WO | 2021/065312 A1 | 4/2021 |
| WO | 2021/117724 A1 | 6/2021 |
| WO | 2021/141921 A1 | 7/2021 |
| WO | WO 21/141135 | 7/2021 |
| WO | 2022/173534 A1 | 8/2022 |
| WO | 2022/221921 A1 | 10/2022 |
| WO | 2022/261506 A1 | 12/2022 |
| WO | 2023/004451 A1 | 2/2023 |
| WO | 2023/089559 A1 | 5/2023 |
| WO | 2023/111808 A1 | 6/2023 |
| WO | 2023/172273 A1 | 9/2023 |
| WO | 2024/095159 A1 | 5/2024 |
| WO | 2024/102879 A1 | 5/2024 |
| WO | 2024/105483 A1 | 5/2024 |
| WO | 2024/105484 A1 | 5/2024 |
| WO | 2024/171153 A1 | 8/2024 |

OTHER PUBLICATIONS

Anjana, P.S. et al., "Study on Self Balancing Motorcycle Using the Concept of Reinforcement Learning," International Research Journal of Engineering and Technology (IRJET), vol. 7, Issue 4, Apr. 2020, pp. 6524-6531.

Arthur S Agatston et al., Quantification ofcoronary artery calcium using ultrafast computed tomography, Journal of the American College of Cardiology, Mar. 15, 1990 , vol. 15, No. 4, pp. 827-832.

Bax, Maxim et al., "Comparative differences in the atherosclerotic disease burden between the epicardial coronary arteries: quantitative plaque analysis on coronary computed tomography angiography", European Society of Cardiology, European Heart Journal—Cardiovascular Imaging (2021) 22, 322-330, published ahead-of-print online Nov. 11, 2020, 9 pages total.

Benjamin, Mina M, Rabbat, Mark G., "Machine learning-based advances in coronary computed tomography angiography," Editorial, Quantitative imaging in Medicine and Sugery, vol. 11, No. Jun. 6, 2021, http://dx.doi.org/10.21037/qims-21-99.

Eskerud et al., "Total coronary atherosclerotic plaque burden is associated with myocardial ischemia in non-obstructive coronary artery disease", 2021 IJC Heart & Vasculature 35:100831 9 pages (Year: 2021), Elsevier B.V.

Fawaz, Ziad, "Design and Control of a Self-balancing Bicycle Using an Electric Linear Actuator," A thesis submitted in partial fulfillment of the requirements for the degree of Master of Science in Engineering (Electrical Engineering) in the University of Michigan-Dearborn 2019, https://deepblue.lib.umich.edu/bitstream/handle/2027.42/148,871/MastersThesis_FinalDraft (3).pdf?sequence=1, 34 pp.

Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons." Journal of the American College of Cardiology 2014;64 (18): 1929-49. doi: 10.1016/j.jacc.2014.07.017.

Hampe, N., Van Velzen, S. G., Aben, J., Collet, C., & Isgum, I. (2023). Deep Learning-Based Prediction of Fractional Flow Reserve along the Coronary Artery. ArXiv. /abs/2308.04923.

(56)         References Cited

OTHER PUBLICATIONS

Job, Mark, Section 510(k) premarket notification of intent to market device "Plaque View, Model No. CSPV-001 A" as filed and Review, K043111, Department of Health & Human Services, Food and Drug Administration, Nov. 18, 2004, 5 pages, Silver Springs, Maryland.

M. Zreik, N. Lessmann, KW. van Hamersvelt, et al., "Deep learning analysis of the myocardium in coronary CT angiography for identification of patients with functionally significant coronary artery stenosis." Medical Image Analysis 44, 72-85 (2018).

M. Zreik, R. W. van Hamersvelt, N. Khalili, et al., "Deep Learning Analysis of Coronary Arteries in Cardiac CT Angiography for Detection of Patients Requiring Invasive Coronary Angiography," IEEE Transactions on Medical Imaging 39, 1545-1557 (2020).

Narula et al., 2021, SCCT 2021 expert consensus document of coronary computed tomographic angiography: a report of the Society of Cardiovascular Computed Tomography, Journal of Cardiovascular Computed Tomography.

Rongero, Jeff D., Section 510(k) premarket notification of intent to market device "Vessel Analysis and Autoplaque for ORS Visual" as filed and Review, K122429, Department of Health & Human Services, Food and Drug Administration, Nov. 28, 2012, 11 pages, Silver Springs, Maryland.

Smith, John, Section 510(k) premarket notification of intent to market device "Adjunctive cardiovascular status indicator" as filed and Review, K231335, Department of Health & Human Services, Food and Drug Administration, Sep. 8, 2023, 9 pages, Silver Springs, Maryland.

The Copenhagen Wheel, https://senseable.mit.edu/copenhagenwheel/, website pages, 2 pages, printed on Oct. 2, 2023 (origination date unknown).

U.S. Food and Drug Administration, Nov. 5, 2010, K100868 501(k) Summary, 10 pp.

U.S. Food and Drug Administration, Oct. 2, 2020, K202280 501(k) Summary, 9 pp.

Velivelli, S. L.S., et al., "Antifungal symbiotic peptide NCR044 exhibits unique structure and multifaceted mechanisms of action that confer plant protection.", Proceedings of the National Academy of Sciences, vol. 117, Issue. 27, 2020, pp. 16043-16054.

Won, Philip, Section 510(k) premarket notification of intent to market device "Medical image management and processing system" as filed and Review, K212758, Department of Health & Human Services, Food and Drug Administration, May 19, 2023, 9 pages, Silver Springs, Maryland.

Yang et al., "Prognostic Implications of Comprehensive Whole Vessel Plaque Quantification Using Coronary Computed Tomography Angiography", Jun. 2021 JACC Asia vol. 1 No. 1:37-48 (Year 2021), Elsevier on behalf of the American College of Cardiology Foundation.

Abbara et al., "SCCT Guidelines for the performance and acquisition of coronary computed tomographic angiography: A report of the society of Cardiovascular Computed Tomography Guidelines Committee: Endorsed by the North American Society for Cardiovascular Imaging (NASCI)." Journal of cardiovascular computed tomography 2016; 10(6):435-449.

Abdelrahman et al., Sep. 8, 2020, Coronary computed tomography angiography from clinical uses to emerging technologies, Journal of the American College of Cardiology, 76(10):1226-1243.

Achenbach et al. "Detection of calcified and noncalcified coronary atherosclerotic plaque by contrast-enhanced, submillimeter multidetector spiral computed tomography: a segment-based comparison with intravascular ultrasound." Circulation 2004; 109(1):14-17.

Ahmadi A. et al. "Do Plaques rapidly progress prior to myocardial infarction? The interplay between plaque vulnerability and progression." Circ Res. 2015; 117(1):99-104.

Ahmadi et al., "Association of Coronary Stenosis and Plaque Morphology with Fractional Flow Reserve and Outcomes." JAMA cardiology 2016; 1 (3):350-357. doi: 10.1001/jamacardio.2016. 0263 [published Online First: Jul. 22, 2016].

Ahmadi et al., 2018, Lesion-Specific and Vessel-Related Determinants of Fractional Flow Reserve Beyond Coronary Artery Stenosis, JACCL Cardiovascular Imaging, 11(4):521-530.

Al'Aref et al. "Clinical Applications of machine learning in cardiovascular disease and its relevance to cardiac imaging." Eur Heart J. Jul. 27, 2018. [Epub ahead of print].

Al'Aref et al., "High-risk atherosclerotic plaque features for cardiovascular risk assessment in the Prospective Multicenter Imaging Study for Evaluation of Chest Pain trial", Cardiovascular Diagnosis and Therapy, vol. 9, No. 1, Feb. 2019. pp. 89-93.

Antonopoulos et al., "Detecting Human coronary inflammation by imaging perivascular fat", Sci. Transl. Med. 9, eaal2658 (2017) Jul. 12, 2017.

Arbab-Zadeh et al., "Contemporary Reviews in Cardiovascular Medicine, Acute Coronary Events", Amercan Heart Association, Inc., Circulation. 2012;125:1147-1156, Mar. 6, 2012, pp. 1147-1156.

Arbab-Zadeh, et al. "the myth of the vulnerable plaque: transitioning from a focus on individual lesions to atherosclerotic disease burden for coronary artery disease risk assessment." J Am Coll Cardiol. 2015;65: 846-855.

Bakhasi, et al. "Comparative Effectiveness of CT-Derived Atherosclerotic Plaque Metrics for Predicting Myocardial Ischemia." JACC Cardiovasc Imaging. Jul. 1, 20183. doi: 10.2013/j.jcmg.2018.05. 019. [Epub ahead of print].

Baskaran et al., "Dense calcium and lesion-specific ischemia: A comparison of CCTA with fractional flow reserve", Atherosclerosis 260, 2017 pp. 163-168.

Benjamin, et al. "Heart Disease and Stroke Statistics-2018 Update: A Report From the American Heart Association." Circulation. 2018;137: e67-e492.

Bergman "Using Multicoloured Halftsone Screens for Offset Print Quality Monitoring", Linköping Studies in Science and Technology; LiU-TEK-LIC-2005:02.

Blankstein R. et al. " Coronary CTA in the Evaluation of Stable Chest Pain: Clear Benefits, but Not for All." J Am Coll Cardiol 2017; 69 (14): 1771-73. doi: 10.1016/j.jacc.2017.02.011 [published Online First: Apr. 8, 2017].

Boogers, et al. "Automated Quantification of Coronary Plaque with Computed Tomography: Comparison with Intravascular Ultrasound using a Dedicated Registration Algorithm for Fusion-Based Quantification", Epub, (2012).

Boussoussou et al., 2023, The effect of patient and imaging characteristics on coronary CT angiography assessed perocoronary adipose tissue attenuation and gradient, Journal of Cardiovascular Computed Tomography, 17:34-42.

Budde et al., Sep. 15, 2021, CT-derived fractional flow reserve (FFRct) for functional coronary artery evaluation in the follow-up of patients after heart transplantation, European Radiology, https://doi.org/10/1007/s00330-0921-08246-5.

Budoff MJ, et al. "Diagnostic performance of 64-multidetector row coronary computed tomographic angiography for evaluation of coronary artery stenosis in individuals without know coronary artery disease: results from the prospective multicenter ACCU-RACY (Assessment by Coronary Computed Tomography of Individuals Undergoing Invasive Coronary Angiography) trial." *J Am Coll Cardiol* 2008; 52(21): 1724-32.

Bzdok "Classical Statistics and Statistical Learning in Imaging Neuroscience." Front Neurosci. 2017; 11:543.

Calvert, et al. "Association between IVUS Findings and Adverse Outcomes in Patients with Coronary Artery Disease: the VIVA (VH-IVUS in Vulnerable Atherosclerosis) Study." JACC Cardiovasc Imaging. 2011;4: 894-901.

Celeng, et al. "Non-invasive and Invasive Imaging of Vulnerable Coronary Plaque." trends Cardiovasc Med. 2016;26-538-47.

Cerqueira et al. "Standardized myocardial segmentation and nomenclature for tomographic imaging of the heart. A statement for healthcare professionals from the Cardiac Imaging Committee of the Council on Clinical Cardiology of the American Heart Association." Int J Cardiovasc Imaging 2002; 18(1): 539-42.

Chang et al., "Coronary Atherosclerotic Precursors of Acute Coronary Syndromes", Journal of the American College of Cardiology, vol. 71, No. 22, Jun. 5, 2018. pp. 2511-2522.

(56) References Cited

OTHER PUBLICATIONS

Chang et al., "Selective Referral Using CCTA Versus Direct Referral for Individuals Referred to Invasive Coronary Angiography for Suspected Cad", JACC: Cardiovascular Imaging, vol. 12, No. 7, Jul. 2019. pp. 1303-1312.

Chrencik et al., Sep. 2019, Quantitative assessment of carotid plaque morphology (geometry and tissue composition) using computed tomography angiography, Journal of Vascular Surgery, 70(3):858-868.

Chung et al. "Image Segmentation Methods for Detecting Blood Vessels in Angiography", 2006 9th Int. Conf. Control, Automation, Robotics and Vision, Singapore, Dec. 5-8, 2006, ICARCV 2006, pp. 1424-1429.

Costopoulos, et al. "Intravascular Ultrasound and Optical Coherence Tomography Imaging of Coronary Atherosclerosis." Int J Cardiovasc Imaging. 2016;32: 189-200.

Cury et al., 2022, CAD-RADS™ 2.0—2022 coronary artery disease—reporting and data system an expert consensus document of the Society of Cardiovascular Computed Tomography (SCCT), the American College of Cardiology (ACC), the American College of Radiology (ACR) and the North America Society of Cardiovascular Imaging (NASCI), Journal of Cardiovascular Computed Tomography, https://doi.org/10.1016/j.jcct.2022.07.002.

Cury, et al. "CAD-RADS™ Coronary Artery Disease—Reporting and Data System. An Expert consensus documents of the Society of Cardiovascular Computed Tomography (SCCT), the American College of Radiology (ACR) and the North American Society for Cardiovascular Imaging (NASCI)." Endorsed by the American College of Cardiology. J Cardiovasc Compute Tomogr. 2016;10: 269-81.

Danad et al. "Comparison of Coronary CT Angiography, SPECT, PET, and Hybrid Imaging for Diagnosis of Ischemic Heart Disease Determined by Fractional Flow Reserve." JAMA Cardiol 2017; 2(10): 1100-07. doi 10.1001/jamacardio.2017.2471 [published Online First: Aug. 17, 2017].

De Bruyne B. et al. "Fractional flow reserve-guided PCI for stable coronary artery disease." The New England journal of medicine 2014; 371 (13):1208-17. doi: 10.1056/NEJMoal408758 [published Online First: Sep. 2, 2014].

De Bruyne et al., Sep. 13, 2012, Fractional flow reserve-guided PCA versus medical therapy in stable coronary disease, The New England Journal of Medicine, 367(11):991-1001.

De Graaf, et al. "Automatic Quantification and Characterization of Coronary Atherosclerosis with Computed Tomography Coronary Angiography: Cross-Correlation with Intravascular Ultrasound Virtual Histology", Int J Cardiovasc, pp. 1177-1190, (2013).

De Graaf, et al. "Feasibility of an Automated Quantitative Computed Tomography Angiography-Derived Risk Stratification of Patients with Suspected CAD." Am J Cardiol (2014).

DeLong ER, et al. "Comparing the areas under two or more correlated receiver operating characteristic curves: a nonparametric approach." Biometrics 1988; 44 (3): 837-45. [published Online First: Sep. 11, 1988].

Dey et al., "Direct Quantitative In Vivo Comparison of Calcified Atherosclerotic Plaque on Vascular MRI and CT by Multimodality Image Registration" Journal of Magnetic Resonance Imaging 23:345-354 (2006).

Dey et al., 2018, Integrated prediction of lesion-specific ischemia from quantitative coronary CT Angiography using machine learning: a multicenter study, European Radiology, 28(6):2655-2664.

Dey, et al. "Comparison of Quantitative Atherosclerotic Plaque Burden from Coronary CT Angiography in Patients with First Acute Coronary Syndrome and Stable Cad" J Cardiovasc Comput tomogr (2014).

Dey, et al. "Non-Invasive Measurement of Coronary Plaque from Coronary CT Angiography and its Clinical Implication", Expert Review of Cardiovascular Therapy (2013).

Diaz-Zamudio, et al. "Automated Quantitative Plaque Burden from Coronary CT Angiography Non-Invasively Predicts Hemodynamic Significance by Using Fractional Flow Reserve in Intermediate Coronary Lesions." Radiology (2015).

Douglas et al., "Outcomes of Anatomical versus Functional Testing for Coronary Artery Disease", N Engl J Med. Apr. 2, 2015, p. 1291-1300.

Douglas et al., Aug. 2, 2016, 1-year outcomes of FFRCT-guided care in patients with suspected coronary disease, Journal of the American College of Cardiology, 68(5):435-445.

Driessen et al., "Adverse Plaque Characteristic Relate More Strongly With Hyperemic Fractional Flow Reserve and Instantaneous Wave-Free Ratio Than With Resting Instantaneous Wave-Free Ratio", JACC: Cardiovascular Imaging, 2019, in 11 pages.

Driessen et al., "Effect of Plaque Burden and Morphology on Myocardial Blood Flow and Fractional Flow Reserve", Journal of the American College of Cardiology, vol. 71, No. 5, 2018 p. 499-509.

Dwivedi et al., "Evaluation of Atherosclerotic Plaque in Non-invasive Coronary Imaging", Korean Circulation Journal, Feb. 2018. 48(2), pp. 124-133.

Ehara et al. "Spotty calcification typifies the culprit plaque in patients with acute myocardial infarction: an intravascular ultrasound study." Circulation 2004; 110(22): 3424-9.

Erickson BJ, et al. "Machine Learning for Medical Imaging." Radiographics 2017; 37(2) pp. 505-515.

Ferencik et al., "Use of High-Risk Coronary Atherosclerotic Plaque Detection for Risk Stratification of Patients With Stable Chest Pain", JAMA Cardiol, Feb. 2018 in 19 pages.

Ferencik, et al. "Computed Tomography-Based High-Risk Coronary Plaque Score to Predict ACS Among Patients with Acute Chest Pain" Journal of Cardiovascular Computed Tomography, (2015).

Fihn et al. "2012 ACCF/AHA/ACP/AATS/PCNA/SCAI/STS Guideline for the Diagnosis and the Management of Patients With Stable Ischemic Heart Disease: Executive Summary: A Report of the American College of Cardiology Foundation/American Heart Association Task Force on Practice Guidelines, and the American College of Physicians, American Association for Thoracic Surgery, Preventive Cardiovascular Nurses Association, Society for Cardiovascular Angiography and Interventions, and Society of Thoracic Surgeons." J Am Coll Cardio 2012;60(24):2564-603. doi: 10.1016/c.cacc.2012.07.012 [published Online First: Nov. 28, 2012].

Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons." Journal of the American College of Cardiology 2014;64 (18): 1929-49. doi:10.1016/j.jacc.2014.07.017 [published Online First: Aug. 1, 2014].

Friedman et al., "Additive logistic regression: a statistical view of boosting (With discussion and a rejoinder by the authors)." Ann Statist. 2000; 28(2) pp. 337-407.

Funama et al., Sep. 2017, Improved estimation of coronary plaque and luminal attenuation using a vendor-specific model-based iterative reconstruction algorithm in contrast-enhanced CT coronary angiography. Academic Radiology 24(9):1070-1078.

Gaemperli et al. "Cardiac hybrid imaging." Eur Heart J 2011; 32(17): 2100-8.

Gaur et al., "Coronary plaque quantification and fractional flow reserve by coronary computed tomography angiography identify ischaemia-causing lesions", European Heart Journal, 2016 pp. 1220-1227.

Goff, et al. "2013 ACC/AHA Guidelines on the Assessment of Cardiovascular Risk: a Report of the American College of Cardiology/American Heart Association Task Force on Practice Guidelines." J Am Coll Cardiol. 2014;63: 2935-59.

Gogas, et al. "Assessment of Coronary Atherosclerosis by IVUS and IVUS-based Imaging Modalities: Profession and Regression Studies, Tissue Composition and Beyond." Int J Cardiovasc Imaging. 2011;27: 225-37.

(56)     References Cited

OTHER PUBLICATIONS

Goldstein et al., "Moving beyond regression techniques in cardiovascular risk prediction: applying machine learning to address analytic challenges." Eur Heart J. 2017; 38(23) pp. 1805-1814.

Greenwood et al. "Effect of Care Guided by Cardiovascular Magnetic Resonance, Myocardial Perfusion Scintigraphy, or NICE Guidelines on Subsequent Unnecessary Angiography Rates: The CE-MARC 2 Randomized Clinical Trial." JAMA 2016; 316(10): 1051-60. doi: 10.1001/jama.2016.12680 [published Online First: Aug. 30, 2016.

Gupta et al., Apr. 8, 2015, Moving beyond luminal stenosis: imaging strategies for stroke prevention in asymptomatic carotid stenosis, Cerebrovascular Diseases, 39:253-261.

Guyon et al., "An introduction to variable and feature selection." J Mach Learn Res. 2003; 3:1157-1182.

Hadamitzky et al., "Optimized Prognostic Score for Coronary Computed Tomographic Angiography", Journal of the American College of Cardiology, vol. 62, No. 5, 2013, pp. 468-476.

Hall et al., "Benchmarking attribute selection techniques for discrete clas data mining." IEEE Transaction on Knowledge and Data Engineering 2003; 15(6): pp. 1437-1447.

Hall et al., "The WEKA data mining software: an update." SIGKDD Explor News. 2009; 11(1) pp. 10-18.

Han et al. "Incremental role of resting myocardial computed tomography perfusion for predicting physiologically significant coronary artery disease: A machine learning approach." J Nucl Cardiol. 2018; 25(1) pp. 223-233.

Han et al., "Quantitative measurement of lipid rich plaque by coronary computed tomography angiography: A correlation of histology in sudden cardiac death", Atherosclerosis, 2018 pp. 426-433.

Hausleiter et al. "Estimated radiation dose associated with cardiac CT angiography." JAMA 2009; 301(5): 500-7.

Heo et al., "Optimal boundary detection method and window settings for coronary atherosclerotic plaque volume analysis in coronary computed tomography angiography: comparison with intravascular ultrasound", Eur Radiol, (2016) 26:31, pp. 3190-3198.

Hesse et al. "EANM/ESC procedural guidelines for myocardial perfusion imaging in nuclear cardiology." Eur J Nucl Med Mol Imaging 2005; 32 (7): 855-97. doi: 10.1007/s00259-005-1779-y.

Howard G et al. "Cigarette smoking and progression of atherosclerosis: The Atherosclerosis Risk in Communities (AIRC) Study." JAMA 1998; 279(2) pp. 119-124.

Hundley WG et al. "Society for Cardiovascular Magnetic Resonance guidelines for reporting cardiovascular magnetic resonance examinations." J Cardiovasc Magn Reson 2009; 11:5.

Kanamori et al. "Robust Loss Functions for Boosting" Neural Computation. 2007; 19(8) pp. 2183-2244.

Kang et al., Apr. 2013, Automated Knowledge-Based Detection of Nonobstructive and Obstructive Arterial Lesions from Coronary CT Angiography. Medical Physics, 40(4):041912-1-041912-10.

Kang, et al. "Structured Learning Algorithm for Detection of Nonobstructive and Obstructive Coronary Plaque Lesions from Computed Tomography Angiography", Journal of Medical Imaging, (2015).

Kanitsar et al., 2002, CPR—curved planar reformation, IEEE Visualization, DOI: 10.1109/VISUAL.2002.1183754, 8 pp.

Karlof et al., 2019, Correlation of computed tomography with carotid plaque transcriptomes associates calcification with lesion-stabilization, atherosclerosis, 288:175-185.

Karlof et al., 2021, Carotid plaque phenotyping by correlating plaque morphology from computed tomography angiography with transcriptional profiling, Eur. J. Vas. Endovas. Surg., 62:716-726.

Kim et al., "Natural History of Diabetic Coronary Atherosclerosis by Quantitative Measurement of Serial Coronary Computed Tomographic Angiography", JACC: Cardiovascular Imaging, vol. 11, No. 10, 2018 pp. 1461-1471.

Klass O, et al. "Coronary plaque imaging with 256-slice multidetector computed tomography: interobserver variability of volumetric lesion parameters with semiautomatic plaque analysis software", *Int J Cardiovasc Imaging*, (2010). 26; pp. 711-720.

Klein et al. :Diagnostic quality of time-averaged ECG-Gated CT data, SPIE medical imaging, 2019.

Knuiman et al. "An Empirical comparison of multivariable methods for estimating risk of death from coronary heart disease." J. Cardiovasc Risk. 1997; 4(2): pp. 127-134.

Kolossvary, et al. "Radiomic Features Are Superior to Conventional Quantitative Computed Tomographic Metrics to Identify Coronary Plaques with Napkin-Ring Sign." Circ Cardiovasc Imaging. 2017;10.

Koo BK, et al. "Diagnosis of ischemia-causing coronary stenoses by noninvasive fractional flow reserve computed from coronary computed tomographic angiograms. Results from the prospective multicenterDISCOVERY-FLOW (Diagnosis of Ischemia-Causes Stenoses Obtained Via Noninvasive Fractional Flow Reserve) study." J Am Coll Cardiol 2011; 58 (19): 1989-97. doi: 10.1016/j.jacc.2011. 06.066 [published Online First: Oct. 29, 2011].

Kramer et al. "Standardized cardiovascular magnetic resonance imaging (CMR) protocols, society for cardiovascular magnetic resonance: board of trustees task force on standardized protocols." J Cardiovasc Magn Reson 2008; 10:35. doi: 10.1186/1532-429X-10-35.

Kwan et al., "Bridging the gap for lipid lowering therapy: plaque regression, coronary computed tomographic angiography, and imaging-guided personalized medicine." Expert Rev Cardiovasc Ther. 2017; 15(7): pp. 547-558.

Kwee et al., Apr. 2010, Systematic review on the association between calcification in carotid plaques and clinical ischemic symptoms, Journal of Vascular Surgery, 51(4):1015-1025.

Lee et al., "Differences in Progression to Obstructive Lesions per High-Risk Plaque Features and Plaque Volumes. With CCTA", JACC: Cardiovascular Imaging, 2019 in 9 pages.

Lee et al., "Identification of High-Risk Plaques Destined to Cause Acute Coronary Syndrome Using Coronary Computed Tomographic Angiography and Computational Fluid Dynamics", JACC: Cardiovascular Imaging, vol. 12, No. 6, Jun. 2019. pp. 1032-1043.

Lee et al., "Quantification of Coronary Atherosclerosis in the Assessment of Coronary Artery Disease." Circ Cardiovasc Imaging. 2018; 11(7): e007562.

Lee et al., Rationale and design of the Coronary Computed Tomographic Angiography for Selective Cardiac Catheterization: Relation to Cardiovascular Outcomes, Cost Effectiveness and Quality of Life (CONSERVE) trial:, Am Heart J, 2017; vol. 186, pp. 48-55.

Lee et al., "Rationale and design of the Progression of AtheRosclerotic PlAque Determined by Computed TomoGraphic Angiography Imaging (PARADIGM) registry: A comprehensive exploration of plaque progression and its impact on clinical outcomes from a multicenter serial coronary computed tomographic angiography study", American Heart Journal, vol. 182. 2016 pp. 72-79.

Lee et al., "Reproducibility in the assessment of noncalcified coronary plaque with 256-slice multi-detector CT and automated plaque analysis software", Int J Cardiovasc Imaging; 2010; 26:237-244.

Lee et al., 2018, Effects of Statins on Coronary Atherosclerotic Plaques—The PARADIGM (Progression of AtheRosclerotic PlAque Determined by Computed TomoGraphic Angiography Imaging) Study, JACC: Cardiovascular Imaging, 11(10):1475-1484.

Leipsic et al. "SCCT guidelines for the interpretation and reporting of coronary CT angiography: a report of the Society of Cardiovascular Computed Tomography Guidelines Committee" J Cardiovasc Comput Tomogr 2014; 8(5): 342-58.

Libby P. "Mechanisms of acute coronary syndromes and their implications for therapy." N Engl J Med. 2013; 368: 2004-13.

Lu et al., "Central Core Laboratory versus Site Interpretation of Coronary CT Angiography: Agreement and Association with Cardiovascular Events in the PROMISE Trial", Radiology: vol. 287, No. 1, Apr. 2018, pp. 87-95.

Lundberg, et al. "A Unified Approach to Interpreting Model Predictions." 31st Conference on Neural Information Processing Systems (NIPS 2017).

MacAlpin, Feb. 1980, Contribution of dynamic vascular wall thickening to luminal narrowing during coronary arterial constriction, Circulation, 60(2):296-301.

Mancio, Jennifer, et al. "Perivascular adipose tissue and coronary atherosclerosis." Hear 104.20 (2018): 1654-1662. (Year: 2018).

(56)          References Cited

OTHER PUBLICATIONS

Maurovich-Horvat et al., 2014, Comprehensive plaque assessment by coronary CT angiography, Nature Reviews Cardiology, 11(7):390-402.

Maurovich-Horvat, et al. "Comprehensive Plaque Assessment by Coronary CT Angiography", Nature Reviews, (2014).

Maurovich-Horvat, et al. "The napkin-ring sign indicates advanced atherosclerotic lesions in coronary CT angiography.", JACC Cardiovasc Imaging 2012; 5(12): 1243-52.

Meijboom et al. "Diagnostic accuracy of 64-slice computed tomography coronary angiography: a prospective, multicenter, multivendor study." J Am Coll Cardiol 2008; 52 (25): 2135-44. doi: 10.1016/j. jacc.2008.08.058.

Melikian et al. "Fractional flow reserve and myocardial perfusion imaging in patients with angiographic multivessel coronary artery disease." JACC Cardiovasc Interv 2010; 3 (3): 307-14. doi: 10.1016/j.jcin.2009.12.010 [published Online First: Mar. 20, 2010].

Mettler et al. "Effective doses in radiology and diagnostic nuclear medicine: a catalog." Radiology 2008; 248(1): 254-63.

Michail et al., Jan. 2021, Feasibility and validity of computed tomography-derived fractional flow reserve in patients with severe aortic stenosis, Circ. Cardiovasc., Interv. 14:e009586,.

Miller et al. "Diagnostic performance of coronary angiography by 61-row CT." N Engel J Med 2008; 359 (22): 2324-36. doi: 10.1056/NEJMoa0806576 [published Online First: Nov. 29, 2008].

Min et al. "Prognostic value of multidetector coronary computed tomographic angiography for predication of all-cause mortality" J Am Coll Cardio 2007; 50(12): 1161-70.

Min et al., "Atherosclerosis, Stenosis, and Ischemia", JACC: Cardiovascular Imaging, vol. 11, No. 4, Apr. 2018. pp. 531-533.

Min et al., "Diagnostic accuracy of fractional flow reserve from anatomic CT angiography." JAMA 2012; 038 (12): 1237-45. doi: 10.1001/2012.jama.11274 [published Online First: Aug. 28, 2012].

Min et al., "The Immediate Effects of Statins on Coronary Atherosclerosis", JACC: Cardiovascular Imaging, vol. 11, No. 6, Jun. 2018. pp. 839-841.

Min et al., 2022, Coronary CTA plaque volume severity stages according to invasive coronary angiography and FFR, Journal of Cardiovascular Computed Tomography, https://doi.org/10.1016/j.jcct.2002.03.001.

Min, "Atherosclerotic plaque characterization: a need for a paradigm shift for prediction of risk", European Heart Journal—Cardiovascular Imaging, Oct. 2017. pp. 1340-1341.

Min, "Chess and Coronary Artery Ischemia: Clinical Implications of Machine-Learning Applications", Circulation: Cardiovascular Imaging, 2018 in 4 pages.

Min, et al. "Rationale and Design of the CONFIRM (Coronary CT Angiography Evaluation for Clinical Outcomes: An International Multicenter) Registry." J Cardiovasc Comput Tomogr. 2011;5: 84-92.

Mintz GS. "Intravascular Imaging of Coronary Calcification and its Clinical Implications." JACC Cardiovasc Imaging. 2015;8: 461-471.

Montalescot et al. "2013 ESC guidelines on the management of stable coronary artery disease: the Task Force on the management of stable coronary artery disease of the European Society of Cardiology." Eur Heart J 2013;34(35: 2949-3003. doi: 10.1093/eurheartj/eht296 [published Online First: Sep. 3, 2013].

Motoyama et al. "Atherosclerotic plaque characterization by 0.5-mm-slice multislice computed tomographic imaging." Circ J 2009; 71(3): 363-6.

Motoyama et al. "Computed tomographic angiography characteristics of atherosclerotic plaques subsequently resulting in acute coronary syndrome." J Am Coll Cardiol 2009; 54(1): 49-57.

Motoyama et al. "Multislice computed tomographic characteristics of coronary lesions in acute coronary syndromes." J Am Coll Cardiol 2007; 50(4): 319-26.

Motwani et al., "Machine learning for prediction of all-cause mortality in patients with suspected coronary artery disease: a 5-year multicentre prospective registry analysis", European Heart Journal, 2017, pp. 500-507.

Murgia et al., Aug. 2020, Plaque imaging vol. analysis: technique and application, Cardiovasc Diagn Ther, 10(4):1032-1047.

Naghavi, et al. From Vulnerable Plaque to Vulnerable Patient: a call for new definitions and risk assessment strategies: Part I. Circulation. 2003; 108: 1664-72.

Nair, et al. "Automated Coronary Plaque Characterisation with intravascular ultrasound backscatter: ex vivo validation." EuroIntervention. 2007; 3: 113-20.

Nakanishi R. et al. "Plaque progression assessed by a novel semi-automated quantitative plaque software on coronary computed tomography angiography between diabetes and non-diabetes patients: A propensity-score matching study." Atherosclerosis 2016; 255 pp. 73-79.

Nakazato et al., "Additive diagnostic value of atherosclerotic plaque characteristics to non-invasive FFR for identification of lesions causing ischaemia: results from a prospective international multicentre trial", http://www.pcronline.com/eurointervention/ahead_of_print/201509-02/ in 9 pages.

Nakazato et al., "Aggregate Plaque vol. by Coronary Computed Tomography Angiography Is Superior and Incremental to Luminal Narrowing for Diagnosis of Ischemic Lesions of Intermediate Stenosis Severity", Journal of the American College of Cardiology, vol. 62, No. 5, 2013 pp. 460-467.

Nakazato et al., "Atherosclerotic plaque characterization by CT angiography for identification of high- risk coronary artery lesions: a comparison to optical coherence tomography", European Heart Journal - Cardiovascular Imaging, vol. 16, 2015. pp. 373-379.

Nakazato et al., "Quantification and characterisation of coronary artery plaque vol. and adverse plaque features by coronary computed tomographic angiography: a direct comparison to intravascular ultrasound", Eur Radiol (2013) 23, pp. 2109-2117.

Nakazato et al., "Relationship of low- and high -density lipoproteins to coronary artery plaque composition by CT angiography", Journal of Cardiovascular Computed Tomography 7, 2013, pp. 83-90.

Neglia et al. "Detection of significant coronary artery disease by noninvasive anatomical and functionalimaging." Circ Cardiovasc Imaging 2015; 8 (3) doi: 10.1161/CIRCIMAGING.114.002179 [published Online First: Feb. 26, 2015].

Newby et al., "Coronary CT Angiography and 5-Year Risk of Myocardial Infarction", The New England Journal of Medicine, Aug. 25, 2018, pp. 924-933.

Newby et al., "CT coronary angiography in patients with suspected angina due to coronary heart disease (SCOT-HEART): an open-label, parallel-group, multicentre trial", www.thelancet.com, vol. 385. Jun. 13, 2015, pp. 2383-2391.

Nicholls et al. "Intravascular ultrasound-derived measures of coronary atherosclerotic plaque burden and clinical outcome." J Am Coll Cardiol. 2010; 55(21): pp. 2399-2407.

Nicholls, et al. "Effect of Evolocumab on Coronary Plaque Composition." J Am Coll Cardiol. 2018;72: 2012-2021.

Norgaard et al., 2020, Clinical outcomes following real-world computed tomography angiography-derived factional flow reserve testing in chronic coronary syndrome patients with calcification, European Heart Journal-Cardiovascular Imaging, doi:10.1093/ehjc/jeaa173.

Norgaard et al., Apr. 1, 2014, Diagnostic performance of noninvasive fractional flow reserve derivedfrom coronary computed tomography angiography in suspected coronary artery disease, Journal of the American College of Cardiology, 63(12):1145-1155.

Obaid, D.R., et al. "Atherosclerotic Plaque Composition and Classification Identified by Coronary Computed Tomography: Assessment of CT-Generated Plaque Maps Compared with Virtual Histology Intravascular Ultrasound and Histology." Circulation: Cardiovascular Imaging 6.5 (2013): 655-664. (Year: 2013).

Obaid, Daniel R., et al. "Coronary CT angiography features of ruptured and high-risk atherosclerotic plaques: correlation with intra-vascular ultrasound." Journal of Cardiovascular Computed Tomography 11.6 (2017): 455-461. (Year: 2017).

(56)          References Cited

OTHER PUBLICATIONS

Oikonomou et al., Aug. 28, 2018, Non-invasive detection of coronary inflammation using computed tomography7 and prediction of residual cardiovascular risk (the CRIPS CT study): a post-hoc analysis of prospective outcome data, The Lancet, 382(10151): 929-939.

Okubo, Ryo, et al. "Pericoronary adipose tissue ratio is a stronger associated factor of plaque vulnerability than epicardial adipose tissue on coronary computed tomography angiography." Heart and vessels 32.7 (2017): 813-822. (Year: 2017).

Otsuka et al. "Napkin-ring sign on coronary CT angiography for the prediction of acute coronary syndrome." JACC Cardiovasc Imaging 2013; 6(4): 448-57.

Ovrehus et al., "CT-based total vessel plaque analyses improves prediction of hemodynamic significance lesions as assessed by fractional flow reserve in patients with stable angina pectoris", Journal of Cardiovascular Computed Tomography 12, 2018 pp. 344-349.

Ovrehus, et al. "Reproducibility of Semi-Automatic Coronary Plaque Quantification in Coronary CT Angiography with Sub-mSv Radiation Dose." *J Cardiovasc Comput Tomogr*, (2016).

Papadopoulou et al., 2013, Reproducibility of CT Angiography Data Analysis Using Semiautomated Plaque Quantification Software: Implications for the Design of Longitudinal Studies, Int J Cardiovasc Imaging, 29:1095-1104.

Papadopoulou, et al. "Detection and Quantification of Coronary Atherosclerotic plaque by 64-slice multidetector CT: A systematic head-to-head comparison with intravascular ultrasound." Atherosclerosis. 2011;219: 163-70.

Park et al., "Atherosclerotic Plaque Characteristics by CT Angiography Identify Coronary Lesions That Cause Ischemia", JACC: Cardiovascular Imaging, vol. 8, No. 1, 2015 in 10 pages.

Park, et al. "Clinical Feasibility of 3D Automated Coronary Atherosclerotic Plaque Quantification Algorithm on Coronary Computed Tomography Angiography: Comparison with Intravascular Ultrasound" European Radiology (2015), 25: 3073-3083.

Park, et al. "Visual-functional Mismatch between Coronary Angiography and Fractional Flow Reserve." JACC Cardiovasc Interv. 2012; 5: 1029-36.

Patel et al., 2019, 1-year impact on medical practice and clinical outcomes of FFRCT, JACC: Cardiovascular Imaging, https://doi.org/10.,1016/j.jcmg.2019.03.003, 9 pp.

Pavlou et al., "A note on obtaining correct marginal predictions from a random intercepts model for binary outcomes." BMC Med Res Methodol 2015; 15:59. doi: 10.1186/s12874-015-004606 [published Online First: Aug. 6, 2015].

Pedregosa, et al. "Scikit-learn: Machine Learning in Python." Journal of Machine Learning Research, 2011;12: 2825-2830.

Picano et al. "The appropriate and justified use of medical radiation in cardiovascular imaging: a position document of the ESC Associations of Cardiovascular Imaging, Percutaneous Cardiovascular Interventions and Electrophysiology." Eur Heart J 2014; 35(10): 665-72.

Puchner et al., Mar. 2015, High-Risk Coronary Plaque at Coronary CT Angiography is Associated with NAFLD, Independent of Coronary Plaque and Stenosis Burden, J Cardiovasc Comput Tomogr., 274(3):693-701.

Puchner, et al. "High-Risk Plaque Detected on Coronary CT Angiography Predicts Acute Coronary Syndrome Independent of Significant Stenosis in Patients with Acute Chest Pain" *J Am Coll Cardiol* 2014.

Raff, et al. "SCCT guidelines for the interpretation and reporting of coronary computed tomographic angiography" *J Cardiovasc Comput Tomogr* 2009: 3(2): 122-36.

Rehani et al. "ICRP Publication 117. Radiological protection in fluoroscopically guided procedures performed outside the imaging department." Ann ICRP 2010; 40(6): 1-102.

Rizvi et al., "Diffuse coronary artery disease among other atherosclerotic plaque characteristics by coronary computed tomography angiography for predicting coronary vessel-specific ischemia by fractional flow reserve", Atherosclerosis 258, 2017 pp. 145-151.

Rizvi et al., "Rationale and Design of the CREDENCE Trial: computed Tomographic evaluation of atherosclerotic Determinants of myocardial Ischemia", BMC Cardiovascular Disorders, 2016, in 10 pages.

Roy-Cardinal et al. "Intravascular Ultrasound Image Segmentation: A Three-Dimensional Fast-Marching Method Based on Grey Level Distributions", IEEE Transactions on Medical Imaging, vol. 25, No. 5, May 2006.

Rozie et al., 2009, Atherosclerotic plaque volume and composition in symptomatic carotid arteries assess with the multidetector CT angiography; relationship with severity of stenosis and cardiovascular risk factors, Eur Radiol, 19:2294-2301.

Sabir, A et al. Measuring Noncalcified Coronary Atherosclerotic Plaque Using Voxel Analysis with MDCT Angiography: Phantom Validation: American Journal of Roentgenology, Apr. 2008; vol. 190, No. 4, pp. 242-246.

Samady H. et al. "Coronary artery wall shear is associated with progression and transformation of atherosclerotic plaque and arterial remodeling in patients with coronary artery disease." American Heart Association Circulation, vol. 124, Issue 7, Aug. 16, 2011, pp. 779-788.

Schinkel et al. "Noninvasive evaluation of ischaemic heart disease: myocardial perfusion imaging or stress echocardiography?" European Heart Journal (2003) 24, 789-800.

Schlett et al. "How to assess non-calcified plaque in CT angiography: delineation methods affect diagnostic accuracy of low-attenuation plaque by CT for lipid-core plaque in history." Euro Heart J Cardiovasc Imaging 2013; 14(11): 1099-105.

Schuurman et al. "Prognostic Value of Intravascular Ultrasound in Patients with Coronary Artery Disease." J Am Coll Cardiol. 2018;72: 2003-2011.

Seghier et al., "Lesion identification using unified segmentation-normalisation models and fuzzy clustering" NeuroImage 40(2008) 1253-1266.

Seifarth, et al. "Histopathological Correlates of the Napkin-Ring Sign Plaque in Coronary CT Angiography." Send to Atherosclerosis. 2012;224: 90-6.

Sharma et al., "Stress Testing Versus CT Angiography in Patients With Diabetes and Suspected Coronary Artery Disease", Journal of the American College of Cardiology, vol. 73, No. 8, 2019 pp. 893-902.

Shaw et al. "Optimal medical therapy with or without percutaneous coronary intervention to reduce ischemic burden: results from the Clinical Outcomes Utilizing Revascularization and Aggressive Drug Evaluation (COURAGE) trail nuclear substudy." Circulation 2008; 117 (10): 1283-91. doi: 10.116/CIRCULATIONAHA.107.743963.

Shaw et al. "Why all the focus on cardiac imaging?" JAAC Cardiovasc Imaging 2010; 3(7): 789-94 doi: 10.16/j.jcmg.2010.05.004.

Sheahan et al., Feb. 2018, Atherosclerotic plaque tissue: noninvasive quantitative assessment of characteristics with software-aided measurements from conventional CT angiography, Radiology, 286(2):622-631.

Shin S. et al., "Impact of Intensive LDL Cholesterol Lowering on Coronary Artery Atherosclerosis Progression: A Serial CT Angiography Study." JACC Cardiovasc Imaging. 2017; 10(4) pp. 437-446.

Siasos, et al. "Local Low Shear Stress and Endothelial Dysfunction in Patients with Nonobstructive Coronary Atherosclerosis." J Am Coll Cardiol. 2018;71: 2092-2102.

Song et al. "Comparison of machine learning techniques with classical statistical models in predicting health outcomes." Stud Health Technol Inform. 2004; 107(Pt 1) pp. 736-740.

Staruch, et al. "Automated Quantitative Plaque Analysis for Discrimination of Coronary Chronic Total Occlusion and Subtotal Occlusion in Computed Tomography Angiography", *J Thoracic Imaging*, (2016).

Stone, et al. "A prospective natural-history study of coronary atherosclerosis." N Engl J Med 2011; 364(3): 226-35.

Stuijfzand, et al. "Stress Myocardial Perfusion Imaging vs Coronary Computed Tomographic Angiography for Diagnosis of Invasive Vessel-Specific Coronary Physiology Predictive Modeling Results

(56) References Cited

OTHER PUBLICATIONS

From the Computed Tomographic Evaluation of Atherosclerotic Determinants of Myocardial Ischemia (CREDENCE) Trial", JAMA Cardiology, doi:10.1001/jamacardio.2020.3409, Aug. 19, 2020.

Sun et al., Mar. 2017, Carotid plaque lipid content and fibrous cap status predict systemic cv outcomes, JACC: Cardiovascular Imaging, 10(3):241-249.

Sun, et al. "Diagnostic Value of Multislice Computed Tomography Angiography in Coronary Artery Disease: a Meta-Analysis." Eur J Radiol. 2006;60: 279-86.

Taylor et al., "Patient-Specific Modeling of Cardiovascular Mechanics", Annu. Rev. Biomed. Eng. 2009.11:109-139.

Thim, et al. "Unreliable Assessment of Necrotic Core by Virtual Histology Intravascular Ultrasound in Porcine Coronary Artery Disease." Circ Cardiovasc Imaging. 2010;3: 384-91.

Thygesen, et al. "Third Universal Definition of Myocardial Infarction." Glob Heart. 2013;7: 275-95.

Tian, et al. "Distinct Morphological Features of Ruptured Culprit Plaque for Acute Coronary Events Compared to those with Silent Rupture and Thin-Cap Fibroatheroma: a Combined Optical Coherence Tomography and Intravascular Ultrasound Study." J Am Coll Cardiol. 2014;63: 2209-16.

Tilkemeier et al., "American Society of Nuclear Cardiology information statement: Standardized reporting matrix for radionuclide myocardial perfusion imaging." J Nucl Cardiol 2006; 13 (6): e157-71. doi: 10.1016/j.nuclcard.2006.08.014.

Tomey MI, et al. "Advances in the understanding of plaque composition and treatment options: year in review." J Am Coll Cardio. 2014; 63(16) pp. 1604-1616.

Tonino et al., "Angiographic versus functional severity of coronary artery stenoses in the FAME study fractional flow reserve versus angiography in multivessel evaluation." Journal of the American College of Cardiology 2010; 55 (25): 2816-21. doi: 10.1016/j.jacc.2009.11-096 [published Online First: Jun. 29, 2010].

U.S. Food and Drug Administration, Nov. 5, 2019, K190868 501 (k) Summary, 10 pp.

Van Ooijen, et al. "Coronary Artery Imaging with Multidetector CT: Visualization Issues" Radio Graphics, vol. 23. (2003).

Van Rosendael et al., "Maximization of the usage of coronary CTA derived plaque information using a machine learning based algorithm to improve risk stratification; insights from the CONFIRM registry", Journal of Cardiovascular Computed Tomography 12, 2018, pp. 204-209.

Van Rosendael et al., "Quantitative Evaluation of High-Risk Coronary Plaque by Coronary CTA and Subsequent Acute Coronary Events", JACC: Cardiovascular Imaging, vol. 12, No. 8, Aug. 2019. pp. 1568-1571.

Versteylen MO, et al. "Additive value of semiautomated quantification of coronary artery disease usingcardiac computed tomographic angiography to predict future acute coronary syndrome." J Am Coll Cardiol. 2013; 61(22): pp. 2296-2305.

Virmani, et al. "Atherosclerotic plaque progression and vulnerability to rupture: angiogenesis as a source of intraplaque hemorrhage." Arterioscler Thromb Vasc Biol. 2005; 25: 2054-61.

Virmani, et al. "Lessons from sudden coronary death: a comprehensive morphological classification scheme for atherosclerotic lesions." Arterioscler Thromb Vasc Biol. 2000;20: 1262-75.

Virmani, et al. "Pathology of the Vulnerable Plaque." J Am Coll Cardiol. 2006; 47: C13-8.

Wei, et al. "Computerized Detection of Noncalcified Plaques in Coronary CT Angiography: Evaluation of Topological Soft Gradient Prescreening Method and Luminal Analysis" *Med Phys*, (2014).

Weir-Maccall et al., "Impact of Non-obstructive left main disease on the progression of coronary artery disease: A Paradigm substudy", Journal of Cardiovascular Computed Tomography 12, 2018, pp. 231-237.

Weisenfeld et al. "Automatic Segmentation of Newborn Brain MRI", NIH PA Author Manuscript 2010.

Williams et al. "Use of Coronary Computed Tomographic Angiography to Guide Management of Patients with Coronary Disease." Journal of American College of Cardiology 2016; 67 (15) : 1759-68. doi: 10.1016/J.Jacc.2016.02.026 [published Online First: Apr. 16, 2016].

Williams et al., "Coronary Artery Plaque Characteristics Associated With Adverse Outcomes in the SCOT-HEART Study", Journal of the American College of Cardiology, vol. 73, No. 3, Jan. 29, 2019. pp. 291-301.

Wilson et al. "Prediction of coronary heart disease using risk factor categories" Circulation 1998; 97(18) pp. 1837-1847.

Wintermark et al., May 2008, High-resolution CT imaging of carotid artery atherosclerotic plaques, Am J Neuroradiol, 29:875-882.

Won et al., "Longitudinal assessment of coronary plaque volume change related to glycemic status using serial coronary computed tomography angiography: A Computed TomoGraphic Angiography Imaging) substudy", Journal of Cardiovascular Computed Tomography 13, 2019 pp. 142-147.

Won et al., "Longitudinal quantitative assessment of coronary plaque progression related to body mass index using serial coronary computed tomography angiography", European Heart Journal—Cardiovascular Imaging, 2019 pp. 591-599.

Wu et al., Jun. 11, 2018, Group normalization, arXiv:1803.08494v3, [cs.CV], 10 pp.

Yang, et al. "Automatic centerline extraction of coronary arteries in coronary computed tomographic angiography" *The International Journal of Cardiovascular Imaging*, 28:921-933. (2012).

Yokoya K, et al. "Process of progression of coronary artery lesions from mild or moderate stenosis to moderate or severe stenosis: A study based on four serial coronary arteriograms per year." Circulation 1999; 100(9):903-909.

Zeb I et al. "Effect of statin treatment on coronary plaque progression—a serial coronary CT angiography study." Atherosclerosis. 2013; 231(2):198-204.

Zhao Z., et al. "Dynamic nature of nonculprit coronary artery lesion morphology in STEMI: a serial IVUS analysis from HORIZONS-AMI trial." JACC Cardiovasc Imaging, 2013; 6(1):86-95.

Zreik et al., Dec. 10, 2018, A recurrent CNN for automatic detection and classification of coronary artery plaque and stenosis in coronary CT angiography, arXiv:1803/04360v4, 11 pp.

International Search Report and Written Opinion for Application No. PCT/US20/15035 dated Apr. 14, 2020, in 20 pages.

International Preliminary Report on Patentability for Application No. PCT/US2020/015035 dated Jul. 27, 2021, in 7 pages.

International Search Report and Written Opinion for Application No. PCT/US2021/012218 dated Mar. 17, 2021, in 11 pages.

International Search Report and Written Opinion for Application No. PCT/US2021/037919 dated Oct. 6, 2021, in 12 pages.

International Search Report and Written Opinion for Application No. PCT/US22/40816 dated Mar. 1, 2023, in 16 pages.

Tonino et al., Jan. 15, 2009, Fractional flow reserve versus angiography for guiding percutaneous coronary interventions, The New England Journal of Medicine, 360(3):213-224.

Xu et al., Aug. 2023, ELIXR: Towards a general purpose X-ray artificial intelligence system through alignment of large language models and radiology vision encoders, arXiv.2308.01317 [cs.CV], 54 pp.

International Search Report and Written Opinion for Application No. PCT/US23/63972 dated Aug. 9, 2023, in 17 pages.

* cited by examiner

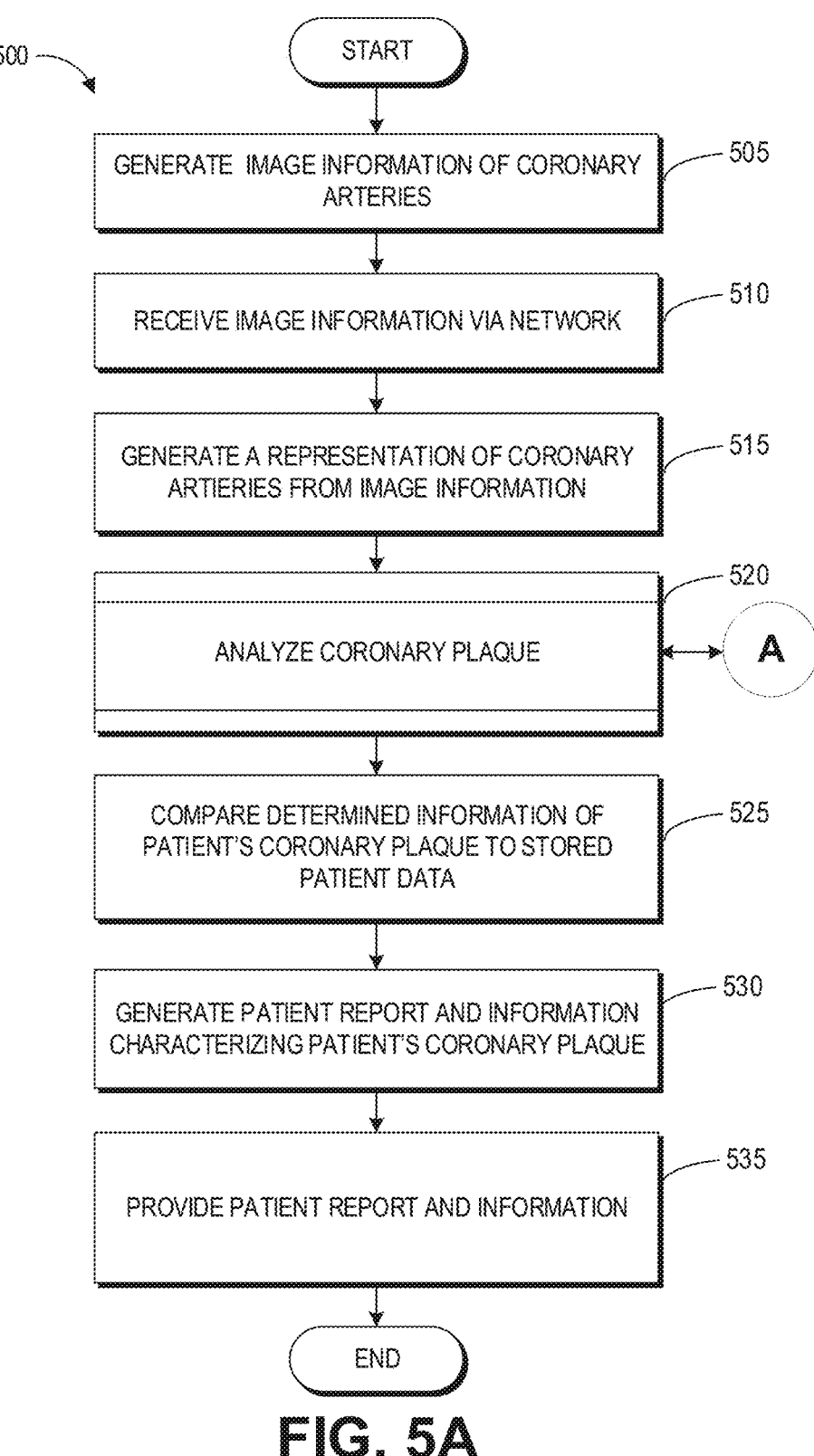

500 —

START

GENERATE  IMAGE INFORMATION OF CORONARY ARTERIES — 505

RECEIVE IMAGE INFORMATION VIA NETWORK — 510

GENERATE A REPRESENTATION OF CORONARY ARTIERIES FROM IMAGE INFORMATION — 515

ANALYZE CORONARY PLAQUE — 520          A

COMPARE DETERMINED INFORMATION OF PATIENT'S CORONARY PLAQUE TO STORED PATIENT DATA — 525

GENERATE PATIENT REPORT AND INFORMATION CHARACTERIZING PATIENT'S CORONARY PLAQUE — 530

PROVIDE PATIENT REPORT AND INFORMATION — 535

END

FIG. 5A

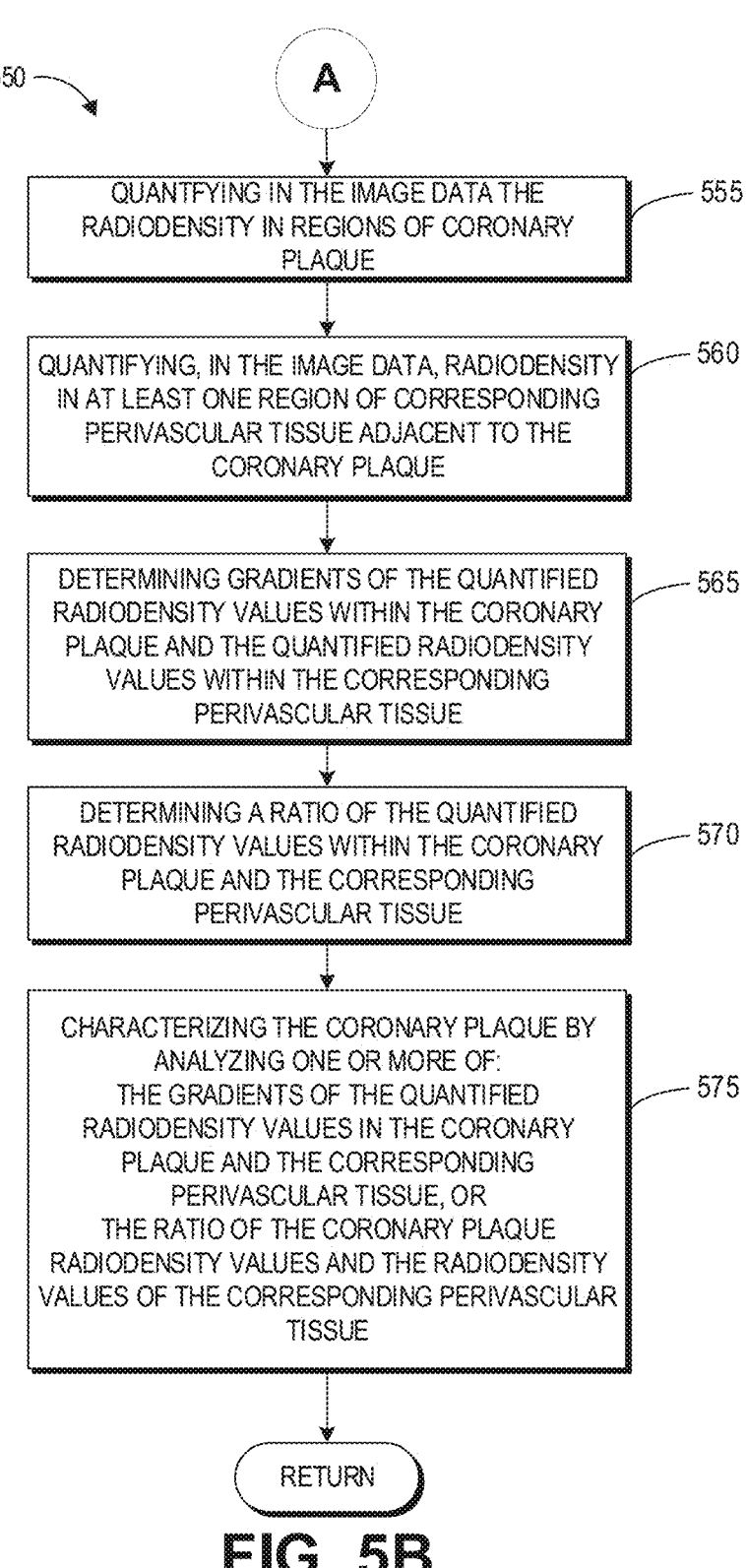

550

A

QUANTFYING IN THE IMAGE DATA THE RADIODENSITY IN REGIONS OF CORONARY PLAQUE — 555

QUANTIFYING, IN THE IMAGE DATA, RADIODENSITY IN AT LEAST ONE REGION OF CORRESPONDING PERIVASCULAR TISSUE ADJACENT TO THE CORONARY PLAQUE — 560

DETERMINING GRADIENTS OF THE QUANTIFIED RADIODENSITY VALUES WITHIN THE CORONARY PLAQUE AND THE QUANTIFIED RADIODENSITY VALUES WITHIN THE CORRESPONDING PERIVASCULAR TISSUE — 565

DETERMINING A RATIO OF THE QUANTIFIED RADIODENSITY VALUES WITHIN THE CORONARY PLAQUE AND THE CORRESPONDING PERIVASCULAR TISSUE — 570

CHARACTERIZING THE CORONARY PLAQUE BY ANALYZING ONE OR MORE OF:
THE GRADIENTS OF THE QUANTIFIED RADIODENSITY VALUES IN THE CORONARY PLAQUE AND THE CORRESPONDING PERIVASCULAR TISSUE, OR
THE RATIO OF THE CORONARY PLAQUE RADIODENSITY VALUES AND THE RADIODENSITY VALUES OF THE CORRESPONDING PERIVASCULAR TISSUE — 575

RETURN

FIG. 5B

CONTRAST IN THE PROXIMAL
PORTION OF THE CORONARY LUMEN
605

VESSEL
665

652

661

650

610 FIBROUS PLAQUE / MEDIUM
ATTENUATION PLAQUE

625 FAT OUTSIDE OF
VESSEL JUXAPOSED
TO THE PLAQUE

662

FIBROUS PLAQUE / MED-
HIGH ATTENUATION
620

615 NECROTIC CORE PLAQUE /
LOW ATTNUATION

663

640 FAT OUTSIDE OF
THE VESSEL
JUXTAPOSED
TO THE PLAQUE

642

635 PLAQUE / VERY HIGH
ATTENUATION

630 FIBROUS PLAQUE / LOW-MED ATTENUATION

CONTRAST IN THE PROXIMAL
PORTION OF THE CORONARY LUMEN
605

610 FIBROUS PLAQUE / MEDIUM
ATTENUATION  PLAQUE

VESSEL
665

625 FAT OUTSIDE OF VESSEL
JUXAPOSED TO THE
PLAQUE

673

674

660

661

655

672

FIBROUS PLAQUE / MED-
620 HIGH ATTENUATION

615  NECROTIC CORE PLAQUE /
LOW ATTNUATION

650

663

671

640  FAT OUTSIDE OF THE
VESSEL JUXTAPOSED
TO THE PLAQUE

670

642

635    PLAQUE / VERY HIGH
ATTENUATION

630  FIBROUS PLAQUE / LOW-MED ATTENUATION

|  | Overall | (-) Culprit | (+) Culprit | p |
|---|---|---|---|---|
| *Number of Lesions* | *965* | *843* | *122* | |
| Number of Lesions with HRP Morphology (n (%)) | 28 ( 2.9) | 9 ( 1.1) | 19 (15.6) | <0.001 |
| Number of Lesions Stratified by DELP (n (%)) | | | | |
| 90° | 5 (0.5) | 4 (0.5) | 1 (0.8) | 1 |
| 180° | 33 (3.4) | 21 (2.5) | 12 (9.8) | <0.001 |
| 270° | 30 (3.1) | 10 (1.2) | 20 (16.4) | <0.001 |
| 360° | 17 (1.8) | 4 (0.5) | 13 (10.7) | <0.001 |
| >180° | 38 (3.9) | 14 (1.7) | 24 (19.7) | <0.001 |
| Number of Lesions Stratified by LDNC Shape (n (%)) | | | | |
| Round | 14 (1.5) | 4 (0.5) | 10 (8.2) | <0.001 |
| Bean-Shaped | 29 (3.0) | 11 (1.3) | 18 (14.8) | <0.001 |
| Lobular | 23 (2.4) | 8 (0.9) | 15 (12.3) | <0.001 |
| Crescent | 22 (2.3) | 18 (2.1) | 4 (3.3) | 0.641 |
| Round or Bean-Shaped | 37 (3.8) | 15 (1.8) | 22 (18.0) | <0.001 |

FIG. 9B

| | OVERALL | (-) ACS | (+) ACS | P |
|---|---|---|---|---|
| *NUMBER OF PATIENTS* | 454 | 228 | 226 | |
| TOTAL PLAQUE VOLUME (MM$^3$) (MEAN (SD)) | 335.74 (332.65) | 312.19 (333.76) | 359.50 (330.57) | 0.13 |
| LOW-DENSITY NON-CALCIFIED PLAQUE VOLUME (MM$^3$) (MEAN (SD)) | 1.70 (5.94) | 0.82 (2.73) | 2.59 (7.88) | 0.001 |
| NON-CALCIFIED PLAQUE VOLUME (MM$^3$) (MEAN (SD)) | 210.12 (195.46) | 187.31 (186.67) | 233.12 (201.75) | 0.012 |
| CALCIFIED PLAQUE VOLUME (MM$^3$) (MEAN (SD)) | 123.65 (175.98) | 124.06 (184.86) | 123.24 (166.97) | 0.961 |
| PERCENT ATHEROMA VOLUME (%) (MEAN (SD)) | 23.31 (9.53) | 22.85 (9.83) | 23.77 (9.21) | 0.303 |
| LOW-DENSITY NON-CALCIFIED PLAQUE PERCENT (%) (MEAN (SD)) | 0.42 (1.46) | 0.24 (0.81) | 0.60 (1.89) | 0.008 |
| NON-CALCIFIED PLAQUE PERCENT (%) (MEAN (SD)) | 72.02 (20.87) | 71.01 (21.79) | 73.05 (19.90) | 0.298 |
| CALCIFIED PLAQUE PERCENT (%) (MEAN (SD)) | 27.56 (21.07) | 28.76 (21.90) | 26.35 (20.18) | 0.225 |
| MINIMAL LUMEN DIAMETER (MM) (MEAN (SD)) | 1.72 (0.52) | 1.77 (0.51) | 1.67 (0.53) | 0.038 |
| MAXIMUM REMODELING INDEX (MEAN (SD)) | 1.47 (0.24) | 1.45 (0.22) | 1.49 (0.25) | 0.106 |
| MAXIMUM LESION LENGTH (MEAN (SD)) | 50.66 (38.49) | 48.81 (39.74) | 52.54 (37.18) | 0.303 |
| MAXIMUM DS$_{AI-QCT}$ (%) (MEAN (SD)) | 37.89 (21.62) | 34.56 (20.77) | 41.25 (21.98) | 0.001 |
| NUMBER OF LESIONS STRATIFIED BY MAXIMUM DS$_{AI-QCT}$ (N (%)) | | | | |
| 0% | 5 (1.1) | 2 (0.9) | 3 (1.3) | 0.992 |
| 1-24% | 144 (31.7) | 88 (38.6) | 56 (24.8) | 0.002 |
| 25-49% | 169 (37.2) | 85 (37.3) | 84 (37.2) | 1 |
| 50-69% | 78 (17.2) | 31 (13.6) | 47 (20.8) | 0.056 |
| 70-99% | 58 (12.8) | 22 (9.6) | 36 (15.9) | 0.062 |
| 100% | 0 (0.0) | 0 (0.0) | 0 (0.) | . |
| NUMBER OF LESIONS STRATIFIED BY NUMBER OF HRP MORPHOLOGY DEPOSITS (N (%)) | | | | |
| 0 HRP MORPHOLOGY DEPOSITS | 407 (89.6) | 221 (96.9) | 186 (82.3) | <0.001 |
| 1 HRP MORPHOLOGY DEPOSIT | 28 (6.2) | 4 (1.8) | 24 (10.6) | <0.001 |
| 2 HRP MORPHOLOGY DEPOSITS | 8 (1.8) | 1 (0.4) | 7 (3.1) | 0.072 |
| ≥3 HRP MORPHOLOGY DEPOSITS | 11 (2.4) | 2 (0.9) | 9 (4.0) | 0.065 |
| NUMBER OF LESIONS STRATIFIED BY NUMBER OF LDNC DEPOSITS (N (%)) | | | | |
| 0 LDNC DEPOSITS | 354 (78.0) | 198 (86.8) | 156 (69.0) | <0.001 |
| 1 LDNC DEPOSIT | 33 (7.3) | 10 (4.4) | 23 (10.2) | 0.028 |
| 2 LDNC DEPOSITS | 21 (4.6) | 4 (1.8) | 17 (7.5) | 0.007 |
| ≥3 LDNC DEPOSITS | 46 (10.1) | 16 (7.0) | 30 (13.3) | 0.04 |

FIG. 9C

| NUMBER OF PATIENTS WITH ≥1 HRP MORPHOLOGY LESION (N (%)) | 47 (10.4) | 7 (3.1) | 40 (17.7) | <0.001 |
|---|---|---|---|---|
| NUMBER OF PATIENTS STRATIFIED BY NUMBER OF HRP MORPHOLOGY LESION (N (%)) | | | | |
| 0 HRP MORPHOLOGY LESIONS | 407 (89.6) | 221 (96.9) | 186 (82.3) | <0.001 |
| 1 HRP MORPHOLOGY LESION | 43 (9.5) | 5 (2.2) | 38 (16.8) | <0.001 |
| 2 HRP MORPHOLOGY LESIONS | 3 (0.7) | 2 (0.9) | 1 (0.4) | 1 |
| >3 HRP MORPHOLOGY LESIONS | 1 (0.2) | 0 (0.0) | 1 (0.4) | 0.996 |
| MAXIMUM DS$_{AI-QCT}$ LESION LOCATION (N (%)) | | | | 0.8 |
| LAD | 236 (52.0) | 121 (53.1) | 115 (50.9) | |
| LCX | 72 (15.9) | 37 (16.2) | 35 (15.5) | |
| RCA | 146 (32.2) | 70 (30.7) | 76 (33.6) | |

DS$_{AI-QCT}$ DIAMETER STENOSIS MEASURED USING ARTIFICIAL-INTELLIGENCE ENABLED QUANTITATIVE COMPUTED TOMOGRAPHY

FIG. 9C(Continued)

| Patient Demographics | Missing | Overall | (-) ACS | (+) ACS | P-value |
|---|---|---|---|---|---|
| *Number of Patients* | | 456 | 230 | 226 | |
| Age (yrs) | | 62±11 | 62±10 | 62±12 | 0.945 |
| Sex (M), n (%) | 19 | 285 (62.5) | 142 (61.7) | 143 (63.3) | 0.809 |
| BMI | 111 | 27.3±4.9 | 27.12 (4.69) | 27.52 (5.12) | 0.396 |
| Race, n (%) | | | | | |
| Caucasian | | 214 (46.9) | 108 (47.0) | 106 (46.9) | 1 |
| African | | 15 (3.3) | 9 (3.9) | 6 (2.7) | 0.624 |
| Latin American | | 2 (0.4) | 1 (0.4) | 1 (0.4) | 1 |
| East Asian | | 105 (23.0) | 52 (22.6) | 53 (23.5) | 0.918 |
| South Asian | | 4 (0.9) | 1 (0.4) | 3 (1.3) | 0.369 |
| Middle Eastern | | 1 (0.2) | 0 (0.0) | 1 (0.4) | 0.496 |
| Other | | 4 (0.9) | 3 (1.3) | 1 (0.4) | 0.623 |
| Hypertension, n (%) | 2 | 283 (62.3) | 140 (60.9) | 143 (63.8) | 0.578 |
| Diabetes Mellitus, n (%) | | 118 (25.9) | 74 (32.2) | 44 (19.5) | 0.003 |
| Family History of CAD, n (%) | 7 | 176 (39.2) | 86 (37.6) | 90 (40.9) | 0.528 |
| Current Smoker, n (%) | 2 | 121 (26.7) | 54 (23.6) | 67 (29.8) | 0.165 |
| Former Smoker, n (%) | 129 | 140 (42.8) | 62 (39.7) | 78 (45.6) | 0.337 |
| Hypercholesterolemia, n (%) | 2 | 245 (54.0) | 121 (52.6) | 124 (55.4) | 0.622 |
| Patients with ACS, n (%) | | 226 (49.6) | 0 (0.0) | 226 (100.0) | <0.001 |
| Time to ACS (years) | | 2.71±2.74 | 3.78±2.38 | 1.63±2.65 | <0.001 |

FIG. 9J

| Number of Lesions | Overall | (< Culprit Lesion | (≥ Culprit Lesion | Adjusted Hazard Ratio (95% CI) | P-value |
|---|---|---|---|---|---|
|  | 965 | 843 | 122 |  |  |
| Total Plaque Volume (mm³) | 50.36±112.76 | 35.21±87.42 | 154.99±188.37 | 1.003 [1.003, 1.004] | <0.001 |
| LD-NCP Volume (mm³) | 0.44±3.02 | 0.22±2.20 | 1.99±6.03 | 1.037 [1.003, 1.071] | 0.032 |
| Non-Calcified Plaque Volume (mm³) | 32.45±75.08 | 22.39±54.22 | 101.98±137.38 | 1.005 [1.004, 1.006] | <0.001 |
| Calcified Plaque Volume (mm³) | 17.34±47.35 | 12.61±41.40 | 50.02±68.59 | 1.006 [1.004, 1.008] | <0.001 |
| Percent Atheroma Volume (mm³) | 23.98±14.33 | 22.24±13.33 | 36.10±15.20 | 1.054 [1.043, 1.065] | <0.001 |
| LD-NCP Percent (%) | 0.29±1.93 | 0.22±1.92 | 0.77±1.92 | 1.086 [1.035, 1.139] | <0.001 |
| Non-Calcified Plaque Percent (%) | 80.57±24.16 | 80.67±22.75 | 79.95±32.34 | 0.996 [0.986, 1.006] | 0.45 |
| Calcified Plaque Percent (%) | 22.60±25.22 | 21.14±24.17 | 32.65±29.71 | 1.014 [1.010, 1.018] | <0.001 |
| Minimum Lumen Diameter (mm) | 2.44±0.82 | 2.44±0.82 | 2.44±0.85 | 0.831 [0.643, 1.073] | 0.156 |
| Remodeling Index | 1.24±0.18 | 1.23±0.17 | 1.36±0.23 | 1.274 [1.186, 1.368] | <0.001 |
| Lesion Length (mm) | 17.07±23.05 | 13.75±18.70 | 40.21±34.54 | 1.022 [1.018, 1.026] | <0.001 |
| Remodeling Index ≥1.1 with LD-NCP (n (%)) | 95 (9.84) | 56 (6.64) | 39 (31.97) | 5.360 [3.629, 7.918] | <0.001 |
| $DS_{A\text{-}QCT}$ (%) | 16.18±17.62 | 13.65±15.32 | 33.61±22.11 | 1.048 [1.040, 1.055] | <0.001 |
| Number of Lesions with $DS_{A\text{-}QCT}$ Severity (n (%)) |  |  |  |  |  |
| 0% | 178 (18.45) | 169 (20.05) | 9 (7.38) | 0.263 [0.145, 0.475] | <0.001 |
| 1-24% | 556 (57.62) | 518 (61.45) | 38 (31.15) | 0.329 [0.227, 0.477] | <0.001 |
| 25-49% | 169 (17.51) | 126 (14.95) | 43 (35.25) | 3.157 [2.111, 4.720] | <0.001 |
| 50-69% | 37 (3.83) | 17 (2.02) | 20 (16.39) | 6.444 [3.944, 10.529] | <0.001 |
| 70-99% | 25 (2.59) | 13 (1.54) | 12 (9.84) | 8.085 [4.174, 15.661] | <0.001 |
| 100% | 0 (0.00) | 0 (0.00) | 0 (0.00) |  | - |
| Lesions with HRP Morphology (n (%)) | 28 (2.90) | 9 (1.07) | 19 (15.57) | 8.253 [4.785, 14.234] | <0.001 |
| Lesion Location (n (%)) |  |  |  |  |  |
| LAD | 322 (33.37) | 253 (30.01) | 69 (56.56) | 2.824 [1.946, 4.097] | <0.001 |
| LCx | 207 (21.45) | 188 (22.30) | 19 (15.57) | 0.572 [0.340, 0.962] | 0.035 |
| RCA | 436 (45.18) | 402 (47.69) | 34 (27.87) | 0.479 [0.308, 0.747] | 0.001 |

FIG. 9K

| | OVERALL | (-) ACS | (+) ACS | ADJUSTED HAZARD RATIO [95% CI] | P-VA |
|---|---|---|---|---|---|
| NUMBER OF PATIENTS | 456 | 230 | 226 | | |
| TOTAL PLAQUE VOLUME (MM³) | 334.33±332.61 | 309.48±333.57 | 359.63±330.45 | 1.000 [1.000, 1.001] | |
| LD-NCP VOLUME (MM³) | 1.69±5.93 | 0.82±2.71 | 2.59±7.88 | 1.028 [1.013, 1.044] | < |
| NON-CALCIFIED PLAQUE VOLUME (MM³) | 209.26±195.47 | 185.68±186.67 | 233.26±201.64 | 1.001 [1.000, 1.001] | |
| CALCIFIED PLAQUE VOLUME (MM³) | 123.11±175.79 | 122.98±184.41 | 123.24±166.97 | 1.000 [0.999, 1.000] | |
| PERCENT ATHEROMA VOLUME (MM³) | 23.23±9.64 | 22.65±10.01 | 23.83±9.22 | 1.000 [0.987, 1.014] | |
| LD-NCP PERCENT (%) | 0.42±1.46 | 0.24±0.81 | 0.60±1.89 | 1.101 [1.056, 1.148] | < |
| NON-CALCIFIED PLAQUE PERCENT (%) | 72.02±20.87 | 71.01±21.79 | 73.05±19.90 | 1.004 [0.998, 1.011] | |
| CALCIFIED PLAQUE PERCENT (%) | 27.56±21.07 | 28.76±21.90 | 26.36±20.18 | 0.995 [0.989, 1.001] | |
| MEAN NUMBER OF LESIONS (N (%)) | 7.63 (3.76) | 7.47 (3.72) | 7.80 (3.80) | 1.028 [0.996, 1.061] | |
| MINIMUM LUMEN DIAMETER (MM) | 1.72±0.52 | 1.77±0.51 | 1.67±0.53 | 0.834 [0.651, 1.068] | |
| REMODELING INDEX | 1.47±0.24 | 1.45±0.22 | 1.49±0.25 | 1.537 [0.837, 2.821]* | |
| MAX LESION LENGTH (MM) | 50.66±38.49 | 48.81±39.74 | 52.54±37.18 | 1.000 [0.997, 1.004] | |
| REMODELING INDEX ≥1.1 WITH LD-NCP (N (%)) | 155 (33.99) | 64 (27.83) | 91 (40.27) | 1.398 [1.056, 1.850] | |
| MAX DS_AIQCT (%) | 37.73±21.71 | 34.26±20.93 | 41.25±21.97 | 1.007 [1.001, 1.014] | |
| NUMBER OF LESIONS WITH MAX DS_AIQCT SEVERITY (N (%)) | | | | | |
| 0% | 7 (1.54) | 4 (1.74) | 3 (1.33) | 0.886 [0.335, 2.340] | |
| 1-24% | 144 (31.58) | 88 (38.26) | 56 (24.78) | 0.700 [0.521, 0.940] | |
| 25-49% | 169 (37.06) | 85 (36.96) | 84 (37.17) | 1.056 [0.807, 1.382] | |
| 50-69% | 78 (17.11) | 31 (13.48) | 47 (20.80) | 1.160 [0.823, 1.635] | |
| 70-99% | 58 (12.72) | 22 (9.57) | 36 (15.93) | 1.322 [0.885, 1.975] | |
| 100% | 0 (0.00) | 0 (0.00) | 0 (0.00) | - | |

FIG. 9M

| | | | | | |
|---|---|---|---|---|---|
| PATIENTS WITH ≥1HRP MORPHOLOGY LESION (N (%)) | 47 (10.31) | 7 (3.04) | 40 (17.70) | 2.484 [1.778, 3.470] | < |
| PATIENTS WITH HRP MORPHOLOGY LESIONS (N (%)) | | | | | |
| 0 | 409 (89.69) | 223 (96.96) | 186 (82.30) | 0.403 [0.288, 0.563] | < |
| 1 | 46 (9.43) | 5 (2.17) | 38 (16.81) | 2.676 [1.923, 3.724] | < |
| 2 | 3 (0.66) | 2 (0.87) | 1 (0.44) | 0.463 [0.065, 3.295] | |
| ≥3 | 1 (0.22) | 0 (0.00) | 1 (0.44) | ~ | |
| MAX DS$_{AI\text{-}QCT}$ LOCATION (N (%)) | | | | | |
| LAD | 235 (51.54) | 121 (52.61) | 144 (50.44) | 0.907 [0.698, 1.179] | |
| LC$_X$ | 72 (15.79) | 37 (16.09) | 35 (15.49) | 0.911 [0.638, 1.303] | |
| RCA | 147 (32.24) | 70 (30.43) | 77 (34.07) | 1.198 [0.911, 1.577] | |

FIG. 9M(Continued)

(a) Forest Plot of Association of Low-Density Non-Calcified Plaque With Acute Coronary Syndrome (b) Bar Graph of Patient Frequencies

(a) High-Risk Plaque Morphology

*2 High-Risk Morphologic Features*

(d) ACS Event-Free Survival Rate

Epicardial Fat Side

Myocardium Side (a)

Training Cohort (163 Territories)

$$(Eq. 1)\ Invasive\ FFR = Y * \frac{Minimal\ Lumen\ Area^{b, Lumen}}{Subtended\ Myocardial\ Mass^{b, Myo}}$$

Testing Cohort (71 Territories)

$$(Eq. 2)\ FFR_{Myo} = 0.96 * \frac{Minimal\ Lumen\ Area^{0.11}}{Subtended\ Myocardial\ Mass^{0.08}}$$

SYSTEMS, DEVICES, AND METHODS FOR NON-INVASIVE IMAGE-BASED PLAQUE ANALYSIS AND RISK DETERMINATION

PRIORITY AND RELATED APPLICATIONS

This application is a continuation of U.S. application Ser. No. 18/179,921, filed Mar. 7, 2023, which claims priority to U.S. Provisional Application No. 63/269,136, filed Mar. 10, 2022, U.S. Provisional Application No. 63/362,108, filed Mar. 29, 2022, U.S. Provisional Application No. 63/362, 856, filed Apr. 12, 2022, U.S. Provisional Application No. 63/364,078, filed May 3, 2022, U.S. Provisional Application No. 63/364,084, filed May 3, 2022, U.S. Provisional Application No. 63/365,381, filed May 26, 2022, U.S. Provisional Application No. 63/368,293 filed Jul. 13, 2022, and U.S. Provisional Application No. 63/381,210, filed Oct. 27, 2022, and each of the above-listed applications is incorporated by reference herein in its entirety. Any and all applications for which a foreign or domestic priority claim is identified in the Application Data Sheet as filed with the present application are hereby incorporated by reference under 37 CFR 1.57.

This application is related to U.S. Pat. No. 10,813,612, filed Jan. 23, 2020, U.S. Pat. No. 11,501,436, filed Jan. 5, 2021, and U.S. Pat. No. 11,302,001, filed Aug. 4, 2021, and U.S. application Ser. No. 17/820,439, filed Aug. 17, 2022, and each of the above-listed patents and patent applications is incorporated by reference herein in its entirety.

BACKGROUND

The present application relates to non-invasive image-based plaque analysis and risk determination.

SUMMARY

Various embodiments described herein relate to systems, devices, and methods for non-invasive image-based plaque analysis and risk determination. In particular, in some embodiments, the systems, devices, and methods described herein are related to analysis of one or more regions of plaque, such as for example coronary plaque, based on one or more distances, volumes, shapes, morphologies, embeddedness, and/or axes measurements. For example, in some embodiments, the systems, devices, and methods described herein are related to plaque analysis based on one or more of distance between plaque and vessel wall, distance between plaque and lumen wall, length along longitudinal axis, length along latitudinal axis, volume of low density non-calcified plaque, volume of total plaque, a ratio(s) between volume of low density non-calcified plaque and volume of total plaque, embeddedness of low density non-calcified plaque, and/or the like. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein.

In some embodiments, the systems, devices, and methods are related to facilitating determination of risk of coronary artery disease (CAD) based at least in part on one or more measurements derived from non-invasive medical image analysis. In some embodiments, the systems, devices, and methods comprise accessing a medical image of a subject, wherein the medical image of the subject is obtained non-invasively, analyzing medical image of the subject to identify one or more arteries, identifying one or more regions of plaque within the one or more coronary arteries, analyzing the identified one or more regions of plaque to identify one or more regions of low density non-calcified plaque, non-calcified plaque, or calcified plaque based at least in part on density, analyzing, in response to identifying one or more regions of low density non-calcified plaque, the one or more regions of low density non-calcified plaque, wherein the analysis of the one or more regions of low density non-calcified plaque comprises: determining a distance from the one or more regions of low density non-calcified plaque to one or more of a lumen wall or vessel wall, determining a degree of embeddedness of the one or more regions of low density non-calcified plaque in one or more of non-calcified plaque or calcified plaque, and determining a shape of the one or more regions of low density non-calcified plaque, and generating a display of the analysis of the one or more regions of low density non-calcified plaque to facilitate determination of a risk of CAD of the subject based at least in part on the analysis of the one or more regions of low density non-calcified plaque.

In some embodiments, a determination of the distance from the one or more regions of low density non-calcified plaque to the lumen wall below a predetermined threshold is indicative of an unstable plaque or high risk of CAD. In some embodiments, the distance from the one or more regions of low density non-calcified plaque to one or more of the lumen wall or vessel wall is determined on a three-dimensional basis. In some embodiments, the distance from the one or more regions of low density non-calcified plaque to one or more of the lumen wall or vessel wall is determined based on a two-dimensional image. In some embodiments, the two-dimensional image is obtained by taking a two-dimensional slice perpendicular to a longitudinal axis of a straightened multiplanar view of the one or more arteries. In some embodiments, the two-dimensional image is obtained by taking a two-dimensional slice resulting in a largest two-dimensional area of the low-density non-calcified plaque. In some embodiments, the distance from the one or more regions of low density non-calcified plaque to the lumen wall is determined by determining a shortest distance between a boundary of the one or more regions of low density non-calcified plaque and a boundary of the lumen wall. In some embodiments, the distance from the one or more regions of low density non-calcified plaque to the vessel wall is determined by determining a shortest distance between a boundary of the one or more regions of low density non-calcified plaque and a boundary of the vessel wall. In some embodiments, the one or more arteries comprises one or more coronary or carotid arteries. In some embodiments, one or more axes of the one or more regions of low density non-calcified plaque comprises one or more of a major axis on a longitudinal plane, minor axis on a longitudinal plane, major axis on a latitudinal plane, or minor axis on a latitudinal plane. In some embodiments, the one or more axes are determined on a three-dimensional basis. In some embodiments, the one or more axes are determined based on one or more two-dimensional images. In some embodiments, the longitudinal plane is obtained by taking a two-dimensional slice parallel to a longitudinal axis of a straightened multiplanar view of the one or more arteries. In some embodiments, the longitudinal plane is obtained by taking a two-dimensional slice resulting in a longest major axis of the longitudinal plane. In some embodiments, the degree of embeddedness of the one or more regions of low density non-calcified plaque is determined based at least in part by graphically overlaying a protractor on the one or more regions of low density non-calcified plaque on the medical image. In some embodiments, a higher degree of embeddedness of the one or more regions of low density non-calcified plaque is indicative of an unstable plaque or high risk of CAD. In some embodiments, the shape of the one or more regions of low density non-calcified plaque is determined as one or more of a crescent, round, lobular, or bean shape. In some embodiments, determination of a round or bean shape of the one or more regions of low density non-calcified plaque is indicative of an unstable plaque or high risk of CAD. In some embodiments, the shape of the one or more regions of low density non-calcified plaque is determined based at least in part by a machine learning algorithm. In some embodiments, the analysis of the one or more regions of low density non-calcified plaque further comprises determining one or more lengths of one or more axes of the one or more regions of low density non-calcified plaque. In some embodiments, the shape of the one or more regions of low density non-calcified plaque is determined based at least in part on the one or more determined lengths of the one or more axes. In some embodiments, the shape of the one or more regions of low density non-calcified plaque is determined based at least in part on determining a standard deviation among the one or more determined lengths of the one or more axes. In some embodiments, the analysis of the one or more regions of low density non-calcified plaque further comprises determining a volume of the one or more regions of low density non-calcified plaque, determining a volume of the one or more regions of plaque, and determining a ratio of the volume of the one or more regions of low density non-calcified plaque to the volume of the one or more regions of plaque. In some embodiments, the volume of the one or more regions of low density non-calcified plaque is determined based on the one or more determined lengths of the one or more axes of the one or more regions of low density non-calcified plaque. In some embodiments, a determination of the volume of the one or more regions of low density non-calcified plaque above a predetermined threshold is indicative of unstable plaque or high risk of CAD. In some embodiments, a determination of the volume of the one or more regions of plaque above a predetermined threshold is indicative of unstable plaque or high risk of CAD. In some embodiments, a determination of the ratio of the volume of the one or more regions of low density non-calcified plaque to the volume of the one or more regions of plaque above a predetermined threshold is indicative of unstable plaque or high risk of CAD. In some embodiments, the density comprises absolute density. In some embodiments, the density comprises radiodensity. In some embodiments, the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Other embodiments disclosed herein relate to systems, devices, and methods are related to cardiovascular risk and/or disease state assessment using image-based analysis of vessel surface and/or coordinates of features. In some embodiments, assessment of cardiovascular risk and/or disease state generated using the systems, methods, and devices herein can be utilized to diagnose and/or generate a proposed treatment for a patient.

Other embodiments disclosed herein relate to systems, devices, and methods are related to cardiovascular risk and/or disease and/or state assessment using image-based analysis of one or more regions and/or features of non-calcified plaque and/or calcified plaque. In some embodiments, assessment of cardiovascular risk and/or disease and/or state generated using the systems, methods, and devices herein can be utilized to diagnose and/or generate a proposed treatment for a patient.

Other embodiments disclosed herein relate to systems, devices, and methods are related to cardiovascular risk and/or disease and/or state assessment using modified and/or normalized image analysis-based plaque parameters. In some embodiments, assessment of cardiovascular risk and/or disease and/or state generated using the systems, methods, and devices herein can be utilized to diagnose and/or generate a proposed treatment for a patient.

Other embodiments disclosed herein relate to relate to systems, devices, and methods for generation of a patient-specific report on the risk and/or state assessment, diagnosis, and/or treatment of cardiovascular disease, including for example coronary artery disease (CAD). In particular, in some embodiments, the systems, devices, and methods are configured to generate an immersive patient-specific report on the patient's cardiovascular disease risk, state, diagnosis, and/or treatment. In some embodiments, the systems, devices, and methods are configured to generate an immersive patient-specific report based at least in part on image-based analysis, for example of one or more plaque and/or vessel parameters.

Other embodiments disclosed herein relate to cardiovascular risk and/or disease and/or state assessment using normalized image analysis-based plaque parameters. In some embodiments, assessment of cardiovascular risk and/or disease and/or state generated using the systems, methods, and devices herein can be utilized to diagnose and/or generate a proposed treatment for a patient.

Other embodiments disclosed herein relate to systems, devices, and methods for non-invasive image-based determination of fractional flow reserve (FFR) and/or ischemia. In particular, in some embodiments, the systems, devices, and methods are related to FFR and/or ischemia analysis of arteries, such as coronary, aortic, and/or carotid arteries using one or more image analysis techniques. For example, in some embodiments, the systems, methods, and devices can be configured to derive one or more stenosis and/or normal measurements from a medical image, which can be obtained non-invasively, and use the same to derive an assessment of FFR and/or ischemia. In some embodiments, the systems, methods, and devices can be configured to apply one or more allometric scaling laws to one or more stenosis and/or normal measurements to derive and/or generate an assessment of FFR and/or ischemia.

In some embodiments, a computer-implemented method of facilitating determination of risk of coronary artery disease (CAD) based at least in part on one or more measurements derived from non-invasive medical image analysis comprises: accessing, by a computer system, a medical image of a subject, wherein the medical image of the subject is obtained non-invasively; analyzing, by the computer system, the medical image of the subject to identify one or more arteries; identifying, by the computer system, one or more regions of plaque within the one or more coronary arteries; analyzing, by the computer system, the identified one or more regions of plaque to identify one or more regions of low density non-calcified plaque, non-calcified plaque, or calcified plaque based at least in part on density, analyzing, in response to identifying one or more regions of low density non-calcified plaque, the one or more regions of low density non-calcified plaque, wherein the analysis of the one or more regions of low density non-calcified plaque comprises: determining a distance from the one or more regions of low density non-calcified plaque to one or more of a lumen wall or vessel wall; determining a degree of embeddedness of the one or more regions of low density non-calcified plaque by one or more of non-calcified plaque or calcified plaque; and determining a shape of the one or more regions of low density non-calcified plaque; and generating, by the computer system, a display of the analysis of the one or more regions of low density non-calcified plaque to facilitate determination of one or more of a risk of CAD of the subject based at least in part on the analysis of the one or more regions of low density non-calcified plaque, wherein the computer system comprises a computer processor and an electronic storage medium.

In some embodiments of the computer-implemented method, a determination of the distance from the one or more regions of low density non-calcified plaque to the lumen wall below a predetermined threshold is indicative of an unstable plaque or high risk of CAD. In some embodiments of the computer-implemented method, the distance from the one or more regions of low density non-calcified plaque to one or more of the lumen wall or vessel wall is determined on a three-dimensional basis. In some embodiments of the computer-implemented method, the distance from the one or more regions of low density non-calcified plaque to one or more of the lumen wall or vessel wall is determined based on a two-dimensional image. In some embodiments of the computer-implemented method, the two-dimensional image is obtained by taking a two-dimensional slice perpendicular to a longitudinal axis of a straightened multiplanar view of the one or more arteries. In some embodiments of the computer-implemented method, the two-dimensional image is obtained by taking a two-dimensional slice resulting in a largest two-dimensional area of the low-density non-calcified plaque. In some embodiments of the computer-implemented method, the distance from the one or more regions of low density non-calcified plaque to the lumen wall is determined by determining a shortest distance between a boundary of the one or more regions of low density non-calcified plaque and a boundary of the lumen wall. In some embodiments of the computer-implemented method, the distance from the one or more regions of low density non-calcified plaque to the vessel wall is determined by determining a shortest distance between a boundary of the one or more regions of low density non-calcified plaque and a boundary of the vessel wall. In some embodiments of the computer-implemented method, the one or more arteries comprises one or more coronary or carotid arteries.

In some embodiments of the computer-implemented method, the one or more axes of the one or more regions of low density non-calcified plaque comprises one or more of a major axis on a longitudinal plane, minor axis on a longitudinal plane, major axis on a latitudinal plane, or minor axis on a latitudinal plane. In some embodiments of the computer-implemented method, the one or more axes are determined on a three-dimensional basis. In some embodiments of the computer-implemented method, the one or more axes are determined based on one or more two-dimensional images. In some embodiments of the computer-implemented method, the longitudinal plane is obtained by taking a two-dimensional slice parallel to a longitudinal axis of a straightened multiplanar view of the one or more arteries. In some embodiments of the computer-implemented method, the longitudinal plane is obtained by taking a two-dimensional slice resulting in a longest major axis of the longitudinal plane. In some embodiments of the computer-implemented method, the latitudinal plane is obtained by taking a two-dimensional slice perpendicular to a longitudinal axis of a straightened multiplanar view of the one or more arteries. In some embodiments of the computer-implemented method, the latitudinal plane is obtained by taking a two-dimensional slice perpendicular to the major axis on the longitudinal plane. In some embodiments of the computer-implemented method, the latitudinal plane is obtained by taking a two-dimensional slice resulting in a largest two-dimensional area of the low-density non-calcified plaque. In some embodiments of the computer-implemented method, one or more of analyses of the one or more regions of low density non-calcified plaque is performed by the computer system.

In some embodiments of the computer-implemented method, the degree of embeddedness of the one or more regions of low density non-calcified plaque is determined based at least in part by graphically overlaying a protractor on the one or more regions of low density non-calcified plaque on the medical image. In some embodiments of the computer-implemented method, a higher degree of embeddedness of the one or more regions of low density non-calcified plaque is indicative of an unstable plaque or high risk of CAD. In some embodiments of the computer-implemented method, the shape of the one or more regions of low density non-calcified plaque is determined as one or more of a crescent, round, lobular, or bean shape. In some embodiments of the computer-implemented method, determination of a round or bean shape of the one or more regions of low density non-calcified plaque is indicative of an unstable plaque or high risk of CAD. In some embodiments of the computer-implemented method, the shape of the one or more regions of low density non-calcified plaque is determined based at least in part by a machine learning algorithm.

In some embodiments of the computer-implemented method, the analysis of the one or more regions of low density non-calcified plaque further comprises determining one or more lengths of one or more axes of the one or more regions of low density non-calcified plaque. In some embodiments of the computer-implemented method, the shape of the one or more regions of low density non-calcified plaque is determined based at least in part on the one or more determined lengths of the one or more axes. In some embodiments of the computer-implemented method, the shape of the one or more regions of low density non-calcified plaque is determined based at least in part on determining a standard deviation among the one or more determined lengths of the one or more axes. In some embodiments of the computer-implemented method, the analysis of the one or more regions of low density non-calcified plaque further comprises: determining a volume of the one or more regions of low density non-calcified plaque; determining a volume of the one or more regions of plaque; and determining a ratio of the volume of the one or more regions of low density non-calcified plaque to the volume of the one or more regions of plaque. In some embodiments of the computer-implemented method, the volume of the one or more regions of low density non-calcified plaque is determined based on the one or more determined lengths of the one or more axes of the one or more regions of low density non-calcified plaque. In some embodiments of the computer-implemented method, a determination of the volume of the one or more regions of low density non-calcified plaque above a predetermined threshold is indicative of unstable plaque or high risk of CAD. In some embodiments of the computer-implemented method, a determination of the volume of the one or more regions of plaque above a predetermined threshold is indicative of unstable plaque or high risk of CAD. In some embodiments of the computer-implemented method, a determination of the ratio of the volume of the one or more regions of low density non-calcified plaque to the volume of the one or more regions of plaque above a predetermined threshold is indicative of unstable plaque or high risk of CAD.

In some embodiments of the computer-implemented method, the density comprises absolute density. In some embodiments of the computer-implemented method, the density comprises radiodensity. In some embodiments of the computer-implemented method, the one or more regions of plaque are identified as low density non-calcified plaque when a radiodensity value is between about −189 and about 30 Hounsfield units. In some embodiments of the computer-implemented method, the one or more regions of plaque are identified as non-calcified plaque when a radiodensity value is between about 31 and about 350 Hounsfield units. In some embodiments of the computer-implemented method, the one or more regions of plaque are identified as calcified plaque when a radiodensity value is between about 351 and 2500 Hounsfield units. In some embodiments of the computer-implemented method, the medical image comprises a Computed Tomography (CT) image. In some embodiments of the computer-implemented method, the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS). In some embodiments of the computer-implemented method, the method further comprises generating, by the computer system, an assessment of risk of CAD of the subject or risk of the one or more regions of plaque based at least in part on the analysis of the one or more regions of low density non-calcified plaque. In some embodiments of the computer-implemented method, the method further comprises generating, by the computer system, a recommended treatment for the subject based at least in part on the analysis of the one or more regions of low density non-calcified plaque.

In some embodiments, a system for facilitating determination of risk of coronary artery disease (CAD) based at least in part on one or more measurements derived from non-invasive medical image analysis comprises: one or more computer readable storage devices configured to store a plurality of computer executable instructions; and one or more hardware computer processors in communication with the one or more computer readable storage devices and configured to execute the plurality of computer executable instructions in order to cause the system to: access a medical image of a subject, wherein the medical image of the subject is obtained non-invasively; analyze the medical image of the subject to identify one or more arteries; identify one or more regions of plaque within the one or more coronary arteries; analyze the identified one or more regions of plaque to identify one or more regions of low density non-calcified plaque, non-calcified plaque, or calcified plaque based at least in part on density, facilitate analyzing, in response to identifying one or more regions of low density non-calcified plaque, the one or more regions of low density non-calcified plaque, wherein the analysis of the one or more regions of low density non-calcified plaque comprises: determining a distance from the one or more regions of low density non-calcified plaque to one or more of a lumen wall or vessel wall; determining a degree of embeddedness of the one or more regions of low density non-calcified plaque by one or more of non-calcified plaque or calcified plaque; and determining a shape of the one or more regions of low density non-calcified plaque; and generate a display of the analysis of the one or more regions of low density non-calcified plaque to facilitate determination of one or more of a risk of CAD of the subject based at least in part on the analysis of the one or more regions of low density non-calcified plaque.

In some embodiments of the system, a determination of the distance from the one or more regions of low density non-calcified plaque to the lumen wall below a predetermined threshold is indicative of an unstable plaque or high risk of CAD. In some embodiments of the system, the distance from the one or more regions of low density non-calcified plaque to one or more of the lumen wall or vessel wall is determined on a three-dimensional basis. In some embodiments of the system, the distance from the one or more regions of low density non-calcified plaque to one or more of the lumen wall or vessel wall is determined based on a two-dimensional image. In some embodiments of the system, the two-dimensional image is obtained by taking a two-dimensional slice perpendicular to a longitudinal axis of a straightened multiplanar view of the one or more arteries. In some embodiments of the system, the two-dimensional image is obtained by taking a two-dimensional slice resulting in a largest two-dimensional area of the low-density non-calcified plaque. In some embodiments of the system, the distance from the one or more regions of low density non-calcified plaque to the lumen wall is determined by determining a shortest distance between a boundary of the one or more regions of low density non-calcified plaque and a boundary of the lumen wall. In some embodiments of the system, the distance from the one or more regions of low density non-calcified plaque to the vessel wall is determined by determining a shortest distance between a boundary of the one or more regions of low density non-calcified plaque and a boundary of the vessel wall. In some embodiments of the system, the one or more arteries comprises one or more coronary or carotid arteries.

In some embodiments of the system, the one or more axes of the one or more regions of low density non-calcified plaque comprises one or more of a major axis on a longitudinal plane, minor axis on a longitudinal plane, major axis on a latitudinal plane, or minor axis on a latitudinal plane. In some embodiments of the system, the one or more axes are determined on a three-dimensional basis. In some embodiments of the system, the one or more axes are determined based on one or more two-dimensional images. In some embodiments of the system, the longitudinal plane is obtained by taking a two-dimensional slice parallel to a longitudinal axis of a straightened multiplanar view of the one or more arteries. In some embodiments of the system, the longitudinal plane is obtained by taking a two-dimensional slice resulting in a longest major axis of the longitudinal plane. In some embodiments of the system, the latitudinal plane is obtained by taking a two-dimensional slice perpendicular to a longitudinal axis of a straightened multiplanar view of the one or more arteries. In some embodiments of the system, the latitudinal plane is obtained by taking a two-dimensional slice perpendicular to the major axis on the longitudinal plane. In some embodiments of the system, the latitudinal plane is obtained by taking a two-dimensional slice resulting in a largest two-dimensional area of the low-density non-calcified plaque. In some embodiments of the system, one or more of analyses of the one or more regions of low density non-calcified plaque is performed by the computer system.

In some embodiments of the system, the degree of embeddedness of the one or more regions of low density non-calcified plaque is determined based at least in part by graphically overlaying a protractor on the one or more regions of low density non-calcified plaque on the medical image. In some embodiments of the system, a higher degree of embeddedness of the one or more regions of low density non-calcified plaque is indicative of an unstable plaque or high risk of CAD. In some embodiments of the system, the shape of the one or more regions of low density non-calcified plaque is determined as one or more of a crescent, round, lobular, or bean shape. In some embodiments of the system, determination of a round or bean shape of the one or more regions of low density non-calcified plaque is indicative of an unstable plaque or high risk of CAD. In some embodiments of the system, the shape of the one or more regions of low density non-calcified plaque is determined based at least in part by a machine learning algorithm.

In some embodiments of the system, the analysis of the one or more regions of low density non-calcified plaque further comprises determining one or more lengths of one or more axes of the one or more regions of low density non-calcified plaque. In some embodiments of the system, the shape of the one or more regions of low density non-calcified plaque is determined based at least in part on the one or more determined lengths of the one or more axes. In some embodiments of the system, the shape of the one or more regions of low density non-calcified plaque is determined based at least in part on determining a standard deviation among the one or more determined lengths of the one or more axes. In some embodiments of the system, the analysis of the one or more regions of low density non-calcified plaque further comprises: determining a volume of the one or more regions of low density non-calcified plaque; determining a volume of the one or more regions of plaque; and determining a ratio of the volume of the one or more regions of low density non-calcified plaque to the volume of the one or more regions of plaque. In some embodiments of the system, the volume of the one or more regions of low density non-calcified plaque is determined based on the one or more determined lengths of the one or more axes of the one or more regions of low density non-calcified plaque. In some embodiments of the system, a determination of the volume of the one or more regions of low density non-calcified plaque above a predetermined threshold is indicative of unstable plaque or high risk of CAD. In some embodiments of the system, a determination of the volume of the one or more regions of plaque above a predetermined threshold is indicative of unstable plaque or high risk of CAD. In some embodiments of the system, a determination of the ratio of the volume of the one or more regions of low density non-calcified plaque to the volume of the one or more regions of plaque above a predetermined threshold is indicative of unstable plaque or high risk of CAD.

In some embodiments of the system, the density comprises absolute density. In some embodiments of the system, the density comprises radiodensity. In some embodiments of the system, the one or more regions of plaque are identified as low density non-calcified plaque when a radiodensity value is between about −189 and about 30 Hounsfield units. In some embodiments of the system, the one or more regions of plaque are identified as non-calcified plaque when a radiodensity value is between about 31 and about 350 Hounsfield units. In some embodiments of the system, the one or more regions of plaque are identified as calcified plaque when a radiodensity value is between about 351 and 2500 Hounsfield units. In some embodiments of the system, the medical image comprises a Computed Tomography (CT) image. In some embodiments of the system, the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS). In some embodiments of the system, the system is further caused to generate an assessment of risk of CAD of the subject or risk of the one or more regions of plaque based at least in part on the analysis of the one or more regions of low density non-calcified plaque. In some embodiments of the system, the system is further caused to generate a recommended treatment for the subject based at least in part on the analysis of the one or more regions of low density non-calcified plaque.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

A better understanding of the devices and methods described herein will be appreciated upon reference to the following description in conjunction with the accompanying drawings, wherein:

FIG. 5A illustrates an example of a flowchart of a process for analyzing coronary plaque.

FIG. 5B illustrates an example of a flowchart that expands on a portion of the flowchart in FIG. 5A for determining characteristics of coronary plaque.

FIG. 9B illustrates example per-lesion high-risk plaque morphology characteristics derived from a sample study.

FIG. 9C illustrates example per-patient atherosclerotic characteristics stratified by patients with and without an acute coronary syndrome event derived from a sample study.

FIG. 9J illustrates patient demographics stratified by occurrence of acute coronary syndrome in an example study validating some embodiments of systems, methods, and devices described herein.

FIG. 9K illustrates per-lesion atherosclerotic characteristics stratified by non-culprit and culprit lesion precursors in an example study validating some embodiments of systems, methods, and devices described herein.

FIG. 9M illustrates per-patient atherosclerotic characteristics stratified by patients with and without occurrence of acute coronary syndrome in an example study validating some embodiments of systems, methods, and devices described herein.

DETAILED DESCRIPTION

Figure 1:
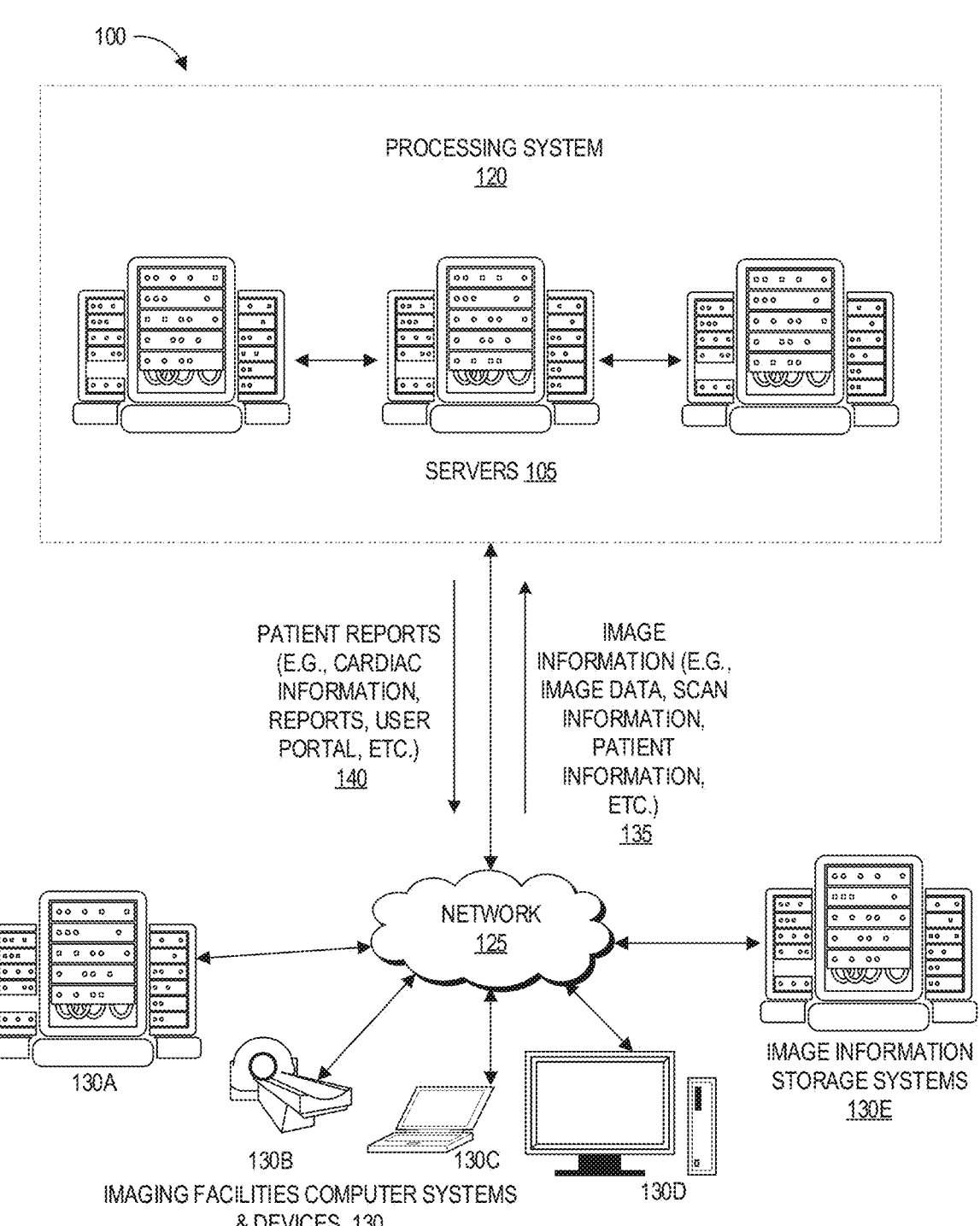
FIG. 1 depicts a schematic of an example of an embodiment of a system 100 that includes a processing system configured to characterize coronary plaque.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Disclosed herein are systems, devices, and methods for non-invasive image-based plaque analysis and risk determination. In particular, in some embodiments, the systems, devices, and methods described herein are related to analysis of one or more regions of plaque, such as for example coronary plaque, based on one or more distances, volumes, shapes, morphologies, embeddedness, and/or axes (or dimension) measurements. "Plaque" or "a region of plaque" or "one or more regions of plaque" may be referred to simply as "plaque" for ease of reference unless otherwise indicated, explicitly or by context. For example, in some embodiments, the systems, devices, and methods described herein are related to plaque analysis based on one or more of distance between plaque and a vessel wall, distance between plaque and a lumen wall, length along longitudinal axis of plaque, length along latitudinal axis of plaque, volume of low density non-calcified plaque, volume of total plaque, a ratio(s) between volume of low density non-calcified plaque and volume of total plaque, embeddedness of low density non-calcified plaque, and/or the like. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein.

Also disclosed herein are systems, methods, and devices for cardiovascular risk and/or state assessment using image-based analyses. In particular, in some embodiments, the systems, devices, and methods are related to cardiovascular risk and/or disease state assessment using image-based analysis of vessel surface and/or coordinates of features. In some embodiments, assessment of cardiovascular risk and/or disease state generated using the systems, methods, and devices herein can be utilized to diagnose and/or generate a proposed treatment for a patient.

Also disclosed herein are systems, methods, and devices for cardiovascular risk and/or state assessment using image-based analyses, where in some embodiments, the systems, devices, and methods are related to cardiovascular risk and/or disease state assessment using image-based analysis of vessel surface and/or coordinates of features. In some embodiments, assessment of cardiovascular risk and/or disease state generated using the systems, methods, and devices herein can be utilized to diagnose and/or generate a proposed treatment for a patient.

Also disclosed herein are systems, methods, and devices for cardiovascular risk and/or state assessment using image-based analyses, where in some embodiments the systems, devices, and methods are related to cardiovascular risk and/or disease and/or state assessment using modified and/or normalized image analysis-based plaque parameters. In some embodiments, assessment of cardiovascular risk and/or disease and/or state generated using the systems, methods, and devices herein can be utilized to diagnose and/or generate a proposed treatment for a patient.

Disclosed herein are systems, methods, and devices for generation of a patient-specific report on the risk and/or state assessment, diagnosis, and/or treatment of cardiovascular disease, including for example coronary artery disease (CAD). In particular, in some embodiments, the systems, devices, and methods are configured to generate an immersive patient-specific report on the patient's cardiovascular disease risk, state, diagnosis, and/or treatment. In some embodiments, the systems, devices, and methods are configured to generate an immersive patient-specific report based at least in part on image-based analysis, for example of one or more plaque and/or vessel parameters. In some embodiments, the systems, devices, and methods are configured to view the patient's cardiovascular disease state or risk from a point of view within one or more arteries of the patient. In some embodiments, the systems, devices, and methods are configured to graphically view and/or track actual or hypothetical progression of the patient's cardiovascular disease state or risk based on actual or proposed treatment from a point of view within one or more arteries of the patient.

Disclosed herein are systems, methods, and devices for cardiovascular risk and/or state assessment using image-based analyses, wherein in some embodiments the systems, devices, and methods are related to cardiovascular risk and/or disease and/or state assessment using normalized image analysis-based plaque parameters. In some embodiments, assessment of cardiovascular risk and/or disease and/or state generated using the systems, methods, and devices herein can be utilized to diagnose and/or generate a proposed treatment for a patient.

Disclosed herein are systems, devices, and methods for non-invasive image-based determination of fractional flow reserve (FFR) and/or ischemia. In particular, in some embodiments, the systems, devices, and methods are related to FFR and/or ischemia analysis of arteries, such as coronary, aortic, and/or carotid arteries using one or more image analysis techniques. For example, in some embodiments, the systems, methods, and devices can be configured to derive one or more stenosis and/or normal measurements from a medical image, which can be obtained non-invasively, and use the same to derive an assessment of FFR and/or ischemia. In some embodiments, the systems, methods, and devices can be configured to apply one or more allometric scaling laws to one or more stenosis and/or normal measurements to derive and/or generate an assessment of FFR and/or ischemia.

Coronary heart disease affects over 17.6 million Americans. The current trend in treating cardiovascular health issues is generally two-fold. First, physicians generally review a patient's cardiovascular health from a macro level, for example, by analyzing the biochemistry or blood content or biomarkers of a patient to determine whether there are high levels of cholesterol elements in the bloodstream of a patient. In response to high levels of cholesterol, some physicians will prescribe one or more drugs, such as statins, as part of a treatment plan in order to decrease what is perceived as high levels of cholesterol elements in the bloodstream of the patient.

The second general trend for currently treating cardiovascular health issues involves physicians evaluating a patient's cardiovascular health through the use of angiography to identify large blockages in various arteries of a patient. In response to finding large blockages in various arteries, physicians in some cases will perform an angioplasty procedure wherein a balloon catheter is guided to the point of narrowing in the vessel. After properly positioned, the balloon is inflated to compress or flatten the plaque or fatty matter into the artery wall and/or to stretch the artery open to increase the flow of blood through the vessel and/or to the heart. In some cases, the balloon is used to position and expand a stent within the vessel to compress the plaque and/or maintain the opening of the vessel to allow more blood to flow. About 500,000 heart stent procedures are performed each year in the United States.

However, a recent federally funded $100 million study calls into question whether the current trends in treating cardiovascular disease are the most effective treatment for all types of patients. The recent study involved over 5,000 patients with moderate to severe stable heart disease from 320 sites in 37 countries and provided new evidence showing that stents and bypass surgical procedures are likely no more effective than drugs combined with lifestyle changes for people with stable heart disease. Accordingly, it may be more advantageous for patients with stable heart disease to forgo invasive surgical procedures, such as angioplasty and/or heart bypass, and instead be prescribed heart medicines, such as statins, and certain lifestyle changes, such as regular exercise. This new treatment regimen could affect thousands of patients worldwide. Of the estimated 500,000 heart stent procedures performed annually in the United States, it is estimated that a fifth of those are for people with stable heart disease. It is further estimated that 25% of the estimated 100,000 people with stable heart disease, or roughly 23,000 people, are individuals that do not experience any chest pain. Accordingly, over 20,000 patients annually could potentially forgo invasive surgical procedures or the complications resulting from such procedures.

To determine whether a patient should forego invasive surgical procedures and opt instead for a drug regimen and/or to generate a more effective treatment plan, it can be important to more fully understand the cardiovascular disease of a patient. Specifically, it can be advantageous to better understand the arterial vessel health of a patient. For example, it is helpful to understand whether plaque build-up in a patient is mostly fatty matter build-up or mostly calcified matter build-up, because the former situation may warrant treatment with heart medicines, such as statins, whereas in the latter situation a patient should be subject to further periodic monitoring without prescribing heart medicine or implanting any stents. However, if the plaque build-up is significant enough to cause severe stenosis or narrowing of the arterial vessel such that blood flow to heart muscle might be blocked, then an invasive angioplasty procedure to implant a stent may likely be required because heart attack or sudden cardiac death (SCD) could occur in such patients without the implantation of a stent to enlarge the vessel opening. Sudden cardiac death is one of the largest causes of natural death in the United States, accounting for approximately 325,000 adult deaths per year and responsible for nearly half of all deaths from cardiovascular disease. For males, SCD is twice as common as compared to females. In general, SCD strikes people in the mid-30 to mid-40 age range. In over 50% of cases, sudden cardiac arrest occurs with no warning signs.

With respect to the millions suffering from heart disease, there is a need to better understand the overall health of the artery vessels within a patient beyond just knowing the blood chemistry or content of the blood flowing through such artery vessels. For example, in some embodiments of systems, devices, and methods disclosed herein, arteries with "good" or stable plaque or plaque comprising hardened calcified content are considered non-life threatening to patients whereas arteries containing "bad" or unstable plaque or plaque comprising fatty material are considered more life threatening because such bad plaque may rupture within arteries thereby releasing such fatty material into the arteries. Such a fatty material release in the blood stream can cause inflammation that may result in a blood clot. A blood clot within an artery can prevent blood from traveling to heart muscle thereby causing a heart attack or other cardiac event. Further, in some instances, it is generally more difficult for blood to flow through fatty plaque buildup than it is for blood to flow through calcified plaque build-up. Therefore, there is a need for better understanding and analysis of the arterial vessel walls of a patient.

Further, while blood tests and drug treatment regimens are helpful in reducing cardiovascular health issues and mitigating against cardiovascular events (for example, heart attacks), such treatment methodologies are not complete or perfect in that such treatments can misidentify and/or fail to pinpoint or diagnose significant cardiovascular risk areas. For example, the mere analysis of the blood chemistry of a patient will not likely identify that a patient has artery vessels having significant amounts of fatty deposit material bad plaque buildup along a vessel wall. Similarly, an angiogram, while helpful in identifying areas of stenosis or vessel narrowing, may not be able to clearly identify areas of the artery vessel wall where there is significant buildup of bad plaque. Such areas of buildup of bad plaque within an artery vessel wall can be indicators of a patient at high risk of suffering a cardiovascular event, such as a heart attack. In certain circumstances, areas where there exist areas of bad plaque can lead to a rupture wherein there is a release of the fatty materials into the bloodstream of the artery, which in turn can cause a clot to develop in the artery. A blood clot in the artery can cause a stoppage of blood flow to the heart tissue, which can result in a heart attack. Accordingly, there is a need for new technology for analyzing artery vessel walls and/or identifying areas within artery vessel walls that comprise a buildup of plaque whether it be bad or otherwise.

In some embodiments, the systems, devices, and methods described herein are configured to utilize non-invasive medical imaging technologies, such as a CT image or CCTA for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

As will be discussed in further detail, the systems, devices, and methods described herein allow for automatic and/or dynamic quantified analysis of various parameters relating to plaque, cardiovascular arteries, and/or other structures. More specifically, in some embodiments described herein, a medical image of a patient, such as a coronary CT image or CCTA, can be taken at a medical facility. Rather than having a physician eyeball or make a general assessment of the patient, the medical image is transmitted to a backend main server in some embodiments that is configured to conduct one or more analyses thereof in a reproducible manner. As such, in some embodiments, the systems, methods, and devices described herein can provide a quantified measurement of one or more features of a coronary CT image using automated and/or dynamic processes. For example, in some embodiments, the main server system can be configured to identify one or more vessels, plaque, fat, and/or one or more measurements thereof from a medical image. Based on the identified features, in some embodiments, the system can be configured to generate one or more quantified measurements from a raw medical image, such as for example radiodensity of one or more regions of plaque, identification of stable plaque and/or unstable plaque, volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like. Based on the identified features and/or quantified measurements, in some embodiments, the system can be configured to generate a risk and/or disease state assessment and/or track the progression of a plaque-based disease or condition, such as for example atherosclerosis, stenosis, and/or ischemia, using raw medical images. Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures. In some embodiments, the systems, methods, and devices described herein comprise and/or are configured to utilize any one or more of such techniques described in US Patent Application Publication No. US 2021/0319558, which is incorporated herein by reference in its entirety.

As such, in some embodiments, the systems, devices, and methods described herein are able to provide physicians and/or patients specific quantified and/or measured data relating to a patient's plaque and/or ischemia that do not exist today. In some embodiments, such detailed level of quantified plaque parameters from image processing and downstream analytical results can provide more accurate and useful tools for assessing the health and/or risk of patients in completely novel ways.

Disclosed are methods for identification of high-risk plaques using volumetric characterization of coronary plaque and perivascular adipose tissue data by computed tomography (CT) scanning. The volumetric characterization of the coronary plaque and perivascular adipose tissue allows for determination of the inflammatory status of the plaque by CT scanning. This is of use in the diagnosis, prognosis and treatment of coronary artery disease. While certain example embodiments are shown by way of example in the drawings and will herein be described in detail, these embodiments are capable of various modifications and alternative forms. There is no intent to limit example embodiments to the particular forms disclosed, but on the contrary, example embodiments are to cover all modifications, equivalents, and alternatives falling within the scope of example embodiments.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes all combinations of one or more of the associated listed items.

The terminology used herein is for the purpose of describing embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof. In this specification, the term "and/or" picks out each individual item as well as all combinations of them. Unless otherwise defined, all terms (including technical and scientific terms) used herein have the same meaning as commonly understood by one of ordinary skill in the art to which example embodiments belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein. It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

In the drawings, the dimensions of layers and regions are exaggerated for clarity of illustration. It will also be understood that when a layer (or tissue) is referred to as being "on" another layer or tissue, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being 'between' two layers, it can be the only layer between the two layers, or one or more intervening layers may also be present. Like reference numerals refer to like elements throughout.

Overview of Example Processing System to Characterize Coronary Plaque

This disclosure includes methods and systems of using data generated from images collected by scanning a patient's arteries to identify coronary artery plaques that are at higher risk of causing future heart attack or acute coronary syndrome. In particular, the characteristics of perivascular coronary fat, coronary plaque, and/or the coronary lumen, and the relationship of the characteristics of perivascular coronary fat, coronary plaque, and/or the coronary lumen are discussed to determine ways for identifying the coronary plaque that is more susceptible to implication in future ACS, heart attack and death. The images used to generate the image data may be CT images, CCTA images, or images generated using any applicable technology that can depict the relative densities of the coronary plaque, perivascular fat, and coronary lumen. For example, CCTA images may be used to generate two-dimensional (2D) or volumetric (three-dimensional (3-D)) image data, and this image data may be analyzed to determine certain characteristics that are associated with the radiodensities of the coronary plaque, perivascular fat, and/or coronary lumen. In some implementations, the Hounsfield scale is used to provide a measure of the radiodensity of these features. A Hounsfield unit, as is known, represents an arbitrary unit of x-ray attenuation used for CT scans. Each pixel (2D) or voxel (3D) of a feature in the image data may be assigned a radiodensity value on the Hounsfield scale, and then these values characterizing the features may be analyzed.

In various embodiments, processing of image information may include: (1) determining scan parameters (for example, mA (milliampere), kvP (peak kilovoltage)); (2) determining the scan image quality (e.g., noise, signal-to-noise ratio, contrast-to-noise ratio); (3) measuring scan-specific coronary artery lumen densities (e.g., from a point distal to a coronary artery wall to a point proximal to the coronary artery wall to distal to the coronary artery, and from a central location of the coronary artery to an outer location (e.g., outer relative to radial distance from the coronary artery): (4) measuring scan-specific plaque densities (e.g., from central to outer, abruptness of change within a plaque from high-to-low or low-to-high) as a function of their 3D shape; and (5) measuring scan-specific perivascular coronary fat densities (from close to the artery to far from the artery) as a function of its 3D shape.

From these measurements, which are agnostic to any commonly known features of ischemia-causing atherosclerosis, we can determine several characteristics, including but not limited to:

1. A ratio of lumen attenuation to plaque attenuation, wherein the volumetric model of scan-specific attenuation density gradients within the lumen adjusts for reduced luminal density across plaque lesions that are more functionally significant in terms of risk value 2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases.

3. A ratio of lumen attenuation/plaque attenuation/fat attenuation

4. A ratio of #1-3 as a function of 3D shape of atherosclerosis, which can include a 3D texture analysis of the plaque 5. The 3D volumetric shape and path of the lumen along with its attenuation density from the beginning to the end of the lumen.

6. The totality of plaque and plaque types before and after any given plaque to further inform its risk.

7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

Other characteristics can also be determined.

The above listed characteristics/metrics, and others, can be analyzed together to assess the risk of the plaque being implicated in future heart attack, ACS, ischemia or death. This can be done through development and/or validation of a traditional risk score or through machine learning methods. Factors for analysis from the metrics, that are likely to be associated with heart attack, ACS, ischemia or death, may include: (1) a ratio of [bright lumen:dark plaque]; (2) a ratio of [dark plaque:light fat]; (3) a ratio of [bright lumen:dark plaque:light fat]; and (4) a low ratio of [dark lumen:dark myocardium in 1 vessel area]/[lumen:myocardium in another vessel area]. Some improvements in the disclosed methods and systems include: (1) using numerical values from ratios of [lumen:plaque], [plaque:fat] and [lumen:plaque:fat] instead of using qualitative definitions of atherosclerotic features; (2) using a scan-specific [lumen:plaque attenuation] ratio to characterize plaque; (3) using a scan-specific [plaque:fat attenuation] ratio to characterize plaque; (4) using ratios of [lumen:plaque:fat circumferential] to characterize plaque; and (5) integration of plaque volume and type before and after as a contributor to risk for any given individual plaque.

Atherosclerotic plaque features may change over time with medical treatment (colchicine and statin medications) and while some of these medications may retard progression of plaque, they also have very important roles in promoting the change in plaque. While statin medications may have reduced the overall progression of plaque they may also have actually resulted in an increased progression of calcified plaque and a reduction of non-calcified plaque. This change will be associated with a reduction in heart attack or ACS or death, and the disclosed methods can be used to monitor the effects of medical therapy on plaque risk over time. Also, this method can also be used to identify individuals whose atherosclerotic plaque features or [lumen:plaque]/[plaque:fat]/[lumen:plaque:fat] ratios indicate that they are susceptible to rapid progression or malignant transformation of disease. In addition, these methods can be applied to single plaques or to a patient-basis wherein whole-heart atherosclerosis tracking can be used to monitor risk to the patient for experiencing heart attack (rather than trying to identify any specific plaque as being causal for future heart attack). Tracking can be done by automated co-registration processes of image data associated with a patient over a period of time.

FIG. 1 depicts a schematic of an example of an embodiment of a system 100 that includes a processing system 120 configured to characterize coronary plaque. The processing system 120 include one or more servers (or computers) 105 each configured with one or more processors. The processing system 120 includes non-transitory computer memory components for storing data and non-transitory computer memory components for storing instructions that are executed by the one or more processors data communication interfaces, the instructions configuring the one or more processors to perform methods of analyzing image information. A more detailed example of a server/computer 105 is described in reference to FIG. 9G.

The system 100 also includes a network. The processing system 120 is in communication with the network 125. The network 125 may include, as at least a portion of the network 125, the Internet, a wide area network (WAN), a wireless network, or the like. In some embodiments, the processing system 120 is part of a "cloud" implementation, which can be located anywhere that is in communication with the network 125. In some embodiments, the processing system 120 is located in the same geographic proximity as an imaging facility that images and stores patient image data. In other embodiments, the processing system 120 is located remotely from where the patient image data is generated or stored.

FIG. 1 also illustrates in system 100 various computer systems and devices 130 (e.g., of an imaging facility) that are related to generating patient image data and that are also connected to the network 125. One or more of the devices 130 may be at an imaging facility that generates images of a patient's arteries, a medical facility (e.g., a hospital, doctor's office, etc.) or may be the personal computing device of a patient or care provider. For example, as illustrated in FIG. 1, an imaging facility server (or computer) 130A may be connected to the network 125. Also, in this example, a scanner 130B in an imaging facility may be connected to the network 125. One or more other computer devices may also be connected to the network 125. For example, a laptop 130C, a personal computer 130D, and/or and an image information storage system 130E may also be connected to the network 125, and communicate with the processing system 120, and each other, via the network 125.

In some examples, the scanner 130B can be a computed tomography (CT) scanner that uses a rotating X-ray tube and a row of detectors to measure X-ray attenuations by different tissues in the body and form a corresponding image. In another example, a scanner 130B can use a spinning tube ("spiral CT") in which an entire X-ray tube and detectors are spun around a central axis of the area being scanned. In another example, the scanner 130B can utilize electron beam tomography (EBT). In another example, the scanner 130B can be a dual source CT scanner with a two X-ray tube system. The methods and systems described herein can also use images from other CT scanners. In some examples, the scanner 130B is a photon counting CT scanner, a spectral CT scanner, or a dual energy CT scanner. A photon counting CT scanner, a spectral CT scanner, or a dual energy CT scanner can help provide more detailed higher resolution images that better show small blood vessels, plaque, and other vascular pathologies, and allow for the determination of absolute material densities over relative densities. In general, a photon counting CT scanner uses an X-ray detector to count photons and quantifies the energy, determining the count of the number of photons in several discrete energy bins, resulting in higher contrast-to-noise ratio, and improved spatial resolution and spectral imaging compared to conventional CT scanners. Each registered photon is assigned to a specific bin depending on its energy, such that each pixel measures a histogram of the incident X-ray spectrum. This spectral information provides several advantages, First, it can be used to quantitatively determine the material composition of each pixel in the reconstructed CT image, as opposed to the estimated average linear attenuation coefficient obtained in a conventional CT scan. The spectral/energy information can be used to remove beam hardening artifacts that occur higher linear attenuation of many materials that shifts mean energy of the X-ray spectrum towards higher energies. Also, use of more than two energy bins allows discrimination between objects (bone, calcifications, contrast agents, tissue, etc.). In some embodiments, images generated using a photon counting CT scanner allows assessment of plaques at different monochromatic energies as well as different polychromatic spectra (e.g., 100 kvp, 120 kvp, 140 kvp, etc.), and this can change definition of non-calcified and calcified plaques compared to conventional CT scanners. A spectral CT scanner uses different X-ray wavelengths (or energies) to produce a CT scan. A dual energy CT scanner uses separate X-ray energies to detect two different energy ranges. In an example, a dual energy CT scanner (also known as spectral CT) can use an X-ray detector with separate layers to detect two different energy ranges ('dual layer'). In another example, a dual energy CT scanner can use a single scanner to scan twice using two different energy levels (e.g., electronic kVp switching). Images can be formed from combining the images detected at each different energy level, or the images may be used separately to assess a medical condition of a patient. In addition to providing absolute material densities, a photon counting CT scanner also allows for evaluation of images that are "monochromatic" as opposed to the typical CT, which is polychromatic spectra of light. As noted above, features (e.g., low density non-calcified plaque, calcified plaque, non-calcified plaque) that are depicted images formed using a photon counting CT scanner, a spectral CT scanner, or a dual energy CT scanner may have different radiodensities than those depicted in images formed from a conventional CT scanner, that is, such images may affect or change the definition of calcified and non-calcified plaque. However, radiodensities of calcified and non-calcified plaque, or other features depicted in images formed from a photon counting CT scanner, a spectral CT scanner, or a dual energy CT scanner, can be normalized to correspond to densities of conventional CT scanners and to the densities disclosed herein. Accordingly, the radiodensities disclosed herein can be directly correlated to radiodensities of images generated with a photon counting CT scanner, a spectral CT scanner, or a dual energy CT scanner such that the systems and methods, analysis, plaque densities etc. disclosed herein are directly applicable to images formed from a photon counting CT scanner, a spectral CT scanner, or a dual energy CT scanner, and are directly applicable to images formed from a photon counting CT scanner, a spectral CT scanner, or a dual energy CT scanner that are normalized to equivalent conventional CT scanner radiodensities.

The information communicated from the devices 130 to the processing system 120 via the network 125 may include image information 135. In various embodiments, the image information 135 may include 2D or 3D image data of a patient, scan information related to the image data, patient information, and other imagery or image related information that relates to a patient. For example, the image information may include patient information including (one or more) characteristics of a patient, for example, age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, lab results and the like. In some embodiments, the image information includes identification information of the patient, for example, patient's name, patient's address, driver's license number, Social Security number, or indicia of another patient identification. Once the processing system 120 analyzes the image information 135, information relating to a patient 140 may be communicated from the processing system 120 to a device 130 via the network 125. The patient information 140 may include for example, a patient report. Also, the patient information 140 may include a variety of patient information which is available from a patient portal, which may be accessed by one of the devices 130.

In some embodiments, image information comprising a plurality of images of a patient's coronary arteries and patient information/characteristics may be provided from one or more of the devices 130 to the one or more servers 105 of the processing system 120 via a network 125. The processing system 120 is configured to generate coronary artery information using the plurality of images of the patient's coronary arteries to generate two-dimensional and/or three-dimensional data representations of the patient's coronary arteries. Then, the processing system 120 analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligent techniques, the data representations of the patient's coronary arteries may be compared to other patients' data representations (e.g., that are stored in a database) to determine additional information about the patient's health. For example, based on certain plaque conditions of the patient's coronary arteries, the likelihood of a patient having a heart attack or other adverse coronary effect can be determined. Also, for example, additional information about the patient's risk of CAD may also be determined.

Figure 2:
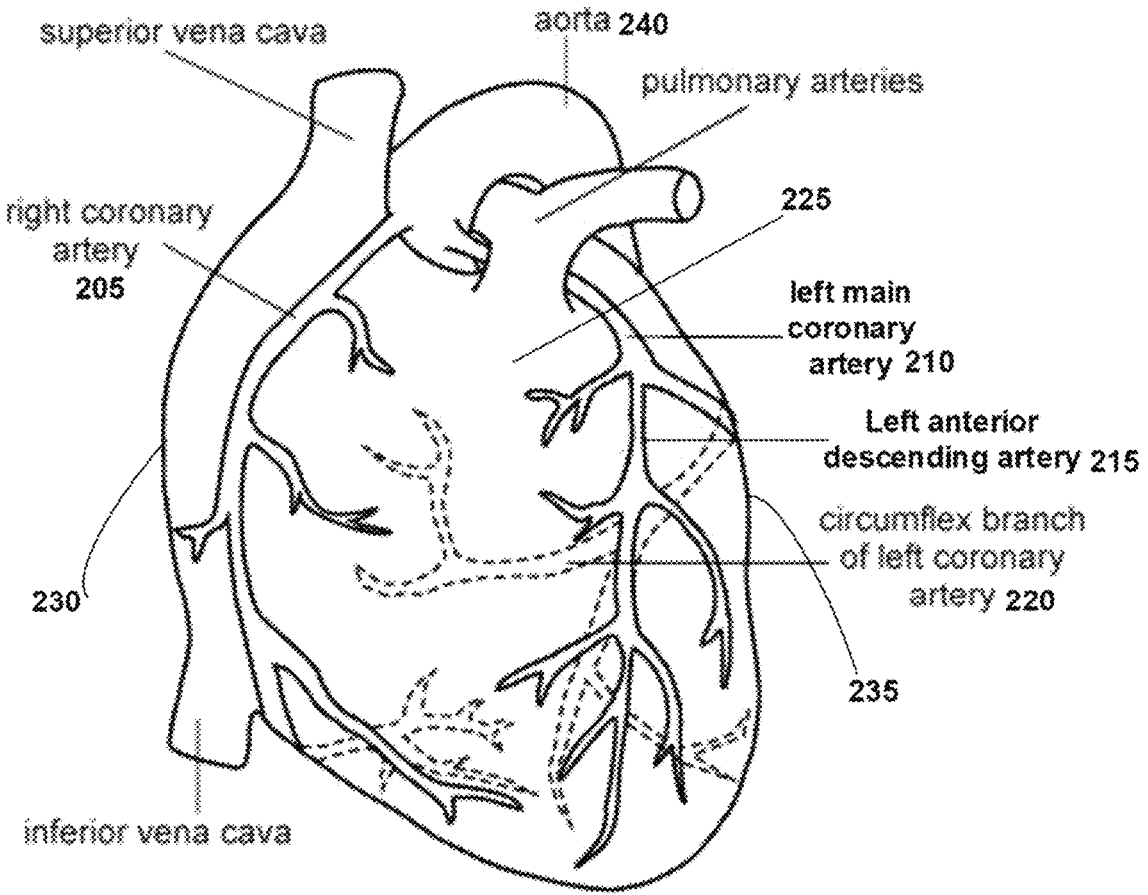
FIG. 2 is a schematic illustrating an example of a heart muscle and its coronary arteries.

FIG. 2 is a schematic illustrating an example of a heart muscle 225 and its coronary arteries. The coronary vasculature includes a complex network of vessels ranging from large arteries to arterioles, capillaries, venules, veins, etc. FIG. 1 depicts a model 220 of a portion of the coronary vasculature that circulates blood to and within the heart and includes an aorta 240 that supplies blood to a plurality of coronary arteries, for example, a left anterior descending (LAD) artery 215, a left circumflex (LCX) artery 220, and a right coronary (RCA) artery 230, described further below. Coronary arteries supply blood to the heart muscle 225. Like all other tissues in the body, the heart muscle 225 needs oxygen-rich blood to function. Also, oxygen-depleted blood must be carried away. The coronary arteries wrap around the outside of the heart muscle 225. Small branches dive into the heart muscle 225 to bring it blood. The examples of methods and systems described herein may be used to determine information relating to blood flowing through the coronary arteries in any vessels extending therefrom. In particular, the described examples of methods and systems may be used to determine various information relating to one or more portions of a coronary artery where plaque has formed which is then used to determine risks associated with such plaque, for example, whether a plaque formation is a risk to cause an adverse event to a patient.

The right side 230 of the heart 225 is depicted on the left side of FIG. 2 (relative to the page) and the left side 235 of the heart is depicted on the right side of FIG. 2. The coronary arteries include the right coronary artery (RCA) 205 which extends from the aorta 240 downward along the right side 230 of the heart 225, and the left main coronary artery (LMCA) 210 which extends from the aorta 240 downward on the left side 235 of the heart 225. The RCA 205 supplies blood to the right ventricle, the right atrium, and the SA (sinoatrial) and AV (atrioventricular) nodes, which regulate the heart rhythm. The RCA 205 divides into smaller branches, including the right posterior descending artery and the acute marginal artery. Together with the left anterior descending artery 215, the RCA 205 helps supply blood to the middle or septum of the heart.

The LMCA 210 branches into two arteries, the anterior interventricular branch of the left coronary artery, also known as the left anterior descending (LAD) artery 215 and the circumflex branch of the left coronary artery 220. The LAD artery 215 supplies blood to the front of the left side of the heart. Occlusion of the LAD artery 215 is often called the widow-maker infarction. The circumflex branch of the left coronary artery 220 encircles the heart muscle. The circumflex branch of the left coronary artery 220 supplies blood to the outer side and back of the heart, following the left part of the coronary sulcus, running first to the left and then to the right, reaching nearly as far as the posterior longitudinal sulcus.

Figure 3:
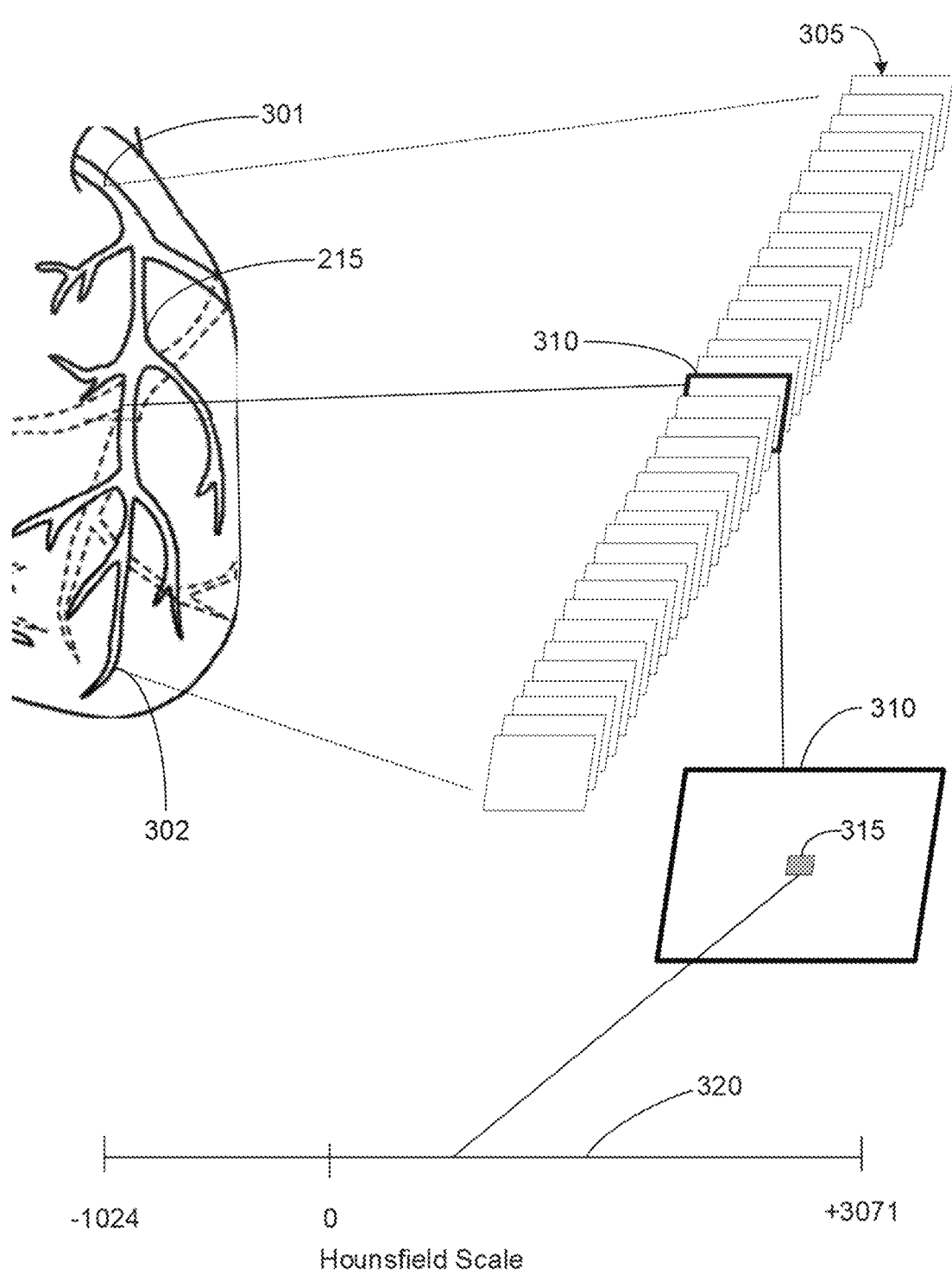
FIG. 3 illustrates an example of a set of images generated from scanning along a coronary artery, including a selected image of a portion of a coronary artery, and how image data may correspond to a value on the Hounsfield Scale.

FIG. 3 illustrates an example of a set of images generated from scanning along a coronary artery, including a selected image of a portion of a coronary artery, and how image data may correspond to a value on the Hounsfield Scale. As discussed in reference to FIG. 1, in addition to obtaining image data, scan information including metrics related to the image data, and patient information including characteristics of the patient may also be collected.

A portion of a heart 225, the LMCA 210, and the LAD artery 215 is illustrated in the example of FIG. 3. A set of images 305 can be collected along portions of the LMCA 210 and the LAD artery 215, in this example from a first point 301 on the LMCA 210 to a second point 302 on the LAD artery 215. In some examples, the image data may be obtained using noninvasive imaging methods. For example, CCTA image data can be generated using a scanner to create images of the heart in the coronary arteries and other vessels extending therefrom. Collected CCTA image data may be subsequently used to generate three-dimensional image models of the features contained in the CCTA image data (for example, the right coronary artery 205, the left main coronary artery 210, the left anterior descending artery 215, the circumflex branch of the left coronary artery 220, the aorta 240, and other vessels related to the heart that appear in the image data.

In various embodiments, different imaging methods may be used to collect the image data. For example, ultrasound or magnetic resonance imaging (MRI) may be used. In some embodiments, the imaging methods involve using a contrast agent to help identify structures of the coronary arteries, the contrast agent being injected into the patient prior to the imaging procedure. The various imaging methods may each have their own advantages and disadvantages of usage, including resolution and suitability of imaging the coronary arteries. Imaging methods which may be used to collect image data of the coronary arteries are constantly improving as improvements to the hardware (e.g., sensors and emitters) and software are made. The disclosed systems and methods contemplate using CCTA image data and/or any other type of image data that can provide or be converted into a representative 3D depiction of the coronary arteries, plaque contained within the coronary arteries, and perivascular fat located in proximity to the coronary arteries containing the plaque such that attenuation or radiodensity values of the coronary arteries, plaque, and/or perivascular fat can be obtained.

Referring still to FIG. 3, a particular image 310 of the image data 305 is shown, which represents an image of a portion of the left anterior descending artery 215. The image 310 includes image information, the smallest point of the information manipulated by a system referred to herein generally as a pixel, for example pixel 315 of image 310. The resolution of the imaging system used to capture the image data will affect the size of the smallest feature that can be discerned in an image. In addition, subsequent manipulation of the image may affect the dimensions of a pixel. As one example, the image 310 in a digital format, may contain 4000 pixels in each horizontal row, and 3000 pixels in each vertical column. Pixel 315, and each of the pixels in image data 310 and in the image data 305, can be associated with a radiodensity value that corresponds to the density of the pixel in the image. Illustratively shown in FIG. 3 is mapping pixel 315 to a point on the Hounsfield scale 320. The Hounsfield scale 320 is a quantitative scale for describing radiodensity. The Hounsfield unit scale linear transformation of the original linear attenuation coefficient measurement into one in which the radiodensity of distilled water at standard pressure and temperature is defined as zero Hounsfield units (HU), while the radiodensity of air at standard pressure and temperature is defined as –1000 HU. Although FIG. 3 illustrates an example of mapping pixel 315 of image 310 to a point on the Hounsfield scale 320, such an association of a pixel to a radiodensity value can also be done with 3D data. For example, after the image data 305 is used to generate a three-dimensional representation of the coronary arteries.

Once the data has been obtained and rendered into a three-dimensional representation, various processes can be performed on the data to identify areas of analysis. For example, a three-dimensional depiction of a coronary artery may be segmented to define a plurality of portions of the artery and identified as such in the data. In some embodiments, the data may be filtered (e.g., smoothed) by various methods to remove anomalies that are the result of scanning or other various errors. Various known methods for segmenting and smoothing the 3D data may be used, and therefore for brevity of the disclosure will not be discussed in any further detail herein.

Figure 4A:
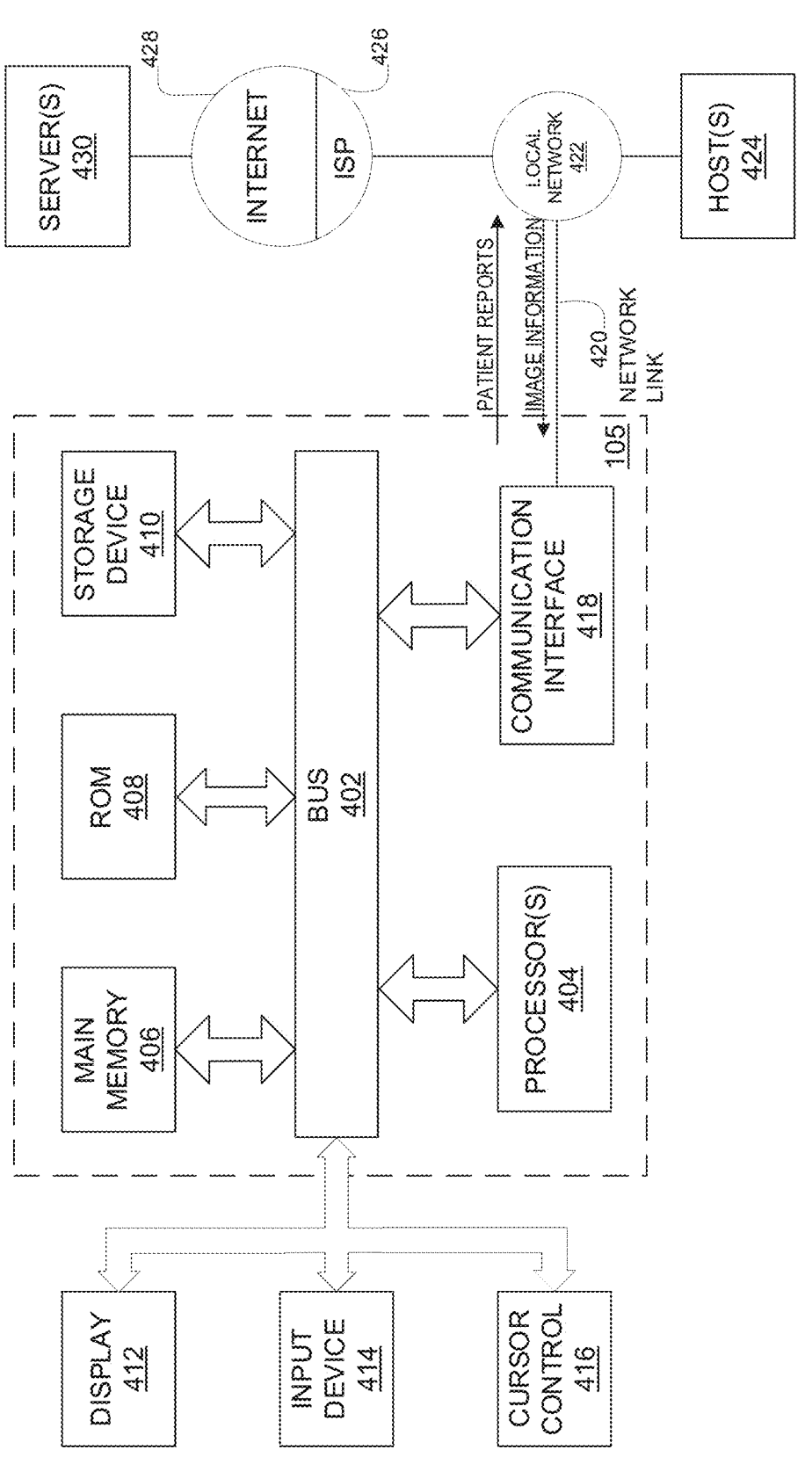
FIG. 4A is a block diagram that illustrates a computer system upon which various embodiments may be implemented.

FIG. 4A is a block diagram that illustrates a computer system 400 upon which various embodiments may be implemented. Computer system 400 includes a bus 402 or other communication mechanism for communicating information, and a hardware processor, or multiple processors, 404 coupled with bus 402 for processing information. Hardware processor(s) 404 may be, for example, one or more general purpose microprocessors.

Computer system 400 also includes a main memory 406, such as a random access memory (RAM), cache and/or other dynamic storage devices, coupled to bus 402 for storing information and instructions to be executed by processor 404. Main memory 406 also may be used for storing temporary variables or other intermediate information during execution of instructions to be executed by processor 404. Such instructions, when stored in storage media accessible to processor 404, render computer system 400 into a special-purpose machine that is customized to perform the operations specified in the instructions. The main memory 406 may, for example, include instructions that analyze image information to determine characteristics of coronary features (e.g., plaque, perivascular fat and coronary arteries) to produce patient reports containing information that characterizes aspects of the patient's health relating to their coronary arteries. For example, one or more metrics may be determined, the metrics including one or more of a slope/gradient of a feature, a maximum density, minimum density, a ratio of a slope of one feature to the slope of another feature, a ratio of a maximum density of one feature to the maximum density of another feature, a ratio of a minimum density of a feature to the minimum density of the same feature, or a ratio of the minimum density of a feature to the maximum density of another feature.

Computer system 400 further includes a read only memory (ROM) 408 or other static storage device coupled to bus 402 for storing static information and instructions for processor 404. A storage device 410, such as a magnetic disk, optical disk, or USB thumb drive (Flash drive), etc., is provided and coupled to bus 402 for storing information and instructions.

Computer system 400 may be coupled via bus 402 to a display 412, such as a cathode ray tube (CRT) or LCD display (or touch screen), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 400 may include a user interface module to implement a GUI that may be stored in a mass storage device as computer executable program instructions that are executed by the computing device(s). Computer system 400 may further, as described below, implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor(s) 404 executing one or more sequences of one or more computer readable program instructions contained in main memory 406. Such instructions may be read into main memory 406 from another storage medium, such as storage device 410. Execution of the sequences of instructions contained in main memory 406 causes processor(s) 404 to perform the process steps described herein. In alternative embodiments, hard-wired circuitry may be used in place of or in combination with software instructions.

Various forms of computer readable storage media may be involved in carrying one or more sequences of one or more computer readable program instructions to processor 404 for execution. For example, the instructions may initially be carried on a magnetic disk or solid state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN (or WAN component to communicate with a WAN). Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the worldwide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

Accordingly, in an embodiment, the computer system 105 comprises a non-transitory computer storage medium storage device 410 configured to at least store image information of patients. The computer system 105 can also include non-transitory computer storage medium storage that stores instructions for the one or more processors 404 to execute a process (e.g., a method) for characterization of coronary plaque tissue data and perivascular tissue data using image data gathered from a computed tomography (CT) scan along a blood vessel, the image information including radiodensity values of coronary plaque and perivascular tissue located adjacent to the coronary plaque. Executing the instructions, the one or more processors 404 can quantify, in the image data, the radiodensity in regions of coronary plaque, quantify in the image data, radiodensity in at least one region of corresponding perivascular tissue adjacent to the coronary plaque, determine gradients of the quantified radiodensity values within the coronary plaque and the quantified radiodensity values within the corresponding perivascular tissue, determine a ratio of the quantified radiodensity values within the coronary plaque and the corresponding perivascular tissue, and characterizing the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

Figure 4B:
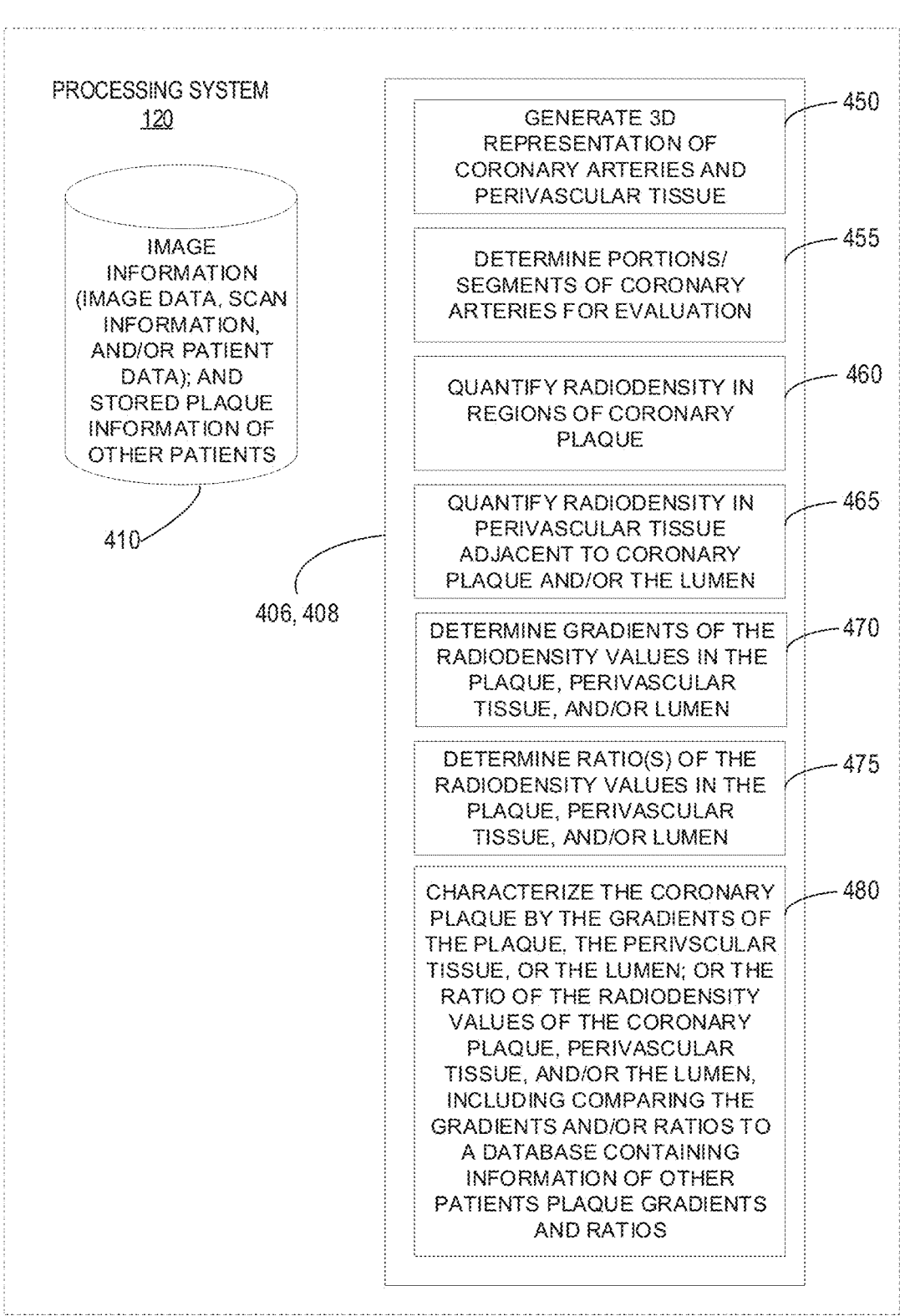
FIG. 4B is a block diagram that illustrates computer modules in a computer system 400 which may implement various embodiments.

FIG. 4B is a block diagram that illustrates examples of representative instructions which may be executed by one or more computer hardware processors in one or more computer modules in a representative processing system (computer system) 120 which may implement various embodiments described herein. As illustrated in FIG. 1, the processing system 120 can be implemented in one computer (for example, a server) or in 2 or more computers (two or more servers). Although the instructions are represented in FIG. 4B as being in seven modules 450, 455, 460, 465, 470, 475, 480, in various implementations the executable instructions may be in fewer modules, including a single module, or more modules.

The processing system 120 includes image information stored on a storage device 410, which may come from the network 125 illustrated in FIG. 1. The image information may include image data, scan information, and/or patient data. In this example, the storage device 410 also includes stored plaque information of other patients. For example, the stored plaque information of other patients may be stored in a database on the storage device 410. In other examples, stored plaque information of other patients is stored on a storage device that is in communication with processing system 120. The other patients' stored plaque information may be a collection of information from one, dozens, hundreds, thousands, tens of thousands, hundreds of thousands, or millions of patients, or more.

The information for each patient may include characterizations of that patient's plaque, such as densities and density gradients of the patient's plaque, and the location of the plaque relative to the perivascular tissue near or adjacent to the plaque. The information for each patient may include patient information. For example, the information may include one or more of sex, age, BMI (body mass index), medication, blood pressure, heart rate, weight, height, race, body habitus, smoking history, history or diagnosis of diabetes, history or diagnosis of hypertension, prior coronary artery disease, family history of coronary artery disease and/or other diseases, or one or more lab results (e.g., blood test results). The information for each patient may include scan information. For example, the information may include one or more of contrast-to-noise ratio, signal-to-noise ratio, tube current, tube voltage, contrast type, contrast volume, flow rate, flow duration, slice thickness, slice spacing, pitch, vasodilator, beta blockers, recon option whether it's iterative or filter back projection, recon type whether it's standard or high resolution, display field-of-view, rotation speed, gating whether it's perspective triggering or retrospective gating, stents, heart rate, or blood pressure. The information for each patient may also include cardiac information. For example, the information may include characterizations of plaque including one or more of density, volume, geometry (shape), location, remodeling, baseline anatomy (for diameter, length), compartments (inner, outer, within), stenosis (diameter, area), myocardial mass, plaque volume, and/or plaque composition, texture, or uniformity.

The processing system 120 also includes memory 406, 408, which may be main memory of the processing system or read only memory (ROM). The memory 406, 408 stores instructions executable by one or more computer hardware processors 404 (groups of which referred to herein as "modules") to characterize coronary plaque. The memory 406, 408 will be collectively referred to, in reference to this diagram, as memory 406 for the sake of brevity. Examples of the functionality that is performed by the executable instructions are described below.

Memory 406 includes module 450 that generates, from the image data stored on the storage device 410, 2-D or 3-D representations of the coronary arteries, including plaque, and perivascular tissue that is located adjacent to or in proximity of the coronary arteries in the plaque. The generation of the 2-D or 3-D representations of the coronary arteries may be done from a series of images 305 (e.g., CCTA images) is described above in reference to FIG. 3. Once the representation of the coronary arteries are generated, different portions or segments of the coronary arteries can be identified for evaluation. For example, portions of interest of the right coronary artery 205, the left anterior descending artery 215, or the circumflex branch of the left coronary artery 220 may be identified as areas of analysis (areas of interest) based on input from a user, or based on a feature determined from the representation of the coronary artery (plaque).

In module 460, the one or more computer hardware processors quantify radiodensity in regions of coronary plaque. For example, the radiodensity in regions of coronary plaque are set to a value on the Hounsfield scale. In module 465, the one or more computer hardware processors quantify radiodensity of perivascular tissue that is adjacent to the coronary plaque, and quantify radiodensity value of the lumen of the vessel of interest. In module 470, the one or more computer hardware processors determine gradients of the radiodensity values of the plaque the perivascular tissue and/or the lumen. In module 475, the one or more computer hardware processors determine one or more ratios of the radiodensity values in the plaque, perivascular tissue, and/or the lumen. Next, in module 480, the one or more computer hardware processors characterize the coronary plaque using the gradients of the plaque, the perivascular tissue, and/or the lumen, and/or characterize ratio of the radiodensity values of the coronary plaque to perivascular tissue and/or the lumen including comparing the gradients and or ratios to a database containing information of other patients' plaque gradients and ratios. For example, the gradients and/or the ratios are compared to patient data that stored on storage device 410. Determining gradients and ratios of the plaque the perivascular tissue and the lumen are described in more detail with reference to FIGS. 6-12.

FIG. 5A illustrates an example of a flowchart of a process 500 for analyzing coronary plaque. At block 505, the process 500 generates image information including image data relating to coronary arteries. In various embodiments, this may be done by a scanner 130B (FIG. 1). At block 510, a processing system may receive image information via a network 125 (FIG. 1), the image information including the image data. At block 515, the process 500 generates a 3D representation of the coronary arteries including perivascular fat and plaque on the processing system. The functionality of blocks 505, 510, and 515, can be performed, for example, using various scanning techniques (e.g., CCTA) to generate image data, communication techniques to transfer data over the network, and processing techniques to generate the 3D representation of the coronary arteries from the image data.

At block 520, the processing system performs a portion of the process 500 to analyze the coronary plaque, which is described in further detail in reference to process 550 of FIG. 5B. Additional details of this process to analyze the coronary plaque in reference to FIGS. 6-12.

FIG. 5B illustrates an example of a flowchart that expands on a portion of the flowchart in FIG. 5A for determining characteristics of coronary plaque. Referring now to FIG. 5B, at block 555, process 550 can utilize the one or more processors 404 to quantify the radiodensity in regions of coronary plaque. At block 560, the process 550 can utilize the one or more processors 404 to quantify, in the image data, radiodensity in at least one region of corresponding perivascular tissue, meaning perivascular tissue that is adjacent to the coronary plaque. At block 565, the process 550 determines gradients of the quantified radiodensity values within the coronary plaque and the quantified radiodensity values within the corresponding perivascular tissue. The one or more processors 404 can be the means to determine these gradients. At block 570, the process 550 may determine a ratio of the quantified radiodensity values within the coronary plaque and the corresponding perivascular tissue. For example, the perivascular tissue that is adjacent to the coronary plaque. The one or more processors 404 can determine these ratios. At block 575, process 550 can utilize the one or more processors 404 to characterize the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue. The process 550 can then return to process 500 as illustrated by the circle A.

Referring again to FIG. 5A, at block 525, the process 500 may compare determined information of a particular patient's coronary plaque to stored patient data, for example patient data stored on storage device 410. An example of the coronary plaque information of a particular patient that can be compared to stored patient data. To better understand the patient's coronary plaque information, and/or to help determine the particular patient's coronary plaque information, one or more of the scan information may be used. Also, when comparing a particular patient's coronary plaque information to previously stored coronary plaque information, one or more characteristics of the patient may be compared, including, for example, one or more of the characteristics of a patient. In some examples, the coronary plaque information of the patient being examined may be compared to or analyzed in reference to a patient who has one or more of the same or similar patient characteristics. For example, the patient being examined may be compared to a patient that has the same or similar characteristics of sex, age, BMI, medication, blood pressure, heart rate, weight, height, race, body habitus, smoking, diabetes, hypertension, prior coronary artery disease, family history, and lab results. Such comparisons can be done through various means, for example machine learning and/or artificial intelligence techniques. In some examples, neural network is used to compare a patient's coronary artery information to numerous (e.g., 10,000+) other patients' coronary artery information. For such patients that have similar patient information and similar cardiac information, risk assessments of the plaque of the patient being examined may be determined.

Figure 6:
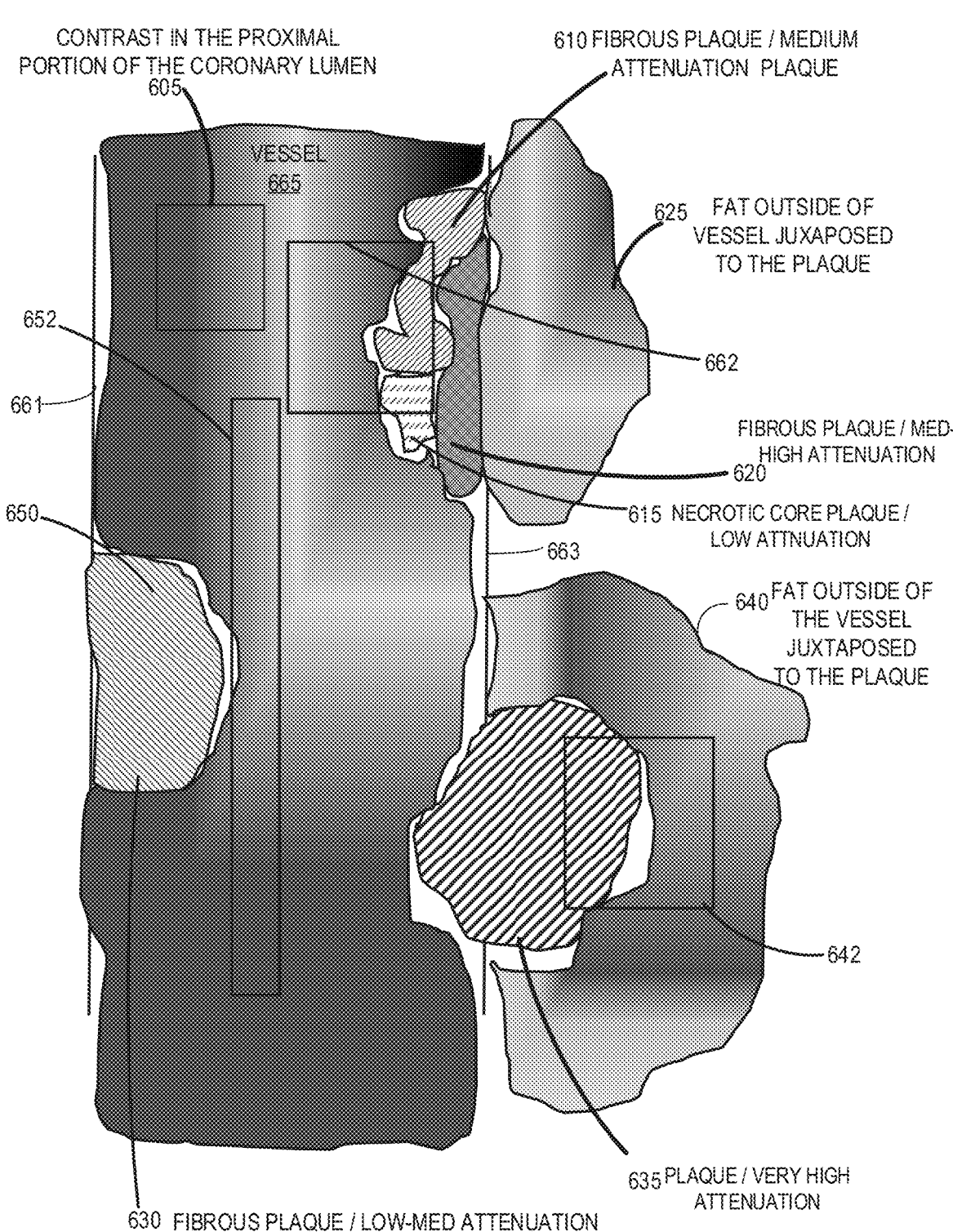
FIG. 6 illustrates a representation of image data depicting an example of a portion of a coronary artery (sometimes referred to herein as a "vessel" for ease of reference).

FIG. 6 illustrates an example of an area, indicated by box 605, where contrast attenuation patterns in a proximal portion of the coronary lumen can be analyzed, box 605 extending from a central area of the vessel 665 towards the vessel wall 661. FIG. 6 illustrates another example of an area, indicated by box 652, where contrast attenuation patterns in a portion of the coronary lumen of vessel 665 can be analyzed, box 652 extending longitudinally relative to vessel 665 from a central area of the vessel 665 towards the vessel wall 661. FIG. 6 further illustrates an example of an area, indicated by box 662, where contrast attenuation patterns of a portion of the lumen, a portion of fibrous plaque 610 and plaque 620 can be analyzed, box 662 thus covering a portion of the vessel 665 and a portion of fibrous plaque 610 and plaque 620. FIG. 6 further illustrates an example of an area indicated by box 642, where contrast attenuation patterns of a portion of plaque 635 and a portion of fat 640 positioned adjacent to plaque 635 can be analyzed, box 642 extending over a portion of plaque 635 and a portion of fat 640. Information determined by analyzing various aspects of the density of coronary artery features (e.g., the lumen, the plaque, and/or the perivascular fat) can be combined with other information to determine characteristics of a patient's arteries. In some examples, the determined information may include for any of the lumen, plaque or perivascular fat, one or more of a slope/gradient of a feature, a maximum density, a minimum density, a ratio of a slope of the density of one feature to the slope of the density of another feature, a ratio of a maximum density of one feature to the maximum density of another feature, a ratio of a minimum density of a feature to the minimum density of the same feature, a directionality of the density ratios, e.g., a density ratio between features facing one way or direction and features facing in an opposite direction (for example, the radiodensity ratio of features facing inwards towards the myocardium and features facing outwards toward the pericardium), or a ratio of the minimum density of a feature to the maximum density of another feature. Such determined information may indicate distinct differences in risks of plaque in a patient. In some examples, determined information (for example as listed above) may be used with a percentage diameter of stenosis to determine characteristics of a patient's arteries.

Still referring to FIG. 6, in an example of the directionality of radiodensity ratios, the density of a portion of the necrotic core plaque 615 to the density of a portion of the vessel 665 (e.g., plaque:vessel inward facing ratio) can be determined and may indicate a certain risk of plaque. In another example of the directionality of radiodensity ratios, the density of a portion of a portion of the vessel 665 to the density of the necrotic core plaque 615 (e.g., vessel:plaque outward facing) can be determined and may indicate a certain risk of plaque. In another example, the density ratio of the necrotic core plaque 615 to the density of a portion of the vessel 665 (e.g., plaque:vessel inward facing ratio) can be compared to the density ratio of the necrotic core plaque 615 to the fibrous plaque 620 (e.g., plaque:plaque outward facing) may indicate a certain risk of plaque. In other examples, features that are adjacently positioned can be used to determine inward and/or outward directional radiodensity values that may be used to indicate a risk associated with plaque. Such ratios may provide distinct differences in risk of plaque. Various embodiments of directional radiodensity values and/or directional radiodensity ratios can be included with any of the other information described herein to indicates plaque risk.

The size of a compartment may be used to also indicate a risk associated with plaque. For example, determination of risk associated with a plaque may be based at least partially on the size of the compartments, such that the ratio of the of the radiodensities affects the determination of risk and the function of the size of the compartments can also affect the determination of risk. While the presence of plaque in a patient where the ratio of plaque:fat may indicate a high risk plaque, if there is only a small amount of plaque (e.g., a small compartment of plaque), it would be of risk than if there was a larger compartment of the same plaque with the same radiodensity ratio of plaque to fat. In one implementation, the size (e.g., a volume) of the compartment a feature (e.g., of lumen, plaque, perivascular tissue (fat), and myocardium) can be determined, and a radiodensity ratio can also be determined, and then the ratio can be weighted based on the size of the compartment. For example, a large compartment can increase the weight of a ratio to make the ratio more indicative of a risk associated with the plaque. Similarly, a small compartment can decrease the weight of a ratio to make the ratio less indicative of a risk associated with the plaque. In an implementation, only the compartment size of the plaque is used to weight (or adjust) the ratio. In an implementation, the compartment size of both of the features that are used in the radiodensity ratio can be used to weight the ratio to determine a resulting risk. In an implementation, the compartment size of one of plaque, lumen, perivascular tissue, or myocardium is used to weight (or adjust) the risk associated with the radiodensity ratio. In an implementation, the compartment size of more than one of plaque, lumen, perivascular tissue, or myocardium is used to weight the risk associated with the radiodensity ratio. Various embodiments of determining plaque risk using compartment size can be included with any of the other information described herein to indicate plaque risk.

Figure 7:
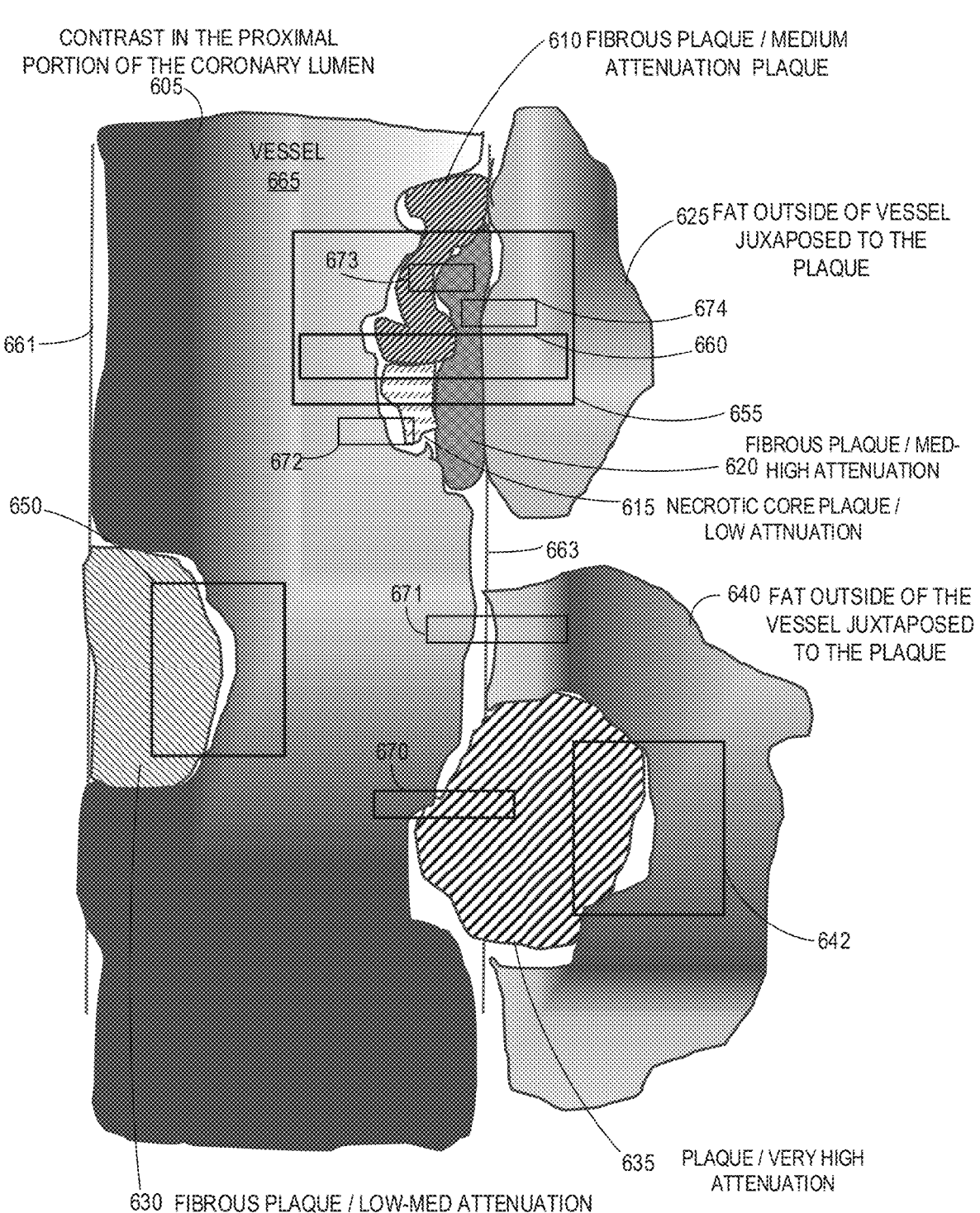
FIG. 7 illustrates the same vessel and features of plaque and fat as illustrated in FIG. 6 and further illustrates additional examples of areas of an artery, and the plaque and/or perivascular fat that is near an artery, that may be analyzed to determine characteristics of a patient's arteries.

FIG. 7 illustrates the same vessel 665 and features of plaque and fat as illustrated in FIG. 6 and further illustrates additional examples of areas of an artery, and plaque and/or perivascular fat near the artery, that may be analyzed to determine characteristics of a patient's arteries. Such areas are indicated in FIG. 7 by rectangular boxes, similar to the illustrations in FIG. 6. Although particular locations of the rectangular boxes are illustrated in FIG. 6 and FIG. 7, these are only examples of areas that may be analyzed. In one example, FIG. 7 illustrates box 660 which includes a portion of the vessel 665, a portion of necrotic core plaque 615, a portion of fibrous plaque 610, a portion of plaque 620, and a portion of fat 625. In another example, FIG. 7 illustrates box 655 which includes a portion of the vessel 665, a portion of the fibers plaque 610 a portion of the plaque 620 the portion of the necrotic core plaque 615, and a portion of fat 625. Box 655 may, in some cases, illustrate the general area for analysis due to the existence of 3 different types of plaque 610, 615, 620, and adjacently disposed fat 625. Particular portions of a general area for analysis may be analyzed to better understand the characteristics formed by adjacent features. For example, FIG. 7 illustrates the general area 665 containing box 660 (described above), box 673, which extends across a portion of fibrous plaque 610 and plaque 620, and box 674 which extends across a portion of plaque 620 and perivascular fat 625. As another example, FIG. 7 also illustrates another box 672 that extends across a portion of the vessel 655 and necrotic core plaque 615. As a further example, FIG. 7 illustrates box 671 that extends across a portion of the vessel 665 and fat 640 juxtaposed to the vessel 665. As a further example, FIG. 7 illustrates box 670 that extends across a portion of the vessel 665 and plaque 635. As indicated above, characteristics of a patient's arteries that can be analyzed based on these features can include but are not limited to:

1. A ratio of lumen attenuation to plaque attenuation, wherein the volumetric model of scan-specific attenuation density gradients within the lumen adjusts for reduced luminal density across plaque lesions that are more functionally significant in terms of risk value.
2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases.
3. A ratio of lumen attenuation/plaque attenuation/fat attenuation.
4. A ratio of #1-3 as a function of 3D shape of atherosclerosis, which can include a 3D texture analysis of the plaque.
5. The 3D volumetric shape and path of the lumen along with its attenuation density from the beginning to the end of the lumen.

6. The totality of plaque and plaque types before and after any given plaque to further inform its risk.

7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

In some embodiments, the systems, devices, and methods described herein can automatically and/or dynamically perform quantified analysis of various parameters relating to plaque, cardiovascular arteries, and/or other structures. For example, rather than having a physician eyeball or make a general assessment of the patient, a medical image can be transmitted to a backend main server in some embodiments that is configured to conduct such analyses, which advantageously can be performed in a consistent, objective, and/or reproducible manner In some embodiments, the systems, methods, and devices described herein can provide a quantified measurement of one or more features of a coronary CT image using automated and/or dynamic processes. For example, in some embodiments, the main server system can be configured to identify one or more vessels, plaque, and/or fat from a medical image. Based on the identified features, in some embodiments, the system can be configured to generate one or more quantified measurements from a raw medical image, such as for example density and/or radiodensity of one or more regions of plaque, identification of stable plaque and/or unstable plaque, perivascular fat, pericoronary adipose tissue (PCAT), fat attenuation index (FAI), volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like.

Based on the identified features and/or quantified measurements, in some embodiments, the system can be configured to generate a risk assessment and/or track the progression of a plaque-based disease or condition, such as for example atherosclerosis, stenosis, ischemia, myocardial infarction, and/or major adverse cardiovascular event (MACE), using raw medical images. As described further herein, in some embodiments the system can perform risk assessment and/or tracking the progression of a plaque-based disease based on other patients' information. For example, by comparing or evaluating features in a patient's medical images and patient information (e.g., age, gender, BMI, medication, blood pressure, heart rate, height, weight, race, whether the patient is a smoker or non-smoker, medical history, family history of disease, etc.) to features in other patients' medical images and their associated patient information including their outcome after a period of time.

Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or response to non-response to medication and/or lifestyle change and/or other treatment and/or invasive procedure. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures.

In some embodiments, image information comprising a plurality of images of a patient's coronary arteries and patient information/characteristics may be provided from one or more of the devices to the one or more servers of the processing system via a network. The processing system is configured to generate coronary artery information using the plurality of images of the patient's coronary arteries to generate two-dimensional and/or three-dimensional data representations of the patient's coronary arteries. Then, the processing system analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligent techniques, the data representations of the patient's coronary arteries may be compared to other patients' data representations (e.g., that are stored in a database) to determine additional information about the patient's health. In some embodiments, the artificial intelligence can be trained using a dataset of other patients' data representations to identify correlations in data. For example, based on certain plaque conditions of the patient's coronary arteries, the likelihood of a patient having a heart attack or other adverse coronary effect can be determined. Also, for example, additional information about the patient's risk of CAD may also be determined.

In some embodiments, the coronary plaque information of a patient being examined may be compared to or analyzed in reference to a patient who has one or more of the same or similar patient characteristics. For example, the patient being examined may be compared to a patient that has the same or similar characteristics of sex, age, BMI, medication, blood pressure, heart rate, weight, height, race, body habitus, smoking, diabetes, hypertension, prior coronary artery disease, family history, and lab results. Such comparisons can be done through various means, for example machine learning and/or artificial intelligence techniques. In some examples, neural network is used to compare a patient's coronary artery information to numerous (e.g., 10,000+) other patients' coronary artery information. For such patients that have similar patient information and similar cardiac information, risk assessments of the plaque of the patient being examined may be determined.

In some embodiments, Deep Learning (DL) methods, machine learning (ML) methods, and artificial intelligence (AI) methods can be used to analyze image information. In an example, this analysis can comprise image segmentation, feature extraction, and classification. In some embodiments, ML methods can comprise image feature extraction and image-based learning from raw data. In some embodiments, the ML method can receive an input of a large training set to learn to ignore variations that could otherwise skew the results of the method. In some embodiments, DL can comprise a Neural Network (NN) with three or more layers that can improve the accuracy of determinations. Advantageously, in some embodiments, DL can obviate the need for pre-processing data and, instead, process raw data. For example, while a human may input a hierarchy of important features of coronary image information for a ML algorithm to make determinations, DL algorithms can determine which features are important and use these features to make determinations. Advantageously, in some embodiments, a DL algorithm can adjust itself for accuracy and precision. In some embodiments, ML and DL algorithms can perform supervised learning, unsupervised learning, and reinforcement learning.

In some embodiments, NN approaches, including convolutional neural networks (CNN) and recurrent convolutional neural networks (RCNN), among others, can be used to analyze information in a manner similar to high-level cognitive functions of a human mind. In some embodiments, a NN approach can comprise training an object recognition system numerous medical images in order to teach it patterns in the images that correlate with particular labels. In some embodiments, a CNN can comprise a NN where the nodes of each layer are clustered, the clusters overlap, and each cluster feeds data to multiple nodes of the next layer. In some embodiments, a RCNN can comprise a CNN where recurrent connections are incorporated in each convolutional layer. Advantageously, in some embodiments, the recurrent connections can make object recognition a dynamic process despite the fact that the input is static.

In some embodiments, the vessel identification algorithm, coronary artery identification algorithm, and/or plaque identification algorithm can be trained on a plurality of medical images wherein one or more vessels, coronary arteries, and/or regions of plaque are pre-identified. Based on such training, for example by use of a CNN in some embodiments, the system can be configured to automatically and/or dynamically identify from raw medical images the presence and/or parameters of vessels, coronary arteries, and/or plaque. In some embodiments, the system can be configured to utilize one or more AI and/or ML algorithms to identify and/or analyze vessels or plaque, derive one or more quantification metrics and/or classifications, and/or generate a treatment plan. In some embodiments, the system can be configured to utilize an AI and/or ML algorithm to identify areas in an artery that exhibit plaque buildup within, along, inside and/or outside the arteries. In some embodiments, input to the AI and/or ML algorithms can include images of a patient and patient information (or characteristics), for example, one or more of age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, or lab results, and the like. In an example where a NN is used, the NN can be trained using information from a plurality of patients, where the information for each patient can include medical images and one or more patient characteristics.

In some embodiments, the system can be configured to utilize one or more AI and/or ML algorithms to automatically and/or dynamically identify one or more regions of plaque using image processing. For example, in some embodiments, the one or more AI and/or ML algorithms can be trained using a CNN on a set of medical images on which regions of plaque have been identified, thereby allowing the AI and/or ML algorithm automatically identify regions of plaque directly from a medical image. In some embodiments, the system can be configured to identify a vessel wall and a lumen wall for each of the identified coronary arteries in the medical image. In some embodiments, the system is then configured to determine the volume in between the vessel wall and the lumen wall as plaque. In some embodiments, the system can be configured to identify regions of plaque based on the radiodensity values typically associated with plaque, for example by setting a predetermined threshold or range of radiodensity values that are typically associated with plaque with or without normalizing using a normalization device.

In some embodiments, the one or more vascular morphology parameters and/or plaque parameters can comprise quantified parameters derived from the medical image. For example, in some embodiments, the system can be configured to utilize an AI and/or ML algorithm or other algorithm to determine one or more vascular morphology parameters and/or plaque parameters. As another example, in some embodiments, the system can be configured to determine one or more vascular morphology parameters, such as classification of arterial remodeling due to plaque, which can further include positive arterial remodeling, negative arterial remodeling, and/or intermediate arterial remodeling. In some embodiments, the classification of arterial remodeling is determined based on a ratio of the largest vessel diameter at a region of plaque to a normal reference vessel diameter of the same region which can be retrieved from a normal database. In some embodiments, the system can be configured to classify arterial remodeling as positive when the ratio of the largest vessel diameter at a region of plaque to a normal reference vessel diameter of the same region is more than 1.1. In some embodiments, the system can be configured to classify arterial remodeling as negative when the ratio of the largest vessel diameter at a region of plaque to a normal reference vessel diameter is less than 0.95. In some embodiments, the system can be configured to classify arterial remodeling as intermediate when the ratio of the largest vessel diameter at a region of plaque to a normal reference vessel diameter is between 0.95 and 1.1.

In some embodiments, the system is configured to classify atherosclerosis of a subject based on the quantified atherosclerosis as one or more of high risk, medium risk, or low risk. In some embodiments, the system is configured to classify atherosclerosis of a subject based on the quantified atherosclerosis using an AI, ML, and/or other algorithm. In some embodiments, the system is configured to classify atherosclerosis of a subject by combining and/or weighting one or more of a ratio of volume of surface area, volume, heterogeneity index, and radiodensity of the one or more regions of plaque.

In some embodiments, the system can be configured to identify one or more regions of fat, such as epicardial fat, in the medical image, for example using one or more AI and/or ML algorithms to automatically and/or dynamically identify one or more regions of fat. In some embodiments, the one or more AI and/or ML algorithms can be trained using a CNN on a set of medical images on which regions of fat have been identified, thereby allowing the AI and/or ML algorithm automatically identify regions of fat directly from a medical image. In some embodiments, the system can be configured to identify regions of fat based on the radiodensity values typically associated with fat, for example by setting a predetermined threshold or range of radiodensity values that are typically associated with fat with or without normalizing using a normalization device.

In some embodiments, the system is configured to utilize an AI, ML, and/or other algorithm to characterize the change in calcium score based on one or more plaque parameters derived from a medical image. For example, in some embodiments, the system can be configured to utilize an AI and/or ML algorithm that is trained using a CNN and/or using a dataset of known medical images with identified plaque parameters combined with calcium scores. In some embodiments, the system can be configured to characterize a change in calcium score by accessing known datasets of the same stored in a database. For example, the known dataset may include datasets of changes in calcium scores and/or medical images and/or plaque parameters derived therefrom of other subjects in the past. In some embodiments, the system can be configured to characterize a change in calcium score and/or determine a cause thereof on a vessel-by-vessel basis, segment-by-segment basis, plaque-by-plaque basis, and/or a subject basis.

In some embodiments, the systems disclosed herein can be used to dynamically and automatically determine a necessary stent type, length, diameter, gauge, strength, and/or any other stent parameter for a particular patient based on processing of the medical image data, for example using AI, ML, and/or other algorithms.

In some embodiments, the system can be configured to utilize an AI and/or ML algorithm to generate the patient-specific report. In some embodiments, the patient-specific report can include a document, AR experience, VR experience, video, and/or audio component.

Figure 8A:
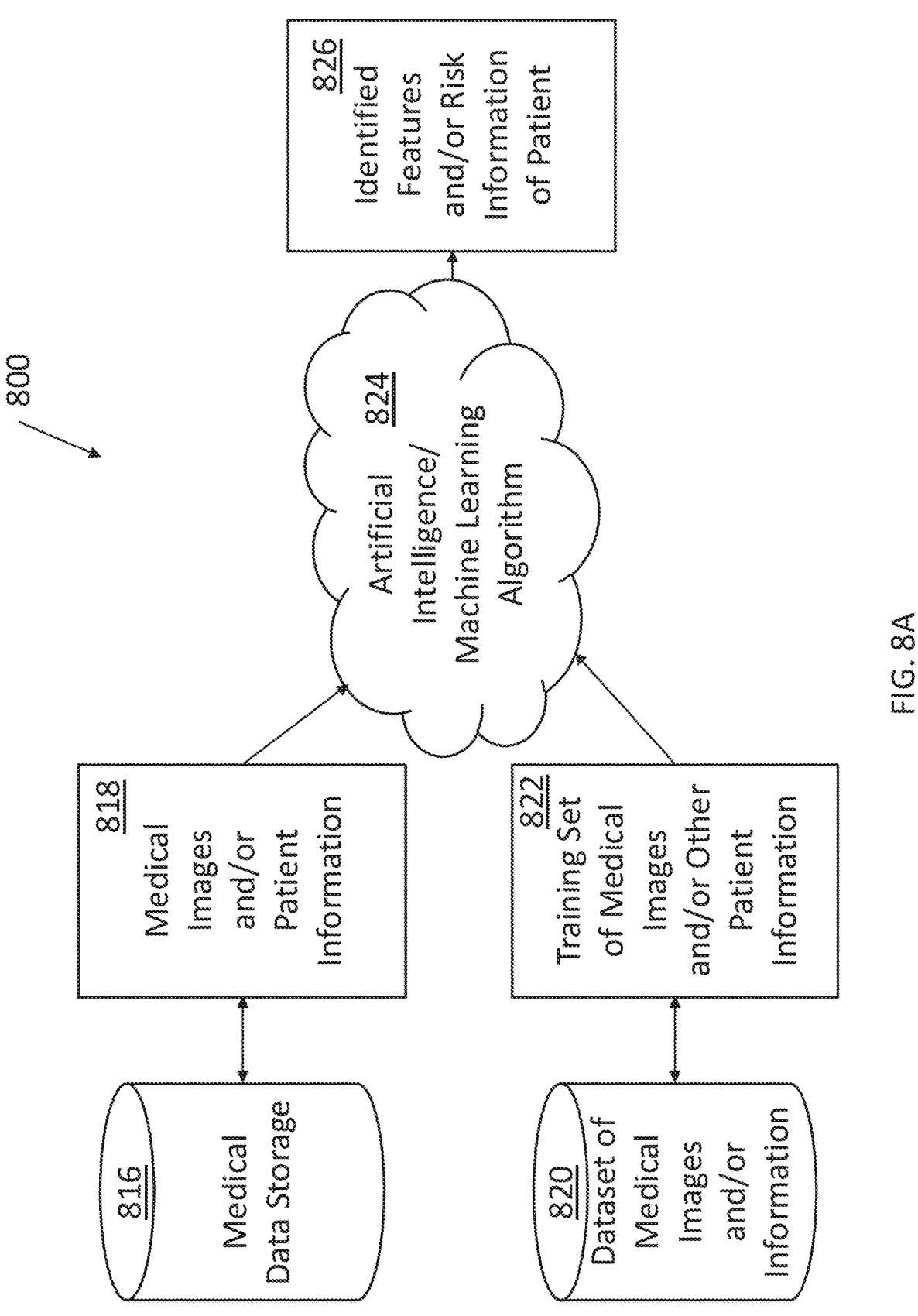
FIG. 8A is a block diagram that illustrates an example process of identifying features of medical images using artificial intelligence or machine learning.

FIG. 8A is a block diagram that illustrates an example of a system and/or process 800 (both referred to here as a "system" for ease of reference) for identifying features and/or risk information of a patient using AI/ML based on non-invasively obtained medical images of the patient and/or patient information. A current patient's medical data including images and/or patient information is first obtained and electronically stored on medical data storage 816 (e.g., cloud storage, hard disk, etc.). The system 800 obtains medical images and/or patient information 818 from the medical data storage 816 and preprocess it, if necessary, for example to re-format it as necessary for further processing. The system 800 can also obtain a training set of medical images and/or patient information 822 from a stored dataset 820 of medical images and/or information of other patients (e.g., hundreds, thousands, tens of thousands, or hundreds of thousands or more of other patients). The medical images and information of other patients can be used to train the AI/ML algorithm 824 prior to processing the medical images and/or patient information 818 of the current patient, as described in further detail in reference to FIGS. 8C and 8D. In some embodiments, the AI/ML algorithm 824 can include one or more NN's, for example, as described in reference to the example NN illustrated in FIG. 8B. The ML/AI 824 processes the medical images and/or patient information 818 of the current patient and generates outputs of identified features and/or risk information 826 of the current patient.

Figure 8B:
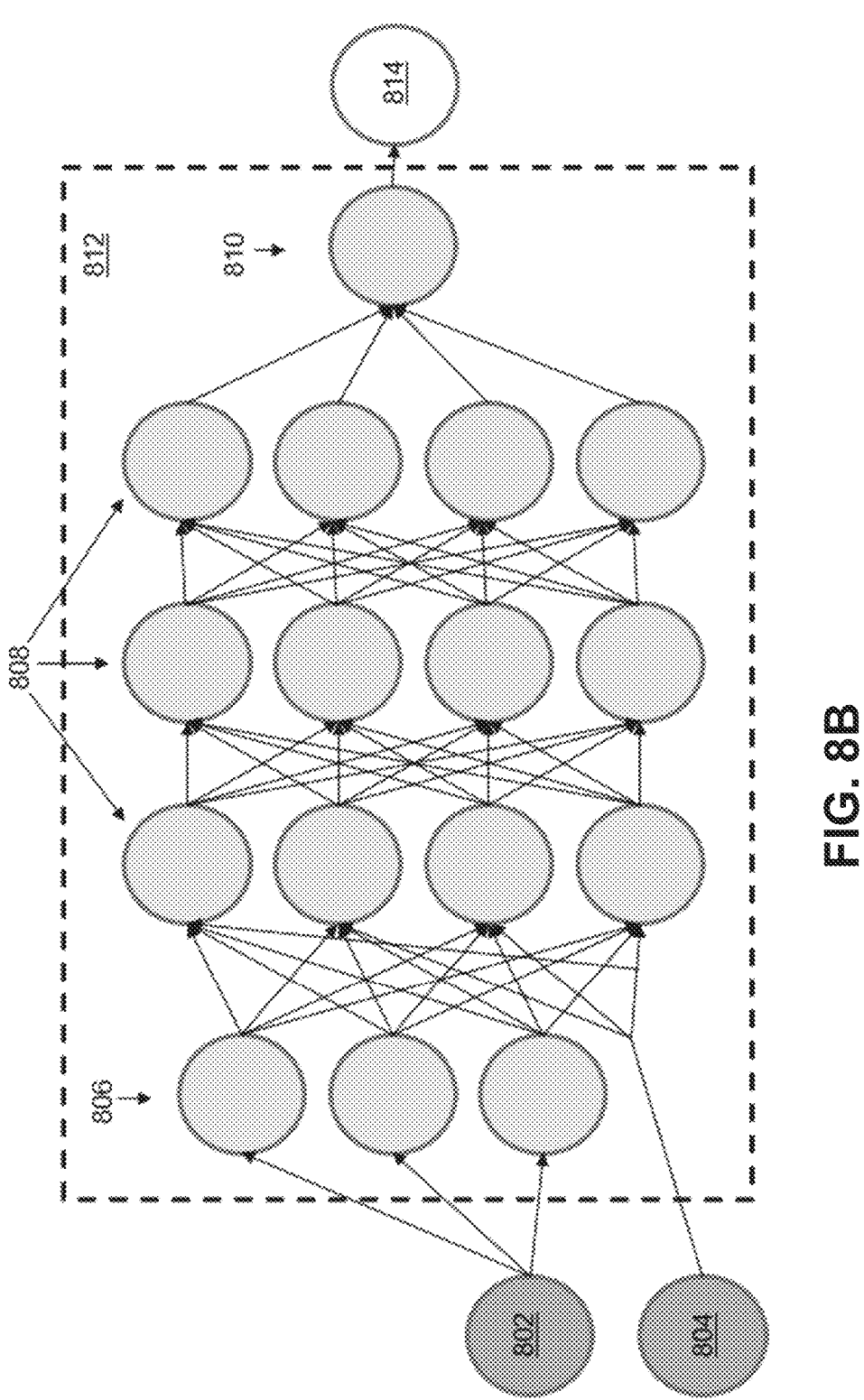
FIG. 8B is a schematic illustrating an example neural network that makes determinations about characteristics of a patient based on medical images.

FIG. 8B is a schematic illustrating an example of a NN 812 that makes determinations 814 about characteristics of a (current) patient based on inputs that include medical images 802. In some embodiments, the NN 812 can be configured to receive other inputs 804. In some embodiments, the other inputs 804 can be medical images of other patients. In some embodiments, the other inputs 804 can be medical history of other patients. In some embodiments, the other inputs 804 can be medical history of the (current) patient. The NN 812 can include an input layer 806. In some embodiments, the NN 812 can be configured to present the training pattern to the input layer 806. In some embodiments, the NN 812 can include one or more hidden layers 808. In some embodiments, the input layer 806 can provide signals to the hidden layers 808, and the hidden layers 808 can receive signals from the input layer 806. In some embodiments, the hidden layers 808 can pass signals to the output layer 810. In some embodiments, one or more hidden layers 808 may be configured as convolutional layers (comprising neurons/nodes connected by weights, the weights corresponding to the strength of the connection between neurons), pooling layers, fully connected layers and/or normalization layers. In some embodiments, the NN 812 may be configured with pooling layers that combine outputs of neuron clusters at one layer into a single neuron in the next layer. In some embodiments, max pooling and/or average pooling may be utilized. In some embodiments, max pooling may utilize the maximum value from each of a cluster of neurons at the prior layer. In some embodiments, back propagation may be utilized, and the corresponding neural network weights may be adjusted to minimize or reduce the error. In some embodiments, the loss function may comprise the Binary Cross Entropy loss function.

In some embodiments, the NN 812 can include an output layer 810. In some embodiments, the output layer 810 can receive signals from the hidden layers 808. In some embodiments, the output layer can generate determinations 814. In some embodiments, the NN 812 can make determinations 814 about characteristics of the patient. In some embodiments, the determinations 814 can include a characterized set of plaque. In some embodiments, the determinations 814 can include a patient's risk of CAD.

Figure 8C:
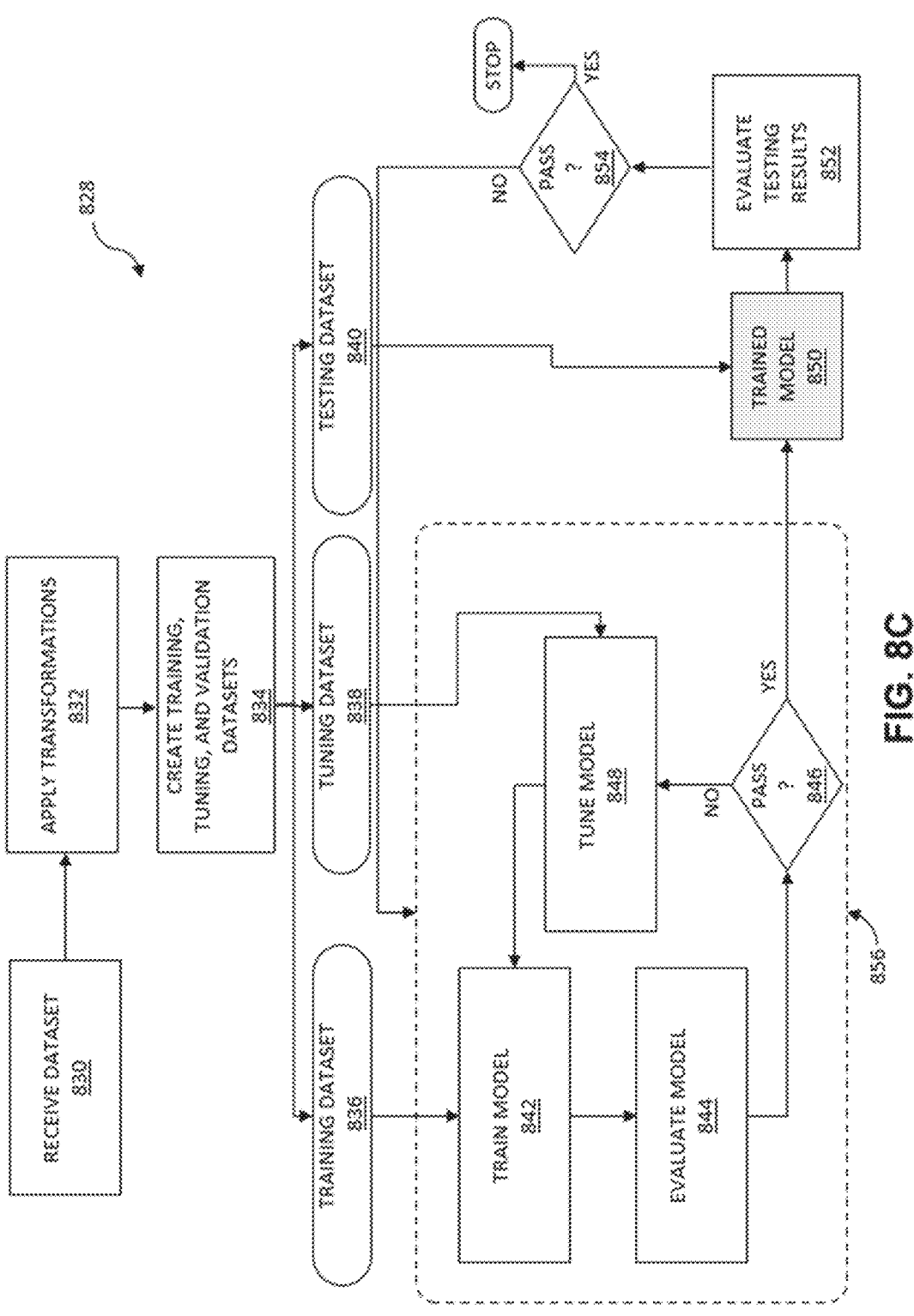
FIG. 8C depicts a flow chart for training an artificial intelligence or machine learning model according to some embodiments.

FIG. 8C depicts an example of a process in a flow diagram for training an artificial intelligence or machine learning model. The process 828 can be performed on a computing system. Various embodiments of such a process for training an AI or ML model may include additional features, and/or may exclude certain illustrated features (for example, when a transformed dataset is accessed such that "apply transformations" in block 832 does not need to be performed.)

As illustrated in the example of FIG. 8C, at block 830 the system receives a dataset that includes patient health information which can include medical images, user surveys, historical test results, genetic information, and/or other patient information (e.g., height, weight, age, etc.). The dataset can also include non-health information, for example, employment information, income information, transportation information, housing information, distances to pharmacies, and/or distances to healthcare providers.

At block 832, one or more transformations may be performed on the data. In an example, data may require transformations to conform to expected input formats to conform with expected formatting, e.g., date formatting, units (e.g., pounds vs kilograms, Celsius vs Fahrenheit, inches vs centimeters, etc.), address conventions, be of a consistent format, and the like. In some embodiments, addresses can be converted, or altered, to be of a consistent format and/or to conform to standards published by the United States Postal Service or a similar postal authority. In some embodiments, the data may undergo conversions to prepare it for use in training an AI or ML algorithm, for example, categorical data may be encoded in a particular manner In some embodiments, nominal data may be encoded using one-hot encoding, binary encoding, feature hashing, or other suitable encoding methods. In some embodiments, ordinal data may be encoded using ordinal encoding, polynomial encoding, Helmert encoding, and so forth. In some embodiments, numerical data may be normalized, for example by scaling data to a maximum of 1 and a minimum of 0 or −1. These are merely examples, and the skilled artisan will readily appreciate that other transformations are possible.

At block 834, the system may create, from the received dataset, training, tuning, and testing/validation datasets. In some embodiments, the training dataset 836 may be used during training to determine features for forming a predictive model. In some embodiments, the tuning dataset 838 may be used to select final models and to prevent or correct overfitting that may occur during training with the training dataset 836, as the trained model should be generally applicable to a broad spectrum of patients. In some embodiments, the testing dataset 840 may be used after training and tuning to evaluate the model. For example, in some embodiments, the testing dataset 840 may be used to check if the model is overfitted to the training dataset. In some embodiments, the system, in training loop 856, may train the model at block 842 using the training dataset 836. In some embodiments, training may be conducted in a supervised, unsupervised, or partially supervised manner. At 844, in some embodiments, the system may evaluate the model according to one or more evaluation criteria. For example, in some embodiments, the evaluation may include determining how often the model determines reasonable scores for a patient's risk of CAD. At 846, in some embodiments, the system may determine if the model meets the one or more evaluation criteria. In some embodiments, if the model fails evaluation, the system may, at 848, tune the model using the tuning dataset 838, repeating the training 842 and evaluation 844 until the model passes the evaluation at 846. In some embodiments, once the model passes the evaluation at 846, the system may exit the model training loop 856. In some embodiments, the testing dataset 836 may be run through the trained model 842 and, at block 844, the system may evaluate the results. In some embodiments, if the evaluation fails, at block 846, the system may reenter training loop 856 for additional training and tuning. If the model passes, the system may stop the training process, resulting in a trained model 850. In some embodiments, the training process may be modified. For example, in some embodiments, the system may not use a tuning dataset 838. In some embodiments, the model may not use a testing dataset 840.

While described above with respect to determining risk scores for CAD, a model can be trained for use in a wide variety of problems.

Figure 8D:
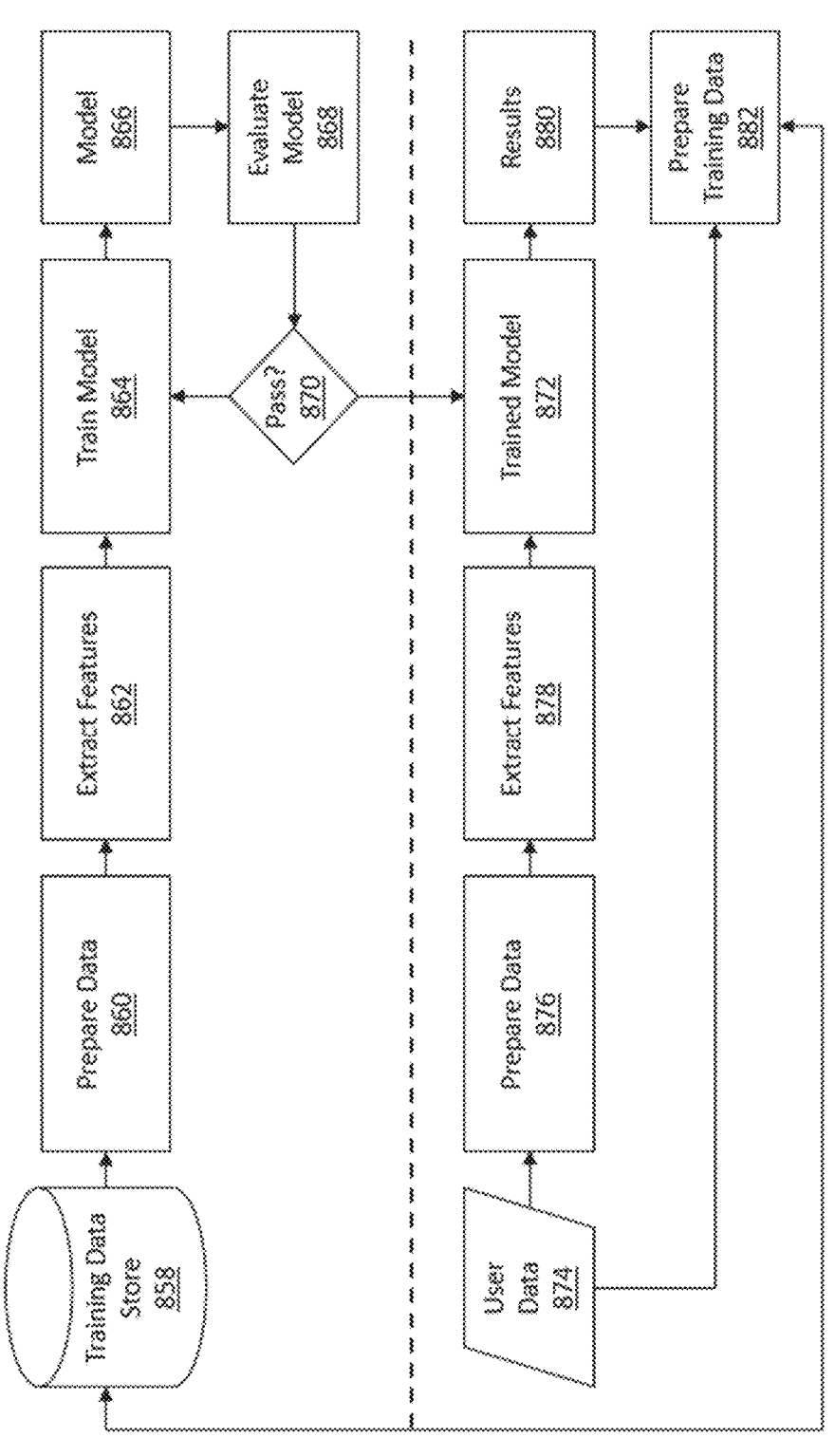
FIG. 8D illustrates an example of training and using an AI/ML model according to some embodiments.

FIG. 8D illustrates an example of a process for training and using an AI/ML model. In some embodiments, the process of FIG. 8D can be used for various purposes, e.g., to determine risk scores of CAD for a patient or to characterize plaque. In some embodiments, training data store 858 can store data for training a model. For example, in some embodiments, training data store 858 can store a patient's medical images, as well as information about patient's health, age, socioeconomic status, employment status, housing arrangements, transportation, and so forth. In some embodiments, the training data can be annotated to include information about user outcomes. For example, in some embodiments, the user outcomes can indicate whether a user had to miss work due to illness, was hospitalized, visited an emergency room, visited an urgent care facility, and so forth. In some embodiments, the training data can indicate whether a user received medication to treat an illness at home, treatments delivered at a hospital or other healthcare facility, did not receive any treatment, and so forth. At block 860, in some embodiments, a system can be configured to prepare the training data if it was not previously prepared for use in training a model. In some embodiments, as described briefly above, preparing the training data can include performing one or more normalization procedures, standardization procedures, and so forth, such as converting units (e.g., between Fahrenheit and Celsius, between inches and centimeters, between pounds and kilograms), converting dates to a standard format, converting times to a standard format, and so forth. In some embodiments, similar treatments or symptoms may be described or coded differently by different healthcare providers. In some embodiments, different providers may use different coding schemes. In some embodiments, even within a particular coding scheme, providers may select different codes to indicate similar information. In some embodiments, a large number of similar codes can lead to variances in coding. Thus, in some embodiments, a code can be changed to another related code. In some embodiments, certain codes can be excluded if they are not relevant to the issue that the model is intended to address. In some embodiments, it can be desirable to exclude certain data as additional data can consume additional computing resources and it can take longer to train a model. However, in some embodiments, exclusions may not be desirable as there can be a risk of excluding a factor that actually is relevant to the patient's risk. In some embodiments, data preparation at block 860 can include modifying or removing coding data, treatment data, and so forth. At block 862, the system can extract features from the training data and, at block 864, can train the model using the training data to produce model 866. At block 868, in some embodiments, the system can evaluate the model to determine if it passes one or more criteria. In some embodiments, at decision point 870, if the model fails, the system can perform additional training. In some embodiments, if, at decision point 870, the model passes, the system can make available trained model 872, which can be the model 872 after training is complete.

In some embodiments, the trained model 872 can be used to evaluate a particular user. The user data 874 can relate to a specific user for whom the outputs of the trained model 872 are desired. At block 876, the system can prepare the data, for example as described above in relations to the stored training data. In some embodiments, at block 878, the system can extract features from the prepared user data. In some embodiments, the system can be configured to feed the extracted features to the trained model 872 to produce results 880. The results 880 can be used to, for example, to determine a risk level associated with the user and/or to determine one or more risk sub-scores for the user.

In some embodiments, the user data 874, the results 880, and other information about the user (e.g., information about the user's outcomes after either receiving or not receiving treatment for plaque-based disease) can be used to train the model. At block 882, in some embodiments, the system can user prepare the user data 874 and the results 880 for use in training. In some embodiments, preparing the data can include, for example, anonymizing the data. For example, in some embodiments, any information about the patient's name, social security number, or other information that could personally identify the patient can be removed. In some embodiments, the system can anonymize the user data 874 in part by altering the user's birthday, for example retaining only the year the user was born (as age is often an important factor in evaluating ask) or the year and month the user was born. In some embodiments, the system can store the prepared data in training data store 858. In some embodiments, the prepared data can be stored, additionally or alternatively, in another database or data store. In some embodiments, the system can retrain the model on periodically, continuously, or whenever an operator indicates to the system that the model should be retrained. Thus, in some embodiments, the trained model 872 can evolve over time, which can result in, for example, improved risk evaluation over time as the model is trained on additional data.

Plaque Morphology/Features Analysis

As discussed herein, disclosed herein are systems, methods, and devices for non-invasive image-based plaque analysis and risk determination. In particular, in some embodiments, the systems, devices, and methods described herein are related to analysis of one or more regions of plaque, such as for example coronary plaque, based on one or more distances, volumes, shapes, morphologies, embeddedness, and/or axes measurements. For example, in some embodiments, the systems, devices, and methods described herein are related to plaque analysis based on one or more of distance between plaque and vessel wall, distance between plaque and lumen wall, length along longitudinal axis, length along latitudinal axis, volume of low density non-calcified plaque, volume of total plaque, a ratio(s) between volume of low density non-calcified plaque and volume of total plaque, embeddedness of low density non-calcified plaque, and/or the like. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein.

More specifically, in some embodiments, the systems, methods, and devices can be configured to analyze a medical image to perform one or more analyses of plaque and/or types of plaque, such as for example low density non-calcified plaque, calcified plaque, non-calcified plaque, and/or the like. In particular, in some embodiments, low density non-calcified plaque can be a focus due to the high-risk generally associated with low density non-calcified plaque. For example, low density non-calcified plaque can have a higher risk of potential rupture compared to other types of plaque, such as regular non-calcified plaque or calcified plaque. A plaque rupture can, in some instances, clog or block a vessel, thereby causing a heart attack or MI. As such, it can be advantageous to analyze one or more features of low density non-calcified plaque, and/or non-calcified plaque and/or calcified plaque, which may correspond to high or low risk of CAD and/or stability or instability of plaque. In some embodiments, the systems, devices, and methods are configured to analyze a medical image, such as a CT or CCTA image, to derive one or more features, measures, and/or characterizations of plaque, such as low density non-calcified plaque, non-calcified plaque, and/or calcified plaque, and use the same to facilitate an assessment or and/or generate an assessment of risk of CAD and/or stability or instability of plaque. Thus, in some embodiments, the systems, devices, and methods can provide an efficient and/or non-invasive method of assessing risk of CAD and/or plaque.

Figure 9A:
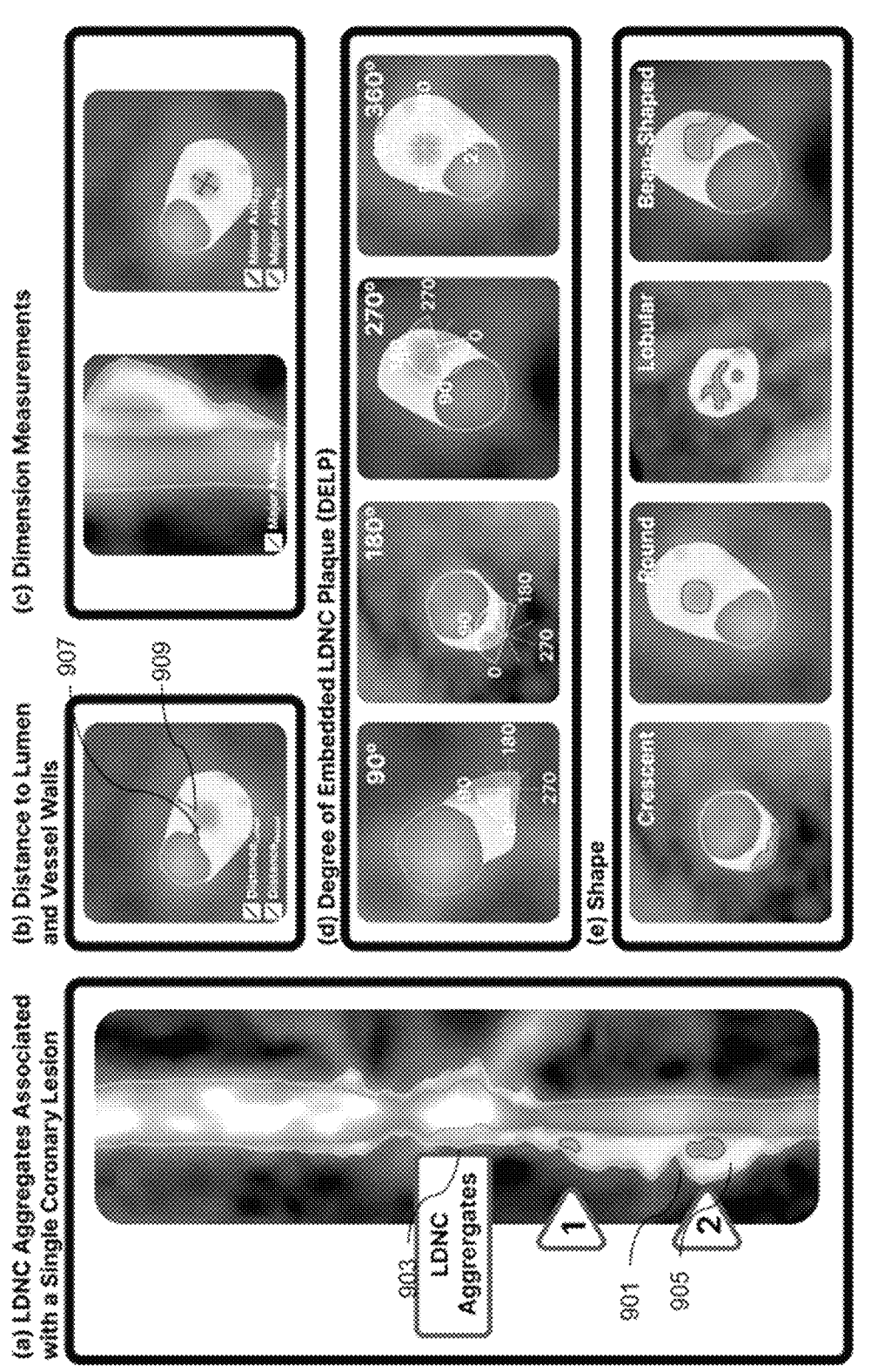
FIG. 9A illustrates examples of sample measurements, dimensions, and/or analyses related to plaque analysis and risk determination, with FIG. 9A(a) illustrating low-density non-calcified (LDNC) aggregates associated with a single coronary lesion, FIG. 9A(b) illustrating distance to lumen and vessel walls, FIG. 9A(c) illustrating dimension axis along a major axis and along a minor axis, FIG. 9A(d) illustrating degree of embeddedness of LDNC plaque (DELP), and FIG. 9A(e) illustrating four different shapes of plaques or regions of plaque, including crescent-shaped, round, lobular, and bean-shaped.

FIG. 9A illustrates examples of sample measurements, dimensions, and/or analyses related to plaque analysis and risk determination. For example, FIG. 9A(a) illustrates an example of low-density non-calcified (LDNC) aggregates associated with a single coronary lesion. FIG. 9A(b) illustrates an example of distances of plaque to lumen and vessel walls. FIG. 9A(c) illustrates an example of dimension axis measurements of plaque along a major axis and along a minor axis. FIG. 9A(d) illustrates examples of degrees of embeddedness of LDNC plaque (DELP). FIG. 9A(e) illustrates examples of four different shapes of plaques or regions of plaque, including plaque that is crescent-shaped, generally round, lobular in shape, and bean-shaped.

As illustrated in FIG. 9A, in some embodiments, the system can be configured to analyze a medical image of a vessel, artery, and/or a portion thereof, such as a coronary lesion. In some embodiments, a particular vessel, artery, and/or lesion can comprise one or more regions of plaque. "Density" and "radiodensity" generally relate to the opacity of a particular material (i.e., the relative inability of radiation to pass through the particular material), that is depicted in a medical image, where the higher the density/radiodensity the higher the opacity of the material. In some embodiments, based on the absolute or material density and/or relative density and/or radiodensity of features in one or more medical images, the system can be configured to characterize a region of plaque into one or more sub-types of plaque. For example, in some embodiments, the system can be configured to characterize a region of plaque as either low density non-calcified plaque, non-calcified plaque, or calcified plaque. In some embodiments the system can be configured to characterize a region of plaque to be one or more of low density non-calcified plaque, non-calcified plaque, or calcified plaque. In some embodiments, calcified plaque can correspond to plaque having a highest density range, low density non-calcified plaque can correspond to plaque having a lowest density range, and non-calcified plaque can correspond to plaque having a density range between calcified plaque and low density non-calcified plaque. For example, in some embodiments, the system can be configured to characterize a particular region of plaque as low density non-calcified plaque when the radiodensity of an image pixel or voxel corresponding to that region of plaque is between about −189 and about 30 Hounsfield units (HU). In some embodiments, the system can be configured to characterize a particular region of plaque as non-calcified plaque when the radiodensity of an image pixel or voxel corresponding to that region of plaque is between about 31 and about 350 HU. In some embodiments, the system can be configured to characterize a particular region of plaque as calcified plaque when the radiodensity of an image pixel or voxel corresponding to that region of plaque is between about 351 and about 2500 HU. In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

In some embodiments, the system can be configured to characterize one or more regions of plaque and generate a display of the same on a straightened multiplanar view or a multiplanar view of a vessel, for example as illustrated in FIG. 9A(a). In the example illustrated in FIG. 9A(a), this particular coronary lesion comprises regions of non-calcified plaque 901 with one or more regions of calcified plaque 903 and two regions of low density non-calcified plaque 905. In some embodiments, the systems, methods, and devices can be configured to perform one or more analyses on one or more regions of plaque, which can be a factor and/or indicator of the stability of plaque and/or risk of CAD or MI. For example, in some embodiments, the systems, methods, and devices can be configured to determine a distance from a region of low density non-calcified plaque to the vessel wall and/or lumen wall. In an example, the distance can be the shortest distance from low density non-calcified plaque to the vessel wall and/or lumen wall, or in another example, the distance can be the average distance from multiple points of low density non-calcified plaque to the vessel wall and/or lumen wall. This is further described in reference to FIG. 9A(b) below. In some embodiments, and as described further in reference to FIG. 9A(c), the systems, methods, and devices can be configured to determine one or more dimensions, such as for example major and/or minor axes, of a region of low density non-calcified plaque. In some embodiments, and as described further in reference to FIG. 9A(d), the systems, methods, and devices can be configured to determine the degree of embeddedness of a low density non-calcified plaque. In some embodiments, and as described further in reference to FIG. 9A(e), the systems, methods, and devices can be configured to determine a shape or morphology of low density non-calcified plaque. In some embodiments, the systems, methods, and devices can be configured to determine a volume or size of low density non-calcified plaque, total plaque, and/or a ratio thereof. In some embodiments, the systems, methods, and devices can be configured to take into account one or some or all of the aforementioned analyses in assessing the stability or instability of plaque and/or risk of CAD or MI on a patient or subject basis, vessel basis, lesion basis, and/or the like. In some embodiments, the systems, methods, and devices can be configured to generate a weighted measure of one or some or all of the aforementioned analyses in assessing the stability or instability of plaque and/or risk of CAD or MI on a patient or subject basis, vessel basis, lesion basis, and/or the like. In some embodiments, the systems, methods, and devices can be configured to utilize one or more artificial intelligence (AI) and/or machine learning (ML) algorithms in performing any one or more of the analyses described herein.

In particular, in some embodiments, the systems, methods, and devices can be configured to measure and/or determine a distance from a region of low density noncalcified plaque to the lumen and/or vessel walls. In some embodiments, the distance from a region of low density non-calcified plaque to the lumen and/or vessel walls can be indicative of the stability of the low density non-calcified plaque and hence be considered a factor in determining the risk of CAD arising from that low density non-calcified plaque. For example, in some embodiments, a low density non-calcified plaque that is closer to the lumen wall can be considered more susceptible to rupture and cause an MI.

In particular, in some embodiments, the system can be configured to determine the shortest distance between a point in the boundary of the region of low density non-calcified plaque and the vessel wall and/or lumen wall. In some embodiments, the system can be configured to determine the distance between a low density non-calcified plaque and the vessel wall and/or lumen wall based on a two-dimensional slice image and/or a three-dimensional rendering.

For example, as illustrated in the example of FIG. 9A(b), in some embodiments, the system can be configured to analyze a two-dimensional slice that renders the largest cross-sectional area of low density non-calcified plaque. In some embodiments, the two-dimensional slice can be perpendicular to a longitudinal axis of the straightened multiplanar view of a vessel. In some embodiments, the system can be configured to automatically and/or semi-automatically determine a distance from a low density non-calcified plaque to the vessel and/or lumen wall. In some embodiments, the system can be configured to assist a user in determining a distance from a low density non-calcified plaque to the vessel and/or lumen wall. For example, in some embodiments, the system can be configured to generate a graphical user interface that allows a user to click on two points on the image, after which the system can automatically determine the distance between the two points. In some embodiments, the system can be configured to utilize a digital caliper to determine a distance between low density non-calcified plaque and vessel or lumen wall.

FIG. 9A(b) illustrates the distance from low density non-calcified plaque to the lumen wall 907, and the distance from low density non-calcified plaque to the vessel wall 909. In some embodiments, the system can be configured to average multiple distances from one or more lumen and/or vessel walls to determine the distance from the region of plaque to the lumen and/or vessel wall. In some embodiments, the boundary of the region of low density non-calcified plaque can be determined at an end of the gradient of plaque densities partially comprising low density non-calcified plaque furthest from the center of the region of low density non-calcified plaque. In some embodiments, the boundary of the region of low density non-calcified plaque can be determined at an end of the gradient of plaque densities partially comprising low density non-calcified plaque closest to the center of the region of low density non-calcified plaque. In some embodiments, the boundary of the region of low density non-calcified plaque can be determined within the gradient of plaque densities partially comprising low density non-calcified plaque between the furthest point from and closest point to the center of the region of low density non-calcified plaque. In some embodiments, a shorter distance between the boundary of the region of low density non-calcified plaque and the lumen and/or vessel wall is indicative of a higher risk of CAD or MI. In some embodiments, a higher distance between the boundary of the region of low density non-calcified plaque and the lumen and/or vessel wall is indicative of a lower risk of CAD or MI. For example, in some embodiments, the system can be configured to characterize risk of CAD or MI as high or low and/or risk of plaque as high or low when a distance, such as the shortest distance, between the boundary of the region of low-density non-calcified plaque and the lumen and/or vessel wall is above or below about 0.0 mm, about 0.1 mm, about 0.2 mm, about 0.3 mm, about 0.4 mm, about 0.5 mm, about mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, and/or any number between, above, or below any of the foregoing.

In some embodiments, the systems, methods, and devices are configured to determine one or more dimensions of a low density non-calcified plaque, as illustrated in FIG. 9A(c). For example, in some embodiments, the system can be configured to measure and/or determine the length of a major and/or minor axis of a region of low density non-calcified plaque. In some embodiments, the system can be configured to measure and/or determine the length of a major and/or minor axis of a region of low density non-calcified plaque automatically or semi-automatically, for example using an image processing algorithm. In some embodiments, the system can be configured to measure and/or determine the length of a major and/or minor axis of a region of low density non-calcified plaque based at least in part on user input, for example using a digital caliper. In some embodiments, the system can be configured to measure and/or determine the length of a major and/or minor axis of a region of low density non-calcified plaque based on a three-dimensional analysis and/or based on one or more two-dimensional images.

For example, as illustrated in the example of FIG. 9A(c), in some embodiments, the system is configured to take a longitudinal slice image of a region of plaque and measure the major and/or minor axis of low density non-calcified plaque. In some embodiments, the longitudinal slice can be taken such that it is parallel to a longitudinal axis of a multiplanar or straightened multiplanar view of a vessel. In some embodiments, the longitudinal slice can be taken such that it shows the longest possible longitudinal axis of the low density non-calcified plaque. In some embodiments, the system can be configured to take a latitudinal slice image of a region of plaque and measure the major and/or minor axis of low density non-calcified plaque. In some embodiments, the latitudinal slice can be taken such that is perpendicular or orthogonal to the longitudinal axis of a multiplanar or straightened multiplanar view of a vessel and/or longitudinal slice. In some embodiments, the longitudinal slice can be taken such that it shows the largest possible cross-sectional area of low density non-calcified plaque. In some embodiments, the system can be configured to determine measurements of one or more orthogonal axes of a low density non-calcified plaque.

In some embodiments, such measurements of one or more axes of a region of low density non-calcified plaque can be utilized by the system for further characterization and/or analysis. For example, in some embodiments, measurement(s) of one or more axes of a region of low density non-calcified plaque can be used as a factor in assessing the stability of plaque and/or risk of CAD or MI of the subject, either directly or indirectly. In some embodiments, the system can be configured to utilize one or more measurements of one or more axes of a region of low density non-calcified plaque to determine and/or estimate the size, volume, and/or shape of low density non-calcified plaque, which in turn can be correlated to an assessment of the stability of plaque and/or risk of CAD or MI. In some embodiments, the system can be configured to directly correlate one or more measurements of one or more axes of a region of low density non-calcified plaque to an assessment of the stability of plaque and/or risk of CAD or MI. In some embodiments, a region of low density non-calcified plaque with a greater area, length, diameter, or volume can correspond to a higher risk of CAD or MI. In some embodiments, a region of low density non-calcified plaque with a smaller area, length, diameter, or volume can correspond to a lower risk of CAD or MI. For example, in some embodiments, the system can be configured to characterize risk of CAD or MI as high or low and/or risk of plaque as high or low when the length or diameter of a region of low-density non-calcified plaque is above or below about 0.0 mm, about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, and/or any number between, above, or below any of the foregoing, and/or corresponding area and/or volume. For example, in some embodiments, the system can be configured to characterize risk of CAD or MI as high or low and/or risk of plaque as high or low when the area of a region of low-density non-calcified plaque is above or below about 0.0 $mm^2$, about 0.01 $mm^2$, about 0.04 $mm^2$, about 0.09 $mm^2$, about 0.16 $mm^2$, about 0.25 $mm^2$, about 0.36 $mm^2$, about 0.49 $mm^2$, about 0.64 $mm^2$, about 0.81 $mm^2$, about 1.0 $mm^2$, about 1.21 $mm^2$, about 1.44 $mm^2$, about 1.69 $mm^2$, about 1.96 $mm^2$, about 2.25 $mm^2$, about 2.56 $mm^2$, about 2.89 $mm^2$, about 3.24 $mm^2$, about 3.61 $mm^2$, about 4.0 $mm^2$, and/or any number between, above, or below any of the foregoing, and/or corresponding length, diameter and/or volume. For example, in some embodiments, the system can be configured to characterize risk of CAD or MI as high or low and/or risk of plaque as high or low when the volume of a region of low-density non-calcified plaque is above or below about 0.0 $mm^3$, about 0.000001 $mm^3$, about 0.000008 $mm^3$, about 0.000027 $mm^3$, about 0.000064 $mm^3$, about 0.000125 $mm^3$, about 0.0.000216 $mm^3$, about 0.0.000343 $mm^3$, about 0.000343 $mm^3$, about 0.0.000729 $mm^3$, about 1.0 $mm^3$, about 1.331 $mm^3$, about 1.728 $mm^3$, about 2.197 $mm^3$, about 2.744 $mm^3$, about 3.375 $mm^3$, about 4.096 $mm^3$, about 4.913 $mm^3$, about 4.913 $mm^3$, about 6.859 $mm^3$, about 8.0 $mm^3$, and/or any number between, above, or below any of the foregoing, and/or corresponding length, diameter and/or area.

In some embodiments, the systems, methods, and devices can be configured to determine an embeddedness of low density non-calcified plaque, for example by regular non-calcified plaque and/or calcified plaque. In some embodiments, the embeddedness of low density non-calcified plaque can be a factor and/or indicator of the stability of plaque and/or risk of CAD or MI, as a more embedded a low-density non-calcified plaque can be more likely to rupture and/or have a thin fibrous cap or more likely to develop a thin fibrous cap. In some embodiments, the system can be configured to determine the embeddedness of low density non-calcified plaque based on the degree of encapsulation of the low density non-calcified plaque by non-calcified plaque or calcified plaque. In some embodiments, the embeddedness of the low density non-calcified plaque is determined by measuring how much of the boundary of the region of the low density non-calcified plaque contacts other types of plaque in relation to how much of the boundary of the region of the low density non-calcified plaque contacts the vessel wall or lumen. In some embodiments, the system can be configured to measure and/or determine the embeddedness of a region of low density non-calcified plaque based on a three-dimensional analysis and/or based on one or more two-dimensional images.

For example, as illustrated in the example of FIG. 9A(d), in some embodiments, the system is configured to take a longitudinal slice image of a region of plaque and measure the embeddedness of low density non-calcified plaque. In some embodiments, the longitudinal slice can be taken such that it is parallel to a longitudinal axis of a multiplanar or straightened multiplanar view of a vessel. In some embodiments, the system can be configured to take a latitudinal slice image of a region of plaque and measure the embeddedness of low density non-calcified plaque. In some embodiments, the latitudinal slice can be taken such that it is perpendicular or orthogonal to the longitudinal axis of a multiplanar or straightened multiplanar view of a vessel and/or longitudinal slice. In an example, when one half of the boundary of the region of the low density non-calcified plaque is in contact with the vessel wall and the other half of the boundary of the region of the low density non-calcified plaque is in contact with calcified plaque, the embeddedness is 180°. In another example, when three-quarters of the boundary of the region of the low density non-calcified plaque is in contact with the vessel wall and the other quarter of the boundary of the region of the low density non-calcified plaque is in contact with calcified plaque, the embeddedness is 90°. In another example, when one quarter of the boundary of the region of the low density non-calcified plaque is in contact with the vessel wall and the other three quarters of the boundary of the region of the low density non-calcified plaque is in contact with calcified plaque, the embeddedness is 270°. In another example, when all of the boundary of the region of the low density non-calcified plaque is in contact with calcified plaque, the embeddedness is 360°. In some embodiments, the system can be configured to determine the embeddedness of low density non-calcified plaque as one or more of about 0°, about 30°, about 60°, about 90°, about 120°, about 150°, about 180°, about 210°, about 240°, about 270°, about 300°, about 330°, about 360°, and/or between a range defined by two of the aforementioned values. In the example illustrated in FIG. 9A(d), in some embodiments, the embeddedness of low density non-calcified plaque is determined to be about 90°, about 180°, about 270°, about 360° in each example. In some embodiments, an embeddedness of low density non-calcified plaque at or above about 270° can be considered a high-risk plaque. In some embodiments, the system can be configured to determine the embeddedness of a region of low density non-calcified plaque automatically or semi-automatically, for example using an image processing algorithm. In some embodiments, the system can be configured to determine the embeddedness of a region of low density non-calcified plaque based at least in part on user input. In some embodiments, the system can be configured to graphically overlay a protractor on a medical image to assist with and/or to display the embeddedness of a region of low density non-calcified plaque.

In some embodiments, the systems, methods, and devices can be configured to determine shape or morphology of a region of low density non-calcified plaque. In some embodiments, the system can be configured to determine and/or characterize the shape or morphology of a low density non-calcified plaque as one or more of a crescent, round, lobular, or bean shape. In some embodiments, the shape or morphology of a low density non-calcified plaque can be a factor and/or indicator of plaque stability and/or risk of CAD. In some embodiments, a crescent shape can have a greater length than width. In some embodiments, a crescent shape can be a thin, curved shape. In some embodiments, a crescent shape can be a narrow shape. In some embodiments, a crescent shape can be a shape resembling a curved or uncurved line. For example, in some embodiments, a crescent-shaped low density non-calcified plaque can be associated with lower risk of CAD or MI. In some instances, this can be because what appears to be a crescent-shaped plaque due to image analysis can potentially correspond to perivascular fat rather than a true low density non-calcified plaque, especially for example if found around or near or adjacent to the vessel wall. In some embodiments, a round shape can have a similar or approximately equal length and width. In some embodiments, a round shape can have a similar or approximately consistent diameter. In some embodiments, a round shape can be a shape similar to a circle or oval. In some embodiments, a bean shape can be a shape comprised of two or three interconnected round and/or crescent shapes. In some embodiments, a bean shape can be a wide shape comprised of interconnected round and/or crescent shapes. In some embodiments, a bean shape can be a distorted round shape. In some embodiments, a bean shape can have an inconsistent diameter. In some embodiments, a round or bean-shaped low density non-calcified plaque can be associated with a higher risk of CAD or MI. In some embodiments, a lobular shape can be a shape comprised of four or more interconnected round and/or crescent shapes. In some embodiments, a lobular shape can be a narrow shape comprised of interconnected round and/or crescent shapes. In some embodiments, a lobular shape can be a distorted crescent shape. In some embodiments, a lobular shaped low-density non-calcified plaque can be associated with higher risk of CAD compared to a crescent shape but lower risk of CAD compared to a bean or round-shaped low density non-calcified plaque. In some embodiments, a low density non-calcified plaque can be classified as lobular v. bean-shape depending on the number of lobes. For example, in some embodiments, a low density non-calcified plaque with more lobes can be classified as lobular, while a low density non-calcified plaque with fewer lobes can be classified as a bean-shape. FIG. 9A(e) illustrates examples of crescent, round, lobular, and/or bean-shaped regions of low density non-calcified plaque.

In some embodiments, the system can be configured to classify the shape or morphology of a region of low density non-calcified plaque automatically or semi-automatically, for example using an image processing algorithm. In some embodiments, the system can be configured to classify the shape or morphology of a region of low density non-calcified plaque based at least in part on user input. In some embodiments, the system can be configured to classify the shape or morphology of a region of low density non-calcified plaque based at least in part on the one or more measures of one or more axes of the low density non-calcified plaque. For example, in some embodiments, the system can be configured to compare the major longitudinal axis, major latitudinal axis, and/or minor latitudinal axis of a region of low density non-calcified plaque in determining the shape of the low density non-calcified plaque. In some embodiments, the system can be configured to take the standard deviation of one or more of the major longitudinal axis, major latitudinal axis, and/or minor latitudinal axis, and classify a low density non-calcified plaque as a round shape when the standard deviation is below a certain predetermined threshold. In some embodiments, a crescent, lobular, and/or bean-shaped low density non-calcified plaque can be associated with a higher standard deviation among axes measurements.

In some embodiments, the systems, devices, and methods can be configured to determine a volume or size of total plaque, low density non-calcified plaque, non-calcified plaque, and/or calcified plaque, and/or a ratio thereof. In some embodiments, the volume or size of total plaque, low density non-calcified plaque, non-calcified plaque, and/or calcified plaque can be a factor and/or indicator in determining the stability of plaque and/or assessing risk of CAD or MI. For example, in some embodiments, a higher volume of total plaque, low density non-calcified plaque, and/or non-calcified plaque can be indicative of a high-risk plaque and/or high risk of CAD. In some embodiments, a high ratio of low density non-calcified plaque to total plaque can be indicative of a high-risk plaque and/or high risk of CAD.

In some embodiments, the system can be configured to determine the size or volume of a region of low density non-calcified plaque automatically or semi-automatically, for example using an image processing algorithm. In some embodiments, the system can be configured to determine the size or volume of a region of low density non-calcified plaque based at least in part on user input. In some embodiments, the system can be configured to determine the size or volume of a region of low density non-calcified plaque based at least in part on the one or more measures of one or more axes of the low density non-calcified plaque.

Sample Study Regarding Plaque Morphology/Features Analysis

As discussed herein, in some embodiments, the systems, methods, and devices are configured to analyze one or more plaque morphology and/or other features as an indicator and/or variable for determining risk of CAD and/or MI. For example, in some embodiments, the systems, methods, and devices can be configured to analyze a medical image to derive one or more plaque parameters and/or vascular parameters, such as total plaque volume, low density non-calcified plaque volume, non-calcified plaque volume, calcified plaque volume, minimal lumen diameter, maximum remodeling index, maximum lesion length, and/or the like. In some embodiments, the systems, methods, and devices can be used to show and/or derive a correlation between one or such features and risk of CAD and/or MI.

FIG. 9B illustrates example per-lesion high-risk plaque morphology characteristics derived from a sample study. As illustrated, FIG. 9B summarizes the frequency of the degree of embedded low-density non-calcified plaque (DELP) and low-density non-calcified (LDNC) deposit shape in non-culprit and culprit lesions ((-) Culprit and (+) Culprit, respectively). In the illustrated sample study, 122 patients were included, wherein the culprit lesion was adjudicated at the time of the acute coronary syndrome (ACS) event.

FIG. 9C illustrates example per-patient atherosclerotic characteristics stratified by patients with and without an acute coronary syndrome event derived from a sample study. In FIG. 9C, per-patient atherosclerotic characteristics are shown stratified by patients without and with an acute coronary syndrome event ((-) ACS and (+) ACS, respectively).

Figure 9D:
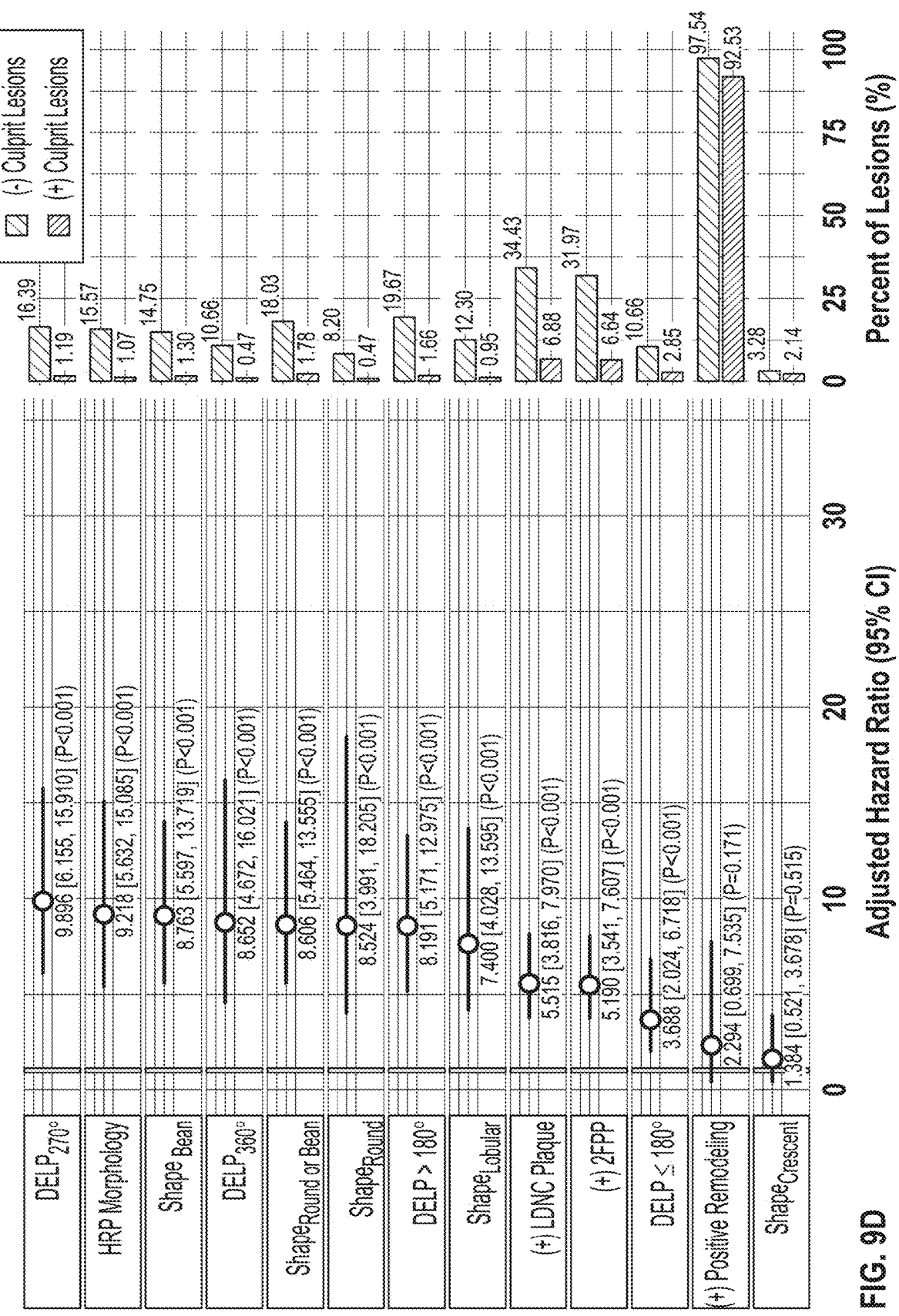
FIG. 9D illustrates example adjusted hazard ratios of the effect of high-risk plaque morphology features on culprit lesion precursors to acute coronary syndrome derived from a sample study.

FIG. 9D illustrates example adjusted hazard ratios of the effect of high-risk plaque morphology features on culprit lesion precursors to acute coronary syndrome derived from a sample study. In the example study summarized in FIG. 9D, 122 patients with 965 coronary lesions were assessed. In this study, all patients underwent culprit lesion adjudication at the time of acute coronary syndrome (ACS). In FIG. 9D, a forest plot of the hazard ratios for degree of embedded low-density non-calcified plaque (DELP) and low-density non-calcified plaque shape (crescent, bean, round, or lobular) is shown, on a per-lesion basis. In the study, high-risk plaque morphology (HRP Morphology) was defined as any lesion with a round or bean-shaped low-density non-calcified deposit, and DELP>180°. Additionally, in FIG. 9D, lesion features such as the presence of low-density non-calcified plaque ((+) LDNC Plaque), positive remodeling ((+) Positive Remodeling), and two feature plaques ((+) 2FPP) are shown for comparison. (+) 2FPP can refer to the presence of both positive remodeling and any amount of low-density non-calcified plaque, for a given lesion. In the study, hazard ratios were adjusted for angina and occurrence of revascularization. Also, in FIG. 9D, proportions of non-culprit ((-) Culprit Lesions) and culprit ((+) Culprit Lesions) are shown for each variable described in the forest plot.

Figure 9E:
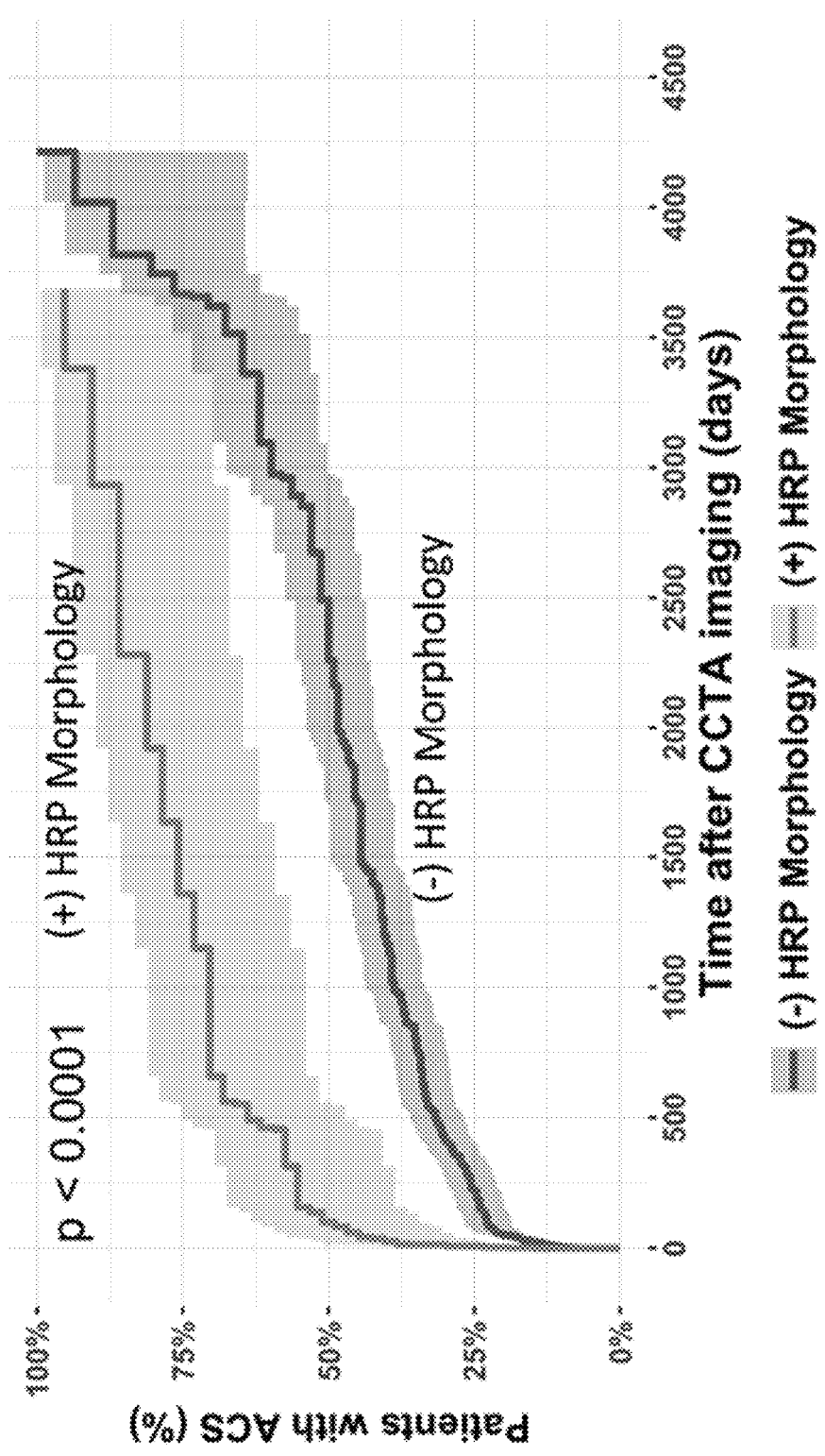
FIG. 9E illustrates an example Kaplan-Meier curve of occurrence of acute coronary syndrome in patients with and without a high-risk plaque morphology lesion derived from a sample study.

FIG. 9E illustrates an example Kaplan-Meier curve of occurrence of acute coronary syndrome in patients with and without a high-risk plaque morphology lesion derived from a sample study. In FIG. 9E, patients without at least one high-risk plaque morphology lesion are shown ((-) HRP Morphology), and patients with at least one high-risk plaque morphology lesion are shown ((+) HRP Morphology).

Plaque Morphology/Features Analysis—Additional Detail

Figure 9F:
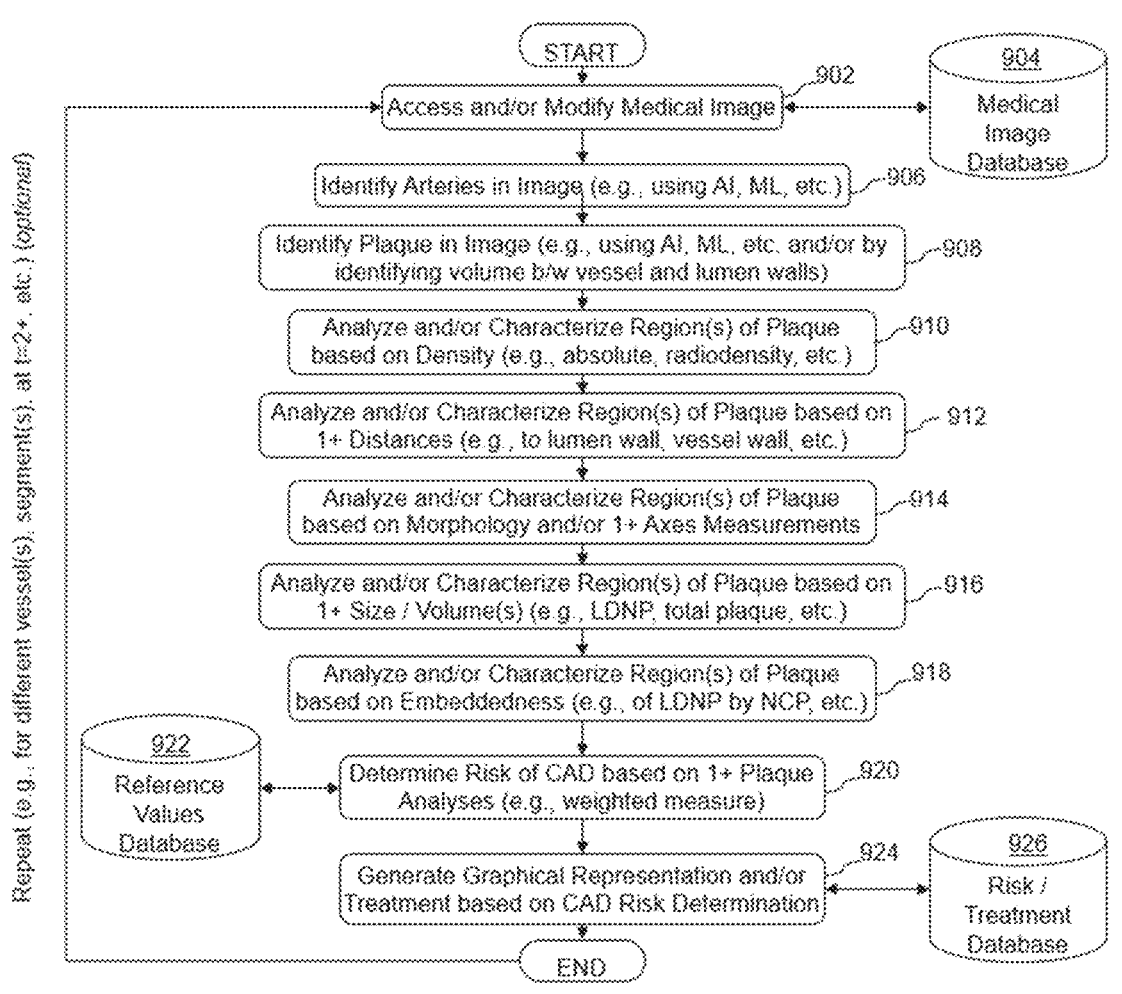
FIG. 9F is a flowchart illustrating an example embodiment(s) of systems, devices, and methods for non-invasive image-based plaque analysis and risk determination.

FIG. 9F is a flowchart illustrating an example embodiment(s) of systems, devices, and methods for non-invasive image-based plaque analysis and risk determination. As illustrated in FIG. 9F, in some embodiments, the system can be configured to access and/or modify one or more medical images at block 902. In some embodiments, the medical image can include one or more arteries, such as coronary, carotid, and/or other arteries of a subject. In some embodiments, the medical image can be stored in a medical image database 904. In some embodiments, the medical image database 904 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 906, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 908, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of (digital) medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 910, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

In some embodiments, at block 912, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, at block 914, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, at block 916, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 918, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 920, the system can be configured to determine a risk of CAD or MI based on one or more plaque analyses described herein, for example in relation to one or more of blocks 902-918. In some embodiments, the system can be configured to utilize some or all of the plaque analyses results. In some embodiments, the system can be configured to generate a weighted measure of some or all of the plaque analyses described herein in determining a risk of CAD. In some embodiments, the system can be configured to refer to one or more reference values of one or more plaque analyses results in determining risk of CAD. For example, in some embodiments, the one or more reference values can comprise one or more values derived from a population with varying states of risks of CAD, wherein the one or more values can comprise one or more of one or more distances to and/or from a low density non-calcified plaque, one or more axes measurements, morphology classification, size and/or volume, and/or embeddedness of low density non-calcified plaque. In some embodiments, the one or more reference values can be stored on a reference values database 922, which can be locally accessible by the system and/or can be located remotely and accessible through a network connection.

In some embodiments, at block 924, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 926, which can be locally accessible by the system and/or can be located remotely and accessible through a network connection. In some embodiments, the plaque risk/treatment database 926 can include reference points or data that relate one or more treatment to cardiovascular disease risk or state determined based on one or more reference plaque analyses values.

In some embodiments, the system can be configured to repeat one or more processes described in relation to blocks 902-926, for example for one or more other vessels, segment, regions of plaque, different subjects, and/or for the same subject at a different time. As such, in some embodiments, the system can provide for longitudinal disease tracking and/or personalized treatment for a subject.

Computer System

Figure 9G:
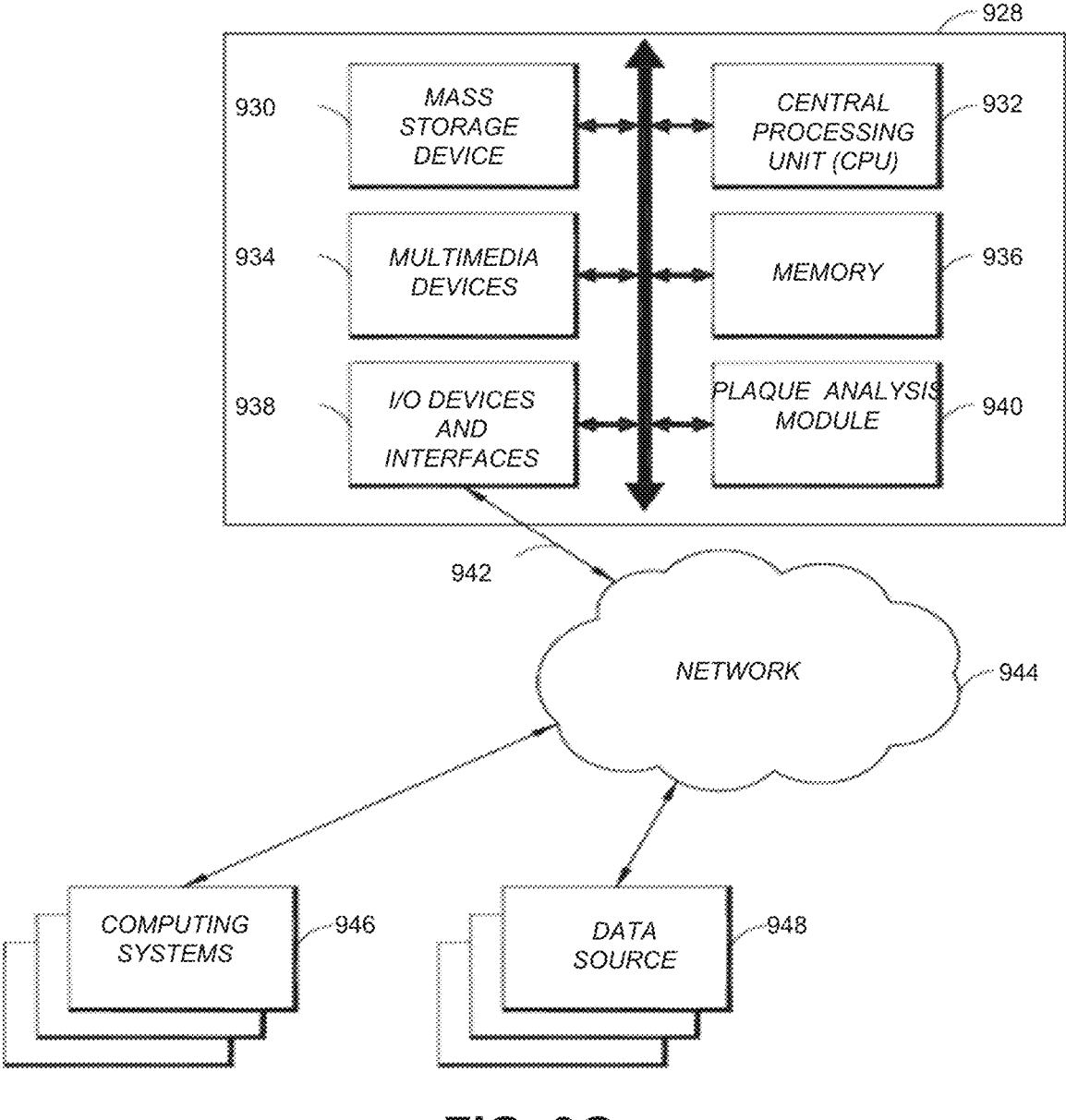
FIG. 9G is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 9G. The example computer system 928 is in communication with one or more computing systems 946 and/or one or more data sources 948 via one or more networks 944. While FIG. 9G illustrates an embodiment of a computing system 928, it is recognized that the functionality provided for in the components and modules of computer system 928 can be combined into fewer components and modules, or further separated into additional components and modules.

The computer system 928 can comprise a Plaque Analysis Module 940 that carries out the functions, methods, acts, and/or processes described herein. The Plaque Analysis Module 940 executed on the computer system 928 by a central processing unit 306 discussed further below.

In general the word "module," as used herein, refers to logic embodied in hardware or firmware or to a collection of software instructions, having entry and exit points. Modules are written in a program language, such as JAVA, C, or C++, or the like. Software modules can be compiled or linked into an executable program, installed in a dynamic link library, or can be written in an interpreted language such as BASIC, PERL, LAU, PHP or Python and any such languages. Software modules can be called from other modules or from themselves, and/or can be invoked in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems, and can be stored on or within any suitable computer readable medium, or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 928 includes one or more processing units (CPU) 932, which can comprise a microprocessor. The computer system 928 further includes a physical memory 936, such as random access memory (RAM) for temporary storage of information, a read only memory (ROM) for permanent storage of information, and a mass storage device 930, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 928 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 928 includes one or more input/output (I/O) devices and interfaces 938, such as a keyboard, mouse, touch pad, and printer. The I/O devices and interfaces 938 can include one or more display devices, such as a monitor, which allows the visual presentation of data to a user. More particularly, a display device provides for the presentation of GUIs as application software data, and multi-media presentations, for example. The I/O devices and interfaces 938 can also provide a communications interface to various external devices. The computer system 928 can comprise one or more multi-media devices 934, such as speakers, video cards, graphics accelerators, and microphones, for example.

Computing System Device/Operating System

The computer system 928 can run on a variety of computing devices, such as a server, a Windows server, a Structure Query Language server, a Unix Server, a personal computer, a laptop computer, and so forth. In other embodiments, the computer system 928 can run on a cluster computer system, a mainframe computer system and/or other computing system suitable for controlling and/or communicating with large databases, performing high volume transaction processing, and generating reports from large databases. The computing system 928 is generally controlled and coordinated by an operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 928 illustrated in FIG. 9G is coupled to a network 944, such as a LAN, WAN, or the Internet via a communication link 942 (wired, wireless, or a combination thereof). Network 944 communicates with various computing devices and/or other electronic devices. Network 944 is communicating with one or more computing systems 946 and one or more data sources 948. The Plaque Analysis Module 914 can access or can be accessed by computing systems 946 and/or data sources 948 through a web-enabled user access point. Connections can be a direct physical connection, a virtual connection, and other connection type. The web-enabled user access point can comprise a browser module that uses text, graphics, audio, video, and other media to present data and to allow interaction with data via the network 944.

The output module can be implemented as a combination of an all-points addressable display such as a cathode ray tube (CRT), a liquid crystal display (LCD), a plasma display, or other types and/or combinations of displays. The output module can be implemented to communicate with input devices 938 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

Other Systems

The computing system 928 can include one or more internal and/or external data sources (for example, data sources 948). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 928 can also access one or more databases 948. The databases 948 can be stored in a database or data repository. The computer system 928 can access the one or more databases 948 through a network 944 or can directly access the database or data repository through I/O devices and interfaces 938. The data repository storing the one or more databases 948 can reside within the computer system 928.

URLs and Cookies

In some embodiments including any of the embodiments disclosed herein (above or below) one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Plaque Morphology/Features Analysis—Additional Study Details

In some embodiments, the systems, methods, and devices described herein are configured to assess plaque morphology non-invasively, for example using coronary CT angiography (CCTA), which can be used to improve the stratification of patients at risk for acute coronary syndrome (ACS). More specifically, in some embodiments, one or more low-density non-calcified plaque (LD-NCP) morphologies described herein can be identified using one or more technologies, such as for example artificial intelligence-enabled quantitative CT (AI-QCT). In some embodiments, the association between such one or more low-density non-calcified plaque (LD-NCP) morphologies with ACS can be compared to, confirmed, and/or strengthened by other high-risk plaque (HRP) features, such as for example napkin ring sign (NRS).

In an example study to confirm the association of such LD-NCP morphologies with ACS, 456 patients from the ICONIC study were included, where all patients underwent CCTA and follow-up for ACS. In the example study, during the follow-up period, ACS occurred in 226 patients. In the example study, using invasive coronary angiography, culprit lesions were adjudicated to CCTA images in 122 patients at the time of ACS. Further, in the example study, LD-NCP morphology was assessed based on shape and the degree of embedded LD-NCP plaque (DELP) following retrospective analysis of CCTA images with AI-QCT.

In the example study, high-risk plaque (HRP) morphology was defined as a lesion with at least one round or bean-shaped LD-NCP deposit with ≥270° degree of embedded low-density non-calcified plaque (DELP). In the example study, it was shown that HRP morphology was strongly associated with culprit lesion precursors (aHR (adjusted Hazard Ratio): 8.253, [4.785, 14.234], p-value<0.001). In the example study, HRP morphology also demonstrated a strong association with ACS (aHR: 2.484, [1.778, 3.470], p-value<0.001). In the example study, HRP morphology was detected in 40 (17.7%) of ACS patients and NRS was detected in 12 (5.3%). In the example study, the median time to ACS in patients without and with HRP morphology was 1845 days and 40 days, respectively (p-value <0.001).

As such, in the example study, it was shown that HRP morphology has a significant association with ACS and culprit lesion precursors and demonstrated a stronger predictor than other HRP features.

As discussed herein, identifying patients at high risk for acute coronary syndrome (ACS) remains one of the most challenging tasks in current cardiovascular disease prevention practice. Despite the abundance of novel ASCVD risk lowering strategies, ACS rates in both primary as well as secondary prevention remain high. Coronary CT angiography (CCTA) imaging can provide non-invasive assessment of atherosclerotic plaque characteristics, as well as coronary artery stenosis. While the presence of obstructive coronary artery disease (CAD) can provide prognostic value, most culprit lesion precursors to ACS can be non-obstructive. As such, in some embodiments, the system can be configured analyze, identify, and/or utilize the presence of one or more qualitative high-risk plaque (HRP) features, such as low-attenuation plaque, positive remodeling, spotty calcifications, or the napkin-ring sign, as indicators of increased risk for ACS. Of note, in some embodiments, the system can be configured to weight obstructive lesions and non-obstructive HRP lesions the same or similarly for risk for ACS.

In some embodiments, the system can be configured to weigh the napkin-ring sign more heavily than other indicators of HRP, as the napkin-ring sign has shown high correspondence with histologic findings of thin fibrous atheroma caps and plaque rupture. More specifically, the napkin ring sign can be a morphologic CCTA finding, wherein low-density non-calcified plaque (LD-NCP) is completely circumscribed by higher-attenuating plaque. However, the clinical value of this feature may be somewhat limited due to its low prevalence and modest sensitivity.

In the example study described herein, the association of LD-NCP shape and the degree of embedded LD-NCP with culprit lesions and ACS was evaluated and demonstrated. For this purpose, in the example study, CCTA images from the multicenter ICONIC study were retrospectively analyzed using an automated artificial intelligence (AI)-enabled web-based software platform. In the example study, after AI-based plaque characterization, LD-NCP morphology was assessed based on shape, e.g., round, bean-shaped, crescent, or lobular, and the degree of embedded LD-NCP (DELP). Additionally, in the example study, the prognostic value of atherosclerotic plaque characteristics measured using AI-based plaque quantification was evaluated. As such, by utilizing identification and/or categorization of LD-NCP morphology based on shape and DELP, some embodiments of the systems, devices, and methods described herein can be used to improve the stratification of patients for risk of ACS.

In the example study utilizing data from the multicenter, international ICONIC (Incident Coronary Syndromes Identified by Computed Tomography) study (NCT02959099), 234 patients who underwent coronary CT angiography (CCTA) prior to acute coronary syndrome (ACS) during follow-up were 1:1 matched to non-ACS controls that underwent CCTA. In the example study, case and control patients underwent propensity score matching based on clinical risk factors for CAD, including age, male sex, history of hypertension and hyperlipidemia, family history of premature CAD, and smoking, as well as coronary stenosis severity as assessed on CCTA, all of which can be used as factors and/or indicators of CAD or ACS in some embodiments of the systems, devices, and methods described herein. In the example study, the culprit coronary lesion was adjudicated to CCTA images at the time of ACS, using invasive coronary angiography (ICA). In the example study, culprit lesions could not be adjudicated in 104 patients with ACS due to no ICA being performed, missing ICA images, or no culprit lesion identified on ICA. In the example study, all CCTA imaging was performed with ≥64 detector row systems and in accordance with SCCT guidelines at the time. In the example study, CCTA images underwent artificial-intelligence enabled quantitative CT (AI-QCT) analysis, similar to some embodiments of systems, devices, and methods described herein. In the example study, the associations between LD-NCP morphology and culprit lesion precursors, as well as ACS were assessed.

In the example study, and in some embodiments described herein, quantitative CT analysis was performed. More specifically, in the example study, and in some embodiments of systems, devices, and methods herein, coronary vessels with a diameter ≥1.5 mm were identified, analyzed and segmented based on the 18-segment SCCT model. In the example study, and in some embodiments herein, the presence of atherosclerosis was defined as any tissue structure >1 mm$^2$ within the coronary artery wall, differentiated from epicardial fat, epicardial tissue, or the coronary lumen. In the example study, and in some embodiments herein, coronary atherosclerotic plaque was characterized using an automated artificial intelligence (AI)-enabled web-based software platform. In the example study, and in some embodiments herein, using Hounsfield unit (HU) ranges, plaque volume was categorized as LD-NCP (<30 HU), non-calcified (30-350 HU), and calcified (>350 HU). In the example study, and in some embodiments herein, percent atheroma volume was calculated as total plaque volume/coronary vessel volume×100%. In the example study, and in some embodiments herein, percent LD-NCP, non-calcified, and calcified plaque was calculated as the specific plaque volume/total plaque volume. In the example study, and in some embodiments herein, diameter stenosis was measured using an AI-enabled quantitative CT method (QCT).

In the example study, and in some embodiments herein, LD-NCP morphology was evaluated. In particular, in the example study, and in some embodiments herein, the morphology of noncontiguous LD-NCP deposits were qualitatively assessed by a level-III qualified CCTA reader (JPE) with consensus agreement with an additional level-III qualified reader (ADC). In the example study, and in some embodiments herein, up to 4 LD-NCP deposits were assessed per coronary plaque. In the example study, and in some embodiments herein, LD-NCP deposits with a maximum axis measurement less than 0.5 mm were ignored, and plaques with less than 0.5 mm3 of LD-NCP were not assessed. In the example study, and in some embodiments herein, the analysis was performed using straightened multiplanar reformatted (SMPR) images with color plaque overlay tool turned on as available in AI-QCT.

Figure 9H:
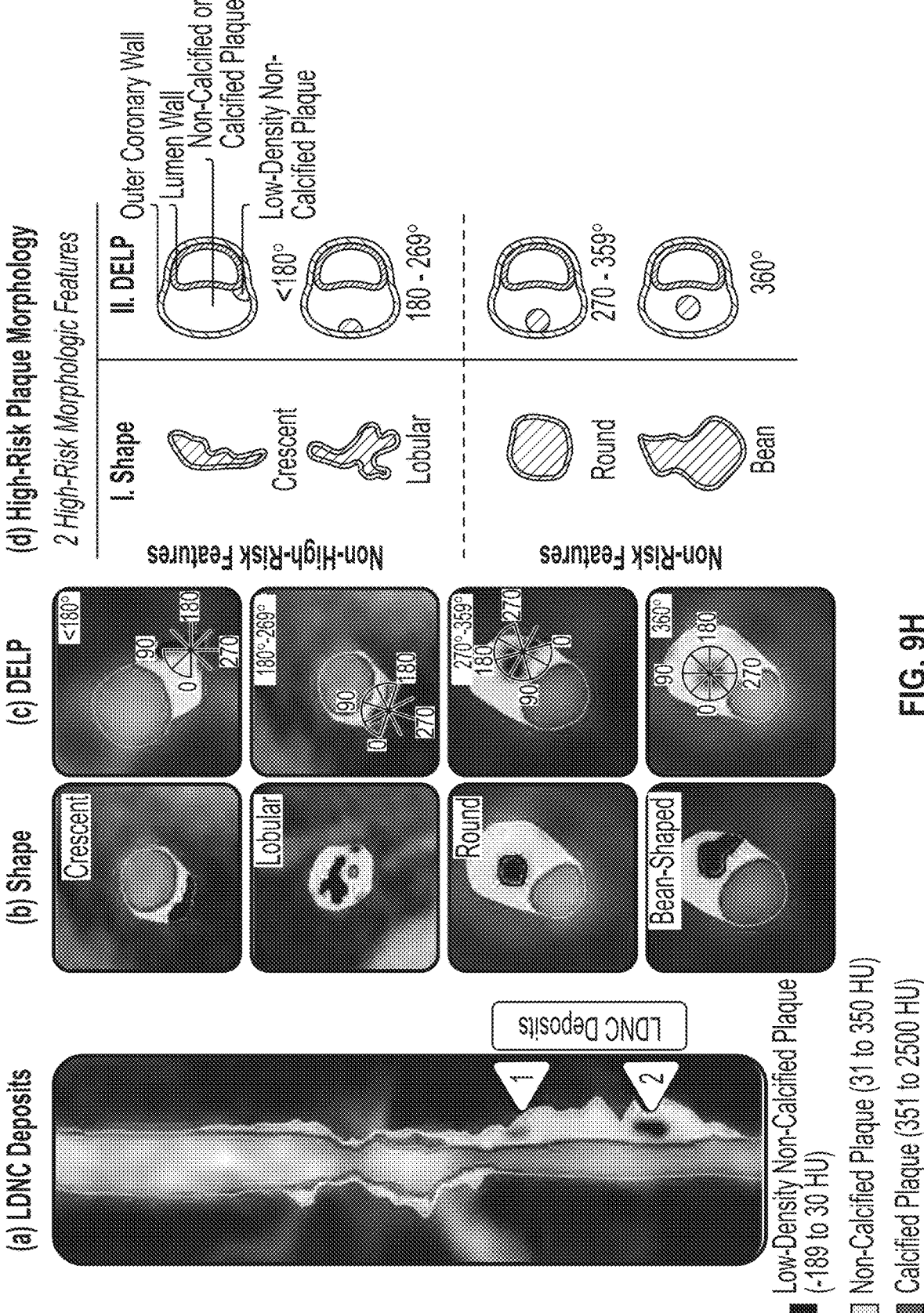
FIG. 9H illustrates an example embodiment(s) of assessing morphology of low-density non-calcified plaque deposits, with FIG. 9H(a) illustrating example LDNC deposits along a vessel, FIG. 9H(b) illustrating shapes or plaque or regions of plaque (e.g., crescent, lobular, round, bean-shaped), FIG. 9H(c) illustrating plaque having various values of DELP (e.g., <180°, 180°-269°, 270°-359°, and 360°), and FIG. 9H(d) illustrating example high-risk plaque morphology).

In the example study, and in some embodiments herein, LD-NCP deposit shape was categorized as crescent, lobular, bean-shaped, and/or round, based on its appearance on cross-sectional and longitudinal SMPR images. FIG. 9H illustrates an example embodiment(s) of assessing morphology of low-density non-calcified plaque deposits. In the example study, and in some embodiments herein, the degree of embedded LD-NCP (DELP) was assessed, based on the extent a LD-NCP deposit was encircled by non-calcified or calcified plaque. In the example study, and in some embodiments herein, using the cross-sectional image with the greatest LD-NCP deposit area, per-plaque DELP was estimated as <180°, 180-269°, 270-359°, or 360°. In the example study, and in some embodiments herein, high-risk plaque (HRP) morphology was defined as a round or bean-shaped LD-NCP deposit with >270° DELP.

In the example study, patient demographic variables were compared between patients without and with occurrence of ACS, using a two-sample t-test for continuous variables, or the chi-squared or Fisher's exact test for categorical variables, depending on sample size. In the example study, and in some embodiments herein, LD-NCP deposit measurements were assessed in association with ACS.

In the example study, the robust variance estimator and marginal Cox regression analysis was used to adjust for patient clustering. In the example study, on a per-patient basis, HRP morphology and atherosclerotic plaque characteristics were assessed in association with occurrence of ACS using marginal Cox regression analysis. In the example study, on a per-lesion basis, HRP morphology and atherosclerotic plaque characteristics were assessed in association with culprit lesion precursors. In the example study, for per-lesion assessment, culprit lesions were compared to all non-culprit lesions within-patient, in patients with ACS and culprit lesion adjudication.

In the example study, event-free survival curve analysis was conducted on a per-patient basis, stratified by patients with at least one HRP morphology lesion, as well as based on the amount of maximum LD-NCP volume in a lesion. In the example study, the Gehan-Breslow test was used to determine statistical significance. Additionally, in the example study, the HRP definition of presence of a lesion with two or more HRPs: low-attenuation plaque, spotty calcifications, or remodeling index $\geq 1.1$ was used to compare the morphology-based HRP described herein.

In the example study, hazard ratios were calculated using time to first ACS event, or event-free follow-up date. In the example study, all hazard ratios were adjusted for interval revascularization and angina severity. In the example study, a p-value <0.05 was considered statistically significant for all analyses conducted for this study. In the example study, continuous variables were represented as MEAN±SD, while categorical variables were shown as number (percentage). In the example study, hazard ratios were represented as HR [95% confidence interval]. In the example study, all statistical analysis was performed using R 4.2.0.

Figure 9I:
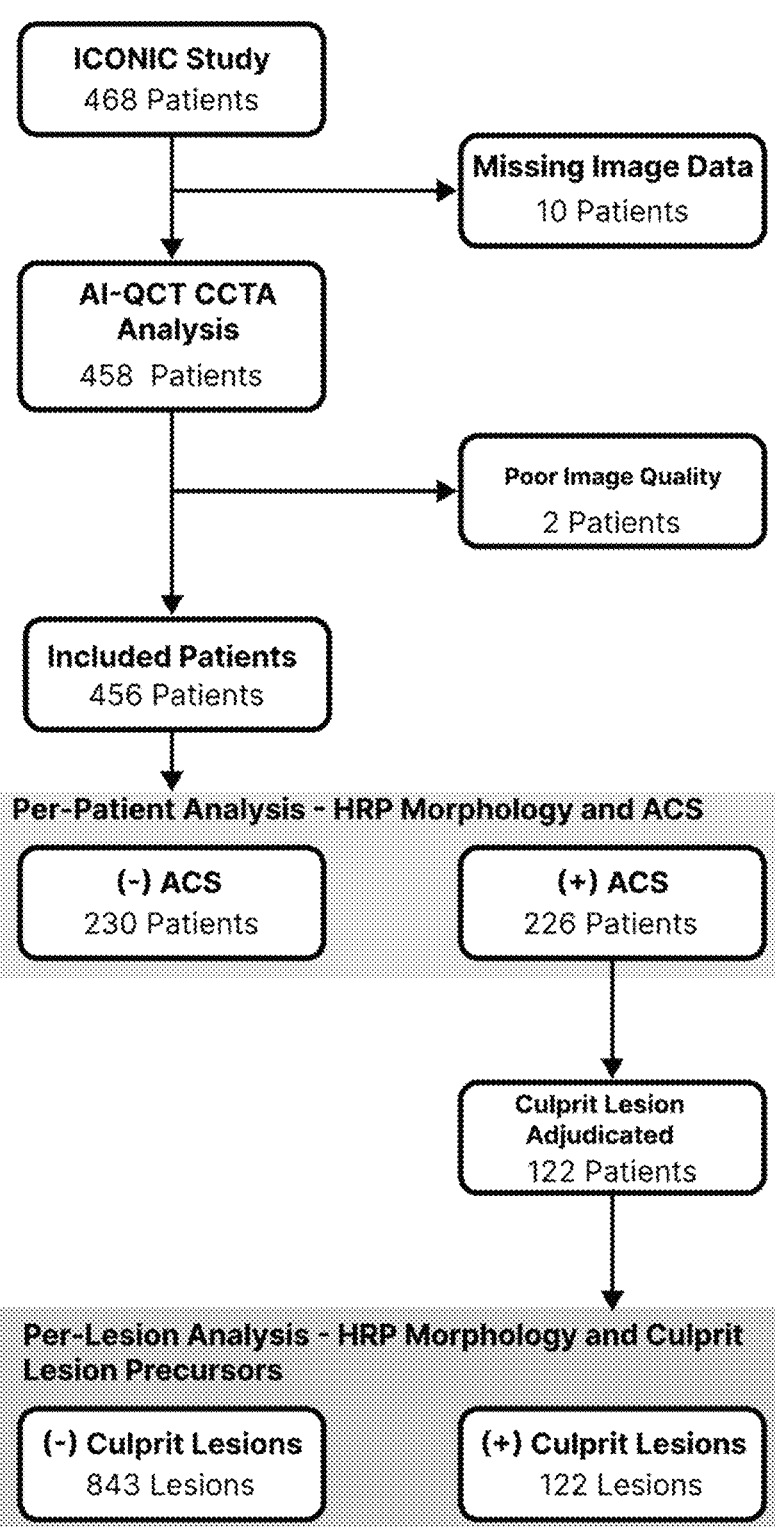
FIG. 9I is a flowchart illustrating analyses of an example study dataset validating some embodiments of the systems, devices, and methods herein.

In the example study, 456/468 patients (97.5%) from the ICONIC study, including 122 patients with culprit lesion adjudication, were included. In the example study, ten patients were excluded due to missing CCTA images, and two patients were excluded due to poor image quality. FIG. 9I is a flowchart illustrating analyses of the example study dataset validating some embodiments of the systems, devices, and methods herein. As illustrate in FIG. 9I, in the example study, high-risk plaque (HRP) morphology was retrospectively analyzed using data from the ICONIC study. In the example study, coronary CT angiography (CCTA) analysis was repeated using an artificial-intelligence enabled quantitative CT analysis (AI-QCT), using the original images from the ICONIC study. In the example study, of the 468 patients in ICONIC, 456 were included in this post-hoc analysis. In the example study, the association of HRP morphology with acute coronary syndrome was assessed on a per-patient basis. In the example study, the association of HRP morphology with culprit lesion precursors was assessed in 122 patients. In the example study, all 122 patients underwent culprit lesion adjudication at the time of the ACS event. FIG. 9J illustrates patient demographics stratified by occurrence of acute coronary syndrome in the example study validating some embodiments of systems, methods, and devices described herein. As illustrated in FIG. 9J, in the example study, 456 patients included a mean follow-up time of 2.71±2.74 years for ACS following CCTA imaging.

As for per-lesion results, in the example study, atherosclerotic plaque characteristics were evaluated in 965 lesions of 122 patients with ACS and culprit lesion adjudication. FIG. 9K illustrates per-lesion atherosclerotic characteristics stratified by non-culprit and culprit lesion precursors in the example study validating some embodiments of systems, methods, and devices described herein. As illustrated in FIG. 9K, in the example study, culprit lesions had a significantly higher plaque of the various atherosclerotic plaque characteristics including total plaque volume, non-calcified plaque volume and LD-NCP volume.

Figure 9L:
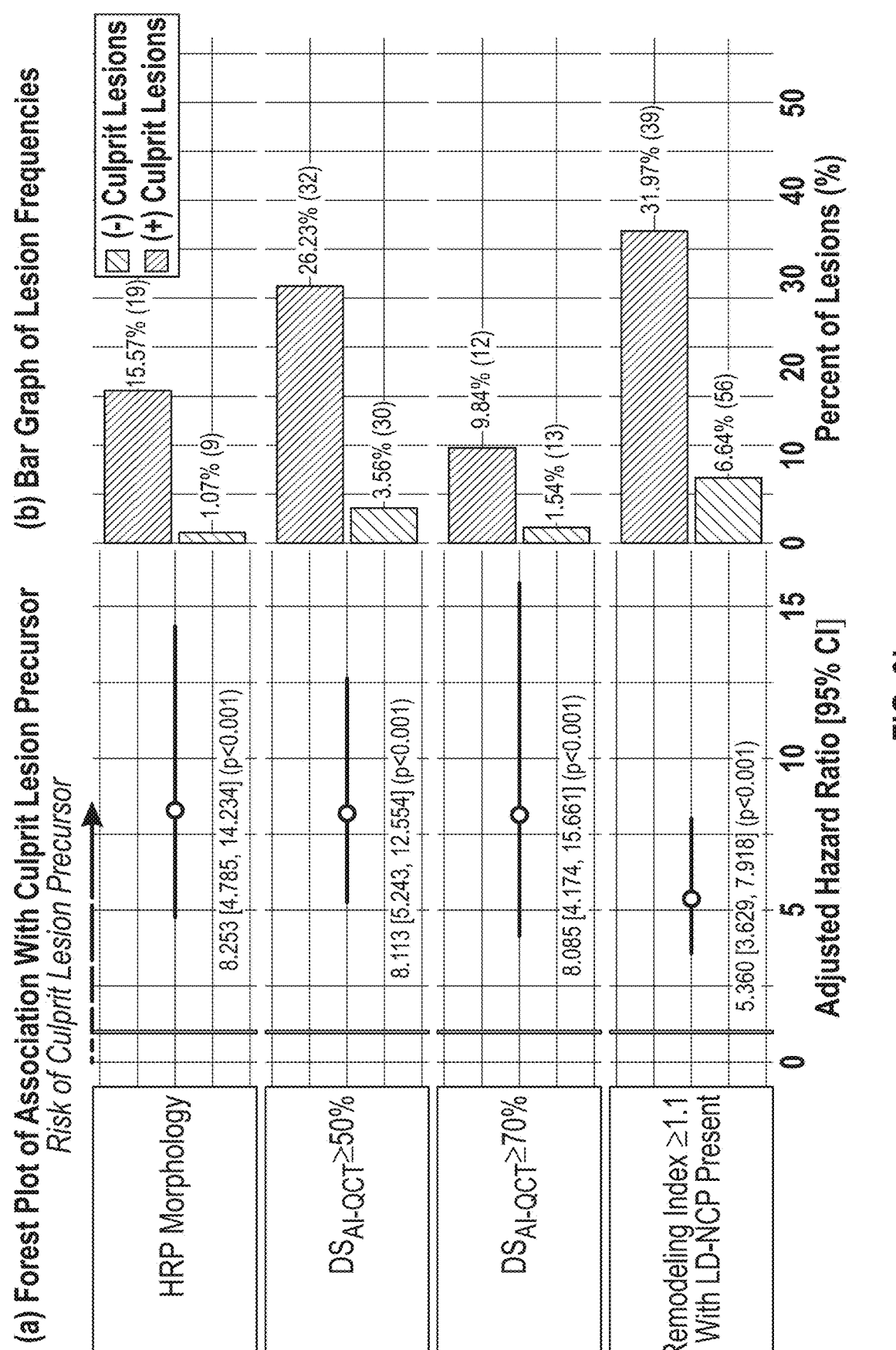
FIG. 9L is a forest plot of hazard ratios of risk for culprit lesion precursors in an example study validating some embodiments of systems, methods, and devices described herein.

FIG. 9L is a forest plot of hazard ratios of risk for culprit lesion precursors in the example study validating some embodiments of systems, methods, and devices described herein. As illustrated in FIG. 9L, in the example study, culprit lesions were identified in 122 patients at the time of an acute coronary syndrome event, using invasive coronary angiography. In the example study, all lesions were adjudicated to a culprit lesion precursor on a previously acquired coronary CT angiography (CCTA) image. In the example study, and in some embodiments described herein, high-risk plaque (HRP) morphology was defined as any lesion with at least one low-density non-calcified plaque (LD-NCP) deposit that was round or bean-shaped with $\geq 270°$ degree of embedded LD-NCP (DELP). In the example study, and in some embodiments described herein, diameter stenosis, measured using artificial intelligence quantitative CT ($DS_{AI\_QCT}$) was assessed for association with culprit lesion precursors. In the example study, and in some embodiments described herein, lesions with a remodeling index $\geq 1.1$ with LD-NCP present were assessed for association with culprit lesion precursors. In the example study, there were 122 culprit lesion precursors and 843 non-culprit lesion precursors. In FIG. 9L, a forest plot and bar graph of the frequency of each variable is shown as a percentage of non-culprit (darker) and culprit lesion precursors (lighter).

As illustrated in FIGS. 9K and 9L, in the example study, 19 (15.57%) of culprit lesions had HRP morphology, e.g., lesions with at least one round or bean-shaped LD-NCP deposit with $\geq 270°$ DELP, (adjusted hazard ratio (aHR): 8.253 [4.785, 14.234]; p-value <0.001). In the example study, per-lesion total plaque volume was 35.21±87.42 mm3 and 154.99±188.37 mm3 for non-culprit and culprit lesions, respectively (aHR: 1.003 [1.003, 1.004]; p-value <0.001). In the example study, LD-NCP volume was 0.22±2.20 mm3 and 1.99±6.03 mm3 for non-culprit and culprit lesions, respectively (aHR: 1.037 [1.003, 1.071]; p-value=0.032). In the example study, $DS_{AI\_QCT}$ was 13.65±15.32% and 33.61±22.11% in non-culprit and culprit lesions (aHR: 1.048 [1.040, 1.055]; p-value <0.001).

As for per-patient results, in the example study, atherosclerotic plaque characteristics from CCTA were evaluated from 456 patients. FIG. 9M illustrates per-patient atherosclerotic characteristics stratified by patients with and without occurrence of acute coronary syndrome in the example study validating some embodiments of systems, methods, and devices described herein. As illustrated in FIG. 9M, in the example study, atherosclerotic characteristics were described for 456 patients, 230 patients without occurrence of acute coronary syndrome (ACS) and 226 patients with ACS ((–) ACS and (+) ACS, respectively). In other words, in the example study, $^{40}/_{47}$ (85.11%) patients with HRP morphology had ACS during follow-up (aHR: 2.484 [1.778, 3.470]; p-value <0.001). In the example study, per-patient total plaque volume was 309.48 (333.57) mm$^3$ and 359.63 (330.45) mm$^3$ for patients without and with ACS, respectively (aHR: 1.000 [1.000, 1.001]; p-value=0.336). In the example study, total LD-NCP volume was 0.82±2.71 mm$^3$ and 2.59±7.88 mm$^3$ for patients without and with ACS, respectively (aHR: 1.028 [1.013, 1.044]; p-value <0.001). In the example study, max DS$_{AI-QCT}$ was 34.26±20.93% and 41.25±21.97% in patients without and with ACS, respectively (aHR: 1.007 [1.001, 1.014]; p-value=0.032).

Figure 9N:
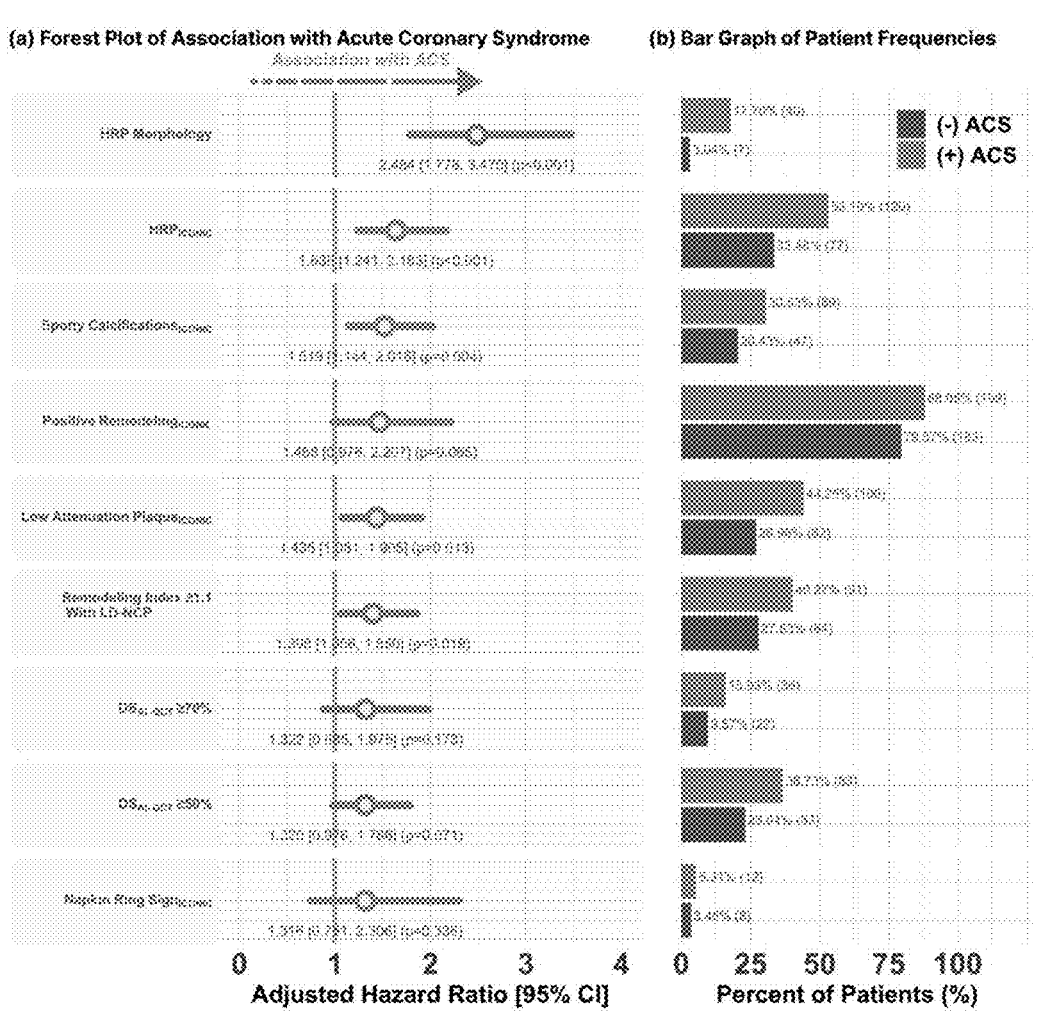
FIG. 9N is a forest plot of hazard ratios of association with acute coronary syndrome derived from an example study validating some embodiments of systems, methods, and devices described herein.

In the example study, the adjusted hazard ratio was significantly higher with the HRP morphology definition compared to the HRP definition based on presence of a lesion with two or more HRPs: low-attenuation plaque, spotty calcifications, or remodeling index ≥1.1 (aHR: 1.638 [1.241, 2.486] vs 2.484 [1.778, 3.470]; p=0.022). FIG. 9N is a forest plot of hazard ratios of association with acute coronary syndrome derived from the example study validating some embodiments of systems, methods, and devices described herein. As illustrated in FIG. 9N, in the example study, hazard ratios were calculated from 226 patients who had acute coronary syndrome (ACS), and 230 matched patients without ACS, following coronary CT angiography imaging. As illustrated in FIG. 9N, the example forest plot demonstrates the association of several variables measured from CCTA. In the example study, high-risk plaque (HRP) morphology, diameter stenosis (DS$_{AI\_QCT}$)≥70% and DS$_{AI\_QCT}$≥50% were assessed in a post-hoc analysis of the ICONIC dataset (red). In the example study, and in some embodiments described herein, HRP defined as the presence of two or more of spotty calcification, remodeling index ≥1.1, or presence of low attenuation plaque (HRP$_{ICONIC}$), presence of a calcification ≤3 mm or 5 cross-sectional slices (Spotty Calcifications$_{ICONIC}$), Presence of remodeling index ≥1.1 (Positive Remodeling$_{ICONIC}$), Presence of low attenuation plaque (<30 HU) (Low Attenuation Plaque$_{ICONIC}$), and Napkin Ring Sign$_{ICONIC}$ were assessed. Further, as illustrated in FIG. 9N, a bar graph derived from the example study demonstrates the frequency and portion of patients with each respective variable, stratified by patients without and with ACS (darker and lighter, respectively).

Figure 9O:
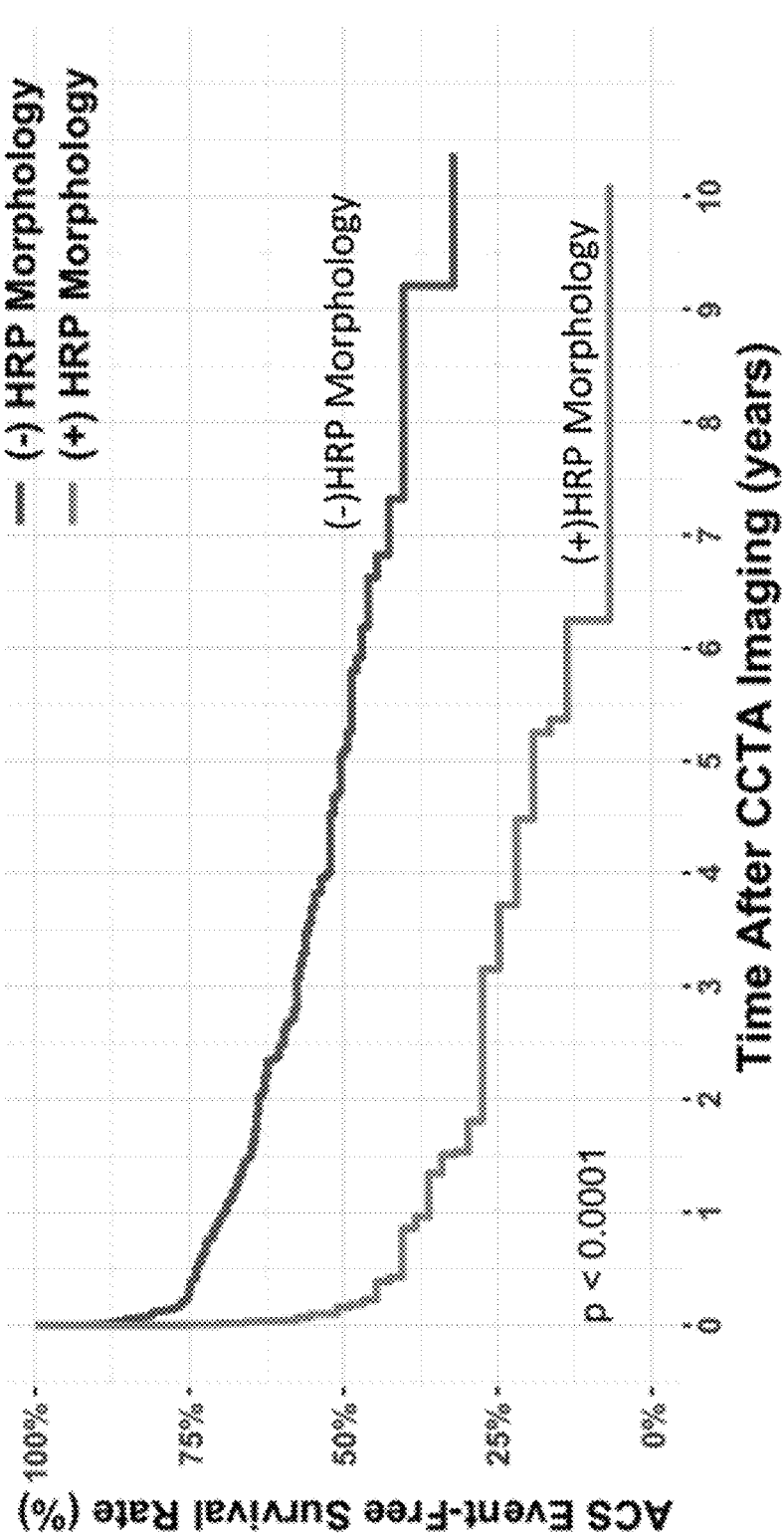
FIG. 9O illustrates acute coronary syndrome event-free survival rate in patients without and with high-risk plaque morphology lesions in an example study validating some embodiments of systems, methods, and devices described herein.

In the example study, and in some embodiments described herein, an acute coronary syndrome event-free survival analysis was performed. In the example study, HRP morphology was detected in 40 (17.7%) of patients experiencing ACS and 7 (3.0%) of those not experiencing ACS; a napkin ring sign (NRS) was detected in 12 (5.3%) of ACS patients and in 8 (3.5%) of non-ACS patients. In the example study, the median time to ACS in patients without and with HRP morphology was 5.06 and 0.11 years, respectively. FIG. 9O illustrates acute coronary syndrome event-free survival rate in patients without and with high-risk plaque morphology lesions in the example study validating some embodiments of systems, methods, and devices described herein. In FIG. 9O, patients with at least one lesion with high-risk plaque morphology (e.g., round or bean-shaped low-density non-calcified plaque (LD-NCP) deposit with ≥270° degree of embedded LD-NCP) are shown ((+) HRP Morphology). In FIG. 9O, patients without at least one HRP morphology lesion are shown((–) HRP Morphology). In the example study, the Gehan-Breslow test was used to compare patient groups. In the example study, overall, 230 patients did not have an ACS event during follow-up, whereas 226 patients did. In the example study, forty-seven patients had at least one HRP morphology lesion, forty of these patients had an ACS event.

Figure 9P:
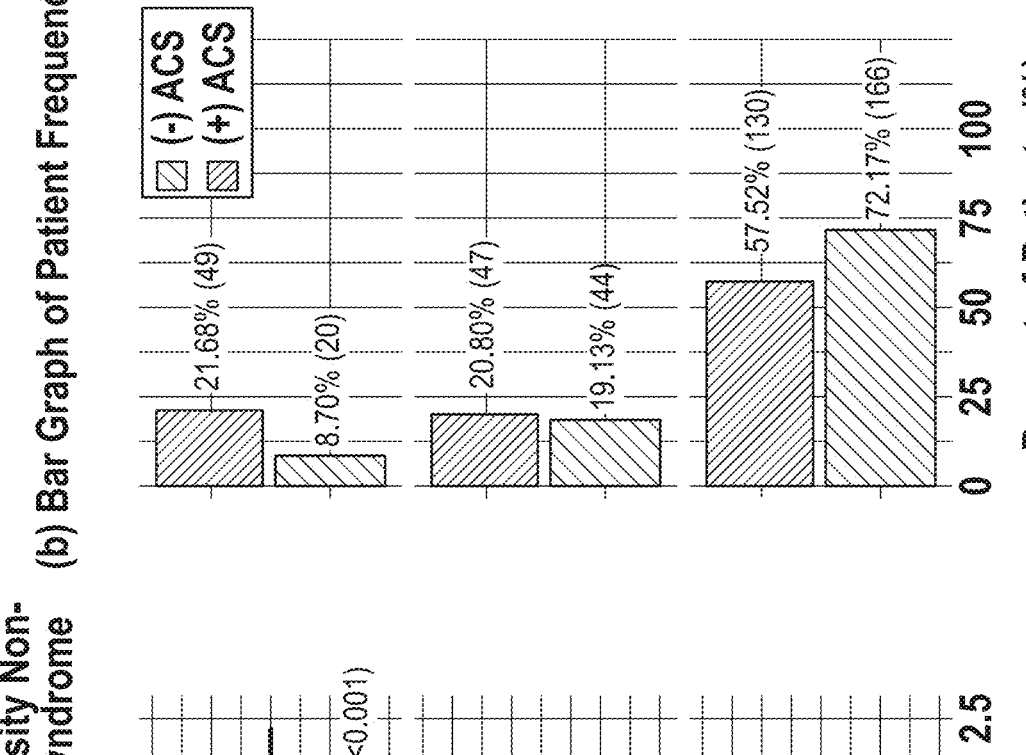
FIG. 9P is a forest plot of hazard ratios of association with low-density non-calcified plaque with acute coronary syndrome derived from an example study validating some embodiments of systems, methods, and devices described herein.

In the example study, and in some embodiments described herein, an incremental association of low-density non-calcified plaque volume with acute coronary syndrome was found on a per-patient basis. In particular, in the example study, patients with a maximum LD-NCP lesion volume ≥2 mm$^3$ were strongly associated with ACS (aHR: 1.767 [1.285, 2.430]; p-value<0.001)). In the example study, patients with a maximum LD-NCP lesion volume >0-1 mm$^3$ were not associated with ACS (aHR: 1.036 [0.734, 1.464]; p-value=0.840)). FIG. 9P is a forest plot of hazard ratios of association with low-density non-calcified plaque with acute coronary syndrome derived from an example study validating some embodiments of systems, methods, and devices described herein. In the example study, hazard ratios were calculated from 226 patients who had acute coronary syndrome (ACS), and 230 matched patients without ACS, following coronary CT angiography imaging In FIG. 9P, the incremental association of the lesion with the maximum low-density non-calcified plaque (LD-NCP) volume per-patient is shown. In the example study, patients were stratified based on the presence of at least one lesion with 0, >0-2, and ≥2 mm3 LD-NCP volume. In FIG. 9P, a forest plot is shown with adjusted hazard rations and 95% confidence intervals, and the bar graph demonstrates the frequency and portion of patients with each respective variable, stratified by patients without and with ACS (darker and lighter, respectively).

Figure 9Q:
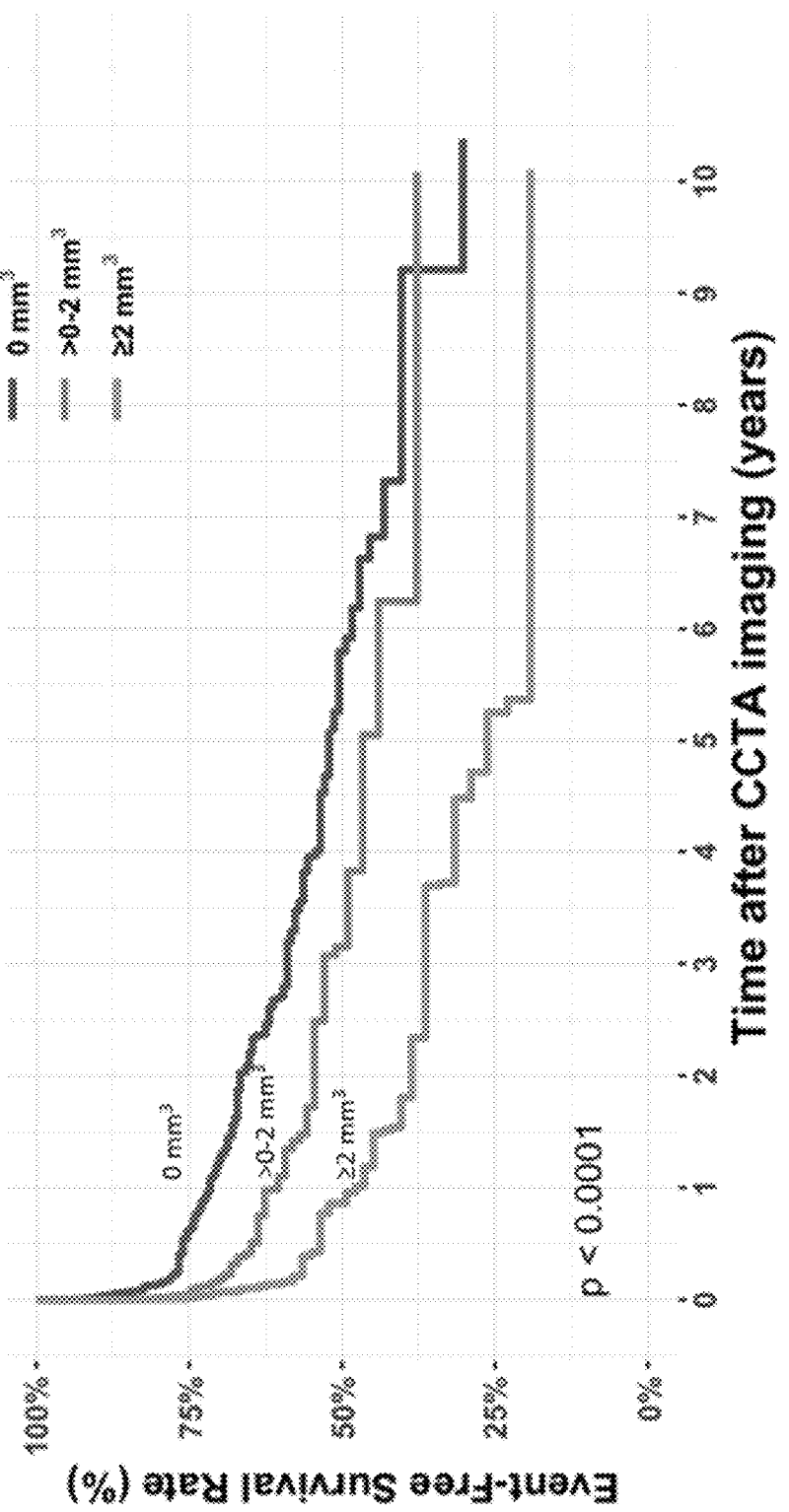
FIG. 9Q illustrates acute coronary syndrome event-free survival rates in patients stratified by the amount of low-density non-calcified plaque volume derived from an example study validating some embodiments of systems, methods, and devices described herein.

FIG. 9Q illustrates acute coronary syndrome event-free survival rates in patients stratified by the amount of low-density non-calcified plaque volume derived from an example study validating some embodiments of systems, methods, and devices described herein. In the example study, and in some embodiments described herein, patients were stratified into 0, >0-2, and >2 mm$^3$ low-density non-calcified plaque (LD-NCP) groups, based the lesion with the maximum volume of LD-NCP. In the example study, the Gehan-Breslow test was used to compare patient stratum with the p-value annotated. As illustrated in FIG. 9Q, in the example study, the median survival times of patients with a maximum LD-NCP lesion volume of 0 mm$^3$, >0-2 mm$^3$, and ≥2 mm$^3$ were 5.80, 3.15, and 0.86 years, respectively.

In the example study, and in some embodiments described herein, HRP defined by one or more features and/or characteristics related to morphology was used and proved superior to both the diameter stenosis analysis, as well as an HRP definition based on two-feature positive plaque in distinguishing ACS patients and matched controls. As discussed, in the example study, and in some embodiments described herein, HRP morphology was strongly associated with early ACS occurrence, based on median time to ACS. Furthermore, in the example study and in some embodiments described herein, on a per-lesion basis, culprit lesion precursors had greater total plaque volume, lesion length, and/or LD-NCP, non-calcified, and/or calcified plaque volumes. In the example study and in some embodiments described herein, on a per-patient basis, ACS patients had greater LD-NCP and non-calcified plaque volume. Collectively, this example study demonstrated the clinical value of HRP morphology, as well as the effectiveness of an automated AI-based method for measuring atherosclerotic plaque characteristics as used in some embodiments described herein. Moreover, in the example study and in some embodiments discussed herein, LD-NCP volume specifically demonstrated increased association with ACS, in patients with a maximum LD-NCP lesion volume ≥2.0 mm³, as compared to patients with a maximum LD-NCP lesion volume <2.0 mm³.

In some embodiments, and as noted in the example study, the pathophysiology of HRP morphology can be important and/or be used as an indicator and/or characteristic of HRP. In particular, in the example study and in some embodiments, crescent and lobular shaped LD-NCP, and plaques with <270° DELP demonstrated a lower risk for ACS and were less frequent culprit lesion precursors. In the example study and in some embodiments described herein, Crescentic and lobular LD-NCP deposits also frequently demonstrated <270° DELP. As such, in some embodiments, a plaque region comprising a bean or round shape with ≥270° DELP can be identified as HRP and/or can be associated with ACS. In some embodiments, a plaque region comprising a bean or round shape alone can be identified as HRP and/or can be associated with ACS. In some embodiments, a plaque region comprising ≥270° DELP can be identified as HRP and/or can be associated with ACS. In some embodiments, and in the example study, LD-NCP deposits with <270° DELP can have a greater intersection with the outer coronary wall. In some embodiments, although plaque instability and rupture is related to the presence of a thin capped fibroatheroma(20), this can be difficult to assess on CCTA due to spatial resolution limitations. In some embodiments, DELP can be considered be a surrogate for the presence of a thin capped fibroatheroma, wherein LD-NCP with a smaller DELP can be located more towards the epicardial coronary vessel wall. Thus, in some embodiments, a smaller DELP implies a greater distance between LD-NCP and the coronary lumen surface, and a lower risk for rupture. Furthermore, in some embodiments, patients with HRP morphology can be precited to experience ACS significantly sooner, implying LD-NCP deposits with ≥270° DELP may be more prone to rupture.

In some embodiments, a napkin-ring sign (NRS) can be considered an indicator and/or characteristic of HRP. In some embodiments, a region of plaque comprising an NRS can comprise histologic correspondence to advance plaque and thin capped fibroatheromas. In some embodiments, NRS is considered to have a strong association with ACS. In some embodiments, HRP morphology features discussed herein can share some similarities with NRS; however, the low prevalence of NRS can limit its clinical utility. In some embodiments, HRP morphology can provide a broader stratum for identifying significant atherosclerosis. For example, in the example study, NRS was shown to have a lower prevalence in comparison to HRP morphology on a per-patient basis.

In some embodiments, the system is configured to identify two-feature positive plaques as HRP. That is, in some embodiments, the system is configured to identify as HRP a region of plaque with a presence of both positive remodeling and low-attenuation plaque. In some embodiments, two-feature positive plaques are considered to be associated with increased risk for ACS.

In the example study, a direct comparison was tested between two-feature positive plaque and HRP based on one or more morphology features, in association with culprit lesion precursors. In the example study, in both outcomes, HRP based on one or more morphology features demonstrated a stronger association, with far less false positive cases, with ACS.

In some embodiments, the presence of one or more HRP features, such as low-attenuation plaque (e.g., plaque <30 HU), positive remodeling, spotty calcifications, and/or NRS is considered to have a strong association with adverse cardiac events. Furthermore, in some embodiments, lesions with HRP are considered more likely to be culprit lesion precursors. In the example study, a direct comparison showed that patients with HRP identified based on one or more morphology features were at greater risk of ACS, as compared to one or more other HRP features.

In some embodiments, the system can be configured to utilize radiomics and CCTA imaging to derive and/or identify geometry features of LD-NCP, which can be used to identify high-risk coronary lesions.

As shown in the example study, the median time to ACS in patients with HRP identified based on one or more morphology features was remarkably reduced compared to HRP identified based on one or more other HRP features. As such, in some embodiments, the system can be configured to utilize HRP identified based on one or more morphology features to stratify patients for high-intensity medical therapies. In some embodiments, the presence of LD-NCP alone is not used to stratify patients for risk of ACS, but rather HRP morphology features, and/or lesion volume of LD-NCP, can be considered to adequately infer risk of ACS.

As such, in some embodiments, high-risk plaque morphology, based on low-density non-calcified plaque for example, can be used to identify patients at very high risk for acute coronary syndrome. Moreover, in some embodiments, patients with a lesion with at least 2 mm³ of low-density non-calcified plaque volume can be considered to be strongly associated with acute coronary syndrome. Thus, in some embodiments, the amount and morphology of low-density non-calcified plaque can be considered when stratifying patients for risk of acute coronary syndrome.

Figure 9R:
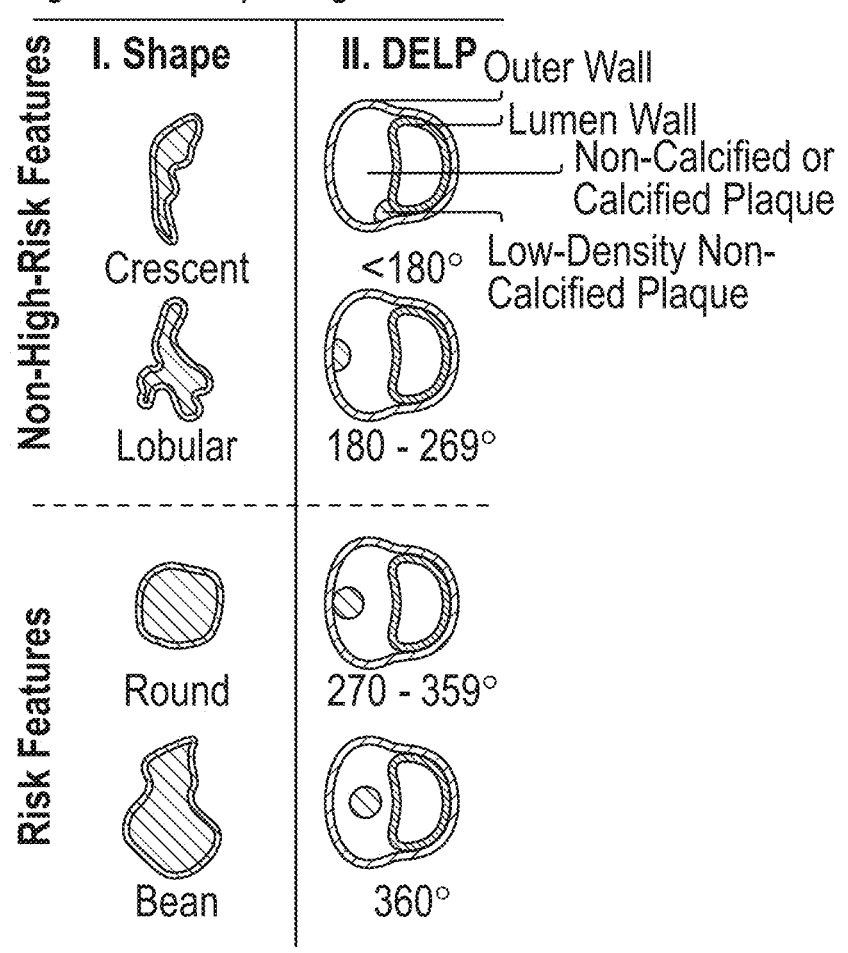
FIG. 9R illustrates how high-risk plaque morphology can be considered to increase risk for acute coronary syndrome in some embodiments.
Figure 9R:
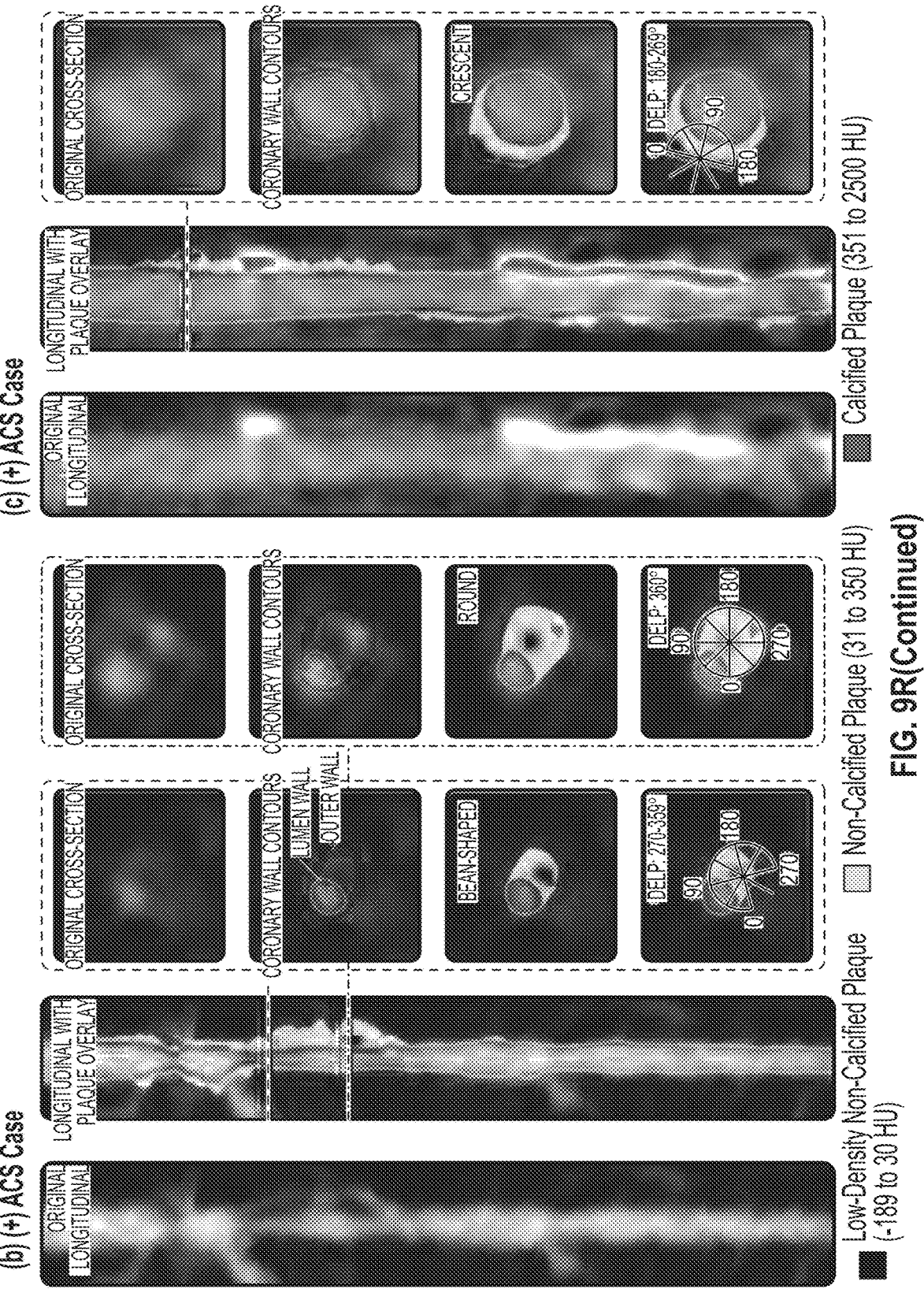
Figure 9R:
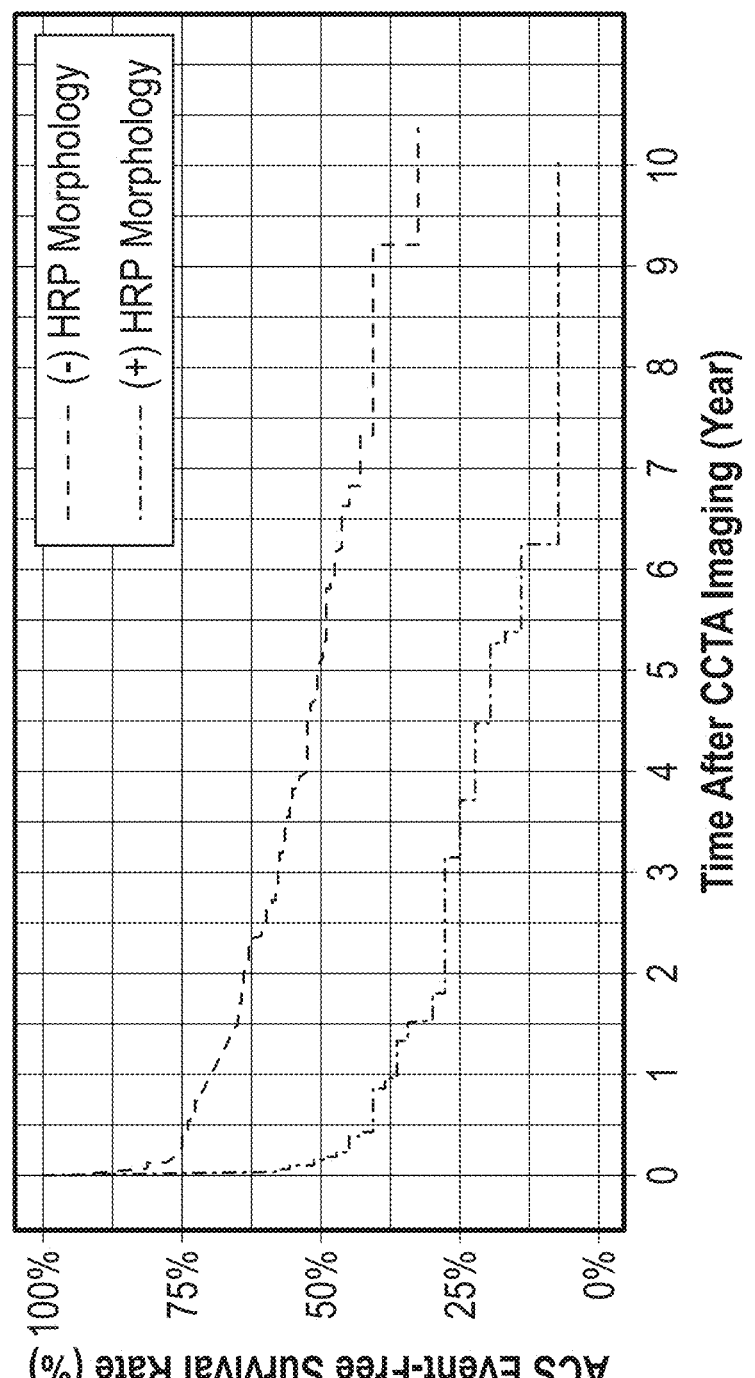

FIG. 9R illustrates how high-risk plaque morphology can be considered to increase risk for acute coronary syndrome in some embodiments. As illustrated, in some embodiments, one or more high-risk plaque morphologies discussed herein can be considered to be strongly associated with acute coronary syndrome and/or culprit lesion precursors. In particular, in some embodiments, crescentic low-density non-calcified plaque can be considered not to be associated with risk for acute coronary syndrome, whereas round or bean-shaped low-density non-calcified plaque can be considered to have greater association with acute coronary syndrome. In some embodiments, artificial intelligence-based quantitative coronary CT angiography can be used to stratify patients for risk of acute coronary syndrome, for example based on one or more morphology features described herein. Further, in some embodiments, the amount of low-density non-calcified plaque can be considered to be associated with increased risk for acute coronary syndrome.

Certain Examples of Embodiments Related to Plaque Morphology/Feature Analysis

The following are non-limiting examples of certain embodiments of systems and methods for determining plaque morphology and/or feature analysis. Other embodiments may include one or more other features, or different features, that are discussed herein.

Embodiment 1: A computer-implemented method of facilitating determination of risk of coronary artery disease (CAD) based at least in part on one or more measurements derived from non-invasive medical image analysis, the method comprising: accessing, by a computer system, a medical image of a subject, wherein the medical image of the subject is obtained non-invasively; analyzing, by the computer system, the medical image of the subject to identify one or more arteries; identifying, by the computer system, one or more regions of plaque within the one or more coronary arteries; analyzing, by the computer system, the identified one or more regions of plaque to identify one or more regions of low density non-calcified plaque, non-calcified plaque, or calcified plaque based at least in part on density, analyzing, in response to identifying one or more regions of low density non-calcified plaque, the one or more regions of low density non-calcified plaque, wherein the analysis of the one or more regions of low density non-calcified plaque comprises: determining a distance from the one or more regions of low density non-calcified plaque to one or more of a lumen wall or vessel wall; determining a degree of embeddedness of the one or more regions of low density non-calcified plaque by one or more of non-calcified plaque or calcified plaque; and determining a shape of the one or more regions of low density non-calcified plaque; and generating, by the computer system, a display of the analysis of the one or more regions of low density non-calcified plaque to facilitate determination of one or more of a risk of CAD of the subject based at least in part on the analysis of the one or more regions of low density non-calcified plaque, wherein the computer system comprises a computer processor and an electronic storage medium.

Embodiment 2: The computer-implemented method of Embodiment 1, wherein a determination of the distance from the one or more regions of low density non-calcified plaque to the lumen wall below a predetermined threshold is indicative of an unstable plaque or high risk of CAD.

Embodiment 3: The computer-implemented method of Embodiment 1, wherein the distance from the one or more regions of low density non-calcified plaque to one or more of the lumen wall or vessel wall is determined on a three-dimensional basis.

Embodiment 4: The computer-implemented method of Embodiment 1, wherein the distance from the one or more regions of low density non-calcified plaque to one or more of the lumen wall or vessel wall is determined based on a two-dimensional image.

Embodiment 5: The computer-implemented method of Embodiment 4, wherein the two-dimensional image is obtained by taking a two-dimensional slice perpendicular to a longitudinal axis of a straightened multiplanar view of the one or more arteries.

Embodiment 6: The computer-implemented method of Embodiment 4, wherein the two-dimensional image is obtained by taking a two-dimensional slice resulting in a largest two-dimensional area of the low-density non-calcified plaque.

Embodiment 7: The computer-implemented method of Embodiment 1, wherein the distance from the one or more regions of low density non-calcified plaque to the lumen wall is determined by determining a shortest distance between a boundary of the one or more regions of low density non-calcified plaque and a boundary of the lumen wall.

Embodiment 8: The computer-implemented method of Embodiment 1, wherein the distance from the one or more regions of low density non-calcified plaque to the vessel wall is determined by determining a shortest distance between a boundary of the one or more regions of low density non-calcified plaque and a boundary of the vessel wall.

Embodiment 9: The computer-implemented method of Embodiment 1, wherein the one or more arteries comprises one or more coronary or carotid arteries.

Embodiment 10: The computer-implemented method of Embodiment 1, wherein the one or more axes of the one or more regions of low density non-calcified plaque comprises one or more of a major axis on a longitudinal plane, minor axis on a longitudinal plane, major axis on a latitudinal plane, or minor axis on a latitudinal plane.

Embodiment 11: The computer-implemented method of Embodiment 10, wherein the one or more axes are determined on a three-dimensional basis.

Embodiment 12: The computer-implemented method of Embodiment 10, wherein the one or more axes are determined based on one or more two-dimensional images.

Embodiment 13: The computer-implemented method of Embodiment 12, wherein the longitudinal plane is obtained by taking a two-dimensional slice parallel to a longitudinal axis of a straightened multiplanar view of the one or more arteries.

Embodiment 14: The computer-implemented method of Embodiment 12, wherein the longitudinal plane is obtained by taking a two-dimensional slice resulting in a longest major axis of the longitudinal plane.

Embodiment 15: The computer-implemented method of Embodiment 12, wherein the latitudinal plane is obtained by taking a two-dimensional slice perpendicular to a longitudinal axis of a straightened multiplanar view of the one or more arteries.

Embodiment 16: The computer-implemented method of Embodiment 12, wherein the latitudinal plane is obtained by taking a two-dimensional slice perpendicular to the major axis on the longitudinal plane.

Embodiment 17: The computer-implemented method of Embodiment 12, wherein the latitudinal plane is obtained by taking a two-dimensional slice resulting in a largest two-dimensional area of the low-density non-calcified plaque.

Embodiment 18: The computer-implemented method of Embodiment 1, wherein one or more of analyses of the one or more regions of low density non-calcified plaque is performed by the computer system.

Embodiment 19: The computer-implemented method of Embodiment 1, wherein the degree of embeddedness of the one or more regions of low density non-calcified plaque is determined based at least in part by graphically overlaying a protractor on the one or more regions of low density non-calcified plaque on the medical image.

Embodiment 20: The computer-implemented method of Embodiment 1, wherein a higher degree of embeddedness of the one or more regions of low density non-calcified plaque is indicative of an unstable plaque or high risk of CAD.

Embodiment 21: The computer-implemented method of Embodiment 1, wherein the shape of the one or more regions of low density non-calcified plaque is determined as one or more of a crescent, round, lobular, or bean shape.

Embodiment 22: The computer-implemented method of Embodiment 21, wherein determination of a round or bean shape of the one or more regions of low density non-calcified plaque is indicative of an unstable plaque or high risk of CAD.

Embodiment 23: The computer-implemented method of Embodiment 1, wherein the shape of the one or more regions of low density non-calcified plaque is determined based at least in part by a machine learning algorithm.

Embodiment 24: The computer-implemented method of Embodiment 1, wherein the analysis of the one or more regions of low density non-calcified plaque further comprises determining one or more lengths of one or more axes of the one or more regions of low density non-calcified plaque.

Embodiment 25: The computer-implemented method of Embodiment 24, wherein the shape of the one or more regions of low density non-calcified plaque is determined based at least in part on the one or more determined lengths of the one or more axes.

Embodiment 26: The computer-implemented method of Embodiment 25, wherein the shape of the one or more regions of low density non-calcified plaque is determined based at least in part on determining a standard deviation among the one or more determined lengths of the one or more axes.

Embodiment 27: The computer-implemented method of Embodiment 24, wherein the analysis of the one or more regions of low density non-calcified plaque further comprises: determining a volume of the one or more regions of low density non-calcified plaque; determining a volume of the one or more regions of plaque; and determining a ratio of the volume of the one or more regions of low density non-calcified plaque to the volume of the one or more regions of plaque.

Embodiment 28: The computer-implemented method of Embodiment 27, wherein the volume of the one or more regions of low density non-calcified plaque is determined based on the one or more determined lengths of the one or more axes of the one or more regions of low density non-calcified plaque.

Embodiment 29: The computer-implemented method of Embodiment 27, wherein a determination of the volume of the one or more regions of low density non-calcified plaque above a predetermined threshold is indicative of unstable plaque or high risk of CAD.

Embodiment 30: The computer-implemented method of Embodiment 27, wherein a determination of the volume of the one or more regions of plaque above a predetermined threshold is indicative of unstable plaque or high risk of CAD.

Embodiment 31: The computer-implemented method of Embodiment 27, wherein a determination of the ratio of the volume of the one or more regions of low density non-calcified plaque to the volume of the one or more regions of plaque above a predetermined threshold is indicative of unstable plaque or high risk of CAD.

Embodiment 32: The computer-implemented method of Embodiment 1, wherein the density comprises absolute density.

Embodiment 33: The computer-implemented method of Embodiment 1, wherein the density comprises radiodensity.

Embodiment 34: The computer-implemented method of Embodiment 33, wherein the one or more regions of plaque are identified as low density non-calcified plaque when a radiodensity value is between about −189 and about 30 Hounsfield units.

Embodiment 35: The computer-implemented method of Embodiment 33, wherein the one or more regions of plaque are identified as non-calcified plaque when a radiodensity value is between about 31 and about 350 Hounsfield units.

Embodiment 36: The computer-implemented method of Embodiment 33, wherein the one or more regions of plaque are identified as calcified plaque when a radiodensity value is between about 351 and 2500 Hounsfield units.

Embodiment 37: The computer-implemented method of Embodiment 1, wherein the medical image comprises a Computed Tomography (CT) image.

Embodiment 38: The computer-implemented method of Embodiment 1, wherein the medical image is obtained using an imaging technique comprising one or more of CT, x-ray, ultrasound, echocardiography, MR imaging, optical coherence tomography (OCT), nuclear medicine imaging, posi-tron-emission tomography (PET), single photon emission computed tomography (SPECT), or near-field infrared spectroscopy (NIRS).

Embodiment 39: The computer-implemented method of Embodiment 1, further comprising generating, by the computer system, an assessment of risk of CAD of the subject or risk of the one or more regions of plaque based at least in part on the analysis of the one or more regions of low density non-calcified plaque.

Embodiment 40: The computer-implemented method of Embodiment 39, further comprising generating, by the computer system, a recommended treatment for the subject based at least in part on the analysis of the one or more regions of low density non-calcified plaque.

Embodiment 41: A system for facilitating determination of risk of coronary artery disease (CAD) based at least in part on one or more measurements derived from non-invasive medical image analysis, the system comprising: one or more computer readable storage devices configured to store a plurality of computer executable instructions; and one or more hardware computer processors in communication with the one or more computer readable storage devices and configured to execute the plurality of computer executable instructions in order to cause the system to: access a medical image of a subject, wherein the medical image of the subject is obtained non-invasively; analyze the medical image of the subject to identify one or more arteries; identify one or more regions of plaque within the one or more coronary arteries; analyze the identified one or more regions of plaque to identify one or more regions of low density non-calcified plaque, non-calcified plaque, or calcified plaque based at least in part on density, facilitate analyzing, in response to identifying one or more regions of low density non-calcified plaque, the one or more regions of low density non-calcified plaque, wherein the analysis of the one or more regions of low density non-calcified plaque comprises: determining a distance from the one or more regions of low density non-calcified plaque to one or more of a lumen wall or vessel wall; determining a degree of embeddedness of the one or more regions of low density non-calcified plaque by one or more of non-calcified plaque or calcified plaque; and determining a shape of the one or more regions of low density non-calcified plaque; and generate a display of the analysis of the one or more regions of low density non-calcified plaque to facilitate determination of one or more of a risk of CAD of the subject based at least in part on the analysis of the one or more regions of low density non-calcified plaque.

Embodiment 42: The system of Embodiment 41, wherein a determination of the distance from the one or more regions of low density non-calcified plaque to the lumen wall below a predetermined threshold is indicative of an unstable plaque or high risk of CAD.

Embodiment 43: The system of Embodiment 41, wherein the distance from the one or more regions of low density non-calcified plaque to one or more of the lumen wall or vessel wall is determined on a three-dimensional basis.

Embodiment 44: The system of Embodiment 41, wherein the distance from the one or more regions of low density non-calcified plaque to one or more of the lumen wall or vessel wall is determined based on a two-dimensional image.

Embodiment 45: The system of Embodiment 44, wherein the two-dimensional image is obtained by taking a two-dimensional slice perpendicular to a longitudinal axis of a straightened multiplanar view of the one or more arteries.

Embodiment 46: The system of Embodiment 44, wherein the two-dimensional image is obtained by taking a two-dimensional slice resulting in a largest two-dimensional area of the low-density non-calcified plaque.

Embodiment 47: The system of Embodiment 41, wherein the distance from the one or more regions of low density non-calcified plaque to the lumen wall is determined by determining a shortest distance between a boundary of the one or more regions of low density non-calcified plaque and a boundary of the lumen wall.

Embodiment 48: The system of Embodiment 41, wherein the distance from the one or more regions of low density non-calcified plaque to the vessel wall is determined by determining a shortest distance between a boundary of the one or more regions of low density non-calcified plaque and a boundary of the vessel wall.

Embodiment 49: The system of Embodiment 41, wherein the one or more arteries comprises one or more coronary or carotid arteries.

Embodiment 50: The system of Embodiment 41, wherein the one or more axes of the one or more regions of low density non-calcified plaque comprises one or more of a major axis on a longitudinal plane, minor axis on a longitudinal plane, major axis on a latitudinal plane, or minor axis on a latitudinal plane.

Embodiment 51: The system of Embodiment 50, wherein the one or more axes are determined on a three-dimensional basis.

Embodiment 52: The system of Embodiment 50, wherein the one or more axes are determined based on one or more two-dimensional images.

Embodiment 53: The system of Embodiment 52, wherein the longitudinal plane is obtained by taking a two-dimensional slice parallel to a longitudinal axis of a straightened multiplanar view of the one or more arteries.

Embodiment 54: The system of Embodiment 52, wherein the longitudinal plane is obtained by taking a two-dimensional slice resulting in a longest major axis of the longitudinal plane.

Embodiment 55: The system of Embodiment 52, wherein the latitudinal plane is obtained by taking a two-dimensional slice perpendicular to a longitudinal axis of a straightened multiplanar view of the one or more arteries.

Embodiment 56: The system of Embodiment 52, wherein the latitudinal plane is obtained by taking a two-dimensional slice perpendicular to the major axis on the longitudinal plane.

Embodiment 57: The system of Embodiment 52, wherein the latitudinal plane is obtained by taking a two-dimensional slice resulting in a largest two-dimensional area of the low-density non-calcified plaque.

Embodiment 58: The system of Embodiment 41, wherein one or more of analyses of the one or more regions of low density non-calcified plaque is performed by the computer system.

Embodiment 59: The system of Embodiment 41, wherein the degree of embeddedness of the one or more regions of low density non-calcified plaque is determined based at least in part by graphically overlaying a protractor on the one or more regions of low density non-calcified plaque on the medical image.

Embodiment 60: The system of Embodiment 41, wherein a higher degree of embeddedness of the one or more regions of low density non-calcified plaque is indicative of an unstable plaque or high risk of CAD.

Embodiment 61: The system of Embodiment 41, wherein the shape of the one or more regions of low density non-calcified plaque is determined as one or more of a crescent, round, lobular, or bean shape.

Embodiment 62: The system of Embodiment 61, wherein determination of a round or bean shape of the one or more regions of low density non-calcified plaque is indicative of an unstable plaque or high risk of CAD.

Embodiment 63: The system of Embodiment 41, wherein the shape of the one or more regions of low density non-calcified plaque is determined based at least in part by a machine learning algorithm.

Embodiment 64: The system of Embodiment 41, wherein the analysis of the one or more regions of low density non-calcified plaque further comprises determining one or more lengths of one or more axes of the one or more regions of low density non-calcified plaque.

Embodiment 65: The system of Embodiment 64, wherein the shape of the one or more regions of low density non-calcified plaque is determined based at least in part on the one or more determined lengths of the one or more axes.

Embodiment 66: The system of Embodiment 65, wherein the shape of the one or more regions of low density non-calcified plaque is determined based at least in part on determining a standard deviation among the one or more determined lengths of the one or more axes.

Embodiment 67: The system of Embodiment 64, wherein the analysis of the one or more regions of low density non-calcified plaque further comprises: determining a volume of the one or more regions of low density non-calcified plaque; determining a volume of the one or more regions of plaque; and determining a ratio of the volume of the one or more regions of low density non-calcified plaque to the volume of the one or more regions of plaque.

Embodiment 68: The system of Embodiment 67, wherein the volume of the one or more regions of low density non-calcified plaque is determined based on the one or more determined lengths of the one or more axes of the one or more regions of low density non-calcified plaque.

Embodiment 69: The system of Embodiment 67, wherein a determination of the volume of the one or more regions of low density non-calcified plaque above a predetermined threshold is indicative of unstable plaque or high risk of CAD.

Embodiment 70: The system of Embodiment 67, wherein a determination of the volume of the one or more regions of plaque above a predetermined threshold is indicative of unstable plaque or high risk of CAD.

Embodiment 71: The system of Embodiment 67, wherein a determination of the ratio of the volume of the one or more regions of low density non-calcified plaque to the volume of the one or more regions of plaque above a predetermined threshold is indicative of unstable plaque or high risk of CAD.

Embodiment 72: The system of Embodiment 41, wherein the density comprises absolute density.

Embodiment 73: The system of Embodiment 41, wherein the density comprises radiodensity.

Embodiment 74: The system of Embodiment 73, wherein the one or more regions of plaque are identified as low density non-calcified plaque when a radiodensity value is between about −189 and about 30 Hounsfield units.

Embodiment 75: The system of Embodiment 73, wherein the one or more regions of plaque are identified as non-calcified plaque when a radiodensity value is between about 31 and about 350 Hounsfield units.

Embodiment 76: The system of Embodiment 73, wherein the one or more regions of plaque are identified as calcified plaque when a radiodensity value is between about 351 and 2500 Hounsfield units.

Embodiment 77: The system of Embodiment 41, wherein the medical image comprises a Computed Tomography (CT) image.

Embodiment 78: The system of Embodiment 41, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 79: The system of Embodiment 41, wherein the system is further caused to generate an assessment of risk of CAD of the subject or risk of the one or more regions of plaque based at least in part on the analysis of the one or more regions of low density non-calcified plaque.

Embodiment 80: The system of Embodiment 79, wherein the system is further caused to generate a recommended treatment for the subject based at least in part on the analysis of the one or more regions of low density non-calcified plaque.

Unfolding of a Vessel

As discussed herein, disclosed herein are systems, methods, and devices for cardiovascular risk and/or disease state assessment using image-based analyses. In particular, in some embodiments, the systems, devices, and methods are related to cardiovascular risk and/or disease state assessment using image-based analysis of vessel surface and/or coordinates of related features. In some embodiments, assessment of cardiovascular risk and/or disease state generated using the systems, methods, and devices herein can be utilized to diagnose and/or generate a proposed treatment for a patient. As such, in some embodiments, the systems, devices, and methods described herein are able to provide physicians and/or patients specific quantified and/or measured data relating to a patient's plaque that do not exist today. For example, in some embodiments, the system can provide a specific numerical value for the volume of stable and/or unstable plaque, the ratio thereof against the total vessel volume, percentage of stenosis, and/or the like, using for example radiodensity values of pixels and/or regions within a medical image. In some embodiments, such detailed level of quantified plaque parameters from image processing and downstream analytical results can provide more accurate and useful tools for assessing the health and/or risk of patients in completely novel ways.

In some embodiments, the systems, devices, and methods described herein can be configured to unfold a generally cylindrical blood vessel, such as a coronary artery, carotid artery, and/or any other blood vessel for example, and flatten out the vessel for further analysis. In other words, in some embodiments, the system is configured to computationally flatten or unfold a generally cylindrical blood vessel, for example using one or more graphical or image-analysis techniques. By doing so, in some embodiments, the system can more easily, more accurately, and/or more quickly evaluate, analyze, and/or diagnose a state or profession of cardiovascular disease, such as plaque or atherosclerosis, and/or use the same for disease tracking and/or treatment purposes. In particular, by flattening out unfolding a generally cylindrical blood vessel, in some embodiments, the system can be configured to expose one or more regions of plaque internal to the vessel. In some embodiments, the exposed part or portion of the plaque can be used to determine the risk of myocardial infarction (MI), ischemia, rapid plaque progression, medication plaque non-responsiveness, need for a stent, need for bypass grafting, and/or the like.

Figure 10A:
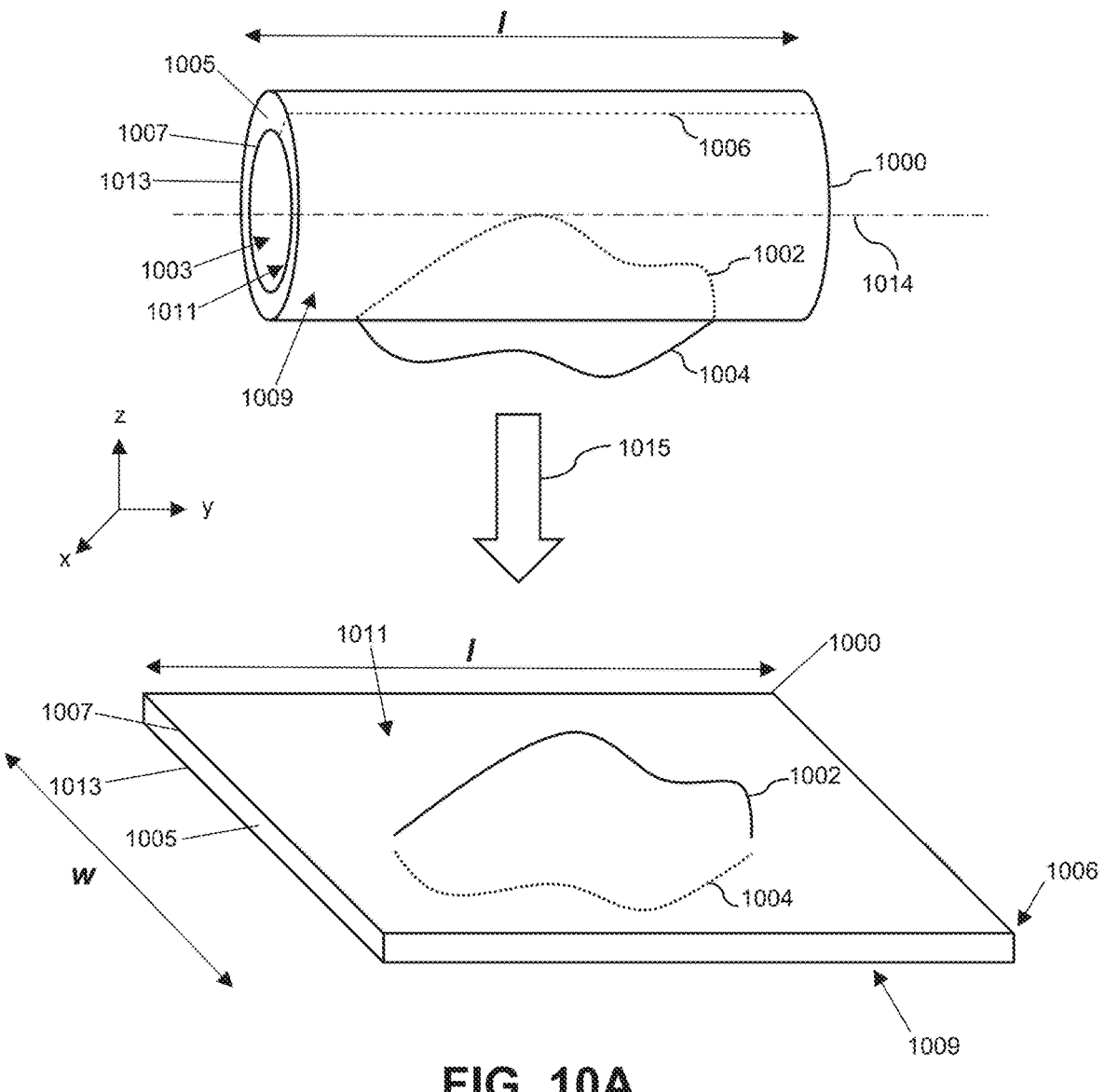
FIG. 10A is a schematic illustrating an example embodiment(s) of systems, methods, and devices for cardiovascular risk and/or disease state assessment using image-based analysis of vessel surface and/or coordinates.

FIG. 10A is a schematic illustrating an example embodiment(s) of systems, methods, and devices for cardiovascular risk and/or disease state assessment using image-based analysis of vessel surface and/or coordinates. As illustrated in the example of FIG. 10A, the system can be configured to unfold or flatten an otherwise generally cylindrical tube of the vessel 1000 to be viewed as a rectangle 1008. More specifically, in some embodiments, the system is configured to identify a generally cylindrical blood vessel 1000, which can include one or more regions of plaque 1002, 1004. In some instances, plaque can be positioned internal to the lumen 1003 (e.g., plaque 1002). In some instances, plaque can be positioned external to the lumen 1003 (e.g., plaque 1004), either inside the vessel wall 1005, or positioned adjacent to the exterior vessel wall 1009 and external to the vessel 1000. In some instances when the plaque is in the vessel wall, the plaque causes the vessel wall to protrude into the lumen. For example, protrude into at least a portion of the space where the lumen would be if not for the plaque causing the vessel wall to extend into that space. In some embodiments, the system can be configured to unfold or flatten the generally cylindrical tube of a vessel 1000 along a hypothetical cut line 1006 that is generally parallel to the longitudinal axis of the vessel 1000, e.g., a hypothetical cut line 1006 that is in a plane that also contains the longitudinal vessel 1000. In some embodiments, for example for ease of processing, prior to the unfolding or flattening of a vessel, the system is configured to generate a straightened representation of an otherwise curvilinear vessel, and process the straightened representation to unfold or flatten the vessel. In an example, the width w of the representation can be the circumference of the vessel, and the length l can be the length of the representation can be the portion of the vessel being evaluated.

In some embodiments, by unfolding the vessel, the system can be configured to view and/or display the internal of a vessel as flat or rectangular view (representation)1008 on a user interface of a display screen, for example, a graphical user display (GUI). In some embodiments, the system can be configured to display the flat or rectangular representation in a three-dimensional (3D) view. In some embodiments, the system can be configured to rotate the 3D view in a 360° manner to allow a medical practitioner to better view and evaluate the plaque. In some embodiments, by doing so, some of the plaque 1002 can be exposed, while some of the plaque 1004 may not be exposed. For example, in some embodiments, regions of plaque facing the internal lumen of the vessel 1002 can be exposed, while regions of plaque 1004 facing outwards of the lumen 1003 may not be exposed. In some embodiments, by flattening or unfolding a cylindrical vessel 1000, the system can be configured to utilize a cartesian or other coordinate system to characterize the surface area of plaque and/or the location and/or position of different components within a region of plaque, which can be used to assess the risk and/or state of cardiovascular disease for a subject more accurately, faster, and/or using less processing power. In some embodiments, the system can be configured to display the flat or rectangular representation in a three-dimensional (3D) view. In some embodiments, the system can be configured to rotate the 3D view in a 360° manner to allow a medical practitioner to better view and evaluate the plaque that is exposed, or unexposed, by flattening the vessel.

In some embodiments, after unfolding or flattening a vessel, the system is configured to analyze different components of a region of plaque, such as for example low-density non-calcified plaque, non-calcified plaque, calcified plaque, and/or the like. In some embodiments, the location and/or position of such individual plaque components and/or the whole region of plaque itself can be analyzed by the system using one or more coordinate systems after flattening and/or unfolding of the vessel.

In some embodiments, by flattening or unfolding the cylindrical tube of the vessel as a rectangle, the system can be configured to visualize and/or analyze the exposed surface area in one or more ways. For example, in some embodiments, once unfolded, the system can be configured to analyze, identify, color, annotate, and/or otherwise graphically alter one or more of the following features: surface area of plaque or exposed plaque, surface area of plaque or exposed plaque compared to total internal surface area of vessel segment, thickness of vessel and/or plaque and/or ratio thereof, composition of plaque (e.g., low-density non-calcified plaque, calcified plaque, and/or non-calcified plaque), stenosis of vessel lumen, remodeling index, heterogeneity of plaque (e.g., as a function or combination of low-density non-calcified plaque, calcified plaque, and/or non-calcified plaque), surface irregularity, surface asymmetry, surface ulceration, depth to one or more plaque components (e.g., low-density non-calcified plaque, calcified plaque, and/or non-calcified plaque), and/or the like.

In some embodiments, the system can be configured to apply a coordinate system to the flattened or unfolded vessel to analyze plaque and/or individual plaque components. For example, in some embodiments, the system can be configured to utilize a cartesian coordinate system, polar coordinate system, cylindrical coordinate system, spherical coordinate system, homogeneous coordinate system, curvilinear coordinate system, log-polar coordinate system, Plücker coordinate system, generalized coordinate system, canonical coordinate system, barycentric coordinate system, and/or trilinear coordinate system.

In some embodiments, the system can be configured to utilize coordinates, such as cartesian coordinates, of plaque and/or individual plaque components to predict and/or assess risk and/or state of cardiovascular disease. In some embodiments, risk and/or disease state assessment can be dependent on the position of the plaque and/or plaque component relative to one or more of: one or more regions of fat, one or more other regions of plaque, vessel lumen, myocardium, myocardial side the of vessel, pericardium, pericardial side of the vessel, epicardial fat, epicardial fat side of the vessel, branch point, bifurcation, trifurcation, or distance from vessel ostium. In some embodiments, the system can be configured to utilize coordinates of plaque and/or plaque components to determine a Euclidian distance from one or more of the foregoing.

Location of Plaque Relative to Myocardium v. Epicardium

Figure 10B:
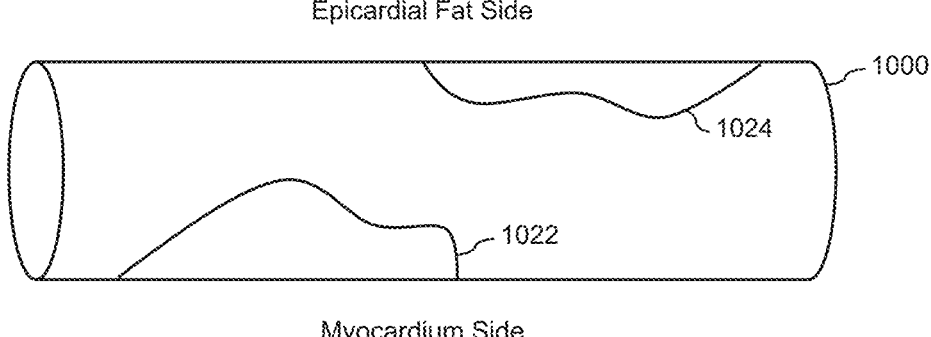
FIG. 10B is a schematic illustrating an example of one or more regions of plaque that are closer to the myocardium versus epicardium.

FIG. 10B is a schematic illustrating an example of one or more regions of plaque that are myocardial v. epicardial fat-adjacent. As illustrated in FIG. 10B, in some instances, plaque can be adjacent, proximal to, near, and/or closer to the myocardium v. epicardium, which can be indicative of risk of cardiovascular disease. For instance, in the example illustrated in FIG. 10B, a first region of plaque 1024 within a vessel 1000 can be adjacent, proximal to, near, and/or closer to the epicardial fat side, while a second region of plaque 1022 within the same vessel 1000 can be adjacent, proximal to, near, and/or closer to the myocardium side. In the illustrated example, the first region of plaque 1024 closer to the epicardial side be associated with a higher risk of disease compared to the second region of plaque 1022 closer to the myocardial side. As such, in some embodiments, the system can be configured to analyze the location of one or more regions of plaque and/or one or more components thereof, for example by mapping to a coordinate system after computationally unfolding a vessel, to determine the location and/or relative location of the region of plaque or a component thereof with respect to the epicardium and/or myocardium. In some embodiments, the analyzed location of the one or more regions of plaque and/or one or more components thereof can be used by the system to determine risk of cardiovascular disease.

Figure 10C:
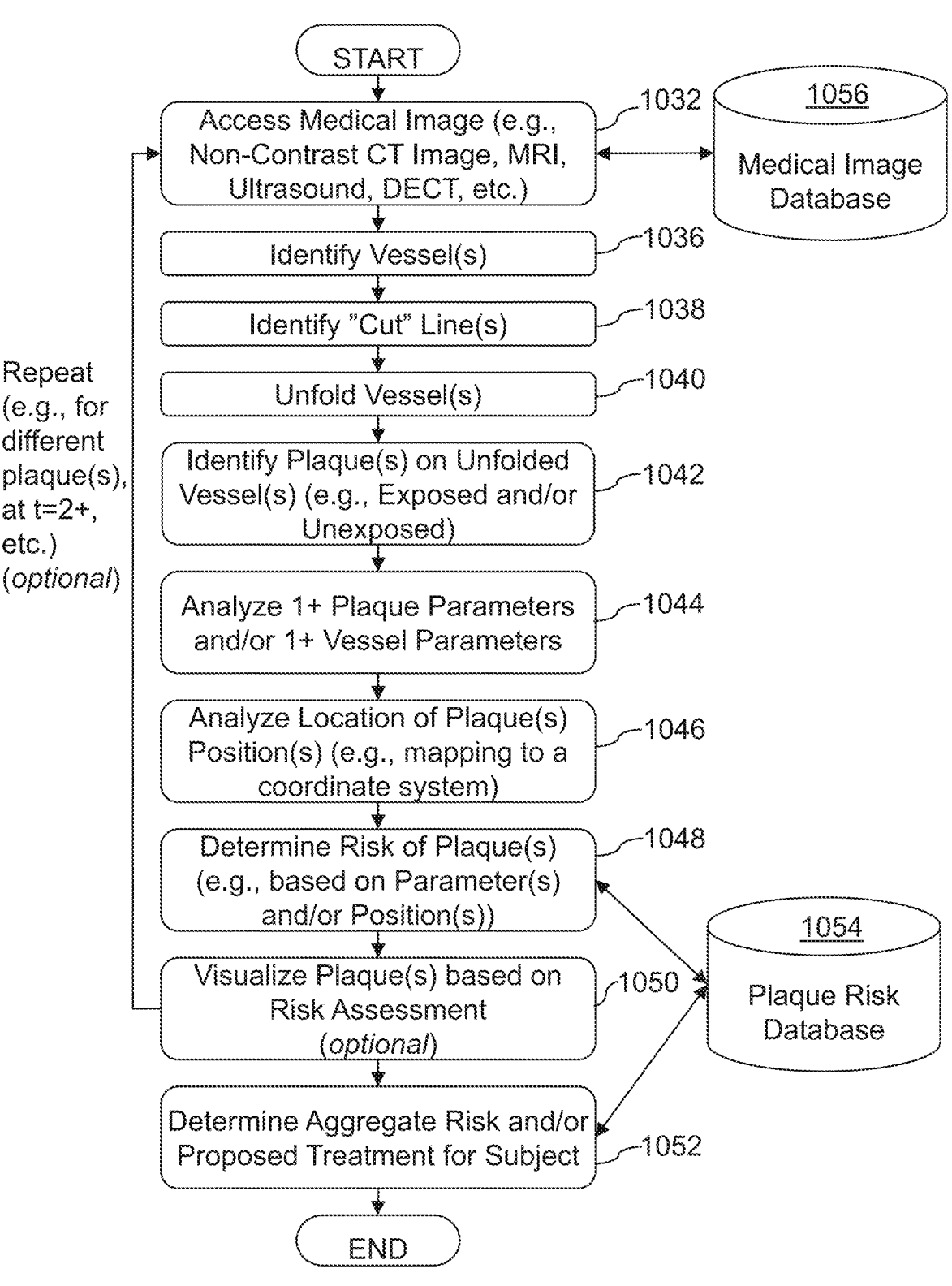
FIG. 10C is a flowchart illustrating an example embodiment(s) of systems, methods, and devices for cardiovascular risk and/or disease state assessment using image-based analysis of vessel surface and/or coordinates.

Cardiovascular Risk and/or Disease State Assessment Using Image-Based Analysis of Vessel Surface and/or Coordinates of Features FIG. 10C is a flowchart illustrating an example embodiment(s) of systems, methods, and devices for cardiovascular risk and/or disease state assessment using image-based analysis of vessel surface and/or coordinates.

As illustrated in FIG. 10C, in some embodiments, the system can be configured to access a medical image at block 1032. In some embodiments, the medical image can include one or more arteries, such as coronary, carotid, and/or other arteries of a subject. In some embodiments, the medical image can be stored in a medical image database 1056. In some embodiments, the medical image database 1056 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1036, the system can be configured to identify one or more vessels or arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1038, the system can be configured to identify a hypothetical and/or computational cut line for one or more vessels. In particular, in some embodiments the hypothetical cut line can be substantially parallel, perpendicular, and/or at another angle with respect to the longitudinal axis of a vessel. In some embodiments, prior to identifying the hypothetical cut line, the system can be configured to computationally straighten out a vessel into a substantially straight cylindrical vessel form. In some embodiments, the system can be configured to utilize one or more AI and/or ML algorithms to automatically and/or dynamically straighten a vessel and/or identify a cut line.

In some embodiments, at block 1040, the system can be configured to computationally unfold a vessel, for example along the hypothetical cut line. In some embodiments, at block 1042, the system can be configured to identify one or more regions of plaque on the unfolded vessel. For example, the one or more regions of plaque can be exposed on the unfolded vessel, which can mean that the plaque was internal to the vessel prior to unfolding. Also, in some instances, the one or more regions of plaque can be unexposed on the unfolded vessel, which can mean that the plaque was external to the vessel prior to unfolding. In some embodiments, the system can be configured to utilize one or more AI and/or ML algorithms to automatically and/or dynamically identify one or more plaques on an unfolded vessel.

In some embodiments, at block 1044, the system can be configured to analyze one or more plaque parameters and/or one or more vessel or vascular parameters. In some embodiments, the one or more vessel parameters and/or plaque parameters can comprise quantified parameters derived from the medical image. For example, in some embodiments, the system can be configured to utilize an AI and/or ML algorithm or other algorithm to determine one or more vessel parameters and/or plaque parameters. As another example, in some embodiments, the system can be configured to determine one or more vessel parameters, such as classification of arterial remodeling due to plaque, which can further include positive arterial remodeling, negative arterial remodeling, and/or intermediate arterial remodeling. In some embodiments, the classification of arterial remodeling is determined based on a ratio of the largest vessel diameter at a region of plaque to a normal reference vessel diameter of the same region which can be retrieved from a normal database. In some embodiments, the system can be configured to classify arterial remodeling as positive when the ratio of the largest vessel diameter at a region of plaque to a normal reference vessel diameter of the same region is more than 1.1. In some embodiments, the system can be configured to classify arterial remodeling as negative when the ratio of the largest vessel diameter at a region of plaque to a normal reference vessel diameter is less than 0.95. In some embodiments, the system can be configured to classify arterial remodeling as intermediate when the ratio of the largest vessel diameter at a region of plaque to a normal reference vessel diameter is between 0.95 and 1.1.

Further, as part of block 1044, in some embodiments, the system can be configured to determine a geometry and/or volume of one or more regions of plaque and/or one or more vessels or arteries. For example, the system can be configured to determine if the geometry of a particular region of plaque is round or oblong or other shape. In some embodiments, the geometry of a region of plaque can be a factor in assessing the stability of the plaque. As another example, in some embodiments, the system can be configured to determine the curvature, diameter, length, volume, and/or any other parameters of a vessel or artery from the medical image.

In some embodiments, as part of block 1044, the system can be configured to determine a volume and/or surface area of a region of plaque and/or a ratio or other function of volume to surface area of a region of plaque, such as for example a diameter, radius, and/or thickness of a region of plaque. In some embodiments, a plaque having a low ratio of volume to surface area can indicate that the plaque is stable. As such, in some embodiments, the system can be configured to determine that a ratio of volume to surface area of a region of plaque below a predetermined threshold is indicative of stable plaque.

In some embodiments, as part of block 1044, the system can be configured to determine a heterogeneity index of a region of plaque. For instance, in some embodiments, a plaque having a low heterogeneity or high homogeneity can indicate that the plaque is stable. As such, in some embodiments, the system can be configured to determine that a heterogeneity of a region of plaque below a predetermined threshold is indicative of stable plaque. In some embodiments, heterogeneity or homogeneity of a region of plaque can be determined based on the heterogeneity or homogeneity of radiodensity values within the region of plaque. As such, in some embodiments, the system can be configured to determine a heterogeneity index of plaque by generating spatial mapping, such as a three-dimensional histogram, of radiodensity values within or across a geometric shape or region of plaque. In some embodiments, if a gradient or change in radiodensity values across the spatial mapping is above a certain threshold, the system can be configured to assign a high heterogeneity index. Conversely, in some embodiments, if a gradient or change in radiodensity values across the spatial mapping is below a certain threshold, the system can be configured to assign a low heterogeneity index.

In some embodiments, as part of block 1044, the system can be configured to determine a radiodensity of plaque and/or a composition thereof. For example, a high radiodensity value can indicate that a plaque is highly calcified or stable, whereas a low radiodensity value can indicate that a plaque is less calcified or unstable. As such, in some embodiments, the system can be configured to determine that a radiodensity of a region of plaque above a predetermined threshold is indicative of stable stabilized plaque. In addition, different areas within a region of plaque can be calcified at different levels and thereby show different radiodensity values. As such, in some embodiments, the system can be configured to determine the radiodensity values of a region of plaque and/or a composition or percentage or change of radiodensity values within a region of plaque. For instance, in some embodiments, the system can be configured to determine how much or what percentage of plaque within a region of plaque shows a radiodensity value within a low range, medium range, high range, and/or any other classification.

Similarly, in some embodiments, as part of block 1044, the system can be configured to determine a ratio of radiodensity value of plaque to a volume of plaque. For instance, it can be important to assess whether a large or small region of plaque is showing a high or low radiodensity value. As such, in some embodiments, the system can be configured to determine a percentage composition of plaque comprising different radiodensity values as a function or ratio of volume of plaque.

In some embodiments, as part of block 1044, the system can be configured to determine the diffusivity and/or assign a diffusivity index to a region of plaque. For example, in some embodiments, the diffusivity of a plaque can depend on the radiodensity value of plaque, in which a high radiodensity value can indicate low diffusivity or stability of the plaque.

In some embodiments, at block 1046, the system can be configured to analyze the location and/or position of one or more regions of plaque and/or one or more components thereof, such as for example low-density non-calcified plaque, calcified plaque, and/or non-calcified plaque. For example, in some embodiments, the system can be configured to analyze the location and/or position of one or more regions of plaque and/or components thereof by mapping to a coordinate system and/or by determining its Euclidian distance. For example, in some embodiments, the system can be configured to utilize a cartesian coordinate system, polar coordinate system, cylindrical coordinate system, spherical coordinate system, homogeneous coordinate system, curvilinear coordinate system, log-polar coordinate system, Plücker coordinate system, generalized coordinate system, canonical coordinate system, barycentric coordinate system, and/or trilinear coordinate system.

In some embodiments, at block 1048, the system can be configured to determine and/or generate a risk and/or disease state assessment of one or more regions of plaque with respect to cardiovascular disease. For example, in some embodiments, the system can be configured to determine and/or generate a risk and/or disease state assessment of one or more regions of plaque based on one or more vessel and/or plaque parameters and/or position or location of one or more regions of plaque and/or components thereof as discussed herein. In some embodiments, the system can be configured to utilize one or more AI and/or ML algorithms to automatically and/or dynamically determine and/or generate a risk and/or disease state assessment of one or more regions of plaque with respect to cardiovascular disease. In some embodiments, the system can be configured to determine and/or generate a cardiovascular disease risk and/or state assessment of one or more regions of plaque by comparison and/or based on analysis of one or more previous analyses, which can be stored for example on a plaque risk database 1054. In some embodiments, the plaque risk database 1054 can be locally accessible by the system and/or can be located remotely and accessible through a network connection.

In some embodiments, the system can be configured to graphically visualize one or more regions of plaque, components thereof, and/or vessel features at block 1050. For example, the graphical representation can depend on the generated cardiovascular risk and/or disease state assessment. As an illustrative example, the system can be configured to analyze, identify, color, annotate, and/or otherwise graphically alter one or more of the following features: surface area of plaque or exposed plaque, surface area of plaque or exposed plaque compared to total internal surface area of vessel segment, thickness of vessel and/or plaque and/or ratio thereof, composition of plaque (e.g., low-density non-calcified plaque, calcified plaque, and/or non-calcified plaque), stenosis of vessel lumen, remodeling index, heterogeneity of plaque (e.g., as a function or combination of low-density non-calcified plaque, calcified plaque, and/or non-calcified plaque), surface irregularity, surface asymmetry, surface ulceration, depth to one or more plaque components (e.g., low-density non-calcified plaque, calcified plaque, and/or non-calcified plaque), and/or the like. In generating a graphical representation or visualization, in some embodiments, the system can be configured to assign to one or more components or features one or more of color, shading, translucency, three-dimensional annotation, or partial translucency.

In some embodiments, at block 1052, the system can be configured to determine an aggregate cardiovascular risk and/or disease state for a subject based at least in part on the determined risk and/or disease state of one or more regions of plaque. For example, in some embodiments, the system can be configured to generate a weighted average or weighted combination or measure of all or some of the generated cardiovascular disease risks of the one or more regions of plaque. In some embodiments, the generated risk score can be based at least in part on an atherosclerotic cardiovascular disease (ASCVD) risk score. For example, an ASCVD risk score can be determined based on patient information, and then generated risk score can be based in part on the ASCVD risk score. There can be various ways to determine an ASCVD risk score, including using/weighting various patient information to determine an overall ASCVD risk score. In an example, patient information used to determine the ASCVD risk score can include, but is not limited to, age, gender, race, systolic blood pressure, diastolic blood pressure, total cholesterol, high-density lipoprotein (HDL) cholesterol, low-density lipoprotein (LDL) cholesterol, history of diabetes, whether a current or past smoker, hypertension, and/or current medication (e.g., on a statin or aspirin therapy). In an example, the American College of Cardiology indicates use of some or all of this information to determine an ASCVD risk score. In some embodiments, a ASCVD risk score can considered Low-risk if <5%, Borderline risk if 5% to 7.4%, Intermediate risk if 7.5% to 19.9%, and High risk if above 20%. In some embodiments, a current patient's aggregate cardiovascular risk and/or disease state for a subject can be based in part on an ASCVD risk score that is compared to other patients' ASCVD risk scores and outcomes (e.g., that are stored in a database).

In some embodiments, the system can be configured to determine and/or generate a proposed treatment for the subject based at least in part on the determined risk and/or disease state of one or more regions of plaque. In some embodiments, the system can be configured to determine and/or generate a proposed treatment for the subject based at least in part on the aggregate cardiovascular risk and/or disease state for the subject.

In some embodiments, the system can be configured to determine and/or generate an aggregate cardiovascular disease risk and/or state assessment and/or proposed treatment for the subject by comparison and/or based on analysis of one or more previously analyses, which can be stored for example on a plaque risk database 1054. In some embodiments, the plaque risk database 1054 can be locally accessible by the system and/or can be located remotely and accessible through a network connection.

In some embodiments, the system can be configured to repeat one or more processes described in relation to flowchart blocks 1032-1052, for example for one or more other regions of plaque and/or other subjects and/or for the same subject at a different time. As such, in some embodiments, the system can provide for longitudinal disease tracking and/or personalized treatment for a subject.

Computer System

Figure 10D:
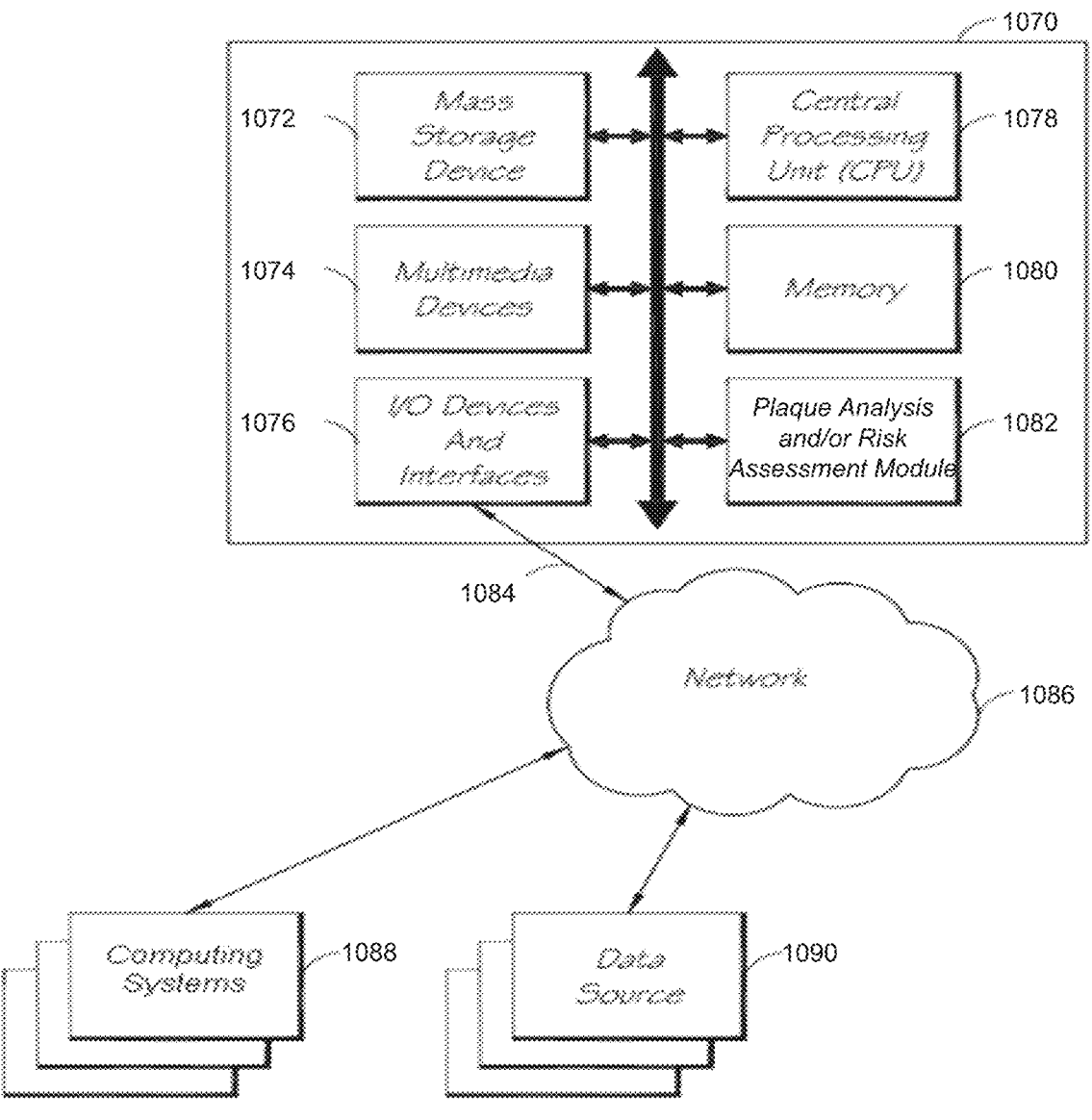
FIG. 10D is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 10D. The example computer system 1070 is in communication with one or more computing systems 1088 and/or one or more data sources 1090 via one or more networks 1086. While FIG. 10D illustrates an embodiment of a computing system 1070, it is recognized that the functionality provided for in the components and modules of computer system 1070 can be combined into fewer components and modules, or further separated into additional components and modules.

The computer system 1070 can comprise a Plaque Analysis and/or Risk Assessment Module 1082 that carries out the functions, methods, acts, and/or processes described herein. The Plaque Analysis and/or Risk Assessment Module 1082 executed on the computer system 1070 by a central processing unit 1078 discussed further below. Other features of the computer system 1070 can be similar to corresponding features of the computer system of FIG. 9G, described above.

Certain Examples of Embodiments Related to Unfolding of a Vessel

The following are non-limiting examples of certain embodiments of systems and methods for analyzing a vessel by unfolding the vessel and characterization of plaque parameters and vessel parameters, and/or other related features. Other embodiments may include one or more other features, or different features, that are discussed herein.

Embodiment 1: A computer-implemented method of assessing a state of cardiovascular disease for a subject based on multi-dimensional information derived from non-invasive medical image analysis, the method comprising: accessing, by a computer system, a medical image of a subject, wherein the medical image of the subject is obtained non-invasively; analyzing, by the computer system, the medical image of the subject to identify one or more arteries, wherein the one or more arteries comprise one or more regions of plaque; identifying, by the computer system, a hypothetical cut line along the one or more arteries, wherein the hypothetical cut line is substantially parallel to a longitudinal axis of the one or more arteries; computationally unfolding, by the computer system, the one or more arteries along the hypothetical cut line; identifying, by the computer system, one or more regions of plaque on the computationally unfolded one or more arteries; identifying, by the computer system, one or more regions of exposed plaque among the one or more regions of plaque on the computationally unfolded one or more arteries; analyzing, by the computer system, the one or more regions of exposed plaque to determine one or more plaque parameters and one or more vessel parameters, wherein the one or more plaque parameters comprises one or more of surface area of plaque, thickness of plaque, composition of plaque, heterogeneity of plaque, or depth to a plaque component, and wherein the one or more vessel parameters comprises one or more of surface area of vessel wall, thickness of vessel wall, stenosis of vessel lumen, remodeling index, surface irregularity, surface asymmetry, or surface ulceration; mapping, by the computer system, the one or more regions of exposed plaque and the computationally unfolded one or more arteries to a coordinate system; analyzing, by the computer system, a position of the one or more regions of exposed plaque based at least in part on the mapping of the one or more regions of exposed plaque and the computationally unfolded one or more arteries to a coordinate system; generating, by the computer system, an assessment of a cardiovascular disease state of the one or more regions of exposed plaque based at least in part on the determined one or more plaque parameters, one or more vessel parameters, and analyzed position of the one or more regions of exposed plaque, wherein the computer system comprises a computer processor and an electronic storage medium.

Embodiment 2: The computer-implemented method of Embodiment 1, wherein the medical image is obtained using an imaging technique comprising one or more of computed tomography (CT), x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 3: The computer-implemented method of Embodiment 1, wherein the hypothetical cut line is identified on a straightened view of the one or more arteries.

Embodiment 4: The computer-implemented method of Embodiment 1, wherein the one or more regions of plaque comprise the one or more regions of exposed plaque and one or more regions of unexposed plaque.

Embodiment 5: The computer-implemented method of Embodiment 1, wherein the coordinate system comprises one or more of a cartesian coordinate system, polar coordinate system, cylindrical coordinate system, spherical coordinate system, homogeneous coordinate system, curvilinear coordinate system, log-polar coordinate system, Plücker coordinate system, generalized coordinate system, canonical coordinate system, barycentric coordinate system, or trilinear coordinate system.

Embodiment 6: The computer-implemented method of Embodiment 1, further comprising: determining, by the computer system, one or more plaque to vessel parameters, the one or more plaque to vessel parameters comprising one or more of a ratio of surface area of plaque to surface area of vessel or a ratio of thickness of plaque to thickness of vessel; and generating, by the computer system, the cardiovascular risk assessment of the subject further based at least in part on the determined one or more plaque to vessel parameters.

Embodiment 7: The computer-implemented method of Embodiment 1, wherein the heterogeneity of plaque is determined by identifying one or more components of plaque within a region of plaque, wherein the one or more components of plaque comprise one or more of low density non-calcified plaque, calcified plaque, or non-calcified plaque.

Embodiment 8: The computer-implemented method of Embodiment 1, wherein the plaque component comprises one or more of low density non-calcified plaque, calcified plaque, or non-calcified plaque.

Embodiment 9: The computer-implemented method of Embodiment 1, wherein the position of the one or more regions of exposed plaque is determined as a Euclidian distance from one or more locations of interest.

Embodiment 10: The computer-implemented method of Embodiment 1, wherein the position of the one or more regions of exposed plaque is determined in relation to one or more of one or more regions of fat, one or more other regions of plaque, vessel lumen, myocardium, myocardial side the of vessel, pericardium, pericardial side of the vessel, epicardial fat, epicardial fat side of the vessel, branch point, bifurcation, trifurcation, or distance from vessel ostium.

Embodiment 11: The computer-implemented method of Embodiment 10, wherein a higher risk is assessed for one or more regions of exposed plaque that is adjacent to the epicardial side of the vessel compared to one or more regions of exposed plaque that is adjacent to the myocardial side of the vessel.

Embodiment 12: The computer-implemented method of Embodiment 1, further comprising generating a graphical representation of the one or more regions of exposed plaque based on the generated cardiovascular disease risk assessment of the one or more regions of exposed plaque.

Embodiment 13: The computer-implemented method of Embodiment 1, wherein generating the graphical representation comprises assigning one or more of color, shading, translucency, three-dimensional annotation, or partial translucency.

Embodiment 14: The computer-implemented method of Embodiment 1, further comprising generating a graphical representation of one or more components within the one or more regions of exposed plaque based on the generated cardiovascular disease risk assessment of the one or more regions of exposed plaque.

Embodiment 15: The computer-implemented method of Embodiment 1, wherein the cardiovascular disease risk assessment of the one or more regions of exposed plaque is generated by utilizing an artificial intelligence or machine learning algorithm based on prior subject image analysis data.

Embodiment 16: The computer-implemented method of Embodiment 1, further comprising generating, by the computer system, cardiovascular disease risk assessment of all regions of exposed plaque within a vessel segment.

Embodiment 17: The computer-implemented method of Embodiment 16, further comprising generating a cardiovascular disease risk assessment of the subject by combining the generated cardiovascular disease risk assessment of all regions of exposed plaque within the vessel segment.

Embodiment 18: The computer-implemented method of Embodiment 17, wherein the cardiovascular disease risk assessment of the subject is generated based at least in part on comparison to a database of previously generated cardiovascular disease risk assessments of other subjects.

Embodiment 19: The computer-implemented method of Embodiment 16, further comprising generating a proposed treatment for the subject by combining the generated cardiovascular disease risk assessment of all regions of exposed plaque within the vessel segment.

Embodiment 20: The computer-implemented method of Embodiment 19, wherein the proposed treatment for the subject is generated based at least in part on comparison to a database of previously proposed treatments of other subjects.

Types of Plaque Composition and Non-Calcium Score Introduction

Disclosed herein are systems, methods, and devices for cardiovascular risk and/or state assessment using image-based analyses. In some embodiments, the systems, devices, and methods are related to cardiovascular risk and/or disease and/or state assessment using image-based analysis of one or more regions and/or features of non-calcified plaque and/or calcified plaque. In some embodiments, assessment of cardiovascular risk and/or disease and/or state generated using the systems, methods, and devices herein can be utilized to diagnose and/or generate a proposed treatment for a patient.

As such, in some embodiments, the systems, devices, and methods described herein are able to provide physicians and/or patients specific quantified and/or measured data relating to a patient's plaque that do not exist today. For example, in some embodiments, the system can provide a specific numerical value for the volume of stable and/or unstable plaque, the ratio thereof against the total vessel volume, percentage of stenosis, and/or the like, using for example radiodensity values of pixels and/or regions within a medical image. In some embodiments, such detailed level of quantified plaque parameters from image processing and downstream analytical results can provide more accurate and useful tools for assessing the health and/or risk of patients in completely novel ways.

As discussed herein, disclosed herein are systems, methods, and devices for cardiovascular risk and/or disease state assessment using image-based analyses. In particular, in some embodiments, the systems, devices, and methods are related to cardiovascular risk and/or disease state assessment using image-based analysis of one or more regions and/or features of non-calcified plaque and/or calcified plaque. In some embodiments, assessment of cardiovascular risk and/or disease and/or state generated using the systems, methods, and devices herein can be utilized to diagnose and/or generate a proposed treatment for a patient.

In particular, in some embodiments, the systems, devices, and methods described herein can be configured to identify and/or analyze one or more regions of non-calcified plaque. Generally speaking, a region of plaque can be classified as non-calcified and/or calcified. In some embodiments, the system can be configured to identify and/or classify one or more regions of plaque as calcified and/or non-calcified. In some embodiments, within non-calcified plaque, the system can be configured to further classify certain non-calcified plaque as low-density non-calcified plaque. As described herein, generally speaking, non-calcified plaque can be considered more dangerous, while calcified plaque can be considered more stable. In other words, in some embodiments, the system can be configured to characterize non-calcified plaque as unstable plaque, while calcified plaque as stable plaque, as non-calcified plaque is the type of plaque that can rupture or cause sudden myocardial infarction heart attack, whereas non-calcified plaque can remain stable without causing a heart attack.

In some embodiments, as part of quantitative phenotyping, the system can be configured to identify and/or characterize different types and/or regions of plaque, for example based on density, absolute density, material density, relative density, and/or radiodensity. For example, in some embodiments, the system can be configured to characterize a region of plaque into one or more sub-types of plaque. For example, in some embodiments, the system can be configured to characterize a region of plaque as one or more of low density non-calcified plaque, non-calcified plaque, or calcified plaque. In some embodiments, calcified plaque can correspond to plaque having a highest density range, low density non-calcified plaque can correspond to plaque having a lowest density range, and non-calcified plaque can correspond to plaque having a density range between calcified plaque and low density non-calcified plaque. For example, in some embodiments, the system can be configured to characterize a particular region of plaque as low density non-calcified plaque when the radiodensity of an image pixel or voxel corresponding to that region of plaque is between about −189 and about 30 Hounsfield units (HU). In some embodiments, the system can be configured to characterize a particular region of plaque as non-calcified plaque when the radiodensity of an image pixel or voxel corresponding to that region of plaque is between about 31 and about 350 HU. In some embodiments, the system can be configured to characterize a particular region of plaque as calcified plaque when the radiodensity of an image pixel or voxel corresponding to that region of plaque is between about 351 and about 2500 HU.

In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

In some embodiments, the system can be configured to determine and/or characterize the burden of atherosclerosis based at least in part on volume of plaque. In some embodiments, the system can be configured to analyze and/or determine total volume of plaque and/or volume of low-density non-calcified plaque, non-calcified plaque, and/or calcified plaque. In some embodiments, the system can be configured to perform phenotyping of plaque by determining a ratio of one or more of the foregoing volumes of plaque, for example within an artery, lesion, vessel, and/or the like.

Despite the risks associated with non-calcified plaque, certain techniques focus more on features of calcified plaque as opposed to non-calcified plaque. For example, in some instances, calcium scores can be used as a marker for assessing the state of cardiovascular health or disease for a subject. In an example, a coronary artery calcium score is a determination or measurement of the amount of calcium in the walls of the arteries that supply the heart muscle. Traditionally, calcium scores have been used to estimate the risk of a heart attack or stroke, for example, in the next 5-10 years. There are many technical shortcomings, however, of focusing solely on calcium scores. For one, a high or increased calcium score alone is not representative of any specific cause, either positive or negative. Rather, in general, there can be various possible causes for a high or increased calcium score. For example, in some cases, a high or increased calcium score can be an indicator of significant heart disease and/or that the patient is at increased risk of a heart attack. Also, in some cases, a high or increased calcium score can be an indicator that the patient is increasing the amount of exercise performed, because exercise can convert fatty material plaque within the artery vessel. In some cases, a high or increased calcium score can be an indicator of the patient beginning a statin regimen wherein the statin is converting the fatty material plaque into calcium. Further, even if quantitative image-based techniques are used, merely focusing on calcified plaque alone may not provide an accurate assessment of state of cardiovascular disease for similar reasons.

As such, to address such technical shortcomings, in some embodiments described herein, the systems, devices, and methods are configured to assess cardiovascular risk and/or disease state using image-based analysis of one or more regions and/or features of non-calcified plaque and/or calcified plaque.

Figure 11A:
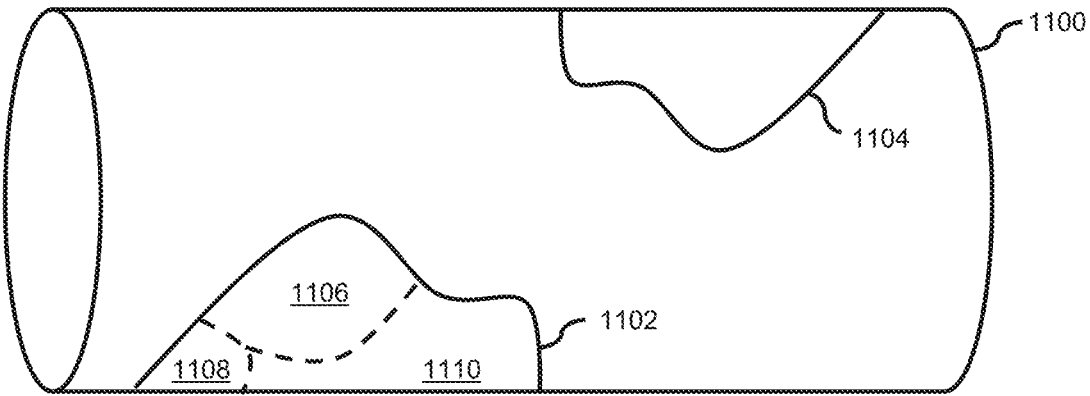
FIG. 11A is a schematic illustrating an example of one or more regions of calcified and/or non-calcified plaque that can be analyzed using image analysis processes by one or more embodiments of the systems, methods, and devices herein for assessment of cardiovascular risk, disease, and/or state.

For example, FIG. 11A is a schematic illustrating an example of one or more regions of calcified and/or non-calcified plaque that can be analyzed using image analysis processes by one or more embodiments of the systems, methods, and devices herein for assessment of cardiovascular risk, disease, and/or state. As illustrated in FIG. 11A, in some embodiments, the systems, methods, and devices described herein can be configured to identify one or more regions of plaque 1102, 1104 within an artery or vessel 1100. In some embodiments, the one or more regions of plaque 1102 can further comprise one or more regions and/or types and/or compositions of plaque 1106, 1108, 1110. In some embodiments, the one or more regions of plaque 1104 can comprise a single type or composition of plaque. In some embodiments, a region of plaque 1102, 1104, 1106, 1108, 1110 can be composed of one or more different types or compositions of plaque. For example, in some embodiments, the system can be configured to analyze, characterize, and/or classify plaque into one of three types: (i) low-density non-calcified plaque, (ii) non-calcified plaque, and (iii) calcified plaque. In some embodiments, the system can be configured to analyze, characterize, and/or classify plaque into one of two types: (i) non-calcified plaque, and (ii) calcified plaque. In some embodiments, the system can be configured to analyze, characterize, and/or classify plaque into one of any number of different types, such as, for example, 1, 2, 3, 4, 5, 6, 7, 8, 9, 10, 15, 20, 25, and/or 30 different types of classifications of plaque. Accordingly, in an example, each of the one or more regions of plaque can be determined to be composed of low-density non-calcified plaque, non-calcified plaque, or calcified plaque. In another example, each of the one or more regions of plaque can be determined to be composed of non-calcified plaque or calcified plaque. In another example, each of the one or more regions of plaque can be determined to be composed of one of a number of different types pf plaque (e.g., 1, 2, 3, or more different types of plaque). In some embodiments, the system can be configured to analyze, characterize, and/or classify plaque into a number of different types within a ranges of defined by two of the aforementioned values of radiodensity of an image pixel or voxel corresponding to that region of plaque.

In some embodiments, the system can be configured to analyze, characterize, and/or classify plaque based on one or more plaque parameters or characteristics. For example, one or more such plaque parameters can include plaque density, radiodensity, location, volume, surface area, geometry, heterogeneity, diffusivity, or ratio between volume and surface area, among others. In an example, radiodensity is determined by the density of information from a medical image. In an example, plaque density is determined based on where radiodensity values are relative to thresholds, e.g., predetermined thresholds. In an example, plaque location relates to one or more characterizations of the plaque location, e.g., proximal vs. middle vs. distal, myocardial vs. pericardial facing, at bifurcation or trifurcation vs. not at bifurcation or trifurcation, plaque location in main vessel vs. branch vessel, and the like. The system can determine plaque volume, surface area, geometry and/or ratio between volume and surface area based on the pixels or voxels identified to be plaque, or a region of plaque, in one or more of the evaluated patient images. In some embodiments, heterogeneity of plaque, or a region of plaque, can be determined by the radiodensity values in a plaque region, for example, the consistency and/or range of radiodensity values in a plaque region. In some embodiments, diffusivity plaque density relates to characterizing the "spread" of the density of plaque in a region. Some of the plaque parameters are determined directly from characterization of the plaque In some embodiments, the system can be configured to utilize one or more image processing, machine learning, and/or artificial intelligence techniques to analyze a medical image to derive one or more such plaque parameters, which can be used to classify plaque. For example, in some embodiments, the system can be configured to classify a particular region of plaque as non-calcified plaque and/or low-density non-calcified plaque if a density or radiodensity value of a pixel representing plaque is lower than a predetermined threshold and/or within a predetermined range. Similarly, in some embodiments, the system can be configured to classify a particular region of plaque as calcified plaque if a density or radiodensity value of a pixel representing plaque is higher than a predetermined threshold and/or within a predetermined range.

In some embodiments, the system can be configured to analyze a medical image to determine one or more other parameters, such as for example vascular parameters and/or relational parameters between plaque and/or vascular parameters. In particular, in some embodiments, vascular parameters can include one or more of vascular volume, diameter, area, cross-sectional area, surface area, length, location, and/or remodeling (e.g., a remodeling index). In some embodiments, relational parameters can include a ratio of surface area of plaque to surface of vessel, ratio of volume of plaque to volume of vessel, and/or a ratio of thickness of plaque to thickness of vessel.

In some embodiments, the system can be configured to analyze one or more plaque parameters of non-calcified and/or calcified plaque and/or any other type or classification of plaque, one or more vascular parameters, and/or one or more relational parameters to assess a risk or state of cardiovascular disease or health of a subject. For example, in some embodiments, the system can be configured to compare one or more plaque parameters, one or more vascular parameters, and/or one or more relational parameters to a reference value database comprising one or more plaque parameters, one or more vascular parameters, and/or one or more relational parameters derived from images of plaque of other subjects with varying states or risks of cardiovascular disease or health, including for example normal values. In some embodiments, based on such analysis of one or more plaque parameters, one or more vascular parameters, and/or one or more relational parameters, the system can be configured to generate an overall plaque score, non-calcified plaque score, non-calcium score, calcified plaque score, and/or calcium score. In some embodiments, the system can be configured to generate an overall plaque score, non-calcified plaque score, non-calcium score, calcified plaque score, and/or calcium score directly from one or more plaque parameters one or more vascular parameters, and/or one or more relational parameters. In some embodiments, the system can be configured to compare the generated overall plaque score, non-calcified plaque score, non-calcium score, calcified plaque score, and/or calcium score to a reference values database comprising one or more overall plaque scores, non-calcified plaque scores, non-calcium scores, calcified plaque scores, and/or calcium scores derived from a population of subjects with varying states of cardiovascular disease and/or health, including for example normal values.

In some embodiments, the system can be configured to assess the risk and/or state of cardiovascular disease or health based on the generated overall plaque score, non-calcified plaque score, non-calcium score, calcified plaque score, and/or calcium score and/or comparison thereof to a reference values database, including for example one or more reference values such as normal values. In some embodiments, a current patient's risk and/or disease state for a subject can be based in part on one or more of an age, gender, race, systolic blood pressure, diastolic blood pressure, total cholesterol, high-density lipoprotein (HDL) cholesterol, low-density lipoprotein (LDL) cholesterol, history of diabetes, whether a current or past smoker, hypertension, current medication, or an ASCVD risk score. In some embodiments, a current's patient's information relating to one or more of age, gender, race, systolic blood pressure, diastolic blood pressure, total cholesterol, high-density lipoprotein (HDL) cholesterol, low-density lipoprotein (LDL) cholesterol, history of diabetes, smoking history, hypertension, current medication, and/or an ASCVD risk score can be used to assess the risk and/or cardiovascular disease or health in addition to their plaque information. In some embodiments, in addition to their plaque information, a current's patient's information relating to one or more of age, gender, race, systolic blood pressure, diastolic blood pressure, total cholesterol, high-density lipoprotein (HDL) cholesterol, low-density lipoprotein (LDL) cholesterol, history of diabetes, smoking history, hypertension, current medication, and/or an ASCVD risk score can be compared to this information of other patients, and/or also their outcomes, to assess the risk and/or cardiovascular disease or health of their that is compared to other patients' ASCVD risk scores and outcomes (e.g., that are stored in a database). In some embodiments, the system can be configured to determine or generate a proposed treatment for the subject based on the assessed risk and/or state of cardiovascular disease or health. For example, the proposed treatment can include one or more of medical therapy (such as statins), interventional therapy (such as stent implantation), and/or lifestyle therapy (such as diet or exercise). In some embodiments, the system can be configured to track the efficacy of a treatment by tracking changes in the overall plaque score, non-calcified plaque score, non-calcium score, calcified plaque score, and/or calcium score, for example compared to a previously generated score for the same subject and/or change relative to a reference values database comprising one or more reference values, such as for example normal values.

As such, in some embodiments, the systems, devices, and methods described herein provide a quantitative and/or image-based solution for generating and/or tracking cardiovascular disease or health by analyzing one or more features of non-calcified and/or calcified plaques.

Figure 11B:
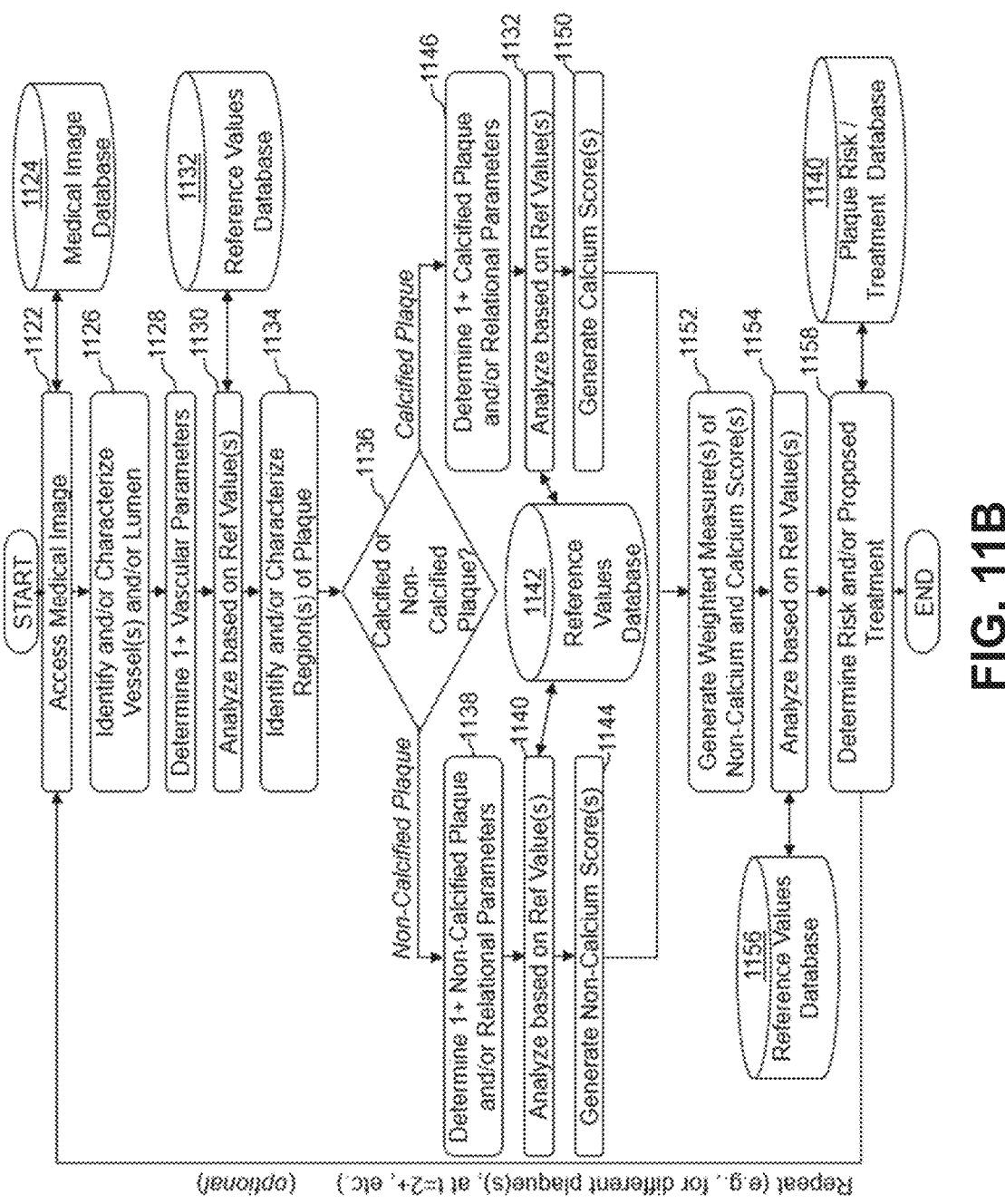
FIG. 11B is a flowchart illustrating an example embodiment of a system, device, and method for cardiovascular risk and/or disease state assessment using image-based analyses of non-calcified and/or calcified plaque.

Cardiovascular Risk and/or Disease State Assessment Using Image-Based Analysis of Calcified and/or Non-Calcified Plaque Features FIG. 11B is a flowchart illustrating an example embodiment(s) of systems, devices, and methods for cardiovascular risk and/or disease state assessment using image-based analyses of non-calcified and/or calcified plaque.

As illustrated in FIG. 11B, in some embodiments, the system can be configured to access a medical image at block 1122. In some embodiments, the medical image can include one or more arteries, such as coronary, carotid, and/or other arteries of a subject. In some embodiments, the medical image can be stored in a medical image database 1124. In some embodiments, the medical image database 1124 can be locally accessible by the system and/or can be located remotely and accessible through a network connection. The medical image can comprise an image obtained using one or more modalities, for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1126, the system can be configured to identify and/or characterize one or more vessels and/or lumen, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1128, the system can be configured to identify and/or determine one or more vascular parameters. In some embodiments, vascular parameters can include one or more of vascular volume, diameter, area, cross-sectional area, surface area, length, location, and/or remodeling. In some embodiments, the system can be configured to analyze the one or more vascular parameters at block 1130. For example, in some embodiments, the system can be configured to compare the one or more vascular parameters derived from the image to one or more reference values of vascular parameters, such as for example normal values. The one or more reference values of vascular parameters can be stored on a reference values database 1132, which can be locally accessible by the system and/or can be located remotely and accessible through a network connection.

In some embodiments, at block 1134, the system can be configured to identify and/or characterize one or more regions of plaque within the medical image. In some embodiments, the system can be configured to utilize one or more AI and/or ML algorithms to automatically and/or dynamically identify and/or characterize one or more regions of plaque using image processing. For example, in some embodiments, the one or more AI and/or ML algorithms can be trained using a Convolutional Neural Network (CNN) on a set of medical images on which one or more regions of plaque have been identified and/or characterized.

The set of medical images used for training the AI and/or ML algorithms ideally includes a large number of images in which regions of plaque have been identified and/or characterized. For example, at least hundreds of images, and more preferably thousands of images, tens of thousands images, hundreds of thousands of images, or more than hundreds of thousands of images (e.g., millions, tens of millions or more). The number of images used to train an AI and/or ML algorithm can increase over time to improve the AI and/or ML algorithm and increase the accuracy of the identification of regions of plaque and increase the accuracy of the characterization of regions of plaque. When trained, the AI and/or ML algorithm can automatically identify and/or characterize regions of plaque directly from a medical image of a subject based on using information in one or more images of the subject, for example, using a neural network trained for feature recognition and/or classification, or another type of AI or ML algorithm.

For example, in some embodiments, the system can be configured to analyze the density and/or radiodensity values and/or heterogeneity or distribution thereof of one or more pixels on a medical image to identify plaque and/or characterize plaque. More specifically, in some embodiments, the system can be configured to identify a particular pixel in an image of a patient as plaque, non-calcified plaque, low-density non-calcified plaque, and/or calcified plaque, and/or any other classification or type of plaque. In some embodiments, the system can be configured to classify a particular pixel or region of plaque as non-calcified plaque when the radiodensity value of the pixel is below a certain predetermined threshold, within a predetermined range, and/or comprises a heterogeneity index or distribution within, under, or above a particular predetermined range or threshold. In some embodiments, the system can be configured to classify a particular pixel or region of plaque as low-density non-calcified plaque when the radiodensity value of the pixel is below a certain predetermined threshold, within a predetermined range, and/or comprises a heterogeneity index or distribution within, under, or above a particular predetermined range or threshold. In some embodiments, the system can be configured to classify a particular pixel or region of plaque as calcified plaque when the radiodensity value of the pixel is above a certain predetermined threshold, within a predetermined range, and/or comprises a heterogeneity index or distribution within, under, or above a particular predetermined range or threshold.

In some embodiments, at block 1136, the system can be configured to determine whether a region of plaque, and/or a particular pixel corresponding to plaque, on the medical image should be classified as calcified or non-calcified plaque. This can be done, for example, based on one or more criteria and/or features and/or techniques discussed herein, including for example AI, ML, imaging processing, and/or the like.

In some embodiments, the system can be configured to utilize a CT or other medical image of a subject as input for performing one or more image analysis techniques to assess a subject, including for example assessing cardiovascular disease risk based on determining a patient's calcified or non-calcified plaque. In particular, by determining a value of non-calcified plaque which may be more indicative of cardiovascular disease risk. Non-calcified plaque is a low attenuation plaque relative to calcified plaque. In some embodiments, such CT image can comprise a contrast-enhanced CT image, in which case some of the analysis techniques described herein can be directly applied, for example to identify or classify plaque. In some embodiments, such CT image can comprise a non-contrast CT image, in which case it can be more difficult to identify and/or determine non-calcified plaque due to its low radiodensity value and overlap with other low radiodensity values components, such as blood for example. In some embodiments, these "low attenuation" plaques may be differentiated between the blood attenuation density and the fat that sometimes surrounds the coronary artery and/or may represent non-calcified plaques of different materials. In some embodiments, the presence of these non-calcified plaques may offer incremental prediction for whether a previously calcified plaque is stabilizing or worsening or progressing or regressing. These findings that are measurable through these embodiments may be linked to the prognosis of a patient, wherein calcium stabilization (that is, higher attenuation densities) and lack of non-calcified plaque by may associated with a favorable prognosis, while lack of calcium stabilization (that is, no increase in attenuation densities), or significant progression or new calcium formation may be associated with a poorer prognosis, including risk of rapid progression of disease, heart attack or other major adverse cardiovascular event.

A quantitative variable that is used in the system and displayed on various portions of a user interface of the system in reference to low-density non-calcified plaque, non-calcified plaque, and calcified plaque, is the Hounsfield unit (HU). As is known, a Hounsfield Unit scale is a quantitative scale for describing radiation, and is frequently used in reference to CT scans as a way to characterize radiation attenuation and thus making it easier to define what a given finding may represent. A Hounsfield Unit measurement is presented in reference to a quantitative scale. Examples of Hounsfield Unit measurements of certain materials are shown in the following table:

| Material | HU |
|---|---|
| Air | −1000 |
| Fat | −50 |
| Distilled Water | 0 |
| Soft Tissue | +40 |
| Blood | +40 to 80 |
| Calcified Plaques | 350-1000+ |
| Bone | +1000 |

In some embodiments, to determine non-calcified and/or low-attenuated plaque from the medical image or non-contrast CT image, the system can be configured to utilize a stepwise approach to first identify areas within the medical image that are clearly non-calcified plaque. In some embodiments, the system can then conduct a more detailed analysis of the remaining areas in the image to identify other regions of non-calcified and/or low-attenuated plaque. By utilizing such compartmentalized or a stepwise approach, in some embodiments, the system can identify or determine non-calcified and/or low-attenuated plaque from the medical image or non-contrast CT image with a faster turnaround rather than having to apply a more complicated analysis to every region or pixel of the image. In some embodiments, predetermined thresholds of radiodensities from a CT image(s) may be used to differentiate plaque types, for example, to differentiate low-density non-calcified plaque (LD-NCP), non-calcified plaque (NCP) and calcified plaque (CP) plaque. In an example for a contrast CT image, LD-NCP is in the range of about −189 to 30 Hounsfield Units (HU), NCP is in the range of about −189 to 350 HU, and CP is in the range of about 350 to 2500 HU. Default or predetermined values can be revised, if desired, for example, using a Plaque Threshold interface displayable on the system. Although default values are provided, users can select different plaque thresholds based on their clinical judgment.

Information pertaining to the length and volume can be determined for a vessel along with plaque and other information (e.g., stenosis information) on a per-vessel and per-lesion level. Users may exclude artifacts from the image they do not want to be considered in the calculations by using the exclusion tool. The following tables indicate certain statistics that are available for vessels, lesions, plaque, and stenosis.

Vessel

| Term | Definition |
|---|---|
| Vessel Length (mm) | Length of a linear coronary vessel |
| Total Vessel Volume (mm3) | The volume of consecutive slices of vessel contours. |
| Total Lumen Volume (mm3) | The volume of consecutive slices of lumen contours |

| Term | Definition |
|---|---|
| Lesion Length (mm) | Linear distance from the start of a coronary lesion to the end of a coronary lesion. |
| Vessel Volume (mm3) | The volume of consecutive slices of vessel contours. |
| Lumen Volume (mm3) | The volume of consecutive slices of lumen contours. |

Plaque

| Term | Definition |
|---|---|
| Total Calcified Plaque Volume (mm3) | Calcified plaque is defined as plaque in between the lumen and vessel wall with an attenuation of greater than 350 HU, or as defined by the user, and is reported in absolute measures by plaque volume. Calcified plaques can be identified in each coronary artery ≥ 1.5 mm in mean vessel diameter. |
| Total Non-Calcified Plaque Volume (mm3) | Non-calcified plaque is defined as plaque in between the lumen and vessel wall with an attenuation of less than or equal to 350, or as defined by the user, HU and is reported in absolute measures by plaque volume. The total non-calcified plaque volume can be |

-continued

| Term | Definition |
|------|-----------|
| | determined to be the sum total of all non-calcified plaques identified in each coronary artery ≥ 1.5 mm in mean vessel diameter. Non-calcified plaque data reported is further broken down into low-density plaque, based on HU density thresholds. |
| Low-Density Non-Calcified Plaque Volume (mm3) | Low-Density-Non-Calcified Plaque is defined as plaque in between the lumen and vessel wall with an attenuation of less than or equal to 30 HU or as defined by the user and is reported in absolute measures by plaque volume. |
| Total Plaque Volume (mm3) | Plaque volume is defined as plaque in between the lumen and vessel wall reported in absolute measures. The total plaque volume is the sum total of all plaque identified in each coronary artery ≥ 1.5 mm in mean vessel diameter or wherever the user places the "End" marker. |

Stenosis

| Term | Definition |
|------|-----------|
| Remodeling Index | Remodeling Index is defined as the mean vessel diameter at a denoted slice divided by the mean vessel diameter at a reference slice. |
| Greatest Diameter Stenosis (%) | The deviation of the mean lumen diameter at the denoted slice from a reference slice, expressed in percentage. |
| Greatest Area Stenosis (%) | The deviation of the lumen area at the denoted slice to a reference area, expressed in percentage |

The system can be configured to identify epicardial fat from the medical image. In some embodiments, the system can be configured to identify epicardial fat by determining every pixel or region within the image that has a radiodensity value below a predetermined threshold and/or within a predetermined range. The exact predetermined threshold value or range of radiodensity for identifying epicardial fat can depend on the medical image, scanner type, scan parameters, and/or the like, which is why a normalization device can be used in some instances to normalize the medical image. For example, in some embodiments, the system can be configured to identify as epicardial fat pixels and/or regions within the medical image or non-contrast CT image with a radiodensity value that is around −100 Hounsfield units and/or within a range that includes −100 Hounsfield units. In particular, in some embodiments, the system can be configured to identify as epicardial fat pixels and/or regions within the medical image or non-contrast CT image with a radiodensity value that is within a range with a lower limit of about −100 Hounsfield units, about −110 Hounsfield units, about −120 Hounsfield units, about −130 Hounsfield units, about −140 Hounsfield units, about −150 Hounsfield units, about −160 Hounsfield units, about −170 Hounsfield units, about −180 Hounsfield units, about −190 Hounsfield units, or about −200 Hounsfield units, and an upper limit of about 30 Hounsfield units, about 20 Hounsfield units, about 10 Hounsfield units, about Hounsfield units, about −10 Hounsfield units, about −20 Hounsfield units, about −30 Hounsfield units, about −40 Hounsfield units, about −50 Hounsfield units, about −60 Hounsfield units, about −70 Hounsfield units, about −80 Hounsfield units, or about −90 Hounsfield units.

In some embodiments, the system can be configured to identify and/or segment arteries on the medical image or non-contrast CT image using the identified epicardial fat as outer boundaries of the arteries. For example, the system can be configured to first identify regions of epicardial fat on the medical image and assign a volume in between epicardial fat as an artery, such as a coronary artery.

In some embodiments, the system can be configured to identify a first set of pixels or regions within the medical image, such as within the identified arteries, as non-calcified or low-attenuated plaque. More specifically, in some embodiments, the system can be configured to identify as an initial set low-attenuated or non-calcified plaque by identifying pixels or regions with a radiodensity value that is below a predetermined threshold or within a predetermined range. For example, the predetermined threshold or predetermined range can be set such that the resulting pixels can be confidently marked as low-attenuated or non-calcified plaque without likelihood of confusion with another matter such as blood. In particular, in some embodiments, the system can be configured to identify the initial set of low-attenuated or non-calcified plaque by identifying pixels or regions with a radiodensity value below around Hounsfield units. In some embodiments, the system can be configured to identify the initial set of low-attenuated or non-calcified plaque by identifying pixels or regions with a radiodensity value at or below around 60 Hounsfield units, around 55 Hounsfield units, around Hounsfield units, around 45 Hounsfield units, around 40 Hounsfield units, around 35 Hounsfield units, around 30 Hounsfield units, around 25 Hounsfield units, around 20 Hounsfield units, around 15 Hounsfield units, around 10 Hounsfield units, around 5 Hounsfield units, and/or with a radiodensity value at or above around 0 Hounsfield units, around 5 Hounsfield units, around 10 Hounsfield units, around 15 Hounsfield units, around 20 Hounsfield units, around 25 Hounsfield units, and/or around 30 Hounsfield units. In some embodiments, the system can be configured to classify pixels or regions that fall within or below this predetermined range of radiodensity values as a first set of identified non-calcified or low-attenuated plaque.

In some embodiments, the system can be configured to identify a second set of pixels or regions within the medical image, such as within the identified arteries, that may or may not represent low-attenuated or non-calcified plaque. This second set of candidates of pixels or regions may require additional analysis to confirm that they represent plaque. In particular, in some embodiments, the system can be configured to identify this second set of pixels or regions that may potentially be low-attenuated or non-calcified plaque by identifying pixels or regions of the image with a radiodensity value within a predetermined range. In some embodiments, the predetermined range for identifying this second set of pixels or regions can be between around 30 Hounsfield units and 100 Hounsfield units. In some embodiments, the predetermined range for identifying this second set of pixels or regions can have a lower limit of around 0 Hounsfield units, 5 Hounsfield units, 10 Hounsfield units, 15 Hounsfield units, 20 Hounsfield units, 25 Hounsfield units, 30 Hounsfield units, 35 Hounsfield units, 40 Hounsfield units, 45 Hounsfield units, 50 Hounsfield units, and/or an upper limit of around 55 Hounsfield units, 60 Hounsfield units, 65 Hounsfield units, 70 Hounsfield units, 75 Hounsfield units, 80 Hounsfield units, 85 Hounsfield units, 90 Hounsfield units, 95 Hounsfield units, 100 Hounsfield units, 110 Hounsfield units, 120 Hounsfield units, 130 Hounsfield units, 140 Hounsfield units, 150 Hounsfield units.

In some embodiments, the system can be configured to conduct an analysis of the heterogeneity of the identified second set of pixels or regions. For example, depending on the range of radiodensity values used to identify the second set of pixels, in some embodiments, the second set of pixels or regions may include blood and/or plaque. Blood can typically show a more homogeneous gradient of radiodensity values compared to plaque. As such, in some embodiments, by analyzing the homogeneity or heterogeneity of the pixels or regions identified as part of the second set, the system can be able to distinguish between blood and non-calcified or low attenuated plaque. As such, in some embodiments, the system can be configured to determine a heterogeneity index of the second set of regions of pixels identified from the medical image by generating spatial mapping, such as a three-dimensional histogram, of radiodensity values within or across a geometric shape or region of plaque. In some embodiments, if a gradient or change in radiodensity values across the spatial mapping is above a certain threshold, the system can be configured to assign a high heterogeneity index and/or classify as plaque. Conversely, in some embodiments, if a gradient or change in radiodensity values across the spatial mapping is below a certain threshold, the system can be configured to assign a low heterogeneity index and/or classify as blood.

In some embodiments, the system can be configured to identify a subset of the second set of regions of pixels identified from the medical image as plaque or non-calcified or low-attenuated plaque. In some embodiments, the system can be configured to combine the first set of identified non-calcified or low-attenuated plaque and the second set of identified non-calcified or low-attenuated plaque. As such, even using non-contrast CT images, in some embodiments, the system can be configured to identify low-attenuated or non-calcified plaque which can be more difficult to identify compared to calcified or high-attenuated plaque due to possible overlap with other matter such as blood.

In some embodiments, the system can also be configured to determine calcified or high-attenuated plaque from the medical image. This process can be more straightforward compared to identifying low-attenuated or non-calcified plaque from the medical image or non-contrast CT image. In particular, in some embodiments, the system can be configured to identify calcified or high-attenuated plaque from the medical image or non-contrast CT image by identifying pixels or regions within the image that have a radiodensity value above a predetermined threshold and/or within a predetermined range. For example, in some embodiments, the system can be configured to identify as calcified or high-attenuated plaque regions or pixels from the medical image or non-contrast CT image having a radiodensity value above around 100 Hounsfield units, around 150 Hounsfield units, around 200 Hounsfield units, around 250 Hounsfield units, around 300 Hounsfield units, around 350 Hounsfield units, around 400 Hounsfield units, around 450 Hounsfield units, around 500 Hounsfield units, around 600 Hounsfield units, around 700 Hounsfield units, around 800 Hounsfield units, around 900 Hounsfield units, around 1000 Hounsfield units, around 1100 Hounsfield units, around 1200 Hounsfield units, around 1300 Hounsfield units, around 1400 Hounsfield units, around 1500 Hounsfield units, around 1600 Hounsfield units, around 1700 Hounsfield units, around 1800 Hounsfield units, around 1900 Hounsfield units, around 2000 Hounsfield units, around 2500 Hounsfield units, around 3000 Hounsfield units, and/or any other minimum threshold.

In some embodiments, the system can be configured to generate a quantized color mapping of one or more identified matters from the medical image. For example, in some embodiments, the system can be configured assign different colors to each of the different regions associated with different matters, such as non-calcified or low-attenuated plaque, calcified or high-attenuated plaque, all plaque, arteries, epicardial fat, and/or the like. In some embodiments, the system can be configured to generate a visualization of the quantized color map and/or present the same to a medical personnel or patient via a GUI. In some embodiments, at block 236, the system can be configured to generate a proposed treatment plan for a disease based on one or more of the identified non-calcified or low-attenuated plaque, calcified or high-attenuated plaque, all plaque, arteries, epicardial fat, and/or the like. For example, in some embodiments, the system can be configured to generate a treatment plan for an arterial disease, renal artery disease, abdominal atherosclerosis, carotid atherosclerosis, and/or the like, and the medical image being analyzed can be taken from any one or more regions of the subject for such disease analysis.

In some embodiments, one or more processes described herein can be repeated. For example, if a medical image of the same subject is taken again at a later point in time, one or more processes described herein can be repeated and the analytical results thereof can be used for disease tracking and/or other purposes.

Further, in some embodiments, the system can be configured to identify and/or determine non-calcified plaque from a DECT or spectral CT image. Similar to the processes described above, in some embodiments, the system can be configured to access a DECT or spectral CT image, identify epicardial fat on the DECT image or spectral CT and/or segment one or more arteries on the DECT image or spectral CT, identify and/or classify a first set of pixels or regions within the arteries as a first set of low-attenuated or non-calcified plaque, and/or identify a second set of pixels or regions within the arteries as a second set of low-attenuated or non-calcified plaque. However, unlike the techniques described above, in some embodiments, such as for example where a DECT or spectral CT image is being analyzed, the system can be configured to identify a subset of those second set of pixels without having to perform a heterogeneity and/or homogeneity analysis of the second set of pixels. Rather, in some embodiments, the system can be configured to distinguish between blood and low-attenuated or noncalcified plaque directly from the image, for example by utilizing the dual or multispectral aspect of a DECT or spectral CT image. In some embodiments, the system can be configured to combine the first set of identified pixels or regions and the subset of the second set of pixels or regions identified as low-attenuated or non-calcified plaque to identify a whole set of the same on the medical image. In some embodiments, even if analyzing a DECT or spectral CT image, the system can be configured to further analyze the second set of pixels or regions by performing a heterogeneity or homogeneity analysis, similar to that described above. For example, even if analyzing a DECT or spectral CT image, in some embodiments, the distinction between certain areas of blood and/or low-attenuated or non-calcified plaque may not be complete and/or accurate.

In some embodiments, if the system determines a particular region of plaque to be non-calcified plaque, at block 1138, the system can be configured to determine one or more non-calcified plaque parameters and/or one or more relational parameters. For example, in some embodiments, one or more non-calcified plaque parameters can include plaque density, radiodensity, location, volume, surface area, geometry, heterogeneity, diffusivity, or ratio between volume and surface area, among others. In some embodiments, one or more relational parameters can include a relationship between any one or more non-calcified plaque parameters and vascular parameters. For example, in some embodiments, one or more relational parameters can include a ratio of surface area of plaque to surface of vessel or lumen, ratio of volume of plaque to volume of vessel or lumen, and/or the like. In some embodiments, the system can be configured to utilize one or more AI and/or ML algorithms to automatically and/or dynamically determine one or more non-calcified plaque parameters and/or relational parameters using image processing. For example, in some embodiments, the one or more AI and/or ML algorithms can be trained using a Convolutional Neural Network (CNN) on a set of medical images on which one or more non-calcified plaque parameters and/or relational parameters have been determined, thereby allowing the AI and/or ML algorithm to automatically determine one or more non-calcified plaque parameters and/or relational parameters directly from a medical image.

In some embodiments, at block 1140, the system can be configured to analyze one or more of the non-calcified plaque parameters and/or relational parameters, for example by comparing to one or more reference values of the same, such as normal values. More specifically, in some embodiments, the system can be configured to access a reference values database 1142 that includes one or more non-calcified plaque parameter and/or relational parameters values derived from other subjects with varying states or risks of cardiovascular disease, including for example normal values. The one or more reference values of non-calcified plaque parameters and/or relational parameters can be stored on a reference values database 1142, which can be locally accessible by the system and/or can be located remotely and accessible through a network connection.

In some embodiments, based on such analysis and/or comparison, the system, at block 1144, can be configured to generate a non-calcium score. In some embodiments, the system can be configured to utilize one or more AI and/or ML algorithms to automatically and/or dynamically generate a non-calcium score. In some embodiments, the non-calcium score can be for the whole subject, for a particular vessel, for a particular lesion, for a particular artery, and/or the like.

In some embodiments, if the system determines a particular region of plaque to be calcified plaque, at block 1146, the system can be configured to determine one or more calcified plaque parameters and/or one or more relational parameters. For example, in some embodiments, one or more calcified plaque parameters can include plaque density, radiodensity, location, volume, surface area, geometry, heterogeneity, diffusivity, or ratio between volume and surface area, among others. In some embodiments, one or more relational parameters can include a relationship between any one or more calcified plaque parameters and vascular parameters. For example, in some embodiments, one or more relational parameters can include a ratio of surface area of plaque to surface of vessel or lumen, ratio of volume of plaque to volume of vessel or lumen, and/or the like. In some embodiments, the system can be configured to utilize one or more AI and/or ML algorithms to automatically and/or dynamically determine one or more calcified plaque parameters and/or relational parameters using image processing. For example, in some embodiments, the one or more AI and/or ML algorithms can be trained using a Convolutional Neural Network (CNN) on a set of medical images on which one or more calcified plaque parameters and/or relational parameters have been determined, thereby allowing the AI and/or ML algorithm to automatically determine one or more calcified plaque parameters and/or relational parameters directly from a medical image.

In some embodiments, at block 1148, the system can be configured to analyze one or more of the calcified plaque parameters and/or relational parameters, for example by comparing to one or more reference values of the same, which may include normal values. More specifically, in some embodiments, the system can be configured to access a reference values database 1142 that includes one or more calcified plaque parameter and/or relational parameters values derived from other subjects with varying states or risks of cardiovascular disease, including for example normal values. The one or more reference values of calcified plaque parameters and/or relational parameters can be stored on a reference values database 1142, which can be locally accessible by the system and/or can be located remotely and accessible through a network connection.

In some embodiments, based on such analysis and/or comparison, the system, at block 1150, can be configured to generate a calcium score. In some embodiments, the system can be configured to utilize one or more AI and/or ML algorithms to automatically and/or dynamically generate a calcium score. In some embodiments, the calcium score can be for the whole subject, for a particular vessel, for a particular lesion, for a particular artery, and/or the like.

In some embodiments, at block 1152, the system can be configured to generate one or more weighted measures of the non-calcium score and/or calcium score. For example, in some embodiments, the system can be configured to generate weighted measures of the non-calcium score and/or calcium score for the subject, for a particular vessel, for a particular lesion, for a particular artery, and/or the like. In some embodiments, the system can be configured to assign a weight to the calcium score and/or non-calcium score in generating the weighted measure. For example, the system can be configured to assign a weight between 0 and 1 to the calcium score and/or non-calcium score. In some embodiments, the system can be configured to weight the calcium score and/or non-calcium score 0, thereby ignoring its effect. In some embodiments, the system can be configured to weight the calcium score and/or non-calcium score 1, thereby focusing exclusively on either the calcium score or the non-calcium score. In some embodiments, the weighted measure can also include one or more other factors or features, such as for example, age, weight, gender, plaque volume, plaque composition, vascular remodeling, high-risk plaque, lumen volume, plaque location (proximal v. middle v. distal), plaque location (myocardial v. pericardial facing), plaque location (at bifurcation or trifurcation v. not at bifurcation or trifurcation), plaque location (in main vessel v. branch vessel), stenosis severity, percentage coronary blood volume, percentage fractional myocardial mass, percentile for age and/or gender, constant or other correction factor to allow for control of within-person, within-vessel, inter-plaque, plaque-myocardial relationships, and/or the like.

In some embodiments, at block 1154, the system can be configured to analyze the weighted measure of non-calcium score and/or calcium score, for example by comparing to one or more reference values of the same, which may include normal values. More specifically, in some embodiments, the system can be configured to access a reference values database 1156 that includes one or more weighted measures of non-calcium and/or calcium scores derived from other subjects with varying states or risks of cardiovascular disease, including for example normal values. The one or more reference values of weighed measures of calcium scores and/or non-calcium scores can be stored on a reference values database 236, which can be locally accessible by the system and/or can be located remotely and accessible through a network connection.

In some embodiments, the reference values databases 1132, 1142, 1656 and/or any portion or component thereof can be part of a single database. In some embodiments, the reference values databases 1132, 1142, 1156 and/or any portion or component thereof can comprise separate databases. In some embodiments, the reference values stored on one or more such reference values databases 1132, 1142, 1156 can be curated, triaged, filtered, or selected based on age, gender, pre-existing medical condition, and/or the like to match the subject for improved accuracy. In an example, when a query is made to the reference value database, one or more characteristics of the subject (e.g., age, gender, race, pre-existing medical condition, whether a smoker, fitness level, and/or the like) may be provided (or associated) with the query, and the reference value(s) selected from the reference values database can be based at least in part, on the provided (or associated) characteristic of the subject.

In some embodiments, based on such analysis and/or comparison, the system, at block 1152, can be configured to determine a risk or state of cardiovascular disease or health of the subject. Further, in some embodiments, based on such analysis and/or comparison, the system, at block 1158, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1140, which can be locally accessible by the system and/or can be located remotely and accessible through a network connection. In some embodiments, the plaque risk/treatment database 1140 can include reference points or data that relate one or more treatment to cardiovascular disease risk or state determined based on one or more weighted measures of non-calcium and/or calcium scores.

In some embodiments, the system can be configured to repeat one or more processes described in relation to blocks

1122-1158 of FIG. 11B, for example, for one or more other regions of plaque and/or other subjects and/or for the same subject at a different time. As such, in some embodiments, the system can provide for longitudinal disease tracking and/or personalized treatment for a subject.

Figure 11C:
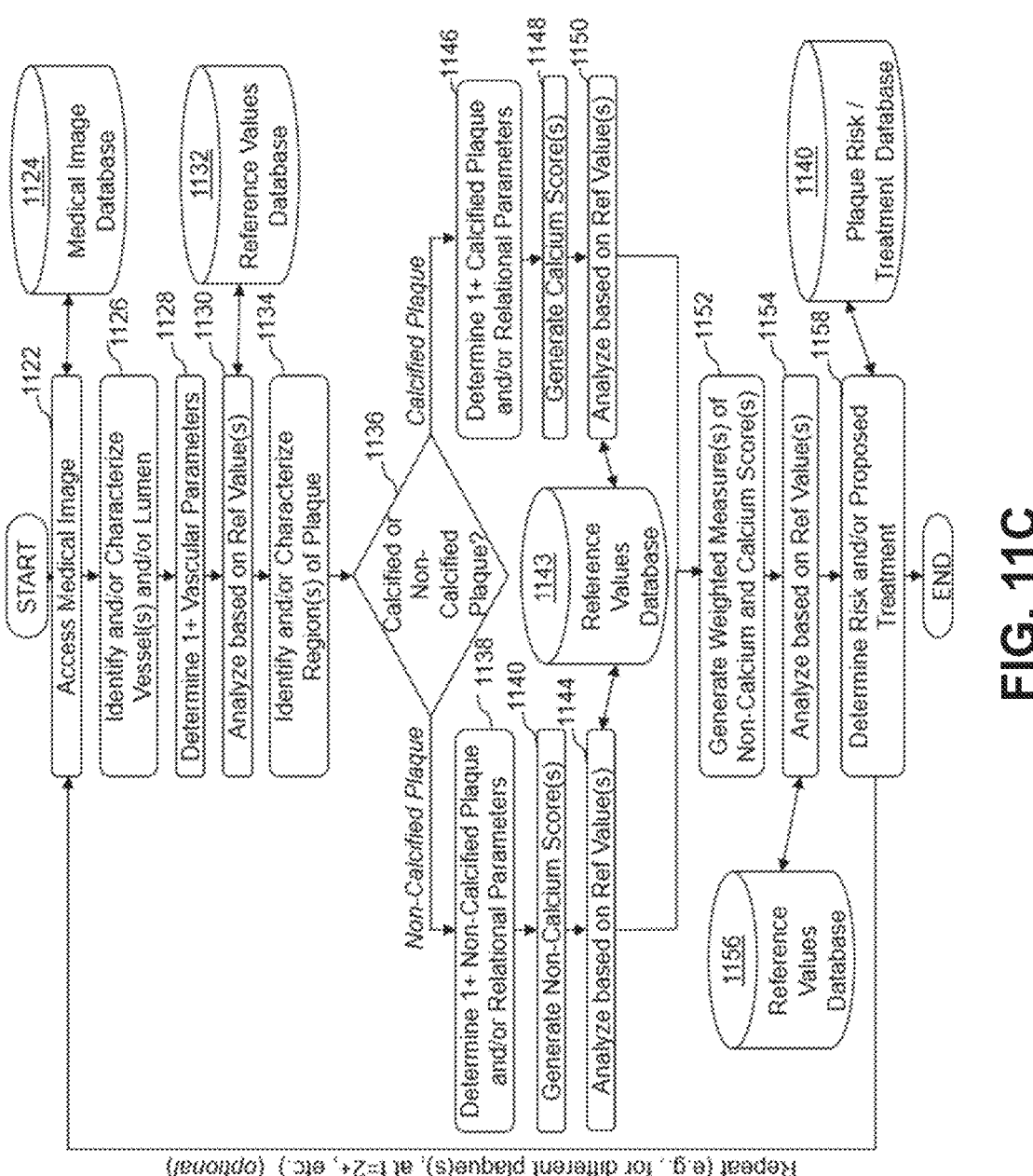
FIG. 11C is a flowchart illustrating another example embodiment of a system, device, and method for cardiovascular risk and/or disease state assessment using image-based analyses of non-calcified and/or calcified plaque.
Figure 11D:
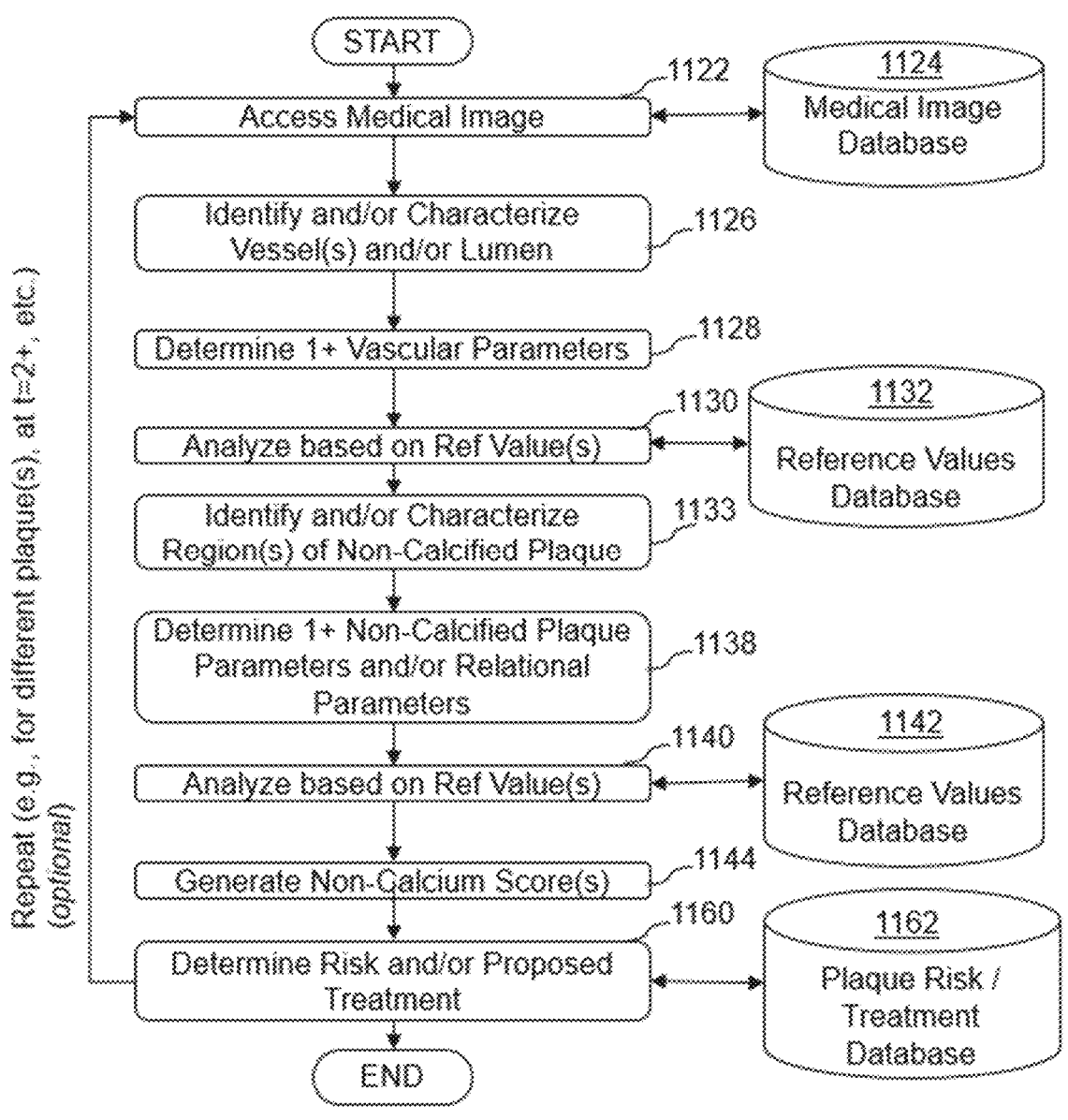
FIG. 11D is a flowchart illustrating example an embodiment of a system, device, and method for cardiovascular risk and/or disease state assessment using image-based analyses of non-calcified plaque.

FIG. 11C is also a flowchart illustrating an example embodiment(s) of systems, devices, and methods for cardiovascular risk and/or disease state assessment using image-based analyses of non-calcified and/or calcified plaque. The same reference numbers in FIGS. 11C and 11D represent similar features and can include any of the features described in reference to either figure.

As illustrated in FIG. 11C, in some embodiments, the system can be configured to generate a non-calcium score and/or calcium score directly from the determined one or more non-calcified plaque parameters, calcified plaque parameters, and/or relational parameters, without referencing reference values and/or normal values. Rather, in some embodiments, the system can be configured to reference values of a non-calcium score and/or calcium score after generating the same based on image processing techniques.

More specifically, in some embodiments, at block 1140, the system can be configured to generate a non-calcium score directly from one or more non-calcified plaque parameters and/or relational parameters without obtaining any information from a reference values database. In some embodiments, the system can be configured to automatically and/or dynamically generate a non-calcium score. In an example, the system can utilize one or more AI and/or ML algorithms to automatically and/or dynamically generate a non-calcium score. In some embodiments, the non-calcium score can be representative of the whole subject. In an example, the non-calcium score can be for the whole subject where two or more areas of the subject are evaluated to determine the non-calcium score, although in some examples the determination of a non-calcium score of a subject can be based on an evaluation of one area of the subject, for example, an artery or region of a vessel that correlates with a non-calcium value of the entire subject. In some embodiments, the non-calcium score can be representative of a particular vessel or a portion of a vessel, the non-calcium score can be representative of a particular lesion, and/or the non-calcium score can be representative of a particular artery.

In some embodiments, at block 1144, after generating a non-calcium score, the system can be configured to analyze the non-calcium score by comparison to one or more reference values of non-calcium scores, such as for example normal values. More specifically, in some embodiments, the system can be configured to access a reference values database 1142 that includes one or more non-calcium score values derived from other subjects with varying states or risks of cardiovascular disease. The one or more reference values of non-calcium scores can be stored on a reference values database 1142, which can be locally accessible by the system and/or can be located remotely and accessible through a network connection.

Similarly, in some embodiments, at block 1148, the system can be configured to generate a calcium score directly from one or more calcified plaque parameters and/or relational parameters without referencing a reference values database for the same. In some embodiments, the system can be configured to utilize one or more AI and/or ML algorithms to automatically and/or dynamically generate a calcium score. In some embodiments, the calcium score can be for the whole subject, for a particular vessel, for a particular lesion, for a particular artery, and/or the like.

In some embodiments, at block 1150, after generating a calcium score, the system can be configured to analyze the calcium score by comparison to one or more reference values of calcium scores, which may include normal values. More specifically, in some embodiments, the system can be configured to access a reference values database 1143 that includes one or more calcium score values derived from other subjects with varying states or risks of cardiovascular disease, such as for example normal values. The one or more reference values of calcium scores can be stored on a reference values database 1143, which can be locally accessible by the system and/or can be located remotely and accessible through a network connection.

In some embodiments, the reference values databases 1132, 1142, 1156, 1143 and/or any portion or component thereof can be part of a single database. In some embodiments, the reference values databases 1132, 1142, 1156, 1143 and/or any portion or component thereof can comprise separate databases. In some embodiments, the reference values stored on one or more such reference values databases 1132, 1142, 1156, 1143 can be curated, triaged, filtered, or selected based on age, gender, pre-existing medical condition, and/or the like to match the subject for improved accuracy.

In some embodiments, the system can be configured to repeat one or more processes described in relation to blocks 1122-1150 in FIG. 11C, for example for one or more other regions of plaque and/or other subjects and/or for the same subject at a different time. As such, in some embodiments, the system can provide for longitudinal disease tracking (e.g., disease tracking over a period of time) and/or personalized treatment for a subject.

Cardiovascular Risk and/or Disease State Assessment Using Image-Based Analysis of Non-Calcified Plaque Features FIG. 11D is a flowchart illustrating an example embodiment(s) of systems, devices, and methods for cardiovascular risk and/or disease state assessment using image-based analyses of non-calcified plaque. The same reference numbers in FIGS. 11B, 11C, and 11D represent similar features and can include any of the features described in reference to either figure.

As illustrated in FIG. 11D, in some embodiments, the system can be configured to generate a non-calcium score and use the non-calcium score alone to determine a risk or state of cardiovascular disease or health of a subject and/or propose a treatment. As discussed herein, non-calcified plaque can be more indicative of cardiovascular risk compared to calcified plaque. As such, a non-calcium score derived from one or more features of non-calcified plaque and/or vascular parameters and/or relational parameters can be strong indicator of cardiovascular risk.

More specifically, as illustrated in FIG. 11D, in some embodiments, the system can be configured to focus on analyzing one or more features of non-calcified plaque. In particular, in some embodiments, at block 1133, the system can be configured to analyze a medical image to identify and/or characterize one or more regions of non-calcified plaque, with or without analyzing one or more regions of calcified plaque.

In some embodiments, based on a non-calcium score generated and/or derived from comparing one or more non-calcified plaque parameters and/or relational parameters to one or more reference values, the system can be configured to determine the risk and/or state of cardiovascular disease or state of the subject at block 1160. Further, in some embodiments, based on a non-calcium score generated and/or derived from comparing one or more non-calcified plaque parameters and/or relational parameters to one or more reference values, the system, at block 1104, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 306, which can be locally accessible by the system and/or can be located remotely and accessible through a network connection. In some embodiments, the plaque risk/treatment database 306 can include reference points or data that relate one or more treatment to cardiovascular disease risk or state determined based on non-calcium scores.

In some embodiments, the databases and/or any portion or component thereof can be part of a single database. In an example, reference values databases 1132, 1142, 1156, 1143 and/or any portion or component thereof can be part of a single database. In another example, reference values databases 1132, 1142, 1156, 1143 and/or any portion or component thereof can comprise separate databases. In another example, the plaque risk/treatment database 1140, 1162 and one or more of the reference values databases 1132, 1142, 1156, 1143 In another example, all or some of the reference values databases 1132, 1142, 1156, 1143 and/or any portion or component thereof can be part of the same database. In some embodiments, the reference values stored on one or more such reference values databases can be curated, triaged, filtered, or selected based on age, gender, race, pre-existing medical condition, and/or any other patient/subject characteristic to match the subject for improved accuracy.

In some embodiments, the system can be configured to repeat one or more processes described in relation to blocks 1122-1160 in FIG. 11D, for example for one or more other regions of plaque and/or other subjects and/or for the same subject at a different time. As such, in some embodiments, the system can provide for longitudinal disease tracking and/or personalized treatment for a subject.

Figure 11E:
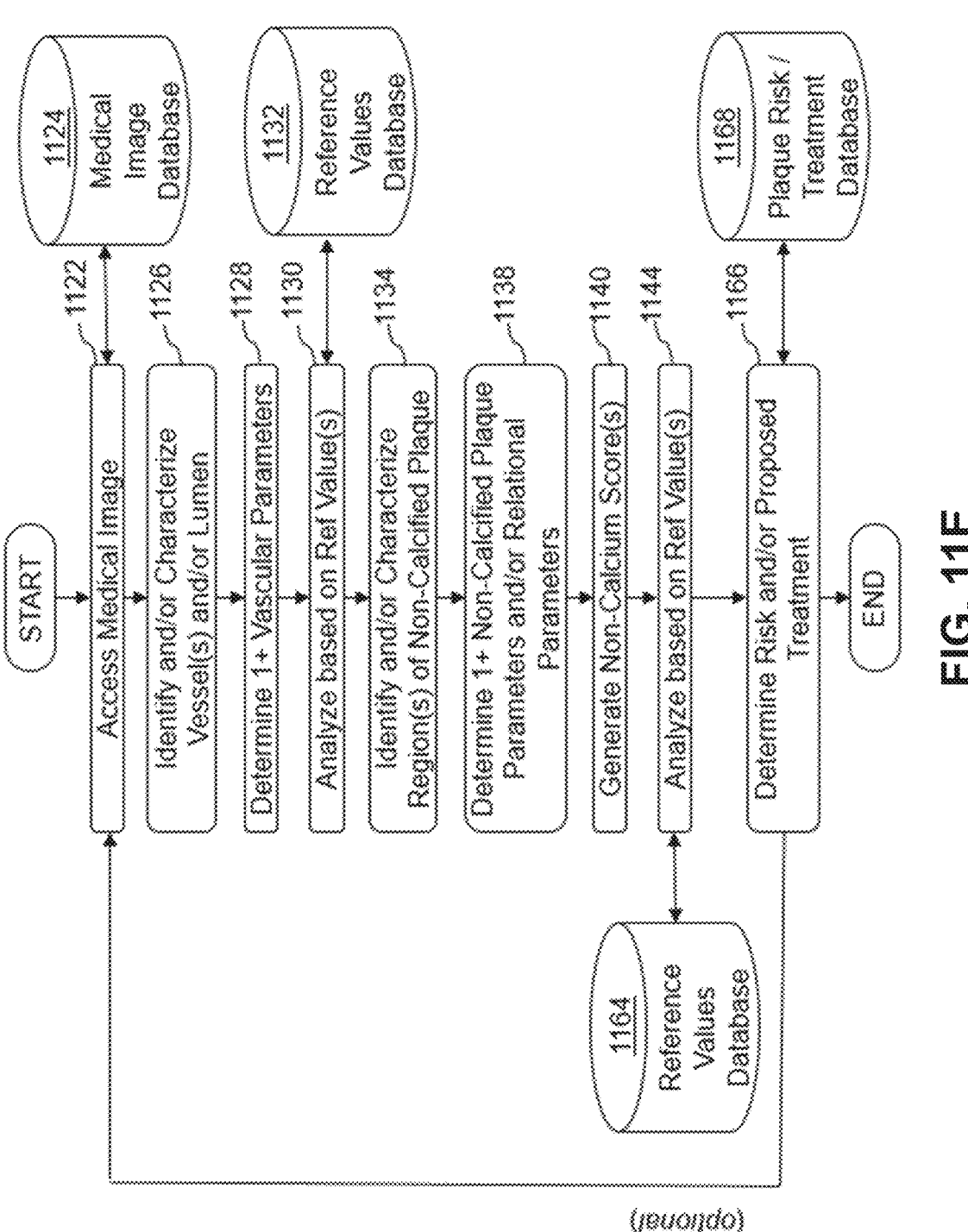
FIG. 11E is a flowchart illustrating example an embodiment of a system, device, and method for cardiovascular risk and/or disease state assessment using image-based analyses of non-calcified plaque.

FIG. 11E is a flowchart illustrating an example embodiment(s) of systems, devices, and methods for cardiovascular risk and/or disease state assessment using image-based analyses of non-calcified plaque. The same reference numbers in FIGS. 11A-E represent similar features and can include any of the features described in reference to either figure.

As illustrated in FIG. 11E, in some embodiments, the system can be configured to generate a non-calcium score and use the non-calcium score alone to determine a risk or state of cardiovascular disease or health of a subject and/or propose a treatment. However, in contrast to some embodiments described herein, in some embodiments as illustrated in FIG. 11E, the system can be configured to generate a non-calcium score directly from the determined one or more non-calcified plaque parameters and/or relational parameters, without referencing reference values and/or normal values. Rather, in some embodiments, the system can be configured to reference values of a non-calcium score after generating the same based on image processing techniques.

More specifically, as illustrated in FIG. 11E, in some embodiments, the system can be configured to generate a non-calcium score at block 1140 and analyze the same based on comparison to one or more reference values at block 1144, which may include normal values. The one or more reference values of non-calcium scores can be stored in a reference values database 1143 as described herein.

In some embodiments, based on a non-calcium score generated and/or derived without referencing reference values, the system can be configured to determine the risk and/or state of cardiovascular disease or state of the subject at block 1166. Further, in some embodiments, based on a non-calcium score generated and/or derived without referencing reference values, the system, at block 1166, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1168, which can be locally accessible by the system and/or can be located remotely and accessible through a network connection. In some embodiments, the plaque risk/treatment database 1168 can include reference points or data that relate one or more treatment to cardiovascular disease risk or state determined based on non-calcium scores derived without reference to reference values and/or normal values.

In some embodiments, the system can be configured to repeat one or more processes described in relation to blocks 1122-1166, for example for one or more other regions of plaque and/or other subjects and/or for the same subject at a different time. As such, in some embodiments, the system can provide for longitudinal disease tracking and/or personalized treatment for a subject.

Computer System

Figure 11F:
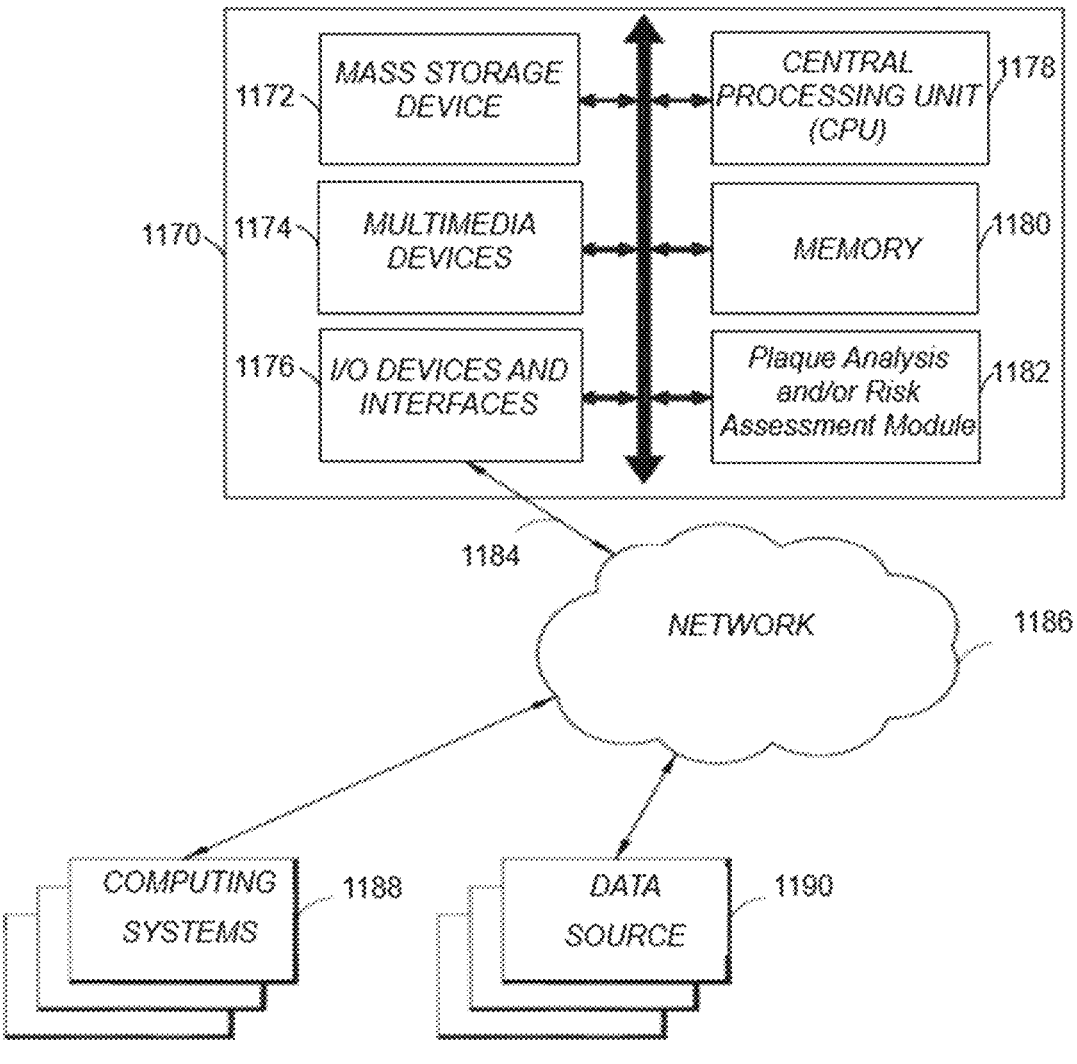
FIG. 11F is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 11F. The example computer system 1170 is in communication with one or more computing systems 1688 and/or one or more data sources 1190 via one or more networks 1186. While FIG. 16F illustrates an embodiment of a computing system 1170, it is recognized that the functionality provided for in the components and modules of computer system 1170 can be combined into fewer components and modules, or further separated into additional components and modules.

The computer system 1170 can comprise a Plaque Analysis and/or Risk Assessment Module 1182 that carries out the functions, methods, acts, and/or processes described herein. The Plaque Analysis and/or Risk Assessment Module 1182 executed on the computer system 1170 by a central processing unit 1178 discussed further below. Other features of the computer system 1170 can be similar to corresponding features of the computer system of FIG. 9G, described above.

Certain Examples of Types of Plaque Composition and Non-Calcium Score

The following are non-limiting examples of certain embodiments of systems and methods for types of plaque composition and non-calcium score. Other embodiments may include one or more other features, or different features, that are discussed herein.

The following are non-limiting examples of certain embodiments of systems and methods for types of plaque composition and non-calcium score. Other embodiments may include one or more other features, or different features, that are discussed herein.

Embodiment 1: A computer-implemented method of assessing a state of cardiovascular disease of a subject based on multi-dimensional information derived from non-invasive medical image analysis, the method comprising: accessing, by a computer system, a medical image of a subject, wherein the medical image of the subject is obtained non-invasively; analyzing, by the computer system, the medical image of the subject to identify one or more arteries, wherein the one or more arteries comprise one or more regions of plaque; determining, by the computer system, one or more vascular parameters associated with the subject by analyzing the one or more arteries identified from the medical image, wherein the one or more vascular parameters comprise one or more of vascular volume, diameter, area, cross-sectional area, surface area, length, location, or remodeling; identifying, by the computer system, the one or more regions of plaque on the medical image; characterizing, by the computer system, one or more of the one or more identified regions of plaque as non-calcified plaque, wherein the one or more identified regions of plaque is characterized as non-calcified plaque when radiodensity values of one or more pixels within the one or more identified regions of plaque is below a predetermined threshold; determining, by the computer system, one or more non-calcified plaque parameters for the one or more characterized non-calcified plaque, the one or more non-calcified plaque parameters comprising one or more of plaque density, radiodensity, location, volume, surface area, geometry, heterogeneity, diffusivity, mass or ratio between volume and surface area; analyzing, by the computer system, one or more of the one or more vascular parameters or one or more non-calcified plaque parameters by comparison to a dataset of values, the values comprising one or more of the one or more vascular parameters or one or more non-calcified plaque parameters derived from a population with varying states of cardiovascular disease; generating, by the computer system, a non-calcium score for the subject, the non-calcium score generated based at least in part by analyzing one or more of the one or more vascular parameters or one or more non-calcified plaque parameters by comparison to a dataset of values; and determining, by the computer system, an assessment of the state of cardiovascular disease of the subject based at least in part on the generated non-calcium score, wherein the computer system comprises a computer processor and an electronic storage medium.

Embodiment 2: The computer-implemented method of Embodiment 1, wherein one or more of the one or more identified regions of plaque is further characterized as non-calcified plaque when distribution of radiodensity values of one or more pixels within the one or more identified regions of plaque is above a predetermined threshold.

Embodiment 3: The computer-implemented method of Embodiment 1, further comprising characterizing, by the computer system, one or more of the one or more identified regions of plaque as calcified plaque, wherein the one or more identified regions of plaque is characterized as calcified plaque when radiodensity values of one or more pixels within the one or more identified regions of plaque is above a predetermined threshold.

Embodiment 4: The computer-implemented method of Embodiment 3, further comprising determining, by the computer system, one or more calcified plaque parameters for the one or more characterized calcified plaque, the one or more calcified plaque parameters comprising one or more of plaque density, radiodensity, location, volume, surface area, geometry, heterogeneity, diffusivity, mass or ratio between volume and surface area.

Embodiment 5: The computer-implemented method of Embodiment 4, further comprising analyzing, by the computer system, one or more of the one or more calcified plaque parameters by comparison to a dataset of values of the one or more calcified plaque parameters derived from a population with varying states of cardiovascular disease.

Embodiment 6: The computer-implemented method of Embodiment 5, further comprising generating, by the computer system, a calcium score for the subject, the calcium score generated based at least in part by analyzing one or more of the one or more calcified plaque parameters by comparison to the dataset of values of the one or more calcified plaque parameters.

Embodiment 7: The computer-implemented method of Embodiment 6, further comprising generating, by the computer system, a weighted measure of the non-calcium score and the calcium score.

Embodiment 8: The computer-implemented method of Embodiment 7, wherein the weighted measure of the non-calcium score and the calcium score is generated by weighting the non-calcium score between 0 and 1 and by weighting the calcium score between 0 and 1.

Embodiment 9: The computer-implemented method of Embodiment 1, wherein the medical image is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS).

Embodiment 10: The computer-implemented method of Embodiment 7, wherein the weighted measure of the non-calcium score and the calcium score is generated by weighting the non-calcium score 1 and the calcium score 0.

Embodiment 11: The computer-implemented method of Embodiment 7, wherein the weighted measure of the non-calcium score and the calcium score is generated by weighting the non-calcium score 0 and the calcium score 1.

Embodiment 12: The computer-implemented method of Embodiment 7, wherein the assessment of the state of cardiovascular disease of the subject is determined based at least in part on the generated weighted measure of the non-calcium score and the calcium score.

Embodiment 13: The computer-implemented method of Embodiment 8, wherein the assessment of the state of cardiovascular disease of the subject is determined by comparing the generated weighted measure of the non-calcium score and the calcium score against a dataset of values of weighted measures of non-calcium score and calcium score for a population with varying states of cardiovascular disease.

Embodiment 14: The computer-implemented method of Embodiment 1, further comprising generating, by the computer system, a treatment for cardiovascular disease for the subject based at least in part on the determined assessment of the state of cardiovascular disease.

Embodiment 15: The computer-implemented method of Embodiment 14, wherein the treatment for cardiovascular disease comprises medical intervention, medical treatment, or lifestyle change.

Embodiment 16: The computer-implemented method of Embodiment 14, further comprising tracking, by the computer system, efficacy of the treatment by determining assessment of the state of cardiovascular disease of the subject at a later point in time after treatment.

Embodiment 17: The computer-implemented method of Embodiment 1, further comprising: determining, by the computer system, one or more relational parameters, the relational parameters comprising one or more of a ratio of surface area of plaque to surface of vessel, ratio of volume of plaque to volume of vessel, or a ratio of thickness of plaque to thickness of vessel; and analyzing, by the computer system, one or more of the one or more relational parameters by comparison to a dataset of values, the values comprising one or more of the one or more relational parameters derived from a population with varying states of cardiovascular disease, wherein the non-calcium score for the subject is further generated based at least in part on the analyzed one or more relational parameters.

Embodiment 18: A system for assessing a state of cardiovascular disease of a subject based on multi-dimensional information derived from non-invasive medical image analysis, the system comprising: one or more computer readable storage devices configured to store a plurality of computer executable instructions; and one or more hardware computer processors in communication with the one or more computer readable storage devices and configured to execute the plurality of computer executable instructions in order to cause the system to: access a medical image of a subject, wherein the medical image of the subject is obtained non-invasively; analyze the medical image of the subject to identify one or more arteries, wherein the one or more arteries comprise one or more regions of plaque; identify the one or more regions of plaque on the medical image; characterize one or more of the one or more identified regions of plaque as non-calcified plaque, wherein the one or more identified regions of plaque is characterized as non-calcified plaque when radiodensity values of one or more pixels within the one or more identified regions of plaque is below a predetermined threshold; determine one or more non-calcified plaque parameters for the one or more characterized non-calcified plaque, the one or more non-calcified plaque parameters comprising one or more of plaque density, radiodensity, location, volume, surface area, geometry, heterogeneity, diffusivity, or ratio between volume and surface area; analyze one or more of the one or more non-calcified plaque parameters by comparison to a dataset of values, the values comprising one or more of the one or more non-calcified plaque parameters derived from a population with varying states of cardiovascular disease; generate a non-calcium score for the subject, the non-calcium score generated based at least in part by analyzing one or more of the one or more non-calcified plaque parameters by comparison to a dataset of values; and determine an assessment of the state of cardiovascular disease of the subject based at least in part on the generated non-calcium score.

Embodiment 19: The system of Embodiment 18, wherein the system is further caused to: characterize one or more of the one or more identified regions of plaque as calcified plaque; determine one or more calcified plaque parameters for the one or more characterized calcified plaque, the one or more calcified plaque parameters comprising one or more of plaque density, radiodensity, location, volume, surface area, geometry, heterogeneity, diffusivity, mass or ratio between volume and surface area; analyze one or more of the one or more calcified plaque parameters by comparison to a dataset of values of the one or more calcified plaque parameters derived from a population with varying states of cardiovascular disease; and generate a calcium score for the subject, the calcium score generated based at least in part by analyzing one or more of the one or more calcified plaque parameters by comparison to the dataset of values of the one or more calcified plaque parameters.

Embodiment 20: The system of Embodiment 19, wherein the system is further caused to generate a weighted measure of the non-calcium score and the calcium score, wherein the assessment of the state of cardiovascular disease of the subject is determined based at least in part on the generated weighted measure of the non-calcium score and the calcium score.

Embodiment 21: The system of Embodiment 20, wherein the weighted measure of the non-calcium score and the calcium score is generated by weighting the non-calcium score between 0 and 1 and by weighting the calcium score between 0 and 1.

Modified and/or Normalized Percent Atheroma Volume (PAV) Introduction

As discussed herein, disclosed herein are systems, methods, and devices for cardiovascular risk and/or disease state assessment using image-based analyses. In particular, in some embodiments, the systems, devices, and methods are related to cardiovascular risk and/or disease and/or state assessment using modified and/or normalized image analysis-based plaque parameters. In some embodiments, assessment of cardiovascular risk and/or disease and/or state generated using the systems, methods, and devices herein can be utilized to diagnose and/or generate a proposed treatment for a patient.

In particular, in some embodiments, the systems, devices, and methods described herein can be configured to analyze one or more non-invasively obtained medical images of a subject, such as a CT image, to determine one or more plaque parameters and/or relational plaque parameters, such as for example percent atheroma volume (PAV). In some embodiments, the systems, devices, and methods described herein can be configured to utilize one or more modified relational plaque parameters, such as a modified version of PAV. PAV can refer to the proportion of total vessel wall volume or total vessel volume occupied by atherosclerotic plaque. As such, analyzing coronary PAV can provide an indication of risk of cardiovascular disease or a major adverse cardiovascular event (MACE), such as a myocardial infarction or heart attack. In some embodiments, one or more medical images obtained from a coronary computed tomography angiography (CCTA) can be used as a non-invasive measure to assess PAV. However, in certain scanners and/or scan parameters, the quality of an image obtained from a CT scan or CCTA can be less than perfect. For example, in some embodiments, small vessels below a certain size can be difficult to analyze, thereby potentially resulting in less than accurate analysis of plaque or PAV within such vessel.

In order to address such technical shortcomings, some embodiments of the systems, devices, and methods described herein are configured to utilize a modified PAV in analyzing a CT or CCTA image. In particular, in some embodiments, the system can be configured to analyze a CT or CCTA image to identify one or more vessels above a certain threshold level and analyze such vessels to determine PAV. In some embodiments, such modified PAV can be further normalized against a physical property of the subject, such as for example body mass, left ventricular (LV) mass, heart mass, and/or the like. In some embodiments, such modified and/or normalized PAV can be compared to a reference database of known modified and/or normalized PAV values, wherein such modified and/or normalized PAV values are obtained by applying the same vessel threshold to medical images obtained from a population with varying levels of plaque and normalized against the same physical property of each subject.

As such, in some embodiments, the systems, devices, and methods described herein can be configured to utilize a modified and/or normalized PAV in assessing the risk of coronary artery disease (CAD) and/or MACE for a subject and/or determine a proposed treatment. By utilizing such modified and/or normalized PAV, it can be possible to address image quality issues arising from CT or CCTA scans, as a modified and/or normalized database of PAV values developed using the same vessel threshold and/or normalized against the same physical property can be used as a reference database.

In some embodiments, the systems, devices, and methods can be configured to apply such vessel threshold prior to analyzing an image for any parameter, such as for example any plaque parameter, vessel parameter, and/or relational parameter between the two, including but not limited to PAV. In some embodiments, any such modified parameter after applying a vessel threshold can be normalized, for example against a physical property of the subject. For example, in some embodiments, the vessel threshold can comprise a diameter of about 2.0 mm, such that the system is configured to ignore any vessels with a diameter below 2.0 mm and analyze only vessel areas with a diameter above 2.0 mm to determine any such parameters. In some embodiments, parameters derived from vessel areas above the vessel threshold can then be normalized against some property of the subject and analyzed by comparison to a database of known parameter values obtained from vessel areas above the same vessel threshold from a population with varying degrees of plaque and/or disease, thereby normalizing the analysis to be independent of the image quality.

In some embodiments, the vessel threshold can be based on volume, diameter, surface area, radius, width, and/or any other variable or parameter related to the vessel. In some embodiments, the vessel threshold can comprise a vessel diameter of about mm, about 9.0 mm, about 8.0 mm, about 7.0 mm, about 6.0 mm, about 5.0 mm, about 4.5 mm, about 4.0 mm, about 3.9 mm, about 3.8 mm, about 3.7 mm, about 3.6 mm, about 3.5 mm, about 3.4 mm, about 3.3 mm, about 3.2 mm, about 3.1 mm, about 3.0 mm, about 2.9 mm, about 2.8 mm, about 2.7 mm, about 2.6 mm, about 2.5 mm, about 2.4 mm, about 2.3 mm, about 2.2 mm, about 2.1 mm, about 2.0 mm, about 1.9 mm, about 1.8 mm, about 1.7 mm, about 1.6 mm, about 1.5 mm, about 1.4 mm, about 1.3 mm, about 1.2 mm, about 1.1 mm, about 1.0 mm, about mm, about 0.8 mm, about 0.7 mm, about 0.6 mm, about 0.5 mm, about 0.4 mm, about 0.5 mm, about 0.4 mm, about 0.3 mm, about 0.2 mm, about 0.1 mm, and/or within a range defined by two of the aforementioned values.

In some embodiments, the system can be configured to utilize a different vessel threshold for different vessels on an image. For example, in some cases, an image can comprise vessels with varying degrees of quality, such that one vessel has a higher image quality than another vessel within the same image due to motion artifact or other reasons. In some embodiments, the system can be configured to apply a higher vessel threshold to a vessel with lower image quality than another vessel with a higher image quality. Similarly, in some embodiments, the system can be configured to apply a lower vessel threshold to a vessel with a higher image quality than another vessel with a lower image quality. In some embodiments, one or more plaque, vessel, and/or relational parameters can be derived from an image after applying different vessel thresholds to different vessels. For example, in some instances, a PAV for one vessel can be derived after removing all vessel areas with a diameter smaller than about 2.0 mm, whereas a PAV for another vessel within the same image can be derived after removing all vessel areas with a diameter smaller than about 1.0 mm.

In some embodiments, the reference database can comprise PAV or other plaque, vessel, and/or relational parameters derived from images after applying varying vessel thresholds to the same and/or different vessels. For example, in some embodiments, the reference database can include PAV derived from one vessel after removing all vessel areas with a diameter smaller than about 2.0 mm, about 1.0 mm, and/or any other vessel threshold as described herein. Then, in some embodiments, if a corresponding vessel in the subject image at hand is applied a vessel threshold of 1.0 mm, then that vessel segment or a parameter derived therefrom can be compared to corresponding vessel segments or parameters derived therefrom in the database after applying a vessel threshold of 1.0 mm (with or without normalizing to a physical property of the subject). Similarly, for another vessel in the subject image or a parameter derived therefrom can be compared to corresponding vessel segments or parameters derived therefrom in the database after applying a vessel threshold of 2.0 mm (with or without normalizing to a physical property of the subject). In other words, different vessel thresholds can be applied to different vessels, and the resulting vessel segments can be normalized and/or compared to vessel segments with different vessel thresholds applied to them in the reference database. As such, in some embodiments, the reference database can include modified and/or normalized parameters for different vessels. As such, in some embodiments, the system can be configured to compare each vessel segment, normalized or not, by comparison to the same vessel segment of different subjects with the same vessel threshold being applied. Thus, in some embodiments, the systems, methods, and devices can be configured to provide dynamic normalization of vessels for improved accuracy and/or analysis independent of image quality.

In some embodiments, the medical image is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS). For example, in some embodiments, images for the reference database can be derived from one or more or a combination of such imaging modalities for varying degrees of image quality.

In some embodiments, after applying a vessel threshold, one or more vessel segments can be analyzed to determine one or more plaque parameters, vessel parameters, and/or relational plaque parameters. For example, the plaque parameters can include absolute plaque density, relative plaque density, composition, calcification, radiodensity, location, volume, surface area, geometry, heterogeneity, diffusivity, and/or ratio between volume and surface area. The vessel parameters can include vessel volume, diameter, area, cross-sectional area, surface area, length, location, and/or remodeling. The relational plaque parameters can include a ratio or other comparison between one or more plaque parameters and one or more vessel parameters, such as for example PAV, PAV on a vessel-by-vessel basis, PAV on a segment-by-segment basis, and/or PAV for the whole heart, ratio of surface area of plaque to surface of vessel or lumen, ratio of volume of plaque to volume of vessel or lumen, and/or the like.

In some embodiments, the system can be configured to assess the risk and/or state of cardiovascular disease or health based on the modified and/or normalized parameter(s) after applying a vessel threshold(s). In some embodiments, the system can be configured to determine or generate a proposed treatment for the subject based on the assessed risk and/or state of cardiovascular disease or health. For example, the proposed treatment can include one or more of medical therapy (such as statins), interventional therapy (such as stent implantation), and/or lifestyle therapy (such as diet or exercise). In some embodiments, the system can be configured to track the efficacy of a treatment by tracking changes in the modified and/or normalized parameter(s), for example compared to previous value(s) for the same subject and/or change relative to a reference values database comprising one or more reference values, such as for example normal values.

As such, in some embodiments, the systems, devices, and methods described herein provide an improved quantitative and/or image-based solution for generating and/or tracking cardiovascular disease or health by modifying and/or normalizing one or more plaque, vessel, and/or relational plaque parameters.

Figure 12A:
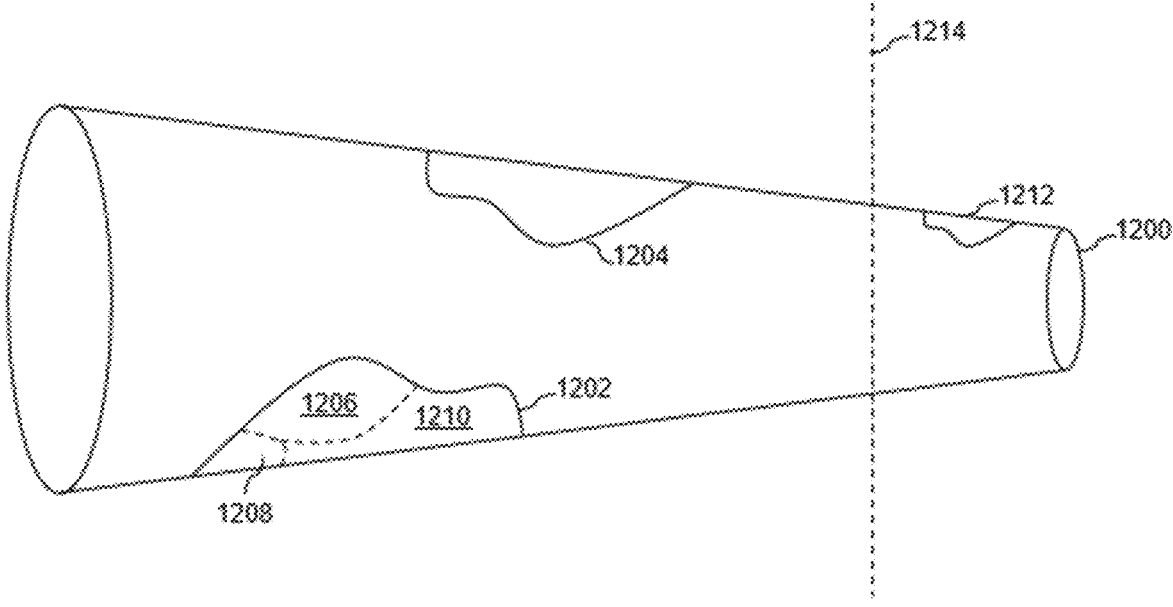
FIG. 12A is a schematic illustrating an example of one or more regions of plaque that can be analyzed using image analysis processes by one or more embodiments of the systems, methods, and devices herein for assessment of cardiovascular risk, disease, and/or state.

As an illustrative example, FIG. 12A provides a schematic example of one or more regions of plaque that can be analyzed using image analysis processes by one or more embodiments of the systems, methods, and devices herein for assessment of cardiovascular risk, disease, and/or state.

As illustrated in FIG. 12A, in some embodiments, the systems, methods, and devices described herein can be configured to analyze one or more vessels 1200 on a medical image. The one or more vessels 1200 can taper along a longitudinal axis such that the diameter of the vessel generally decreases. As described herein, in some embodiments, the quality of the medical image can be such that certain vessel features, such as plaque 1212, in a small or narrow vessel segment can appear less than accurate for analysis purposes. In contrast, certain vessel features, such as some other regions of plaque 1202, 1204, within the same vessel 1200 can have sufficient image quality for analysis purposes. For example, in some embodiments, a region of plaque 1202 appearing in a sufficiently wide vessel segment can be further analyzed by the system to identify and/or determine one or more regions and/or types and/or compositions of plaque 1206, 1208, 1210 within the region of plaque 1202. In some embodiments, the one or more regions of plaque 1204 can comprise a single type or composition of plaque. In some embodiments, a region of plaque 1202, 1204, 1206, 1208, 1210 can comprise one or more different types or compositions of plaque. For example, in some embodiments, the system can be configured to analyze, characterize, and/or classify plaque into one of three types: low-density non-calcified plaque, non-calcified plaque, and calcified plaque. In some embodiments, the system can be configured to analyze, characterize, and/or classify plaque into one of two types: non-calcified plaque and calcified plaque. In some embodiments, the system can be configured to analyze, characterize, and/or classify plaque into one of any number of different types, such as for example 1, 2, 3, 4, 5, 6, 7, 8, 9, 10, 15, 20, 25, and/or 30 different types of classifications of plaque. In some embodiments, the system can be configured to analyze, characterize, and/or classify plaque into a number of different types within a range defined by two of the aforementioned values.

In some embodiments, due to the fact that certain vessel features, such as a region of plaque 1212, within a narrow vessel segment comprises low image quality for analysis, the system can be configured to ignore or remove such features. More specifically, as described herein, in some embodiments, the system can be configured to ignore vessel segments below a certain vessel threshold 1214 and/or features therein from further analysis. As such, in the illustrated example, in some embodiments, the system can be configured to only analyze some of the regions of plaque 1202, 1204 that are above a vessel threshold 1214 and not others 1212 that are below the vessel threshold 1214 within a single vessel 1200. In some embodiments, the system can be further configured to analyze only those regions of plaque 1202, 1204 above the vessel threshold 1214 in determining one or more plaque, vessel, and/or relational plaque parameters, such as PAV. In some embodiments, such modified PAV or other parameter can be normalized, for example against the body mass and/or LV mass and/or heart mass of the subject, and/or compared to a normal values and/or reference values database comprising modified and/or normalized PAV or other parameter values. Based on such analysis, in some embodiments, the system can be configured to determine coronary artery disease (CAD) risk assessment and/or proposed treatment for a subject.

Figure 12B:
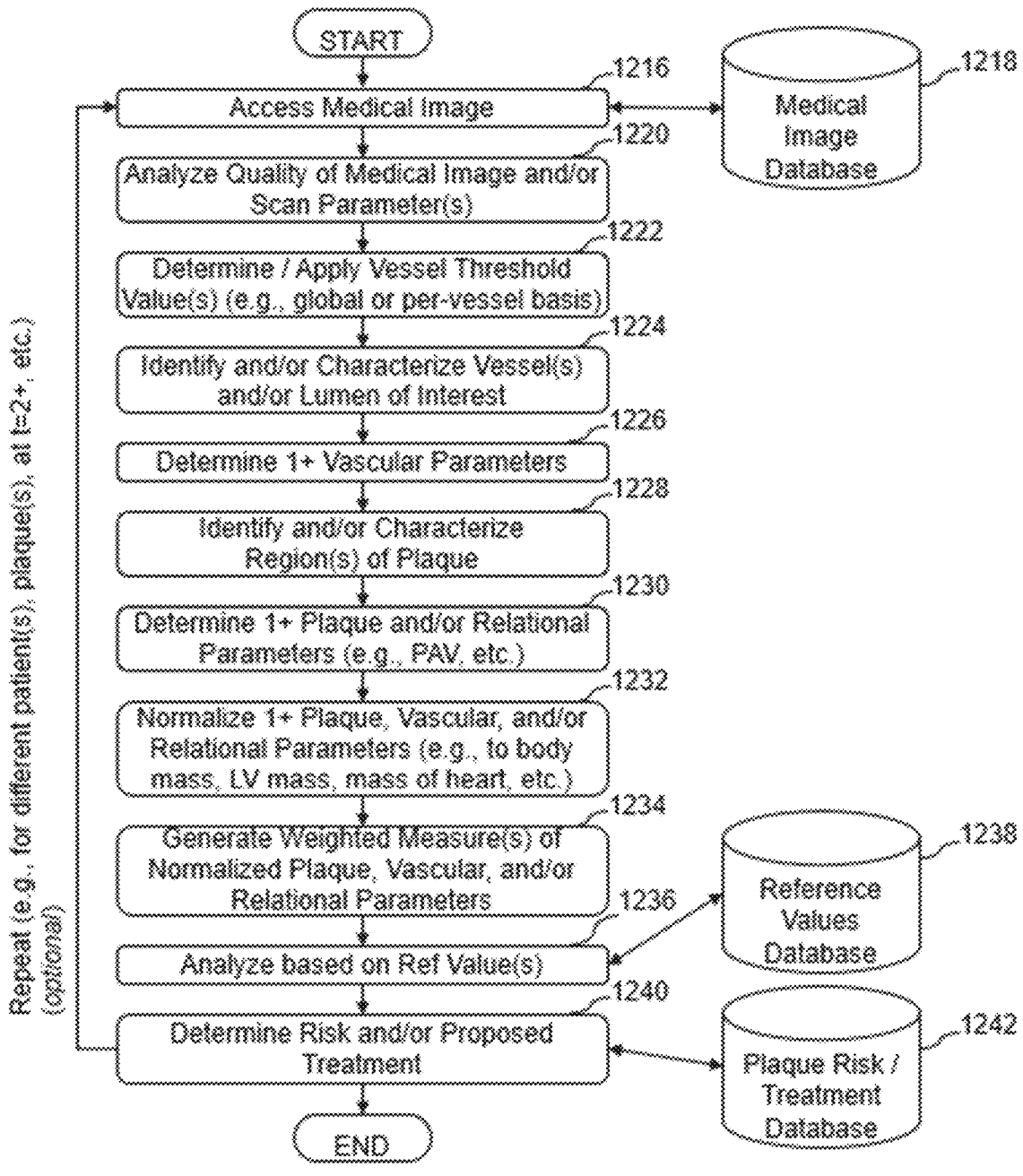
FIGS. 12B-12C are flowcharts illustrating example embodiments of systems, devices, and methods for cardiovascular risk and/or disease state assessment using modified and/or normalized image analysis-based plaque parameters.

Cardiovascular Risk and/or Disease State Assessment Using Modified and/or Normalized Image Analysis-Based Plaque Parameters As described herein, some embodiments of systems, devices, and methods described herein are configured to derive one or more modified plaque parameters, for example by setting a vessel threshold for analysis, from a medical image and use the same for risk assessment and/or treatment assessment for CAD. In some embodiments, such modified plaque parameters can be normalized for comparison and/or analysis against a reference database in determining the risk and/or treatment assessment. FIG. 12B is a flowchart illustrating example embodiments of systems, devices, and methods for cardiovascular risk and/or disease state assessment using modified and/or normalized image analysis-based plaque parameters.

As illustrated in FIG. 12B, in some embodiments, the system can be configured to access a medical image at block 1216. In some embodiments, the medical image can include one or more arteries, such as coronary, carotid, and/or other arteries of a subject. In some embodiments, the medical image can be stored in a medical image database 1218. In some embodiments, the medical image database 1218 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1220, the system can be configured to analyze the quality of the medical image and/or scan parameters. In some embodiments, the system can be configured to analyze the quality of the image as a whole and/or on a vessel-by-vessel or segment-by-segment basis.

In some embodiments, at block 1222, the system can be configured to determine and/or apply a vessel threshold value. As discussed herein, in some embodiments, the vessel threshold value can be determined and/or applied on the image as a whole and/or on a vessel-by-vessel or segment-by-segment basis. The vessel threshold can be predetermined and/or be dynamically determined, automatically, semi-automatically, and/or manually.

In some embodiments, the system can be configured to utilize one or more AI and/or ML algorithms to automatically and/or dynamically determine and/or apply a vessel threshold value. For example, in some embodiments, the one or more AI and/or ML algorithms can be trained using a Convolutional Neural Network (CNN) on a set of medical images on which vessel thresholds have been identified, for example depending on the image quality, thereby allowing the AI and/or ML algorithm automatically determine and/or apply a vessel threshold(s) directly based on a medical image.

In some embodiments, the vessel threshold can be based on volume, diameter, surface area, radius, width, and/or any other variable or parameter related to the vessel. In some embodiments, the vessel threshold can comprise a vessel diameter of about mm, about 9.0 mm, about 8.0 mm, about 7.0 mm, about 6.0 mm, about 5.0 mm, about 4.5 mm, about 4.0 mm, about 3.9 mm, about 3.8 mm, about 3.7 mm, about 3.6 mm, about 3.5 mm, about 3.4 mm, about 3.3 mm, about 3.2 mm, about 3.1 mm, about 3.0 mm, about 2.9 mm, about 2.8 mm, about 2.7 mm, about 2.6 mm, about 2.5 mm, about 2.4 mm, about 2.3 mm, about 2.2 mm, about 2.1 mm, about 2.0 mm, about 1.9 mm, about 1.8 mm, about 1.7 mm, about 1.6 mm, about 1.5 mm, about 1.4 mm, about 1.3 mm, about 1.2 mm, about 1.1 mm, about 1.0 mm, about mm, about 0.8 mm, about 0.7 mm, about 0.6 mm, about 0.5 mm, about 0.4 mm, about 0.5 mm, about 0.4 mm, about 0.3 mm, about 0.2 mm, about 0.1 mm, and/or within a range defined by two of the aforementioned values.

In some embodiments, at block 1224, the system can be configured to identify and/or characterize one or more vessels and/or lumen of interest, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, the one or more vessels and/or lumen of interest can be identified based on the vessel threshold(s) being applied. For example, in some embodiments, the system can be configured to identify and/or characterize only those vessel or lumen segments that qualify and/or are above the vessel threshold, while ignoring other vessel or lumen segments below the vessel threshold. Thus, in some embodiments, the system can be configured to same processing power and increase processing speed by ignoring areas within certain vessels that would only produce sub-par analysis results due to low image quality.

In some embodiments, at block 1226, the system can be configured to identify and/or determine one or more vascular parameters. In some embodiments, vascular parameters can include one or more of vascular volume, diameter, area, cross-sectional area, surface area, length, location, and/or remodeling. The system can be configured to utilize one or more AI and/or ML algorithms to automatically and/or dynamically identify and/or determine one or more vascular parameters using image processing.

In some embodiments, at block 1228, the system can be configured to identify and/or characterize one or more regions of plaque within the medical image. In some embodiments, the one or more regions of plaque can be identified based on the vessel threshold(s) being applied. For example, in some embodiments, the system can be configured to identify and/or characterize only those regions of plaque that are within a vessel segment that qualify and/or are above the vessel threshold, while ignoring other regions of plaque that are within a vessel or lumen segments below the vessel threshold. Thus, in some embodiments, the system can be configured to same processing power and increase processing speed by ignoring areas of plaque within certain vessels that would only produce sub-par analysis results due to low image quality.

In some embodiments, the system can be configured to utilize one or more AI and/or ML algorithms to automatically and/or dynamically identify and/or characterize one or more regions of plaque using image processing. For example, in some embodiments, the one or more AI and/or ML algorithms can be trained using a Convolutional Neural Network (CNN) on a set of medical images on which one or more regions of plaque have been identified and/or characterized, thereby allowing the AI and/or ML algorithm to automatically identify and/or characterize regions of plaque directly from a medical image.

For example, in some embodiments, the system can be configured to analyze the absolute density, relative density, radiodensity values, and/or heterogeneity or distribution thereof of one or more pixels on a medical image to identify and/or characterize plaque. More specifically, in some embodiments, the system can be configured to identify a particular pixel as plaque, non-calcified plaque, low-density non-calcified plaque, and/or calcified plaque, and/or any other classification or type of plaque. In some embodiments, the system can be configured to classify a particular pixel or region of plaque as non-calcified plaque when the radiodensity value of the pixel is below a certain predetermined threshold, within a predetermined range, and/or comprises a heterogeneity index or distribution within, under, or above a particular predetermined range or threshold. In some embodiments, the system can be configured to classify a particular pixel or region of plaque as low-density non-calcified plaque when the radiodensity value of the pixel is below a certain predetermined threshold, within a predetermined range, and/or comprises a heterogeneity index or distribution within, under, or above a particular predetermined range or threshold. In some embodiments, the system can be configured to classify a particular pixel or region of plaque as calcified plaque when the radiodensity value of the pixel is above a certain predetermined threshold, within a predetermined range, and/or comprises a heterogeneity index or distribution within, under, or above a particular predetermined range or threshold.

In some embodiments, at block 1230, the system can be configured to determine one or more non-calcified plaque parameters and/or one or more relational plaque parameters. For example, in some embodiments, the one or more plaque parameters can include absolute plaque density, relative plaque density, composition, calcification, radiodensity, location, volume, surface area, geometry, heterogeneity, diffusivity, and/or ratio between volume and surface area.

The relational plaque parameters can include a ratio or other comparison between one or more plaque parameters and one or more vessel parameters, such as for example PAV, PAV on a vessel-by-vessel basis, PAV on a segment-by-segment basis, and/or PAV for the whole heart, ratio of surface area of plaque to surface of vessel or lumen, ratio of volume of plaque to volume of vessel or lumen, and/or the like.

In some embodiments, the system can be configured to utilize one or more AI and/or ML algorithms to automatically and/or dynamically determine one or more plaque parameters and/or relational plaque parameters using image processing. For example, in some embodiments, the one or more AI and/or ML algorithms can be trained using a Convolutional Neural Network (CNN) on a set of medical images on which one or more plaque parameters and/or relational plaque parameters have been determined, thereby allowing the AI and/or ML algorithm to automatically determine one or more plaque parameters and/or relational plaque parameters directly from a medical image.

In some embodiments, at block 1232, the system can be configured to normalize one or more of the one or more modified plaque parameters, vascular parameters, and/or relational plaque parameters. For example, in some embodiments, the system can be configured to normalize one or more parameters by comparing to a physical property of the subject, such as for example heart mass, LV mass, total vessel volume, age, gender, and/or a combination or weighted measure of the foregoing.

In some embodiments, at block 1234, the system can be configured to generate a weighted measure of the normalized and/or modified one or more parameters. For example, in some embodiments, the system can be configured to assign a weight between 0 and 1 to one or more normalized plaque parameters, vascular parameters, and/or relational plaque parameters. In some embodiments, the system can be configured to assign a weight between 0 and 1, such as for example 0, 0.05, 0.1, 0.15, 0.2, 0.3, 0.4, 0.5, 0.6, 0.7, 0.8, 0.9, 0.99, and 1. In some embodiments, the system can be configured weight one or more parameters 0, thereby ignoring its effect. In some embodiments, the system can be configured to weight one or more parameters 1, thereby focusing exclusively on such parameter. In some embodiments, the weighted measure can also include one or more other factors or features, such as for example, age, weight, gender, plaque volume, plaque composition, vascular remodeling, high-risk plaque, lumen volume, plaque location (proximal v. middle v. distal), plaque location (myocardial v. pericardial facing), plaque location (at bifurcation or trifurcation v. not at bifurcation or trifurcation), plaque location (in main vessel v. branch vessel), stenosis severity, percentage coronary blood volume, percentage fractional myocardial mass, percentile for age and/or gender, constant or other correction factor to allow for control of within-person, within-vessel, inter-plaque, plaque-myocardial relationships, and/or the like.

In some embodiments, at block 1236, the system can be configured analyze the generated weighted measure of the normalized and/or modified one or more of the one or more plaque parameters, vascular parameters, and/or relational plaque parameters. For example, in some embodiments, the system can be configured to analyze the weighted measure against one or more reference values, such as normal values. More specifically, in some embodiments, the system can be configured to access a reference values database 1238 that includes a weighted measure of one or more reference values of one or more normalized and/or modified plaque parameters, vascular parameters, and/or relational plaque parameters. The one or more reference values can be derived from other subjects with varying states or risks of cardiovascular disease, including for example normal values.

In some embodiments, the one or more reference values can be obtained from one or more medical images using the same or similar imaging modalities as the medical image accessed at block 1216. In some embodiments, the one or more reference values can be obtained from analyzing one or more medical image to derive one or more modified plaque, relational plaque, and/or vascular parameters after applying one or more vessel thresholds, including for example the same vessel threshold applied at block 1222. In some embodiments, the one or more reference values can include one or more parameters obtained from a medical image after applying varying different vessel thresholds to the same image and/or vessel. In some embodiments, the one or more reference values can be obtained after normalizing to a physical property, including for example the same physical property used to normalize the one or more parameters in block 1232. In some embodiments, the one or more reference values can include one or more parameters obtained from a medical image after normalizing against a number of varying different physical properties, such as body mass, heart mass, LV mass, and/or the like, to the same image and/or parameter. In some embodiments, a weighted measure of the one or more reference values can be stored on a reference values database 1238, which can be locally accessible by the system and/or can be located remotely and accessible through a network connection.

In some embodiments, based on such analysis and/or comparison, the system, at block 1240, can be configured to determine a risk or state of cardiovascular disease or health of the subject. Further, in some embodiments, based on such analysis and/or comparison, the system, at block 1240, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1242, which can be locally accessible by the system and/or can be located remotely and accessible through a network connection. In some embodiments, the plaque risk/treatment database 1242 can include reference points or data that relate one or more treatment to cardiovascular disease risk or state determined based on one or more normalized and/or modified one or more plaque, vascular, and/or relational plaque parameters.

In some embodiments, the system can be configured to repeat one or more processes described in relation to blocks 1216-1240, for example for one or more other regions of plaque and/or other subjects and/or for the same subject at a different time. As such, in some embodiments, the system can provide for longitudinal disease tracking and/or personalized treatment for a subject.

Figure 12C:
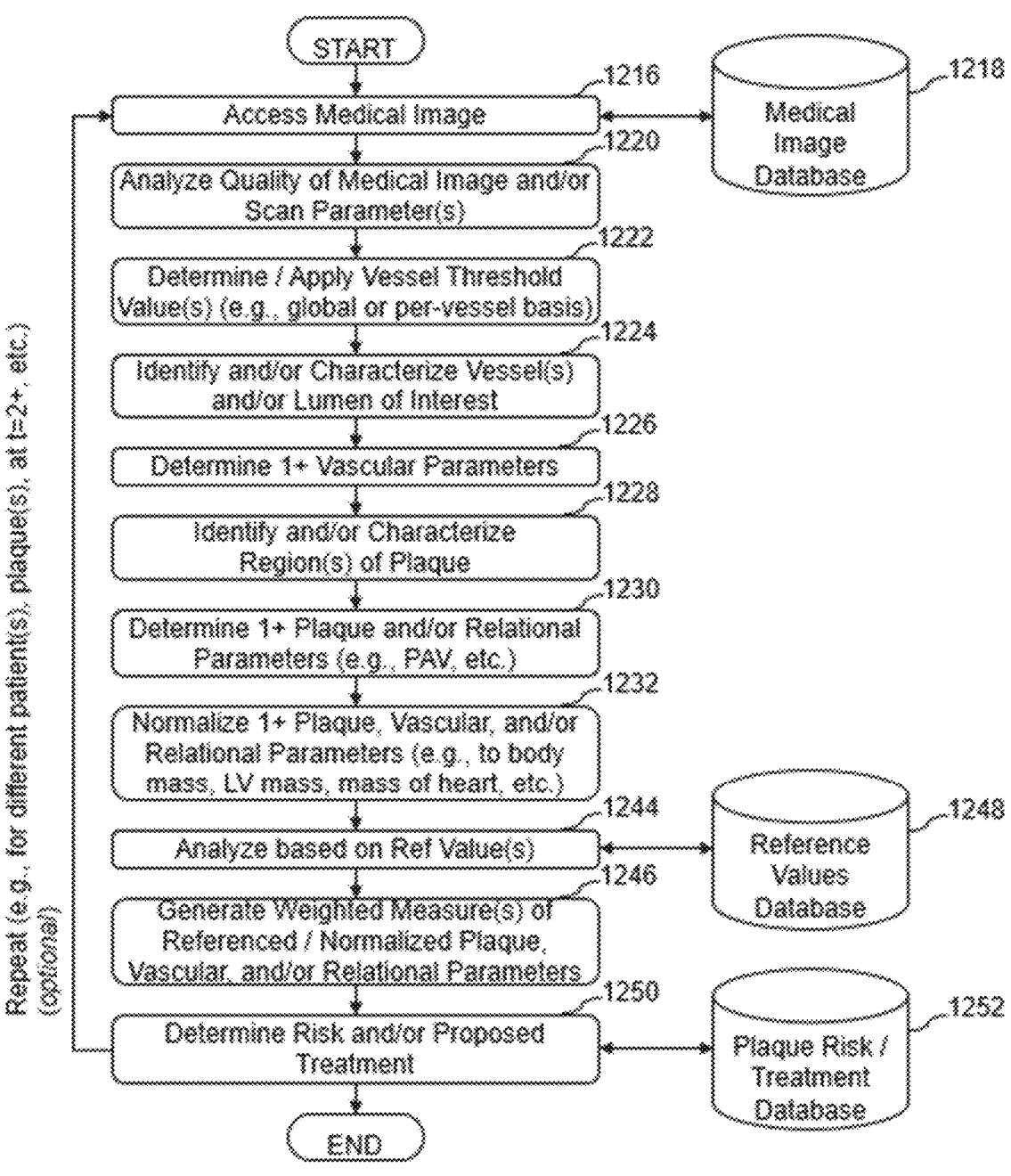

FIG. 12C is also a flowchart illustrating example embodiments of systems, devices, and methods for cardiovascular risk and/or disease state assessment using modified and/or normalized image analysis-based plaque parameters. The same reference numbers in FIGS. 12B and 12C represent similar features and can include any of the features described in reference to either figure.

As illustrated in FIG. 12C, in some embodiments, the system can be configured to analyze one or more normalized plaque, vascular, and/or relational plaque parameters at block 1244 directly without generating a weighted measure of the same. More specifically, in some embodiments, the system can be configured to access a reference values database 1248 that includes one or more reference values of one or more normalized and/or modified plaque parameters, vascular parameters, and/or relational plaque parameters. The one or more reference values can be derived from other subjects with varying states or risks of cardiovascular disease, including for example normal values.

In some embodiments, the one or more reference values can be obtained from one or more medical images using the same or similar imaging modalities as the medical image accessed at block 1216. In some embodiments, the one or more reference values can be obtained from analyzing one or more medical image to derive one or more modified plaque, relational plaque, and/or vascular parameters after applying one or more vessel thresholds, including for example the same vessel threshold applied at block 1222. In some embodiments, the one or more reference values can include one or more parameters obtained from a medical image after applying varying different vessel thresholds to the same image and/or vessel. In some embodiments, the one or more reference values can be obtained after normalizing to a physical property, including for example the same physical property used to normalize the one or more parameters in block 1232. In some embodiments, the one or more reference values can include one or more parameters obtained from a medical image after normalizing against a number of varying different physical properties, such as body mass, heart mass, LV mass, and/or the like, to the same image and/or parameter. In some embodiments, the one or more reference values can be stored on a reference values database 1248, which can be locally accessible by the system and/or can be located remotely and accessible through a network connection.

In some embodiments, at block 1246, the system can be configured to generate a weighted measure of the referenced and/or normalized and/or modified one or more plaque, vascular, and/or relational plaque parameters. For example, in some embodiments, the system can be configured to assign a weight between 0 and 1 to one or more referenced, normalized, and/or modified plaque parameters, vascular parameters, and/or relational plaque parameters. In some embodiments, the system can be configured to assign a weight between 0 and 1, such as for example 0, 0.05, 0.1, 0.15, 0.2, 0.3, 0.4, 0.5, 0.6, 0.7, 0.8, 0.9, 0.99, and 1. In some embodiments, the system can be configured weight one or more parameters 0, thereby ignoring its effect. In some embodiments, the system can be configured to weight one or more parameters 1, thereby focusing exclusively on such parameter. In some embodiments, the weighted measure can also include one or more other factors or features, such as for example, age, weight, gender, plaque volume, plaque composition, vascular remodeling, high-risk plaque, lumen volume, plaque location (proximal v. middle v. distal), plaque location (myocardial v. pericardial facing), plaque location (at bifurcation or trifurcation v. not at bifurcation or trifurcation), plaque location (in main vessel v. branch vessel), stenosis severity, percentage coronary blood volume, percentage fractional myocardial mass, percentile for age and/or gender, constant or other correction factor to allow for control of within-person, within-vessel, inter-plaque, plaque-myocardial relationships, and/or the like.

In some embodiments, the system, at block 1250, can be configured to use the generated weighted measure of the referenced and/or normalized and/or modified one or more plaque, vascular, and/or relational plaque parameters to determine a risk or state of cardiovascular disease or health of the subject. Further, in some embodiments, the system, at block 1250 can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1252, which can be locally accessible by the system and/or can be located remotely and accessible through a network connection. In some embodiments, the plaque risk/treatment database 1252 can include reference points or data that relate one or more treatment to cardiovascular disease risk or state determined based on one or more weighted measures of referenced and/or normalized and/or modified one or more plaque, vascular, and/or relational plaque parameters.

In some embodiments, the reference values databases 1238, 1248 and/or any portion or component thereof can be part of a single database. In some embodiments, the reference values databases 1238, 1248 and/or any portion or component thereof can comprise separate databases. In some embodiments, the reference values stored on one or more such reference values databases 1238, 1248 can be curated, triaged or selected based on age, gender, pre-existing medical condition, and/or the like to match the subject for improved accuracy.

In some embodiments, the plaque risk/treatment databases 1242, 1252 and/or any portion or component thereof can be part of a single database. In some embodiments, the plaque risk/treatment databases 1242, 1252 and/or any portion or component thereof can comprise separate databases. In some embodiments, the plaque risk and/or treatment stored on one or more such plaque risk/treatment databases 1242, 1252 can be curated, triaged or selected based on age, gender, pre-existing medical condition, and/or the like to match the subject for improved accuracy.

In some embodiments, the system can be configured to repeat one or more processes described in relation to blocks 1216-1250, for example for one or more other regions of plaque and/or other subjects and/or for the same subject at a different time. As such, in some embodiments, the system can provide for longitudinal disease tracking and/or personalized treatment for a subject.

Reference Values Database Based on Modified and/or Normalized Image Analysis-Based Plaque Parameters As described herein, some embodiments of systems, devices, and methods described herein are configured to utilize one or more reference values of modified and/or normalized plaque parameters, vessel parameters, and/or relational plaque parameters in assessing CAD risk and/or determining a proposed treatment for a subject. In order to obtain such reference values and/or build a reference values database, some embodiments can be configured to utilize one or more vessel thresholds to modify one or more plaque parameters, vessel parameters, and/or relational plaque parameters. Further, in order to obtain such reference values and/or build a reference values database, some embodiments can be configured to normalize one or more modified plaque parameters, vessel parameters, and/or relational plaque parameters against a physical property of the subject, such as for example body mass, heart mass, LV mass, total vessel volume, and/or the like.

Figure 12D:
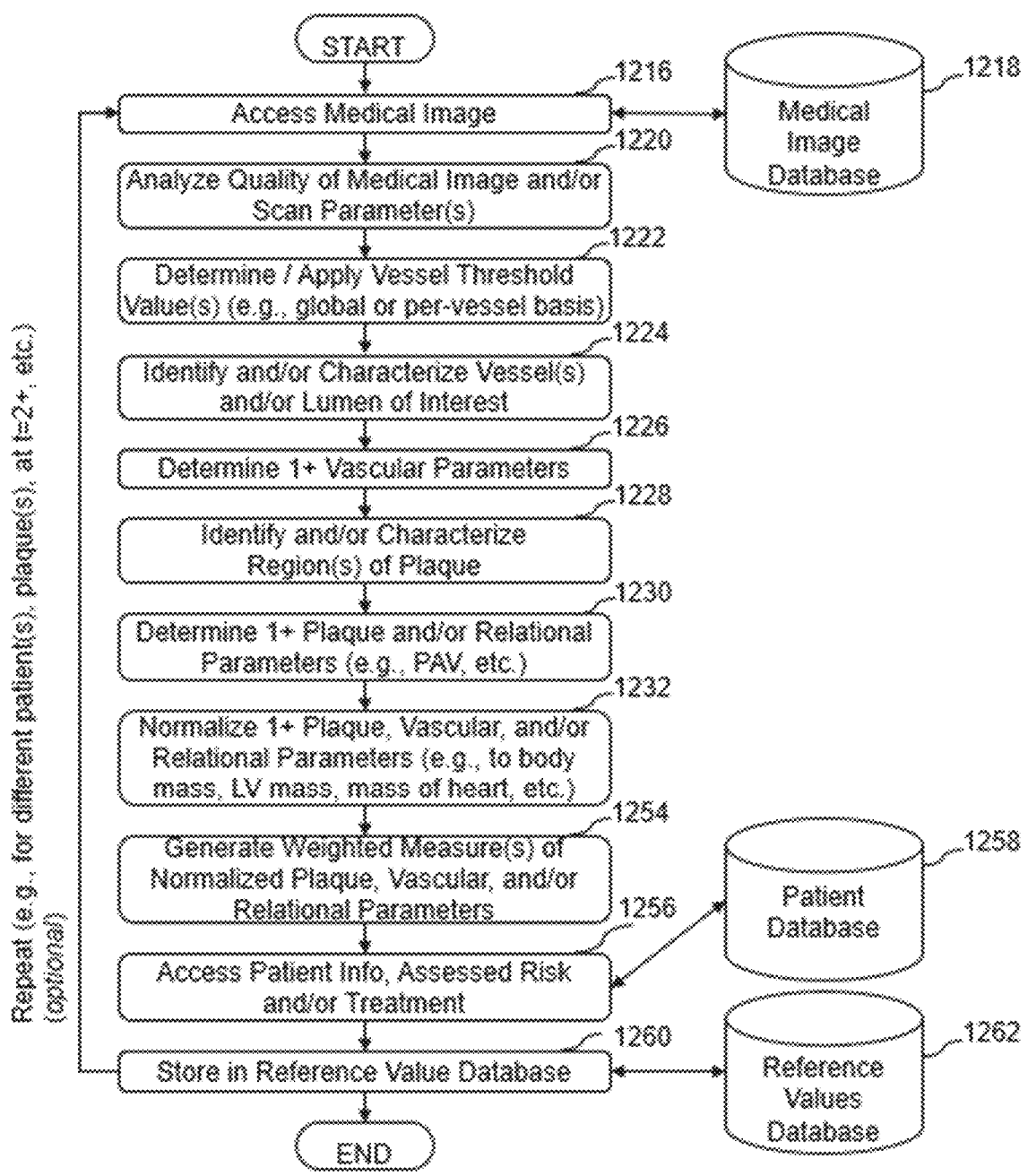
FIG. 12D is a flowchart illustrating example embodiments of systems, devices, and methods for developing a reference values database for cardiovascular risk and/or disease state assessment using modified and/or normalized image analysis-based plaque parameters.

FIG. 12D is a flowchart illustrating example embodiments of systems, devices, and methods for developing a reference values database for cardiovascular risk and/or disease state assessment using modified and/or normalized image analysis-based plaque parameters. The same reference numbers in FIGS. 12D, 12C, 12B represent similar features and can include any of the features described in reference to either figure.

As illustrated in FIG. 12D, in some embodiments, the system can be configured to store one or more normalized and/or modified plaque parameters, vessel parameters, and/or relational plaque parameters in a reference values database 1258. For example, in some embodiments, the system can be configured to store one or more such values in the reference values database 1258 after analysis of a subject, thereby continuously and/or periodically updating the reference database.

More specifically, in some embodiments, at block 1216, the system can be configured to access one or more patient information, assessed CAD risk, and/or proposed or actual treatment, for example by accessing a patient database 1218. In some embodiments, the system can be configured to correlate and/or map the modified and/or normalized one or more plaque parameters, vessel parameters, and/or relational plaque parameters to one or more information accessed from the patient database 1218. In some embodiments, the patient database 1218 can be locally accessible by the system and/or can be located remotely and accessible through a network connection.

In some embodiments, at block 1260, the system can be configured to store the normalized and/or modified one or more plaque parameters, vessel parameters, and/or relational plaque parameters and/or mapping to one or more patient information. For example, in some embodiments, the system can be configured to store one or more of the foregoing on a reference values database 1258 that can be locally accessible by the system and/or can be located remotely and accessible through a network connection.

In some embodiments, the reference values databases 1238, 1248, 1258 and/or any portion or component thereof can be part of a single database. In some embodiments, the reference values databases 1238, 1248, 1258 and/or any portion or component thereof can comprise separate databases. In some embodiments, the reference values stored on one or more such reference values databases 1238, 1248, 1258 can be curated, triaged or selected based on age, gender, pre-existing medical condition, and/or the like to match the subject for improved accuracy.

In some embodiments, the system can be configured to repeat one or more processes described in relation to blocks 1216-1260, for example for one or more other regions of plaque and/or other subjects and/or for the same subject at a different time. As such, in some embodiments, the system can be configured to continuously and/or periodically update the reference values database 1258, thereby continuously improving accuracy.

Computer System

Figure 12E:
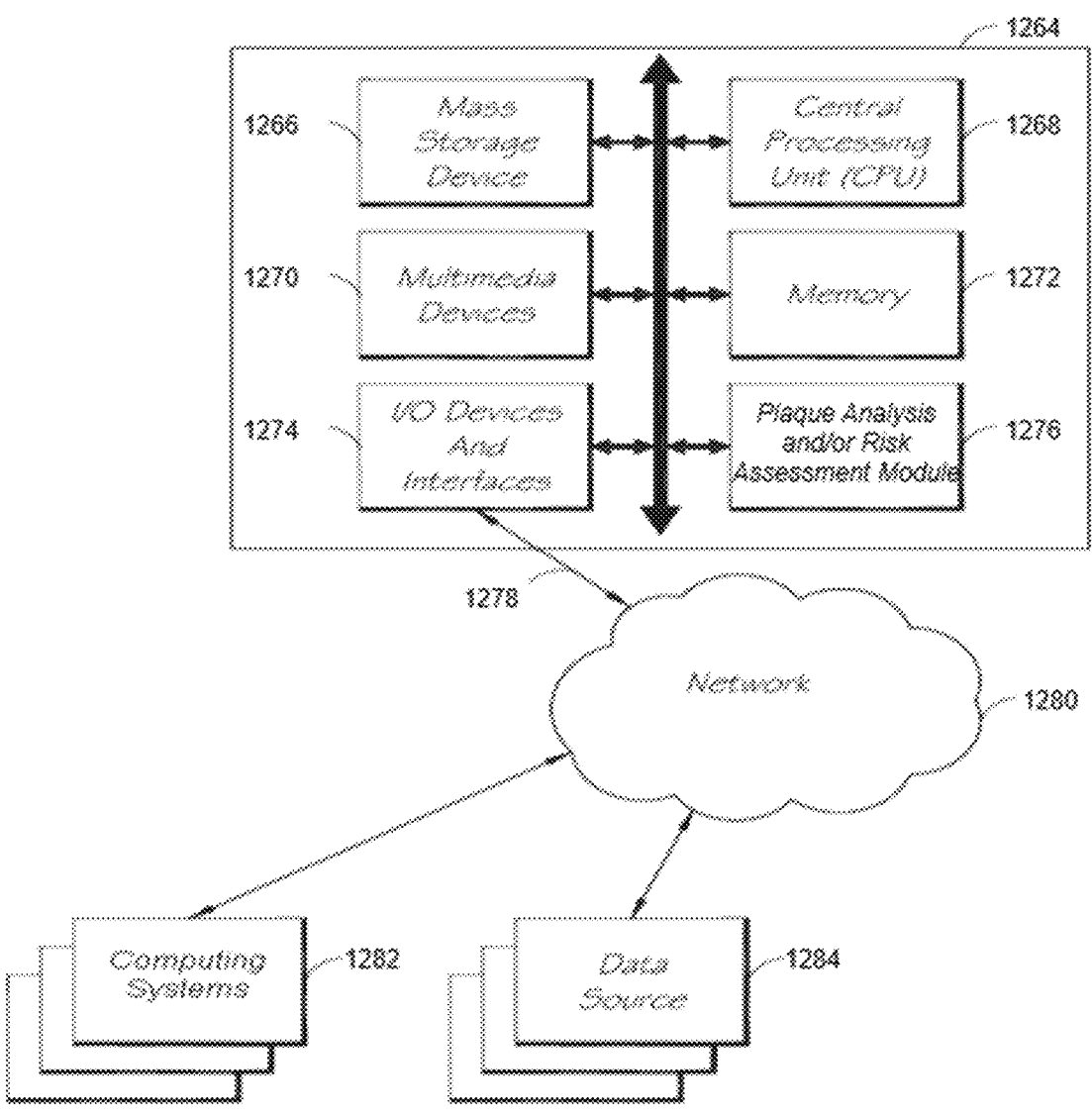
FIG. 12E is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 12E. The example computer system 1264 is in communication with one or more computing systems 1282 and/or one or more data sources 1284 via one or more networks 1280. While FIG. 12E illustrates an embodiment of a computing system 1264, it is recognized that the functionality provided for in the components and modules of computer system 1264 can be combined into fewer components and modules, or further separated into additional components and modules.

The computer system 1264 can comprise a Plaque Analysis and/or Risk Assessment Module 1276 that carries out the functions, methods, acts, and/or processes described herein.

The Plaque Analysis and/or Risk Assessment Module 1276 executed on the computer system 1264 by a central processing unit 1268 discussed further below. Other features of the computer system 1264 can be similar to corresponding features of the computer system of FIG. 9G, described above.

Certain Examples of Embodiments of Modified Percent Atheroma Volume (PAV) and/or Normalized Percent Atheroma Volume The following are non-limiting examples of certain embodiments of systems and methods for determining modified and/or normalized percent atheroma volume (PAV). Other embodiments may include one or more other features, or different features, that are discussed herein.

Embodiment 1: A computer-implemented method of assessing a state of cardiovascular disease of a subject based on one or more normalized relational plaque parameters derived from non-invasive medical image analysis, the method comprising: accessing, by a computer system, a medical image of a subject, wherein the medical image of the subject is obtained non-invasively; analyzing, by the computer system, the medical image of the subject to identify one or more arteries; applying, by the computer system, a vessel threshold to the one or more arteries identified from the medical image to determine one or more arterial sections of interest above the vessel threshold; determining, by the computer system, one or more vascular parameters associated with the subject by analyzing the one or more arterial sections of interest, wherein the one or more vascular parameters comprise one or more of vessel volume, diameter, area, cross-sectional area, surface area, length, location, or remodeling; identifying, by the computer system, one or more regions of plaque in the arterial sections of interest; determining, by the computer system, one or more plaque parameters associated with the one or more regions of plaque, wherein the one or more plaque parameters comprise one or more of plaque density, composition, calcification, radiodensity, location, volume, surface area, geometry, heterogeneity, diffusivity, or ratio between volume and surface area; determining, by the computer system, one or more relational plaque parameters for the subject, the one or more relational plaque parameters determined by comparing the one or more plaque parameters to the one or more vascular parameters; normalizing, by the computer system, the one or more relational plaque parameters for the subject by comparison to one or more physical properties of the subject; analyzing, by the computer system, the normalized one or more relational plaque parameters for the subject by comparison to a dataset of values, the values comprising a plurality of normalized one or more relational plaque parameters derived from applying the vessel threshold to a plurality of medical images of a population with varying states of cardiovascular disease; and determining, by the computer system, an assessment of a state of cardiovascular disease of the subject based at least in part on analysis of the normalized one or more relational plaque parameters for the subject, wherein the computer system comprises a computer processor and an electronic storage medium.

Embodiment 2: The computer-implemented method of Embodiment 1, wherein the vessel threshold comprises about 2.0 mm in diameter.

Embodiment 3: The computer-implemented method of Embodiment 1, wherein the one or more relational plaque parameters comprises percent atheroma volume (PAV).

Embodiment 4: The computer-implemented method of Embodiment 3, wherein the PAV comprises total plaque volume over vessel volume of the one or more arterial sections of interest.

Embodiment 5: The computer-implemented method of Embodiment 3, wherein the PAV comprises non-calcified plaque volume over vessel volume of the one or more arterial sections of interest.

Embodiment 6: The computer-implemented method of Embodiment 3, wherein the PAV comprises low-density non-calcified plaque volume over vessel volume of the one or more arterial sections of interest.

Embodiment 7: The computer-implemented method of Embodiment 1, wherein the vessel threshold comprises about 2.0 mm in diameter, and wherein the one or more relational plaque parameters comprises percent atheroma volume (PAV).

Embodiment 8: The computer-implemented method of Embodiment 1, wherein the one or more physical properties of the subject comprises body mass of the subject.

Embodiment 9: The computer-implemented method of Embodiment 1, wherein the one or more physical properties of the subject comprises left ventricular mass of the subject.

Embodiment 10: The computer-implemented method of Embodiment 9, wherein the left ventricular mass of the subject is determined based at least in part on the medical image of the subject.

Embodiment 11: The computer-implemented method of Embodiment 1, wherein the medical image is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS).

Embodiment 12: The computer-implemented method of Embodiment 1, wherein the vessel threshold varies by vessel.

Embodiment 13: The computer-implemented method of Embodiment 1, wherein the vessel threshold is determined based at least in part on quality of the medical image.

Embodiment 14: The computer-implemented method of Embodiment 1, wherein the assessment of the state of cardiovascular disease of the subject is further determined based at least in part on the one or more vascular parameters or the one or more plaque parameters.

Embodiment 15: The computer-implemented method of Embodiment 1, further comprising: generating, by the computer system, a weighted measure of one or more of the one or more vascular parameters, one or more plaque parameters, or one or more relational plaque parameters, wherein the assessment of the state of cardiovascular disease of the subject is further determined based at least in part on the generated weighted measure.

Embodiment 16: The computer-implemented method of Embodiment 1, further comprising generating, by the computer system, a treatment for cardiovascular disease for the subject based at least in part on the determined assessment of the state of cardiovascular disease.

Embodiment 17: The computer-implemented method of Embodiment 16, wherein the treatment for cardiovascular disease comprises medical intervention, medical treatment, or lifestyle change.

Embodiment 18: The computer-implemented method of Embodiment 16, further comprising tracking, by the computer system, efficacy of the treatment by determining assessment of the state of cardiovascular disease of the subject at a later point in time after treatment.

Embodiment 19: A system for assessing a state of cardiovascular disease of a subject based on one or more normalized relational plaque parameters derived from non-invasive medical image analysis, the system comprising: one or more computer readable storage devices configured to store a plurality of computer executable instructions; and one or more hardware computer processors in communication with the one or more computer readable storage devices and configured to execute the plurality of computer executable instructions in order to cause the system to: access a medical image of a subject, wherein the medical image of the subject is obtained non-invasively; analyze the medical image of the subject to identify one or more arteries; apply a vessel threshold to the one or more arteries identified from the medical image to determine one or more arterial sections of interest above the vessel threshold; determine one or more vascular parameters associated with the subject by analyzing the one or more arterial sections of interest, wherein the one or more vascular parameters comprise one or more of vessel volume, diameter, area, cross-sectional area, surface area, length, location, or remodeling; identify one or more regions of plaque in the arterial sections of interest; determine one or more plaque parameters associated with the one or more regions of plaque, wherein the one or more plaque parameters comprise one or more of plaque density, composition, calcification, radiodensity, location, volume, surface area, geometry, heterogeneity, diffusivity, or ratio between volume and surface area; determine one or more relational plaque parameters for the subject, the one or more relational plaque parameters determined by comparing the one or more plaque parameters to the one or more vascular parameters; normalize the one or more relational plaque parameters for the subject by comparison to one or more physical properties of the subject; analyze the normalized one or more relational plaque parameters for the subject by comparison to a dataset of values, the values comprising a plurality of normalized one or more relational plaque parameters derived from applying the vessel threshold to a plurality of medical images of a population with varying states of cardiovascular disease; and determine an assessment of a state of cardiovascular disease of the subject based at least in part on analysis of the normalized one or more relational plaque parameters for the subject.

Embodiment 20: The system of Embodiment 19, wherein the vessel threshold comprises about 2.0 mm in diameter.

Embodiment 21: The system of Embodiment 19, wherein the one or more relational plaque parameters comprises percent atheroma volume (PAV).

Embodiment 22: The system of Embodiment 21, wherein the PAV comprises total plaque volume over vessel volume of the one or more arterial sections of interest.

Embodiment 23: The system of Embodiment 21, wherein the PAV comprises non-calcified plaque volume over vessel volume of the one or more arterial sections of interest.

Embodiment 24: The system of Embodiment 21, wherein the PAV comprises low-density non-calcified plaque volume over vessel volume of the one or more arterial sections of interest.

Embodiment 25: The system of Embodiment 19, wherein the vessel threshold comprises about 2.0 mm in diameter, and wherein the one or more relational plaque parameters comprises percent atheroma volume (PAV).

Embodiment 26: The system of Embodiment 19, wherein the one or more physical properties of the subject comprises body mass of the subject.

Embodiment 27: The system of Embodiment 19, wherein the one or more physical properties of the subject comprises left ventricular mass of the subject.

Embodiment 28: The system of Embodiment 27, wherein the left ventricular mass of the subject is determined based at least in part on the medical image of the subject.

Embodiment 29: The system of Embodiment 19, wherein the medical image is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS).

Embodiment 30: The system of Embodiment 19, wherein the vessel threshold varies by vessel.

Embodiment 31: The system of Embodiment 19, wherein the vessel threshold is determined based at least in part on quality of the medical image.

Embodiment 32: The system of Embodiment 19, wherein the assessment of the state of cardiovascular disease of the subject is further determined based at least in part on the one or more vascular parameters or the one or more plaque parameters.

Embodiment 33: The system of Embodiment 19, wherein the system is further caused to: generate a weighted measure of one or more of the one or more vascular parameters, one or more plaque parameters, or one or more relational plaque parameters, wherein the assessment of the state of cardiovascular disease of the subject is further determined based at least in part on the generated weighted measure.

Embodiment 34: The system of Embodiment 19, wherein the system is further caused to generate a treatment for cardiovascular disease for the subject based at least in part on the determined assessment of the state of cardiovascular disease.

Embodiment 35: The system of Embodiment 34, wherein the treatment for cardiovascular disease comprises medical intervention, medical treatment, or lifestyle change.

Embodiment 36: The system of Embodiment 34, wherein the system is further caused to track efficacy of the treatment by determining assessment of the state of cardiovascular disease of the subject at a later point in time after treatment.

Immersive Patient-Specific Report Introduction

Disclosed herein are systems, methods, and devices for generation of a patient-specific report on the risk and/or state assessment, diagnosis, and/or treatment of cardiovascular disease, including for example coronary artery disease (CAD). In particular, in some embodiments, the systems, devices, and methods are configured to generate an immersive patient-specific report on the patient's cardiovascular disease risk, state, diagnosis, and/or treatment. In some embodiments, the systems, devices, and methods are configured to generate an immersive patient-specific report based at least in part on image-based analysis, for example of one or more plaque and/or vessel parameters. In some embodiments, the systems, devices, and methods are configured to view the patient's cardiovascular disease state or risk from a point of view within one or more arteries of the patient. In some embodiments, the systems, devices, and methods are configured to graphically view and/or track actual or hypothetical progression of the patient's cardiovascular disease state or risk based on actual or proposed treatment from a point of view within one or more arteries of the patient. In some embodiments, the systems, methods, and devices described herein can allow for virtual consultations and/or physician visits. For example, such virtual consultations or physician visits can take place in a virtual setting, such as the Metaverse, using augmented reality (AR) or virtual reality (VR) technology.

With respect to the millions suffering from heart disease, there is a need to better understand the overall health of the artery vessels within a patient beyond just knowing the blood chemistry or content of the blood flowing through such artery vessels. For example, in some embodiments of systems, devices, and methods disclosed herein, arteries with "good" or stable plaque or plaque comprising hardened calcified content are considered non-life threatening to patients whereas arteries containing "bad" or unstable plaque or plaque comprising fatty material are considered more life threatening because such bad plaque may rupture within arteries thereby releasing such fatty material into the arteries. Such a fatty material release in the blood stream can cause inflammation that may result in a blood clot. A blood clot within an artery can prevent blood from traveling to heart muscle thereby causing a heart attack or other cardiac event. Further, in some instances, it is generally more difficult for blood to flow through fatty plaque buildup than it is for blood to flow through calcified plaque build-up. Therefore, there is a need for better understanding and analysis of the arterial vessel walls of a patient.

Further, while blood tests and drug treatment regimens are helpful in reducing cardiovascular health issues and mitigating against cardiovascular events (for example, heart attacks), such treatment methodologies are not complete or perfect in that such treatments can misidentify and/or fail to pinpoint or diagnose significant cardiovascular risk areas. For example, the mere analysis of the blood chemistry of a patient will not likely identify that a patient has artery vessels having significant amounts of fatty deposit material bad plaque buildup along a vessel wall. Similarly, an angiogram, while helpful in identifying areas of stenosis or vessel narrowing, may not be able to clearly identify areas of the artery vessel wall where there is significant buildup of bad plaque. Such areas of buildup of bad plaque within an artery vessel wall can be indicators of a patient at high risk of suffering a cardiovascular event, such as a heart attack. In certain circumstances, areas where there exist areas of bad plaque can lead to a rupture wherein there is a release of the fatty materials into the bloodstream of the artery, which in turn can cause a clot to develop in the artery. A blood clot in the artery can cause a stoppage of blood flow to the heart tissue, which can result in a heart attack. Accordingly, there is a need for new technology for analyzing artery vessel walls and/or identifying areas within artery vessel walls that comprise a buildup of plaque whether it be bad or otherwise.

Various systems, methods, and devices disclosed herein are directed to embodiments for addressing the foregoing issues and to help educate patients with respect to their particular state of cardiovascular disease, state, or risk. In particular, in some embodiments, the systems, devices, and methods are configured to generate an immersive patient-specific report on the patient's cardiovascular disease risk, state, diagnosis, and/or treatment. In some embodiments, the systems, devices, and methods are configured to generate an immersive patient-specific report based at least in part on image-based analysis, for example of one or more plaque and/or vessel parameters. In some embodiments, the systems, devices, and methods are configured to view the patient's cardiovascular disease state or risk from a point of view within one or more arteries of the patient. In some embodiments, the systems, devices, and methods are configured to graphically view and/or track actual or hypothetical progression of the patient's cardiovascular disease state or risk based on actual or proposed treatment from a point of view within one or more arteries of the patient. In some embodiments, the systems, devices, and methods are configured to generate an immersive virtual visitation experience in which patients may be connected to medical professionals and view any of the generated reports and/or graphical views as described above.

As discussed herein, disclosed herein are systems, methods, and devices for cardiovascular risk and/or disease state assessment using image-based analyses and/or generation of an immersive patient-specific report using the same. In particular, in some embodiments, the systems, devices, and methods are configured to generate an immersive patient-specific report on the patient's cardiovascular disease risk, state, diagnosis, and/or treatment. In some embodiments, the systems, devices, and methods are configured to generate an immersive patient-specific report based at least in part on image-based analysis, for example of one or more plaque and/or vessel parameters.

In some embodiments, the systems, devices, and methods are configured to view the patient's cardiovascular disease state or risk from a point of view within one or more arteries of the patient. For example, the systems, methods, and devices may provide a patient and/or a doctor with an ability to view the patient's blood vessels in an AR and/or VR presentations, for example, from within a blood vessel. This can allow the patient and/or doctor to virtually tour the patient's vasculature, for example, to view potential dangerous plaques.

In some embodiments, the systems, devices, and methods are configured to graphically view and/or track actual or hypothetical progression of the patient's cardiovascular disease state or risk based on actual or proposed treatment from a point of view within one or more arteries of the patient.

Further, in some embodiments, the systems, methods, and devices described herein can allow for virtual consultations and/or physician visits, for example, in the metaverse. In particular, in some embodiments, the systems, methods, and devices described herein provide a metaverse experience in which a patient is able to obtain a virtual consultation with a physician prior to and/or after analysis of the patient's health state and/or risk. In some embodiments, the systems, devices, and methods also provide a virtual consultation in the metaverse to go over the results of a patient-specific report. For example, in some embodiments, the systems, methods, and devices allow for a virtual consultation while the patient is viewing an immersive patient-specific report of the patient's coronary arteries using a virtual reality (VR) device and/or other computing device. In some embodiments, the systems, methods, and devices are also configured to provide consultation, analysis, and/or generation of an immersive patient-specific report on structural heart disease and/or valvular heart disease. More specifically, in some embodiments, the systems, methods, and devices are configured to allow a patient to view inside his or her heart and/or valves to obtain a visceral experience of his or her state and/or risk of structural heart disease and/or valvular heart disease.

As described herein, coronary artery disease (CAD) and/or other cardiovascular and/or coronary heart diseases affect millions of patients in the US alone. Further, by utilizing some systems, devices, and methods described herein, it is possible to quantify and/or more accurately assess the state and/or risk of disease in a subject. For example, some embodiments of systems, devices, and methods described herein can be configured to analyze one or more medical images obtained using non-invasive measures to determine the extent and/or composition of plaque, as well as other plaque parameters and/or vascular parameters. For example, in some embodiments, the system can be configured to utilize one or more artificial intelligence (AI) and/or machine learning (ML) algorithms for determining such parameters. Based on such analyses, in some embodiments, the system can be configured to determine a risk of disease for a subject.

Despite such technical advantages and developments, however, in order to effectively prevent and/or treat disease, it can be equally important to educate patients, physicians, and/or subjects of individual state or risk of disease, such as coronary disease. Effective education and/or reporting can significantly improve outcome, as subjects who have a better understanding will likely adhere better to the proposed treatment, which can include lifestyle changes, exercise, diet, and/or the like. In order to better educate a subject on his or her state of coronary or cardiovascular disease, it can be important to personalize the report. In addition, it can also be important to provide a more real and/or life-like report.

In order to address such goals and technical shortcomings of the current state of technology, some systems, devices, and methods described herein are configured to generate an immersive, patient-specific report to each subject based on analyses of one or more plaque and/or vascular parameters derived from a medical image of that particular subject. As such, in some embodiments, the generated report can be specific to the patient and can include patient-specific parameters, such as for example total volume of plaque, volume of non-calcified plaque, volume of low density plaque, volume of high density plaque, vascular remodeling, and/or the like.

Further, in some embodiments, the systems, methods, and devices described herein can be configured to provide an immersive experience for the subject, for example by generating an interactive and/or immersive viewing experience of the subject's own arteries. More specifically, in some embodiments, the systems, methods, and devices described herein are configured to analyze one or more arteries of the subject to determine the curvature of each artery and/or extent and type of plaque within the one or more arteries. Based on such analyses, in some embodiments, the system can be configured to generate a three-dimensional graphical representation of the actual arteries of the subject, including regions of plaque. In some embodiments, the three-dimensional graphical representation can allow the subject or another user to view his or her arteries from inside or within the arteries to obtain a visceral sense or immersive viewing experience of his or her arteries. Further, in some embodiments, the three-dimensional graphical representation can allow the subject or another user to move around within the arteries, for example in six degrees of freedom (6-DOF) or three degrees of freedom (3-DOF).

In some embodiments, the three-dimensional graphical representation of the one or more arteries can include the one or more regions of plaque such that the subject or another user can view of the total extent of plaque within his or her arteries and obtain a real or life-like sense. In some embodiments, each or some of the regions of plaque (or a portion thereof) can be color-coded based on the level of risk. For example, in some embodiments, a low-risk plaque or highly calcified or high-density plaque can be assigned one color to depict the low risk of that plaque. Similarly, in some embodiments, certain plaques or regions of plaque or a portion thereof can comprise lower density and/or positive remodeling, in which case that plaque, region of plaque, or portion thereof can be assigned a different color. As such, in some embodiments, as the user is "moving" around his or her arteries, the user can see and obtain a visceral sense of how much total plaque, good plaque, and/or bad plaque the user has, thereby increasing the impact of the patient-specific report which can lead to better adherence to treatment and/or outcome.

Further, in some embodiments, the system can be configured to determine a risk of rupture of one or more regions of plaque, for example based on the density, remodeling, and/or any other factor or parameter discussed herein. In some embodiments, if the system determines that the risk of a particular plaque rupturing within a particular timeframe is higher than some predetermined threshold, the system can be configured to animate that plaque rupturing in the three-dimensional representation of the one or more arteries of the subject. As such, in some embodiments, the subject or user can be able to view a plaque rupturing within his or her artery, thereby further increasing the impact of the patient-specific report.

In some embodiments, the systems, methods, and devices described herein can be configured to generate one or more proposed treatments for the subject based on the analyses of the one or more plaque and/or vessel parameters. In some embodiments, based on the generated proposed treatment(s), the system can be configured to determine an expected outcome of the proposed treatment. For example, in some embodiments, the system may determine that the proposed treatment will likely harden or increase the density of one or more plaques by a certain degree over a certain period of time. In some embodiments, the system can be configured to animate that change in plaque(s) in the three-dimensional representation of the one or more arteries of the subject. As such, in some embodiments, the subject can viscerally see the potential effects of a proposed treatment.

In some embodiments, the systems, methods, and devices described herein can be configured to generate an animation or graphical representation of what would happen to the subject's arteries without treatment. For example, in some embodiments, the system may determine that a subject is expected to have a certain amount more of low-density plaque over a certain period of time without treatment. Based on such analyses, in some embodiments, the system can be configured to animate or generate a graphical representation of such change. In some embodiments, such visualization of change in plaque without treatment can be viewed side-by-side and/or in sequence with a visualization of change in plaque with treatment, which can be an effective way to educate the subject and/or improve adherence to treatment.

In some embodiments, the systems, methods, and devices described herein can be configured to track progression of plaque or disease, either with or without treatment. For example, in some embodiments, the systems, methods, and devices can be configured to generate and/or update a graphical representation of the arteries of the subject at a second point in time to track progression of disease or plaque. In some embodiments, if no particular treatment was given to the subject, the system can be configured to track progression of plaque and provide a visual representation of the same to the subject. In some embodiments, if a treatment was assigned to the subject, whether invasive, lifestyle change, or drug treatment, the system can be configured to graphically show the subject the difference if plaque or disease, thereby allowing the subject to visually track his or her progress.

As such, in some embodiments, the systems, methods, and devices described herein can provide an immersive patient-specific view from inside or within the subject's own arteries, thereby providing the subject and/or a physician with a visceral view or sense of the state and/or progression of plaque or disease or CAD. In some embodiments, the immersive patient-specific report can be viewable and/or experienced using a virtual reality (VR) device or headset and/or other computing device. In some embodiments, the immersive patient-specific report can include a voiceover or narrative to guide the user as the user explores around his or her arteries. In some embodiments, the immersive patient-specific report can include one or more sound and/or motion effects, for example associated with when a plaque ruptures, such that a VR headset rumbles or moves otherwise for added effect when a plaque ruptures. In some embodiments, the immersive patient-specific report can include one or more areas that the user can click or otherwise select, which can lead to additional menus or features or descriptions. For example, in some embodiments, if a user selects a region of plaque, the immersive patient-specific report can be configured to notify the user, either orally or graphically or via text, that the region corresponds to plaque, fat, specific type of plaque, and/or the like. In some embodiments, such immersive patient-specific report can have a significant impact on patient education and/or adherence to treatment and/or improved treatment outcome compared to a more traditional paper-based or document report with standard boilerplate description or language.

Further, in some embodiments, the systems, methods, and devices described herein can allow for virtual consultations and/or physician visits, for example, in the metaverse. In particular, in some embodiments, the systems, methods, and devices described herein can provide an immersive virtual consultation and/or visit using a virtual reality (VR) device headset and/or other computing device. In some embodiments, the systems, methods, and devices described herein can allow a patient and physician to communicate using a VR device headset and/or other computing device. In some embodiments, the systems, methods, and devices described herein provide a metaverse experience in which a patient is able to obtain a virtual consultation with a physician through use of avatars rendered in a VR space or otherwise. In some embodiments, the systems, methods, and devices described herein allow avatars of a patient and physician to move, speak, or otherwise interact in a virtual consultation setting.

In particular, in some embodiments, the systems, methods, and devices described herein provide a metaverse experience in which a patient is able to obtain a virtual consultation with a physician prior to and/or after analysis of the patient's health state and/or risk. In some embodiments, the systems, devices, and methods also provide a virtual consultation in the metaverse to go over the results of a patient-specific report. For example, in some embodiments, the systems, methods, and devices allow for a virtual visitation in which a physician may allow for a virtual consultation while the patient is viewing an immersive patient-specific report of the patient's coronary arteries while in the metaverse. For example, in some embodiments, the systems, methods, and devices allow for a virtual consultation while the patient is viewing an immersive patient-specific report of the patient's coronary arteries using a virtual reality (VR) device and/or other computing device.

Figure 13A:
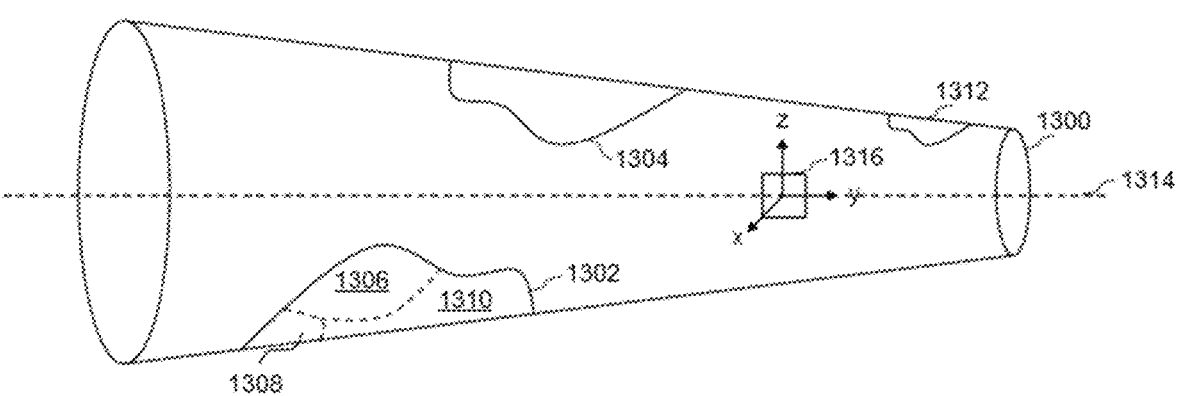
FIG. 13A is a schematic illustrating an example of an embodiment(s) of an immersive patient-specific report on cardiovascular disease risk, state, diagnosis, and/or treatment that can be generated using one or more embodiments of the systems, methods, and devices described herein.

FIG. 13A is a schematic illustrating an example of an embodiment(s) of an immersive patient-specific report on cardiovascular disease risk, state, diagnosis, and/or treatment that can be generated using one or more embodiments of the systems, methods, and devices described herein.

As illustrated in FIG. 13A, in some embodiments, the systems, methods, and devices described herein can be configured to analyze one or more vessels, such as artery 1300A on a medical image. The one or more vessels, such as artery 1300A can taper along a longitudinal axis 1314A such that the diameter of the vessel generally decreases. In some embodiments, artery 1300A can include one or more areas of plaque 1302A, 1304A, 1312A. Further, an area or region of plaque 1302A can further include one or more regions of plaque 1306A, 1308A, 1310A with different plaque compositions. Each or some of the one or more areas of plaque 1302A, 1304A, 1312A and/or portions within a region of plaque 1306A, 1308A, 1310A can comprise a different plaque composition. For example, one or more regions of plaque can comprise low-density plaque, low-density non-calcified plaque, and/or high-density plaque. In some embodiments, the system can be configured to analyze the composition of plaque utilizing one or more image analysis techniques. In some embodiments, the system can be configured to characterize the composition of plaque based on the absolute density and/or relative density, radiodensity, and/or Hounsfield unit of one or more pixels shown on a medical image of plaque.

In some embodiments, the system can be configured to analyze, characterize, and/or classify plaque into one of three types: low-density non-calcified plaque, non-calcified plaque, and calcified plaque. In some embodiments, the system can be configured to analyze, characterize, and/or classify plaque into one of two types: non-calcified plaque and calcified plaque. In some embodiments, the system can be configured to analyze, characterize, and/or classify plaque into one of any number of different types, such as for example 1, 2, 3, 4, 5, 6, 7, 8, 9, 10, 15, 20, 25, and/or 30 different types of classifications of plaque. In some embodiments, the system can be configured to analyze, characterize, and/or classify plaque into a number of different types within a range defined by two of the aforementioned values.

In some embodiments, as described herein, the system can be configured to generate an immersive patient-specific report of the patient's arteries. For example, referring to FIG. 13A as an illustrative example, in some embodiments, the immersive patient-specific report can comprise a graphical representation of an artery 1300A of the subject, which can further include one or more regions of plaque 1302A, 1304A, 1312A. In some embodiments, the immersive patient-specific report can comprise a graphical representation of one or more portions of plaque 1306A, 1308A, 1310A within a region of plaque 1302A. In some embodiments, depending on the type or composition of plaque, the system can be configured to annotate or color each region of plaque 1302A, 1304A, 1306A, 1308A, 1310A, 1312A. As such, in some embodiments, the user can view each region of plaque and know instantaneously the risk factor associated with each region of plaque.

In some embodiments, as described herein, the system can allow a user to view the immersive patient-specific report from a point of view 1316A within an artery. As such, in some embodiments, the user or subject can view from inside his or her artery different regions of plaque, fat, and/or vessel in 3-DOF. In some embodiments, the immersive patient-specific report can allow the user or subject to move around within the artery 1300A, for example in 6-DOF and/or along the longitudinal axis 1316A. In some embodiments, the system can be configured to utilize one or more coordinate systems for processing movement and/or rotation. For example, in some embodiments, the system can be configured to utilize a cartesian coordinate system, polar coordinate system, cylindrical coordinate system, spherical coordinate system, homogeneous coordinate system, curvilinear coordinate system, log-polar coordinate system, Plücker coordinate system, generalized coordinate system, canonical coordinate system, barycentric coordinate system, and/or trilinear coordinate system.

Figure 13B:
FIG. 13B is a schematic illustrating an example of an embodiment(s) of an immersive patient-specific report on cardiovascular disease risk, state, diagnosis, and/or treatment that can be generated using one or more embodiments of the systems, methods, and devices described herein.

FIG. 13B is a schematic illustrating an example of an embodiment(s) of an immersive patient-specific report on cardiovascular disease risk, state, diagnosis, and/or treatment that can be generated using one or more embodiments of the systems, methods, and devices described herein. As illustrated in FIG. 13B, in some embodiments, the system can be configured to allow a user to travel or move across different arteries, such as for example the left coronary artery, right coronary artery, right (acute) marginal artery, circumflex artery, left (obtuse) marginal artery, left anterior descending artery, and/or diagonal arteries. In some embodiments, the system can be configured to generate a three-dimensional graphical representation of all or some of the arteries. In some embodiments, the system can allow a user to select or click into a particular artery, which can then allow the user to move around or view the inside of that particular artery. In some embodiments, to create a three-dimensional graphical representation of one or more arteries, the system can be configured to analyze one or more different slices, such as for example axial, coronal, and/or sagittal views. In some embodiments, the system can be configured to construct a multi-planar reformat or reconstruct of the different slices to generate a three-dimensional graphical representation of one or more arteries. In some embodiments, the system can be configured to add or superimpose one or more plaque and/or fat features onto the three-dimensional graphical representation of one or more arteries or multi-planar reformat or reconstruct. As such, in some embodiments, using non-invasive medical imaging techniques, the system can be configured to generate a three-dimensional representation of one or more actual arteries of the subject, including plaque and/or fat features and/or risk thereof, and provide an immersive viewing experience for the subject from within the vessel or lumen wall of one or more arteries.

Immersive Patient-Specific Report Generation

Figure 13C:
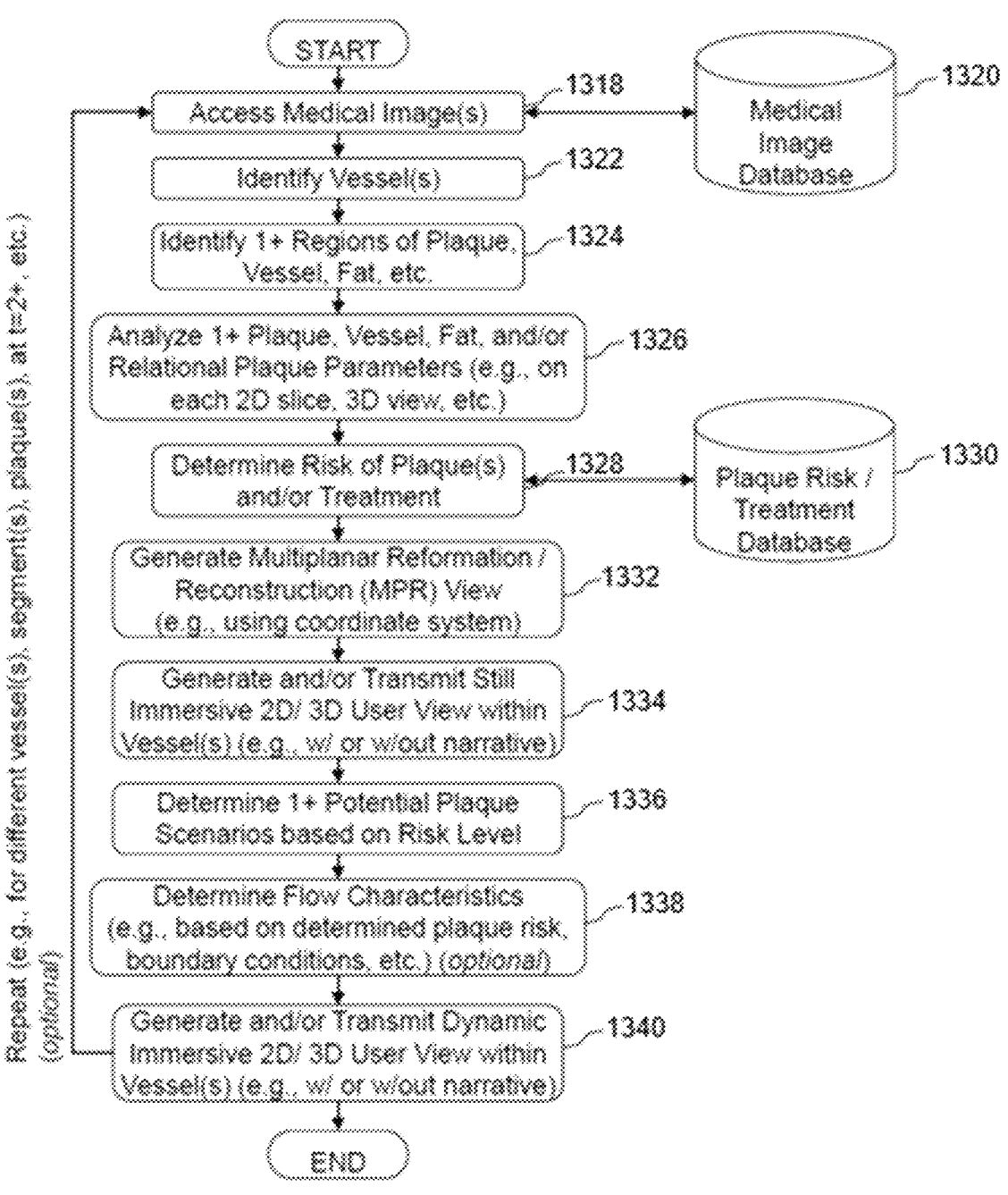
FIG. 13C is a flowchart illustrating an example embodiment(s) of systems, devices, and methods for generation of an immersive patient-specific report on cardiovascular disease risk, state, diagnosis, and/or treatment.

As described herein, some embodiments of systems, devices, and methods described herein are configured to generate an immersive patient-specific report on cardiovascular disease risk, state, and/or treatment, for example using image-based analysis of one or more plaque and/or vessel parameters derived from a medical image. FIG. 13C is a flowchart illustrating an example embodiment(s) of systems, devices, and methods for generation of an immersive patient-specific report on cardiovascular disease risk, state, diagnosis, and/or treatment.

As illustrated in FIG. 13C, in some embodiments, the system can be configured to access a medical image at block 1302C. In some embodiments, the medical image can include one or more arteries, such as coronary, carotid, and/or other arteries of a subject. In some embodiments, the medical image can be stored in a medical image database 1304C. In some embodiments, the medical image database 1304C can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1306C, the system can be configured to identify one or more vessels on the medical image(s), such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more artificial intelligence (AI) and/or machine learning (ML) algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1308C, the system can be configured to identify one or more regions of plaque, one or more regions of fat, and/or one or more other vessel features. In some embodiments, the system can be configured to utilize one or more AI and/or ML algorithms to automatically and/or dynamically identify and/or characterize one or more regions of plaque, one or more regions of fat, and/or one or more other vessel features, for example using image processing. In some embodiments, the one or more AI and/or ML algorithms can be trained using a Convolutional Neural Network (CNN) on a set of medical images on which one or more regions of plaque, one or more regions of fat, and/or one or more other vessel features have been identified and/or characterized, thereby allowing the AI and/or ML algorithm to automatically identify and/or characterize the same directly from a medical image.

In some embodiments, at block 1310C, the system can be configured to analyze one or more plaque parameters, one or more vessel parameters, one or more fat parameters, and/or one or more relational parameters, for example on one or more two-dimensional slices or images and/or on one or more three-dimensional images. In some embodiments, the system can be configured to utilize one or more AI and/or ML algorithms to automatically and/or dynamically identify and/or determine one or more one or more plaque parameters, one or more vessel parameters, one or more fat parameters, and/or one or more relational parameters. For example, in some embodiments, the one or more AI and/or ML algorithms can be trained using a Convolutional Neural Network (CNN) on a set of medical images on which one or more plaque parameters, one or more vessel parameters, one or more fat parameters, and/or one or more relational parameters have been determined, thereby allowing the AI and/or ML algorithm to automatically determine the same directly from a medical image.

In some embodiments, the system can be configured to analyze the absolute density, relative density, radiodensity values, and/or heterogeneity or distribution thereof of one or more pixels on a medical image to identify and/or characterize plaque. More specifically, in some embodiments, the system can be configured to identify a particular pixel as plaque, non-calcified plaque, low-density non-calcified plaque, and/or calcified plaque, and/or any other classification or type of plaque. In some embodiments, the system can be configured to classify a particular pixel or region of plaque as non-calcified plaque when the radiodensity value of the pixel is below a certain predetermined threshold, within a predetermined range, and/or comprises a heterogeneity index or distribution within, under, or above a particular predetermined range or threshold. In some embodiments, the system can be configured to classify a particular pixel or region of plaque as low-density non-calcified plaque when the radiodensity value of the pixel is below a certain predetermined threshold, within a predetermined range, and/or comprises a heterogeneity index or distribution within, under, or above a particular predetermined range or threshold. In some embodiments, the system can be configured to classify a particular pixel or region of plaque as calcified plaque when the radiodensity value of the pixel is above a certain predetermined threshold, within a predetermined range, and/or comprises a heterogeneity index or distribution within, under, or above a particular predetermined range or threshold.

In some embodiments, the one or more plaque parameters can include absolute plaque density, relative plaque density, composition, calcification, radiodensity, location, volume, surface area, geometry, heterogeneity, diffusivity, and/or ratio between volume and surface area. In some embodiments, the one or more fat parameters can include fat density, relative fat density, composition, radiodensity, location, volume, surface area, geometry, heterogeneity, diffusivity, and/or ratio between volume and surface area. In some embodiments, the one or more vessel or vascular parameters can include one or more of vascular volume, diameter, area, cross-sectional area, surface area, length, location, and/or remodeling. In some embodiments, the one or more relational plaque parameters can include a ratio or other comparison between one or more plaque parameters, one or more vessel parameters, and/or one or more fat parameters. For example, in some embodiments, the one or more relational parameter can include percent atheroma volume (PAV), PAV on a vessel-by-vessel basis, PAV on a segment-by-segment basis, and/or PAV for the whole heart, ratio of surface area of plaque to surface of vessel or lumen, ratio of volume of plaque to volume of vessel or lumen, and/or the like.

In some embodiments, at block 1312C, the system can be configured to determine a risk or state of cardiovascular disease or health of one or more regions of plaque and/or the subject, for example based on one or more plaque parameters, one or more vessel parameters, one or more fat parameters, and/or one or more relational parameters derived from the medical image. Further, in some embodiments, at block 1312C, the system can be configured to determine a proposed treatment for one or more regions of plaque and/or the subject. The treatment can include, for example, medical treatment such as statins, interventional treatment such as stent implantation, and/or lifestyle treatment such as exercise or diet.

In some embodiments, in determining the risk or state of cardiovascular disease or health and/or treatment, the system can access a plaque risk/treatment database 1314C, which can be locally accessible by the system and/or can be located remotely and accessible through a network connection. In some embodiments, the plaque risk/treatment database 1314C can include reference points or data that relate one or more treatment to cardiovascular disease risk or state determined based on one or more plaque parameters, one or more vessel parameters, one or more fat parameters, and/or one or more relational parameters.

In some embodiments, the system can be configured to determine the risk or state of cardiovascular disease or health of one or more regions of plaque and/or the subject based on a weighted measure of the one or more plaque parameters, one or more vessel parameters, one or more fat parameters, and/or one or more relational parameters. For example, in some embodiments, the system can be configured to assign a weight between 0 and 1 to one or more plaque parameters, one or more vessel parameters, one or more fat parameters, and/or one or more relational parameters. In some embodiments, the system can be configured to assign a weight between 0 and 1, such as for example 0, 0.05, 0.1, 0.15, 0.2, 0.3, 0.4, 0.5, 0.6, 0.7, 0.8, 0.9, 0.99, and 1. In some embodiments, the system can be configured to weight one or more parameters as 0, thereby ignoring its effect. In some embodiments, the system can be configured to weight one or more parameters as 1, thereby focusing exclusively on such parameter. In some embodiments, the weighted measure can also include one or more other factors or features, such as for example, age, weight, gender, plaque volume, plaque composition, vascular remodeling, high-risk plaque, lumen volume, plaque location (proximal v. middle v. distal), plaque location (myocardial v. pericardial facing), plaque location (at bifurcation or trifurcation v. not at bifurcation or trifurcation), plaque location (in main vessel v. branch vessel), stenosis severity, percentage coronary blood volume, percentage fractional myocardial mass, percentile for age and/or gender, constant or other correction factor to allow for control of within-person, within-vessel, inter-plaque, plaque-myocardial relationships, and/or the like.

In some embodiments, at block 1316C, the system can be configured to generate a multiplanar reformation or multiplanar reconstruction (MPR) view of the one or more arteries. For example, in some embodiments, the system can be configured to analyze a plurality of two-dimensional slices or images obtained from the subject. In some embodiments, the system can be configured to analyze the plurality of two-dimensional slices or images to reconstruct a multiplanar view of one or more arteries in three-dimensions. For example, in some embodiments, the system can be configured to utilize any one or more coordinate systems described herein in generating the MPR view.

In some embodiments, at block 1318C, the system can be configured to generate and/or transmit a still immersive view to a user computing device. For example, in some embodiments, the system can be configured to generate an immersive two-dimensional or three-dimensional view of the inside of one or more arteries or other vessels, including one or more regions of plaque and/or fat, using the MPR view. In some embodiments, the immersive view can be configured to allow a user to explore and/or move around a graphical representation of the one or more arteries or vessels, for example in 3-DOF or 6-DOF. In some embodiments, the still immersive view can include one or more actual curvatures of the one or more arteries or other vessels of the subject. In some embodiments, the still immersive view can include an audio narrative describing different features within the one or more arteries or vessels. In some embodiments, the audio narrative can map and/or follow movement or view of the user inside the one or arteries or vessels. For example, in some embodiments, the system can be configured to play a certain audio narrative based on what the user is focusing on within the immersive view of the artery or vessel.

In some embodiments, at block 1320C, the system can be configured to determine one or more potential plaque scenarios, for example based on the risk assessment of one or more plaques. More specifically, in some embodiments, based on the risk assessment of one or more regions of plaque, the system can be configured to determine the likelihood of a particular plaque rupturing within a particular period of time, such as for example about 1 year, about 2 years, about 3 years, about 4 years, about 5 years, about 6 years, about 7 years, about 8 years, about 9 years, about 10 years, about 15 years, about 20 years, and/or within a range defined by two of the aforementioned values.

In some embodiments, at block 1322C, the system can be configured to determine one or more flow characteristics within the vessel, such as for example fractional flow reserve (FFR). In some embodiments, the system can be configured to determine one or more flow characteristics using the risk assessment of one or more regions of plaque, boundary conditions of the vessel or lumen wall, curvature of the vessel or lumen wall, and/or the like.

In some embodiments, at block 1324C, the system can be configured to generate and/or transmit a dynamic immersive view to a user computing device. For example, in some embodiments, the system can be configured to generate a dynamic immersive two-dimensional or three-dimensional view of the inside of one or more arteries or other vessels, including one or more regions of plaque and/or fat, using the MPR view. In some embodiments, the dynamic immersive view can include one or more dynamically moving features within the vessel. For example, in some embodiments, the dynamic immersive view can include a graphical representation of blood flow, plaque rupturing, and/or the like, to allow the user to obtain a dynamic view and/or experience of what happens and/or what can happen inside his or her arteries or vessels. In particular, in some embodiments, the system can be configured to generate a graphical representation of a particular plaque rupturing if/when the likelihood of such plaque rupturing is determined to be above a particular threshold, for example utilizing one or more processes described in relation to block 1320C. Further, in some embodiments, the system can be configured to generate a graphical representation of blood flow through the vessel based at least in part on one or more flow characteristics determined utilizing one or more processes described in relation to block 1322C. In some embodiments, the system can be configured to generate a graphical representation of a plaque rupturing and how that affects the blood flow within that vessel or artery.

In some embodiments, the dynamic immersive view can be configured to allow a user to explore and/or move around a graphical representation of the one or more arteries or vessels, for example in 3-DOF or 6-DOF. In some embodiments, the dynamic immersive view can include one or more actual curvatures of the one or more arteries or other vessels of the subject. In some embodiments, the dynamic immersive view can include an audio narrative describing different features within the one or more arteries or vessels. In some embodiments, the audio narrative can map and/or follow movement or view of the user inside the one or arteries or vessels. For example, in some embodiments, the system can be configured to play a certain audio narrative based on what the user is focusing on within the dynamic immersive view of the artery or vessel.

In some embodiments, the system can be configured to repeat one or more processes described in relation to blocks 1302C-1324C, for example for one or more other vessels, segments, regions of plaque, other subjects, and/or for the same subject at a different time. For example, in some embodiments, the system can be configured to repeat one or more processes after the same subject is treated with a particular treatment so that the subject can be provided a graphical/visual representation of the actual effects of treatment. As such, in some embodiments, the system can provide for longitudinal disease tracking and/or personalized treatment for a subject. Similarly, in some embodiments, the system can be configured to repeat one or more processes for the same subject after hypothetically treating the subject with a particular treatment, thereby providing the subject with a graphical/visual representation of expected outcomes of a particular treatment.

Computer System

Figure 13D:
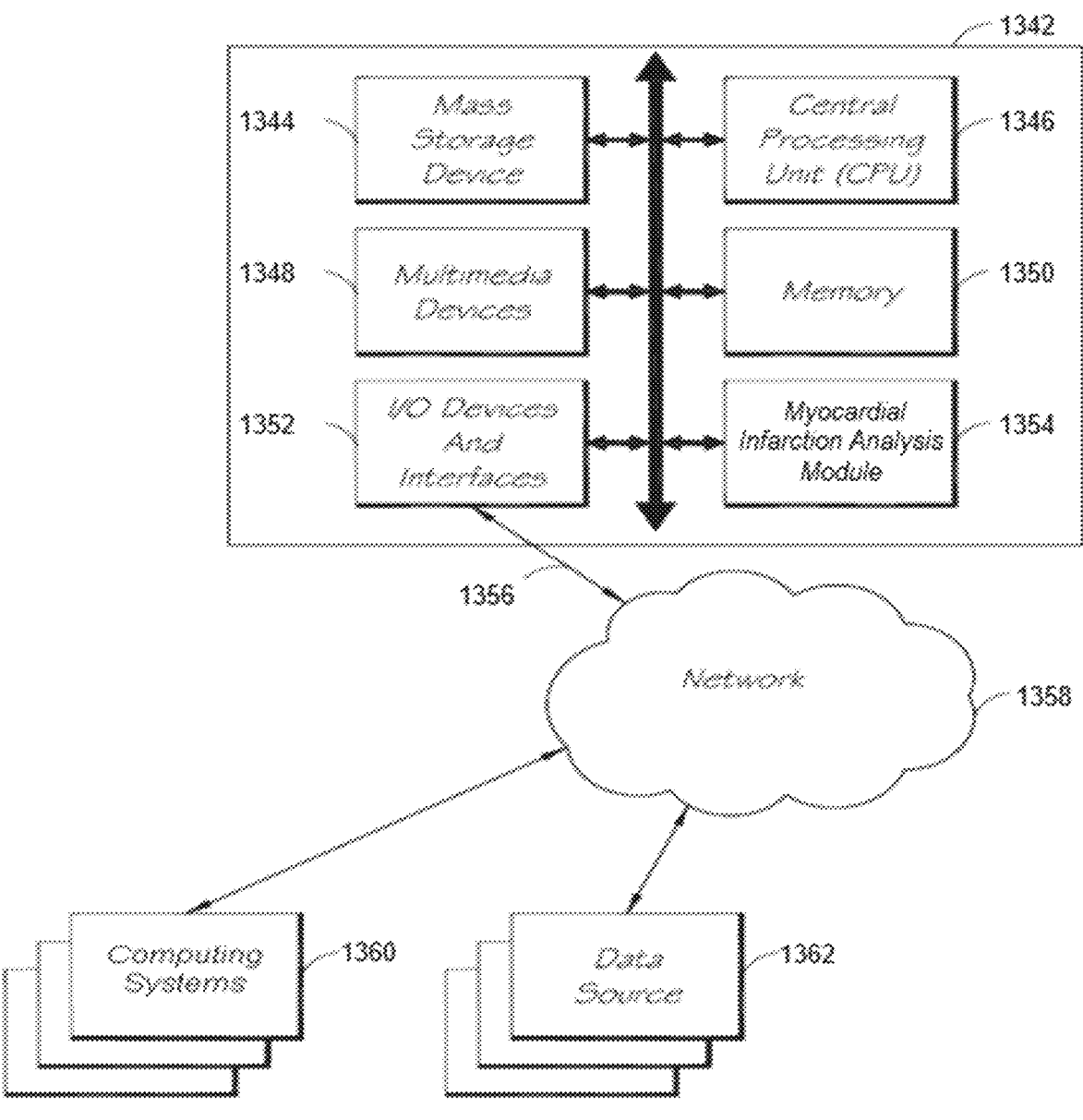
FIG. 13D is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 13D. The example computer system 1302D is in communication with one or more computing systems 1320D and/or one or more data sources 1322D via one or more networks 1318D. While FIG. 13D illustrates an embodiment of a computing system 1302D, it is recognized that the functionality provided for in the components and modules of computer system 1302D can be combined into fewer components and modules, or further separated into additional components and modules.

The computer system 1302D can comprise an Immersive Patient-Specific Report Generation Module 1314D that carries out the functions, methods, acts, and/or processes described herein. The Immersive Patient-Specific Report Generation Module 1314D executed on the computer system 1302D by a central processing unit 1306D discussed further below. Other features of the computer system 1302D can be similar to corresponding features of the computer system of FIG. 9G, described above.

Certain Examples of Embodiments of Immersive Patient-Specific Report

The following are non-limiting examples of certain embodiments of systems and methods of immersive patient-specific report. Other embodiments may include one or more other features, or different features, that are discussed herein.

Embodiment 1: A computer-implemented method of generating an immersive patient-specific report on cardiovascular disease state based on one or more plaque parameters derived from non-invasive medical image analysis, the method comprising: accessing, by a computer system, a medical image of a subject, wherein the medical image of the subject is obtained non-invasively; analyzing, by the computer system, the medical image of the subject to identify one or more arteries, wherein the one or more arteries comprise one or more regions of plaque; determining, by the computer system, one or more vascular parameters associated with the subject by analyzing the one or more identified arteries, wherein the one or more vascular parameters comprise one or more of vessel volume, diameter, area, cross-sectional area, surface area, length, location, or remodeling; identifying, by the computer system, the one or more regions of plaque in the one or more arteries; determining, by the computer system, one or more plaque parameters associated with the one or more regions of plaque, wherein the one or more plaque parameters comprise one or more of plaque density, composition, calcification, radiodensity, location, volume, surface area, geometry, heterogeneity, diffusivity, or ratio between volume and surface area; generating, by the computer system, an assessment of cardiovascular disease state of the one or more regions of plaque based at least in part on the determined one or more plaque parameters and the one or more vascular parameters; generating, by the computer system, a three-dimensional graphical representation of myocardial infarction arising from the one or more regions of plaque when the generated assessment of cardiovascular disease state of the one or more regions of plaque is above a pre-determined threshold level; generating, by the computer system, a three-dimensional multiplanar reformation of the one or more arteries comprising the one or more regions of plaque based at least in part on the determined one or more vascular parameters and the one or more plaque parameters; generating, by the computer system, an immersive three-dimensional graphical representation of the one or more arteries based at least in part on the three-dimensional multiplanar reformation of the one or more arteries, wherein the immersive three-dimensional graphical representation of the one or more arteries comprises the three-dimensional graphical representation of the myocardial infarction arising from the one or more regions of plaque when the generated assessment of cardiovascular disease state of the one or more regions of plaque is above a pre-determined threshold level; and causing, by the computer system, transmission of the immersive three-dimensional graphical representation of the one or more arteries to a user computing device, wherein the immersive three-dimensional graphical representation of the one or more arteries is configured to allow a user to view the state of cardiovascular disease from a point of view positioned inside the one or more arteries, wherein the computer system comprises a computer processor and an electronic storage medium.

Embodiment 2: The computer-implemented method of Embodiment 1, wherein the user computing device comprises a virtual reality (VR) device.

Embodiment 3: The computer-implemented method of Embodiment 1, wherein the pre-determined threshold level is based at least in part on density of the one or more regions of plaque.

Embodiment 4: The computer-implemented method of Embodiment 1, wherein the density of the one or more regions of plaque comprises absolute density.

Embodiment 5: The computer-implemented method of Embodiment 1, wherein the density of the one or more regions of plaque comprises radiodensity.

Embodiment 6: The computer-implemented method of Embodiment 1, wherein the immersive three-dimensional graphical representation of the one or more arteries is configured to allow a user to move the point of view within the one or more arteries in six degrees of freedom.

Embodiment 7: The computer-implemented method of Embodiment 1, wherein the immersive three-dimensional graphical representation of the one or more arteries is configured to allow a user to rotate the point of view within the one or more arteries in three degrees of freedom.

Embodiment 8: The computer-implemented method of Embodiment 1, wherein the immersive three-dimensional graphical representation of the one or more arteries is configured to allow a user to move the point of view within the one or more arteries along a longitudinal axis of the one or more arteries.

Embodiment 9: The computer-implemented method of Embodiment 1, further comprising generating, by the computer system, a treatment for cardiovascular disease for the subject based at least in part on the determined assessment of the state of cardiovascular disease of the one or more regions of plaque.

Embodiment 10: The computer-implemented method of Embodiment 9, further comprising: determining, by the computer system, an expected progression of the state of cardiovascular disease of the one or more regions of plaque based on the treatment; modifying, by the computer system, the immersive three-dimensional graphical representation of the one or more arteries based at least in part on the expected progression of the state of cardiovascular disease of the one or more regions of plaque; and causing, by the computer system, transmission of the modified immersive three-dimensional graphical representation of the one or more arteries to the user computing device, wherein the modified immersive three-dimensional graphical representation of the one or more arteries is configured to allow the user to view the expected progression of the state of cardiovascular disease of the one or more regions of plaque from the point of view positioned within the one or more arteries.

Embodiment 11: The computer-implemented method of Embodiment 9, wherein the treatment for cardiovascular disease comprises medical intervention, medical treatment, or lifestyle change.

Embodiment 12: The computer-implemented method of Embodiment 9, further comprising tracking, by the computer system, efficacy of the treatment by determining assessment of the state of cardiovascular disease of the one or more regions of plaque at a later point in time after treatment.

Embodiment 13: The computer-implemented method of Embodiment 12, further comprising: modifying, by the computer system, the immersive three-dimensional graphical representation of the one or more arteries based at least in part on the assessment of the state of cardiovascular disease of the one or more regions of plaque at the later point in time after treatment of the state of cardiovascular disease; and causing, by the computer system, transmission of the modified immersive three-dimensional graphical representation of the one or more arteries to the user computing device, wherein the modified immersive three-dimensional graphical representation of the one or more arteries is configured to allow the user to view a change in the state of cardiovascular disease of the one or more regions of plaque after treatment from the point of view positioned within the one or more arteries.

Embodiment 14: The computer-implemented method of Embodiment 1, wherein the state of assessment of cardiovascular disease state of the one or more regions of plaque based at least in part on a weighted measure of the one or more plaque parameters and the one or more vascular parameters.

Embodiment 15: The computer-implemented method of Embodiment 1, further comprising: generating, by the computer system, a weighted measure of one or more of the one or more vascular parameters and the one or more plaque parameters, wherein the assessment of the state of cardiovascular disease of the one or more regions of plaque is further determined based at least in part on the generated weighted measure.

Embodiment 16: The computer-implemented method of Embodiment 1, wherein the assessment of the state of cardiovascular disease of the one or more regions of plaque is further determined based at least in part on one or more of age or gender of the subject.

Embodiment 17: The computer-implemented method of Embodiment 1, wherein the medical image is obtained using an imaging technique comprising one or more of computed tomography (CT), x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 18: The computer-implemented method of Embodiment 1, wherein the myocardial infarction arises from one or more of plaque rupture, plaque erosion or calcified nodule.

Embodiment 19: A system for generating an immersive patient-specific report on cardiovascular disease state based on one or more plaque parameters derived from non-invasive medical image analysis, the system comprising: one or more computer readable storage devices configured to store a plurality of computer executable instructions; and one or more hardware computer processors in communication with the one or more computer readable storage devices and configured to execute the plurality of computer executable instructions in order to cause the system to: access a medical image of a subject, wherein the medical image of the subject is obtained non-invasively; analyze the medical image of the subject to identify one or more arteries, wherein the one or more arteries comprise one or more regions of plaque; determine one or more vascular parameters associated with the subject by analyzing the one or more identified arteries, wherein the one or more vascular parameters comprise one or more of vessel volume, diameter, area, cross-sectional area, surface area, length, location, or remodeling; identify the one or more regions of plaque in the one or more arteries; determine one or more plaque parameters associated with the one or more regions of plaque, wherein the one or more plaque parameters comprise one or more of plaque density, composition, calcification, radiodensity, location, volume, surface area, geometry, heterogeneity, diffusivity, or ratio between volume and surface area; generate an assessment of cardiovascular disease state of the one or more regions of plaque based at least in part on the determined one or more plaque parameters and one or more vascular parameters; generate a three-dimensional graphical representation of myocardial infarction arising from the one or more regions of plaque when the generated assessment of cardiovascular disease state of the one or more regions of plaque is above a pre-determined threshold level; generate a three-dimensional multiplanar reformation of the one or more arteries comprising the one or more regions of plaque based at least in part on the determined one or more vascular parameters and the one or more plaque parameters; generate an immersive three-dimensional graphical representation of the one or more arteries based at least in part on the three-dimensional multiplanar reformation of the one or more arteries, wherein the immersive three-dimensional graphical representation of the one or more arteries comprises the three-dimensional graphical representation of the myocardial infarction arising from the one or more regions of plaque when the generated assessment of cardiovascular disease state of the one or more regions of plaque is above a pre-determined threshold level; and cause transmission of the immersive three-dimensional graphical representation of the one or more arteries to a user computing device, wherein the immersive three-dimensional graphical representation of the one or more arteries is configured to allow a user to view the state of cardiovascular disease from a point of view positioned inside the one or more arteries.

Embodiment 20: The system of Embodiment 19, wherein the user computing device comprises a virtual reality (VR) device.

Embodiment 21: The system of Embodiment 19, wherein the pre-determined threshold level is based at least in part on density of the one or more regions of plaque.

Embodiment 22: The system of Embodiment 19, wherein the density of the one or more regions of plaque comprises absolute density.

Embodiment 23: The system of Embodiment 19, wherein the density of the one or more regions of plaque comprises radiodensity.

Embodiment 24: The system of Embodiment 19, wherein the immersive three-dimensional graphical representation of the one or more arteries is configured to allow a user to move the point of view within the one or more arteries in six degrees of freedom.

Embodiment 25: The system of Embodiment 19, wherein the immersive three-dimensional graphical representation of the one or more arteries is configured to allow a user to rotate the point of view within the one or more arteries in three degrees of freedom.

Embodiment 26: The system of Embodiment 19, wherein the immersive three-dimensional graphical representation of the one or more arteries is configured to allow a user to move the point of view within the one or more arteries along a longitudinal axis of the one or more arteries.

Embodiment 27: The system of Embodiment 19, wherein the system is further caused to generate a treatment for cardiovascular disease for the subject based at least in part on the determined assessment of the state of cardiovascular disease of the one or more regions of plaque.

Embodiment 28: The system of Embodiment 27, wherein the system is further caused to: determine an expected progression of the state of cardiovascular disease of the one or more regions of plaque based on the treatment; modify the immersive three-dimensional graphical representation of the one or more arteries based at least in part on the expected progression of the state of cardiovascular disease of the one or more regions of plaque; and cause transmission of the modified immersive three-dimensional graphical representation of the one or more arteries to the user computing device, wherein the modified immersive three-dimensional graphical representation of the one or more arteries is configured to allow the user to view the expected progression of the state of cardiovascular disease of the one or more regions of plaque from the point of view positioned within the one or more arteries.

Embodiment 29: The system of Embodiment 27, wherein the treatment for cardiovascular disease comprises medical intervention, medical treatment, or lifestyle change.

Embodiment 30: The system of Embodiment 27, wherein the system is further caused to track efficacy of the treatment by determining assessment of the state of cardiovascular disease of the one or more regions of plaque at a later point in time after treatment.

Embodiment 31: The system of Embodiment 30, wherein the system is further caused to: modify the immersive three-dimensional graphical representation of the one or more arteries based at least in part on the assessment of the state of cardiovascular disease of the one or more regions of plaque at the later point in time after treatment of the state of cardiovascular disease; and cause transmission of the modified immersive three-dimensional graphical representation of the one or more arteries to the user computing device, wherein the modified immersive three-dimensional graphical representation of the one or more arteries is configured to allow the user to view a change in the state of cardiovascular disease of the one or more regions of plaque after treatment from the point of view positioned within the one or more arteries.

Embodiment 32: The system of Embodiment 19, wherein the state of assessment of cardiovascular disease state of the one or more regions of plaque based at least in part on a weighted measure of the one or more plaque parameters and the one or more vascular parameters.

Embodiment 33: The system of Embodiment 19, wherein the system is further caused to: generate a weighted measure of one or more of the one or more vascular parameters and the one or more plaque parameters, wherein the assessment of the state of cardiovascular disease of the one or more regions of plaque is further determined based at least in part on the generated weighted measure.

Embodiment 34: The system of Embodiment 19, wherein the assessment of the state of cardiovascular disease of the one or more regions of plaque is further determined based at least in part on one or more of age or gender of the subject.

Embodiment 35: The system of Embodiment 19, wherein the medical image is obtained using an imaging technique comprising one or more of computed tomography (CT), x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 36: The system of Embodiment 19, wherein the myocardial infarction arises from one or more of plaque rupture, plaque erosion or calcified nodule.

Normalized Plaque Parameters Introduction

Various systems, methods, and devices disclosed herein are directed to embodiments for addressing the foregoing issues. In particular, various embodiments described herein relate to systems, methods, and devices for cardiovascular risk, disease, and/or state assessment using image-based analyses. In particular, in some embodiments, the systems, devices, and methods are related to cardiovascular risk and/or disease and/or state assessment using normalized image analysis-based plaque parameters. In some embodiments, assessment of cardiovascular risk and/or disease and/or state generated using the systems, methods, and devices herein can be utilized to diagnose and/or generate a proposed treatment for a patient.

In some embodiments, the systems, devices, and methods described herein are configured to utilize non-invasive medical imaging technologies, such as a CT image for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

As will be discussed in further detail, the systems, devices, and methods described herein allow for automatic and/or dynamic quantified analysis of various parameters relating to plaque, cardiovascular arteries, and/or other structures. More specifically, in some embodiments described herein, a medical image of a patient, such as a coronary CT image, can be taken at a medical facility. Rather than having a physician eyeball or make a general assessment of the patient, the medical image is transmitted to a backend main server in some embodiments that is configured to conduct one or more analyses thereof in a reproducible manner. As such, in some embodiments, the systems, methods, and devices described herein can provide a quantified measurement of one or more features of a coronary CT image using automated and/or dynamic processes. For example, in some embodiments, the main server system can be configured to identify one or more vessels, plaque, and/or fat from a medical image. Based on the identified features, in some embodiments, the system can be configured to generate one or more quantified measurements from a raw medical image, such as for example radiodensity of one or more regions of plaque, identification of stable plaque and/or unstable plaque, volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like. Based on the identified features and/or quantified measurements, in some embodiments, the system can be configured to generate a risk and/or disease state assessment and/or track the progression of a plaque-based disease or condition, such as for example atherosclerosis, stenosis, and/or ischemia, using raw medical images. Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures.

As such, in some embodiments, the systems, devices, and methods described herein are able to provide physicians and/or patients specific quantified and/or measured data relating to a patient's plaque that do not exist today. For example, in some embodiments, the system can provide a specific numerical value for the volume of stable and/or unstable plaque, the ratio thereof against the total vessel volume, percentage of stenosis, and/or the like, using for example radiodensity values of pixels and/or regions within a medical image. In some embodiments, such detailed level of quantified plaque parameters from image processing and downstream analytical results can provide more accurate and useful tools for assessing the health and/or risk of patients in completely novel ways.

Disclosed herein are systems, methods, and devices for cardiovascular risk and/or disease state assessment using image-based analyses. In particular, in some embodiments, the systems, devices, and methods are related to cardiovascular risk and/or disease and/or state assessment using normalized image analysis-based plaque parameters. In some embodiments, assessment of cardiovascular risk and/or disease and/or state generated using the systems, methods, and devices herein can be utilized to diagnose and/or generate a proposed treatment for a patient.

In particular, in some embodiments, the systems, devices, and methods described herein can be configured to analyze one or more non-invasively obtained medical images of a subject, such as a CT image, to determine one or more plaque parameters and/or vessel parameters. For example, in some embodiments, the one or more plaque parameters can be associated with one or more regions of plaque and can include one or more of percent atheroma volume (PAV), plaque volume, total plaque volume, volume of non-calcified plaque, volume of calcified plaque, volume of low-attenuated, non-calcified plaque, location, geometry, and/or the like. In some embodiments, the one or more vessel parameters can include one or more of vessel wall volume, curvature, and/or the like. In particular, plaque volume can be a helpful indicator of the disease state of a subject. However, absolute plaque volume may have its limits for a number of reasons. For example, absolute total plaque volume does not take into account the composition of plaque, such as for example calcified versus non-calcified and/or low-attenuated plaque. Also, even if plaque composition is taken into account, there may be variation in plaque volume between subjects due to differences in physical properties of the subjects that are not necessarily related to their disease state. As such, in some embodiments, plaque volume can be normalized for analysis to account for such shortcomings associated with analyzing absolute plaque volume. In particular, in some embodiments, plaque volume can be normalized to the vessel volume using plaque parameters, such as, for example, PAV. PAV can refer to the proportion of total vessel wall volume or total vessel volume occupied by atherosclerotic plaque. In some examples, PAV can be determined on a per vessel basis. As such, in some embodiments, analyzing coronary PAV can provide an indication of risk of cardiovascular disease or a major adverse cardiovascular event (MACE), such as a myocardial infarction or heart attack. In some embodiments, one or more medical images obtained from a coronary computed tomography angiography (CCTA) can be used as a non-invasive measure to assess PAV.

However, in some embodiments, analyzing PAV can also have certain limitations. For example, for certain scanners and/or scan parameters, the quality of an image obtained from a CT scan or CCTA can be less than perfect. For example, in some embodiments, small vessels below a certain size can be difficult to analyze, thereby potentially resulting in less than accurate analysis of plaque or PAV within such vessel. In order to address such technical shortcomings, some embodiments of the systems, devices, and methods described herein are configured to utilize a normalized PAV in analyzing a CT or CCTA image. In particular, in some embodiments, the system can be configured to analyze a CT or CCTA image to identify one or more vessels above a certain threshold level (e.g., a threshold vessel diameter or other thresholds as discussed below) and analyze such vessels to determine PAV. By utilizing such a modified and/or normalized PAV measurement, it can be possible to address image quality issues arising from CT or CCTA scans, as a modified and/or normalized database of PAV values derived using the same vessel threshold can be used as a reference database.

In some embodiments, the systems, devices, and methods can be configured to apply such vessel thresholds prior to analyzing an image for any parameter. For example, parameters can include any plaque parameter, vessel parameter, and/or relational parameter between the two, including but not limited to PAV. In some embodiments, after applying a vessel threshold, any such parameter modified by vessel thresholds can be normalized, for example, against a physical property of the subject. For example, in some embodiments, the vessel threshold can comprise a diameter of about 2.0 mm, such that the system is configured to ignore any vessels with a diameter below 2.0 mm and analyze only vessel areas with a diameter above 2.0 mm to determine any such parameters. Other vessel thresholds can be used as described below. In some embodiments, parameters derived from vessel areas above the vessel threshold can then be normalized against some property of the subject and analyzed by comparison to a database of known parameter values obtained from vessel areas above the same vessel threshold from a population with varying degrees of plaque and/or disease, thereby normalizing the analysis to be independent of the image quality.

In some embodiments, the vessel threshold can be based on volume, diameter, surface area, radius, width, and/or any other variable or parameter related to the vessel. In some embodiments, the vessel threshold can comprise a vessel diameter, radius, or width of about 10.0 mm, about 9.0 mm, about 8.0 mm, about 7.0 mm, about 6.0 mm, about 5.0 mm, about 4.5 mm, about 4.0 mm, about 3.9 mm, about 3.8 mm, about 3.7 mm, about 3.6 mm, about 3.5 mm, about 3.4 mm, about 3.3 mm, about 3.2 mm, about 3.1 mm, about 3.0 mm, about 2.9 mm, about 2.8 mm, about 2.7 mm, about 2.6 mm, about 2.5 mm, about 2.4 mm, about 2.3 mm, about 2.2 mm, about 2.1 mm, about 2.0 mm, about 1.9 mm, about 1.8 mm, about 1.7 mm, about 1.6 mm, about 1.5 mm, about 1.4 mm, about 1.3 mm, about 1.2 mm, about 1.1 mm, about 1.0 mm, about 0.9 mm, about 0.8 mm, about 0.7 mm, about 0.6 mm, about 0.5 mm, about 0.4 mm, about 0.5 mm, about 0.4 mm, about 0.3 mm, about 0.2 mm, about 0.1 mm, and/or within a range defined by two of the aforementioned values. These values can refer, for example, to average diameters, widths, or radii along a vessel. Vessel surface area can be the square of any of these listed values and/or other values both larger and smaller.

In some embodiments, the system can be configured to utilize a different vessel threshold for different vessels on an image. For example, in some cases, an image can comprise vessels with varying degrees of quality, such that one vessel has a higher image quality than another vessel within the same image due to motion artifact or other reasons. The system can be configured to perform an image analysis to determine image qualities for vessels identified therein, for example, using machine learning or artificial intelligence algorithms and/or other image processing techniques. In some embodiments, the system can be configured to apply a higher vessel threshold to a vessel with lower image quality than another vessel with a higher image quality.

Similarly, in some embodiments, the system can be configured to apply a lower vessel threshold to a vessel with a higher image quality than another vessel with a lower image quality. In some embodiments, one or more plaque, vessel, and/or relational parameters can be derived from an image after applying different vessel thresholds to different vessels. For example, in some instances, a PAV for one vessel can be derived after removing all vessel areas with a diameter smaller than about 2.0 mm, whereas a PAV for another vessel within the same image can be derived after removing all vessel areas with a diameter smaller than about 1.0 mm.

In some embodiments, the reference database can comprise PAV or other plaque, vessel, and/or relational parameters derived from images after applying varying vessel thresholds to the same and/or different vessels. For example, in some embodiments, the reference database can include PAVs derived from one vessel after removing all vessel areas with a diameter smaller than about 2.0 mm, about 1.0 mm, and/or any other vessel threshold as described herein. Then, in some embodiments, if a corresponding vessel in the subject image at hand is applied to a vessel threshold of 1.0 mm, then that vessel segment or a parameter derived therefrom can be compared to corresponding vessel segments or parameters derived therefrom in the database after applying a vessel threshold of 1.0 mm (with or without normalizing to a physical property of the subject). Similarly, another vessel in the subject image, or a parameter derived therefrom, can be compared to corresponding vessel segments, or parameters derived therefrom, in the database after applying a vessel threshold of 2.0 mm (with or without normalizing to a physical property of the subject). In other words, different vessel thresholds can be applied to different vessels, and the resulting vessel segments can be normalized and/or compared to vessel segments with different applied vessel thresholds in the reference database. As such, in some embodiments, the reference database can include modified and/or normalized parameters for different vessels. Accordingly, in some embodiments, the system can be configured to compare each vessel segment, normalized or not, to the same vessel segment with the same applied vessel threshold of different subjects. Thus, in some embodiments, the systems, methods, and devices can be configured to provide dynamic normalization of vessels for improved accuracy and/or analysis independent of image quality.

In some embodiments, with or without applying a vessel threshold, one or more vessel segments can be analyzed to determine one or more plaque parameters, vessel parameters, and/or relational plaque parameters. For example, the plaque parameters can include absolute plaque density, relative plaque density, composition, calcification, radiodensity, location, volume, surface area, geometry, heterogeneity, diffusivity, and/or ratio between volume and surface area, among others. The vessel parameters can include vessel volume, diameter, area, cross-sectional area, surface area, length, location, and/or remodeling, among others. The relational plaque parameters can include a ratio or other comparison between one or more plaque parameters and one or more vessel parameters, such as for example PAV, PAV on a vessel-by-vessel basis, PAV on a segment-by-segment basis, and/or PAV for the whole heart, ratio of surface area of plaque to surface of vessel or lumen, ratio of volume of plaque to volume of vessel or lumen, and/or the like.

Figure 14A:
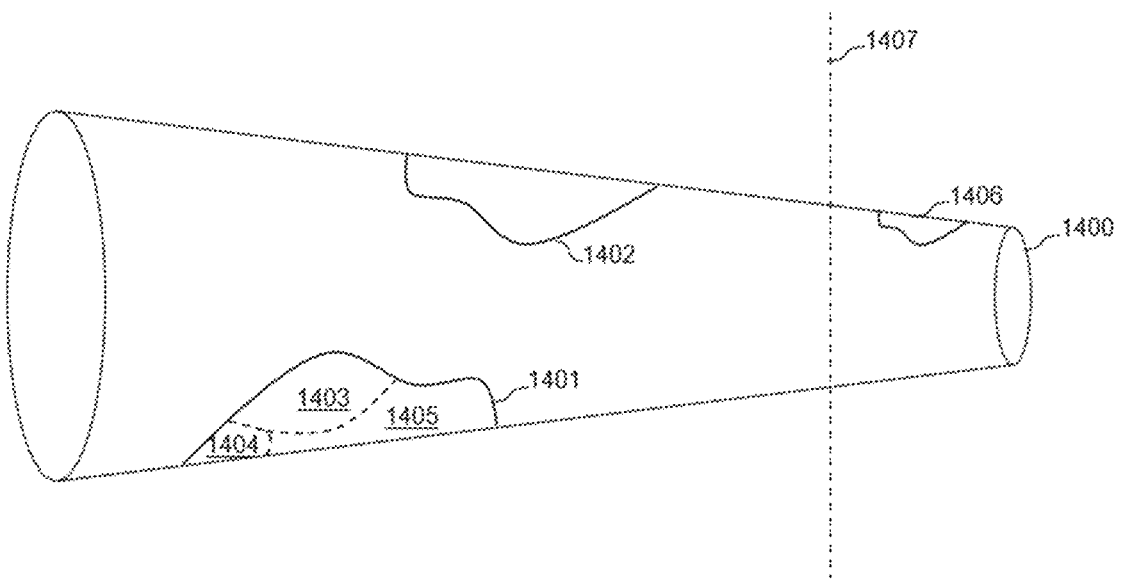
FIG. 14A is a schematic illustrating an example of one or more regions of plaque that can be analyzed using image analysis processes by one or more embodiments of the systems, methods, and devices herein for assessment of cardiovascular risk, disease, and/or state.

As an illustrative example, FIG. 14A provides a schematic example of one or more regions of plaque that can be analyzed using image analysis processes by one or more embodiments of the systems, methods, and devices herein for assessment of cardiovascular risk, disease, and/or state.

As illustrated in FIG. 14A, in some embodiments, the systems, methods, and devices described herein can be configured to analyze one or more vessels 1400 on a medical image. The one or more vessels 1400 can taper along a longitudinal axis such that the diameter of the vessel generally decreases. As described herein, in some embodiments, the quality of the medical image can be such that certain vessel features, such as plaque 1406, in a small or narrow vessel segment can appear less than accurate for analysis purposes. In contrast, certain vessel features, such as some other regions of plaque 1401, 14024, within the same vessel 1400 can have sufficient image quality for analysis purposes. For example, in some embodiments, a region of plaque 1401 appearing in a sufficiently wide vessel segment can be further analyzed by the system to identify and/or determine one or more regions and/or types and/or compositions of plaque 1403, 1404, 1405 within the region of plaque 1401. In some embodiments, a region of plaque 1402 can comprise a single type or composition of plaque. In some embodiments, a region of plaque 1401, 1402, 1403, 1404, 1405 can comprise one or more different types or compositions of plaque. For example, in some embodiments, the system can be configured to analyze, characterize, and/or classify plaque into one of three types: low-density non-calcified plaque, non-calcified plaque, and calcified plaque. In some embodiments, the system can be configured to analyze, characterize, and/or classify plaque into one of two types: non-calcified plaque and calcified plaque. In some embodiments, the system can be configured to analyze, characterize, and/or classify plaque into one of any number of different types, such as for example 1, 2, 3, 4, 5, 6, 7, 8, 9, 10, 15, 20, 25, and/or 30 different types of classifications of plaque. In some embodiments, the system can be configured to analyze, characterize, and/or classify plaque into a number of different types within a range defined by two of the aforementioned values.

In some embodiments, due to the fact that certain vessel features, such as a region of plaque 1406, within a narrow vessel segment comprise low image quality for analysis, the system can be configured to ignore or remove such features. More specifically, as described herein, in some embodiments, the system can be configured to ignore vessel segments below a certain vessel threshold 1407, the vessel threshold 1407 associated with the size of the vessel segment, and/or features therein from further analysis. As such, in the illustrated example, in some embodiments, the system can be configured to only analyze some of the regions of plaque 1401, 1402 that appear in a sufficiently wide vessel segment which is above a vessel threshold 1407 and not other regions of plaque 1406 that are below the vessel threshold 1407 within a single vessel 1400. In some embodiments, the system can be further configured to analyze only those regions of plaque 1401, 1402 within the portion of the vessel above the vessel threshold 1407 in determining one or more plaque, vessel, and/or relational plaque parameters, such as PAV. In some embodiments, the database PAV modified by the vessel threshold or other database parameter can be normalized, for example against the body mass and/or LV mass and/or heart mass of the subject, and/or compared to a normal values and/or reference values database comprising modified and/or normalized PAV or other parameter values. Based on such analysis, in some embodiments, the system can be configured to determine coronary artery disease (CAD) risk assessment and/or proposed treatment for a subject.

Figure 14B:
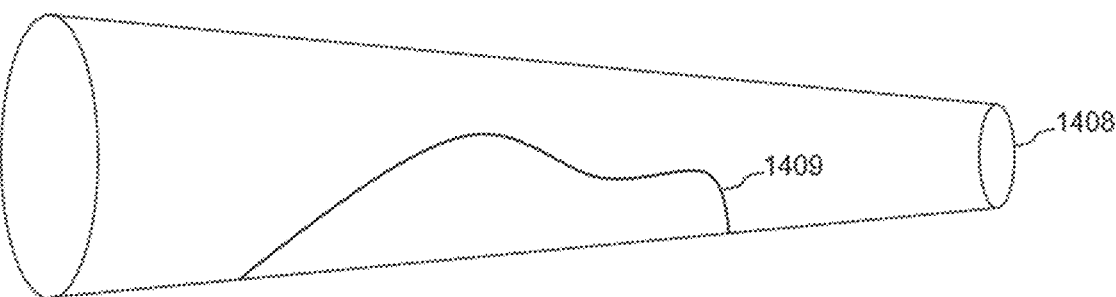
FIGS. 14B-14C are schematics illustrating an example of one or more regions of plaque that can be analyzed using image analysis processes by one or more embodiments of the systems, methods, and devices herein for assessment of cardiovascular risk, disease, and/or state.
Figure 14C:
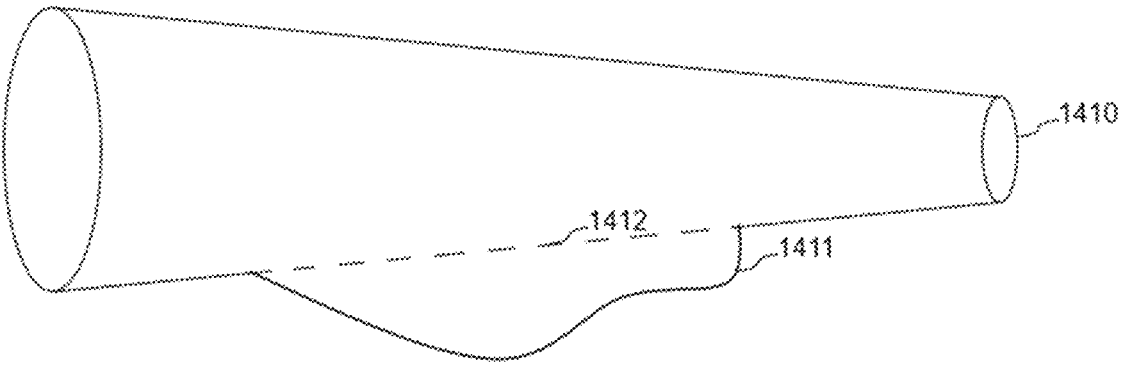

Further, even if PAV, plaque volume, or any other plaque parameter is analyzed either with or without truncating a vessel based on a threshold, there may still be other factors that limit the usefulness and/or indicative nature of such plaque parameter. As an illustrative example, FIGS. 14B-14C are schematics illustrating examples of one or more regions of plaque that can be analyzed using image analysis processes by one or more embodiments of the systems, methods, and devices herein for assessment of cardiovascular risk, disease, and/or state. As illustrated in FIG. 14B, in some instances, a vessel 1408 can include a region of plaque 1409 that is inside the vessel 1408 and thereby obstructs or decreases the vessel volume. In contrast, as illustrated in FIG. 14C, in some instances, a vessel 1410 can include a region of plaque 1411 that is outside the vessel 1410 and thereby does not obstruct or decrease the vessel volume. As such, in both instances illustrated in FIGS. 14B and 14C, even if the plaque volume is the same and even if the plaque composition is the same between the two regions of plaque 1409, 1411, the PAV will be different due to differences in vessel volume of the vessels 1408, 1410. More specifically, the PAV of the region of plaque 1409 inside the vessel 1408 will be higher than the PAV of plaque 1411 outside of the vessel 1410. However, if the volume and composition of the regions of plaque 1409, 1411 are equal, then the potential risk and/or disease state of both vessels 1408, 1410 due to the two regions of plaque 1409, 1411 may be the same. For example, the risk of plaque 1411 rupturing may be the same as the risk of plaque 1409 rupturing. However, PAV values of both regions of plaque 1409, 1411 may indicate otherwise.

As such, to account for such technical shortcomings, in some embodiments described herein, the systems, methods, and devices are configured to normalize and/or modify PAV for more accurate analysis of disease state. For example, in some embodiments, the systems, methods, and devices described herein are configured to generate a hypothetical PAV, wherein plaque volume is normalized against a hypothetical vessel volume that would have been true had the region(s) of plaque not been present. In other words, in some embodiments, the systems, methods, and devices are configured to interpolate a curvature of the vessel wall before and after where a region(s) of plaque exists and determine the hypothetical vessel volume based on the same. For example, in the situation illustrated in FIG. 14B, because the plaque 1409 is wholly within the vessel 1408, the system can simply use the exterior vessel wall as a basis for determining the hypothetical vessel volume. However, in the situation illustrated in FIG. 14C, the system can be configured to use the boundaries of where the plaque 1411 exists as a basis for interpolating the vessel wall curvature to determine a hypothetical vessel wall 1412 had the plaque 1411 not existed. In some embodiments, based on the hypothetical vessel wall 1412, the system can be configured to determine the hypothetical vessel volume. In some embodiments, the system can be configured divide the plaque volume by the hypothetical vessel volume to determine a normalized plaque volume, which can account for differences in actual vessel volume, for example due to positive remodeling.

In some embodiments, the system can be configured to determine a hypothetical PAV for one or more regions of plaque within one or more arteries or vessels identified on a medical image. For example, in some embodiments, the system can be configured to determine a hypothetical PAV for every region of plaque that is present on a medical image and/or vessel and/or artery. In some embodiments, the system can be configured to aggregate all such hypothetical PAV values and compare the same to a reference database of known aggregate hypothetical PAV values to determine the state and/or risk of disease. In some embodiments, the system can be configured to determine a hypothetical PAV for one or more regions of plaque within a particular artery or vessel and compare the same to a reference database of known hypothetical PAV values for that same artery or vessel to determine a state and/or risk of disease for that artery or vessel. In some embodiments, the system can be configured to repeat the process for one or more arteries or vessels and then aggregate the same to determine an overall state and/or risk of disease for the subject.

In some embodiments, the systems, devices, and methods described herein can be configured to normalize plaque volume against a physical property of the subject, such as, for example, left ventricular (LV) mass, to address shortcomings with using plaque volume directly as a proxy for the state or risk of disease. LV mass may refer to the weight of the left ventricle and can be used to determine blood pressure effects on the heart. In general, the higher the LV mass, the more likely there could be an occurrence of a cardiac incident. In some embodiments, the system can be configured to normalize plaque volume, such as total plaque volume, total non-calcified plaque volume, total calcified plaque volume, and/or total low-attenuated non-calcified plaque volume, against LV mass. In some embodiments, LV mass can be derived from a medical image using image processing techniques. In some embodiments, the system can be configured to compare plaque volume normalized to LV mass to a reference database comprising values of plaque volume normalized to LV mass derived from a population with varying degrees of health or disease to assess the risk and/or state of disease of the subject.

In some embodiments, the systems, devices, and methods described herein can be configured to normalize plaque volume appearing in a particular vessel or artery against LV mass subtended by that artery or vessel in which the plaque appears. As such, in some embodiments, plaque can be normalized against subtended LV mass on a vessel-by-vessel basis. As described above, in some embodiments, the system can be configured to normalize plaque volume, such as total plaque volume, total non-calcified plaque volume, total calcified plaque volume, and/or total low-attenuated non-calcified plaque volume, against LV mass subtended by the artery or vessel in which that plaque appears. In some embodiments, the LV mass and/or LV mass subtended by a particular artery can be derived from a medical image using image processing techniques. In some embodiments, the system can be configured to compare plaque volume normalized to LV mass subtended by a vessel in which the plaque appears to a reference database comprising values of plaque volume normalized to LV mass subtended by the vessel in which the plaque appears that can be derived from a population with varying degrees of health or disease to assess the risk and/or state of disease of the subject.

As such, in some embodiments, the systems, devices, and methods described herein can be configured to utilize normalized PAV and/or plaque volume in assessing the risk of coronary artery disease (CAD) and/or MACE for a subject and/or determine a proposed treatment. By utilizing such normalized or modified PAV or plaque volume, it can be possible to address predictability and/or comparability issues arising from image quality issues, positive/negative remodeling, and/or differences arising from physical differences in subjects, and/or the like, by comparing the normalized and/or modified PAV or plaque volume to a reference database of values of normalized and/or modified PAV or plaque volumes derived from a reference population using similar PAV and/or plaque normalization and/or modification techniques.

In some embodiments, the medical image of the subject and/or reference database is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS). For example, in some embodiments, images for the reference database can be derived from one or more or a combination of such imaging modalities for varying degrees of image quality.

In some embodiments, the system can be configured to assess the risk and/or state of cardiovascular disease or health based on the modified and/or normalized plaque parameter(s). In some embodiments, the system can be configured to determine or generate a proposed treatment for the subject based on the assessed risk and/or state of cardiovascular disease or health. For example, the proposed treatment can include one or more of medical therapy (such as statins), interventional therapy (such as stent implantation), and/or lifestyle therapy (such as diet or exercise). In some embodiments, the system can be configured to track the efficacy of a treatment by tracking changes in the modified and/or normalized parameter(s), for example compared to previous value(s) for the same subject and/or change relative to a reference values database comprising one or more reference values, such as, for example, normal values.

As such, in some embodiments, the systems, devices, and methods described herein provide an improved quantitative and/or image-based solution for generating and/or tracking cardiovascular disease or health by modifying and/or normalizing one or more plaque parameters, such as for example PAV, plaque volume, and/or the like.

Cardiovascular Risk and/or Disease State Assessment Using Modified and/or Normalized Image Analysis-Based Plaque Parameters As described herein, some embodiments of systems, devices, and methods described herein are configured to derive one or more modified and/or normalized plaque parameters from a medical image and use the same for risk assessment and/or treatment assessment for CAD. In some embodiments, such modified and/or normalized plaque parameters can be analyzed against a reference database in determining the risk and/or treatment assessment. FIGS. 14D-14G are flowcharts illustrating example embodiment(s) of systems, devices, and methods for cardiovascular risk and/or disease state assessment using modified and/or normalized image analysis-based plaque parameters.

Figure 14D:
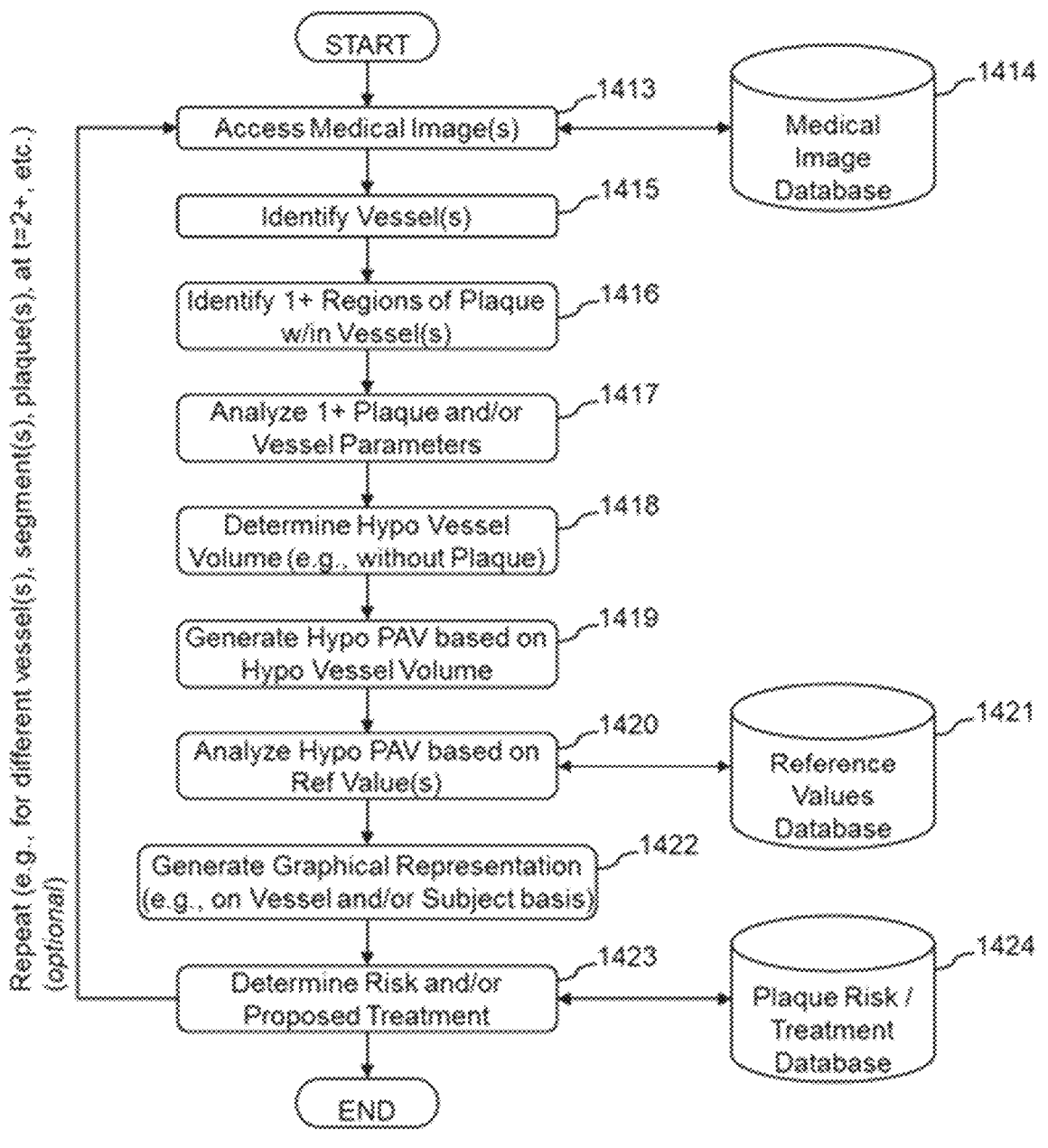
FIGS. 14D-14G are flowcharts illustrating example embodiment(s) of systems, devices, and methods for cardiovascular risk and/or disease state assessment using modified and/or normalized image analysis-based plaque parameters.

As illustrated in FIG. 14D, in some embodiments, the system can be configured to normalize plaque volume against a hypothetical vessel volume without plaque to account for differences in vessel remodeling due to plaque. As such, in some embodiments, the systems, methods, and devices described herein can provide a more accurate benchmark for comparison and/or analysis among different subjects.

In particular, as illustrated in FIG. 14D, in some embodiments, the system can be configured to access a medical image at block 1413. In some embodiments, the medical image can include one or more arteries, such as coronary, carotid, and/or other arteries of a subject. In some embodiments, the medical image can be stored in a medical image database 1414. In some embodiments, the medical image database 1414 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1415, the system can be configured to identify and/or characterize one or more vessels and/or lumen of interest, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1416, the system can be configured to identify one or more regions of plaque within the medical image. In some embodiments, at block 1417, the system can be configured to analyze and/or determine one or more plaque and/or vessel parameters. In some embodiments, the system can be configured to utilize one or more AI and/or ML algorithms to automatically and/or dynamically identify and/or characterize one or more regions of plaque using image processing. For example, in some embodiments, the one or more AI and/or ML algorithms can be trained using a Convolutional Neural Network (CNN) on a set of medical images on which one or more regions of plaque have been identified and/or characterized, thereby allowing the AI and/or ML algorithm to automatically identify and/or characterize regions of plaque directly from a medical image.

For example, in some embodiments, the system can be configured to analyze the absolute density, relative density, radiodensity values, and/or heterogeneity or distribution thereof of one or more pixels on a medical image to identify and/or characterize plaque. More specifically, in some embodiments, the system can be configured to identify a particular pixel as plaque, non-calcified plaque, low-density non-calcified plaque, and/or calcified plaque, and/or any other classification or type of plaque. In some embodiments, the system can be configured to classify a particular pixel or region of plaque as non-calcified plaque when the radiodensity value of the pixel is below a certain predetermined threshold, within a predetermined range, and/or comprises a heterogeneity index or distribution within, under, or above a particular predetermined range or threshold. In some embodiments, the system can be configured to classify a particular pixel or region of plaque as low-density non-calcified plaque when the radiodensity value of the pixel is below a certain predetermined threshold, within a predetermined range, and/or comprises a heterogeneity index or distribution within, under, or above a particular predetermined range or threshold. In some embodiments, the system can be configured to classify a particular pixel or region of plaque as calcified plaque when the radiodensity value of the pixel is above a certain predetermined threshold, within a predetermined range, and/or comprises a heterogeneity index or distribution within, under, or above a particular predetermined range or threshold.

In some embodiments, the one or more plaque parameters can include absolute plaque density, relative plaque density, composition, calcification, radiodensity, location, volume, surface area, geometry, heterogeneity, diffusivity, and/or ratio between volume and surface area. In some embodiments, the one or more vessel parameters can include one or more of vascular volume, diameter, area, cross-sectional area, surface area, length, location, and/or remodeling. In some embodiments, the one or more plaque parameters can include a ratio or other comparison between one or more plaque parameters and one or more vessel parameters, such as for example PAV, PAV on a vessel-by-vessel basis, PAV on a segment-by-segment basis, and/or PAV for the whole heart, ratio of surface area of plaque to surface of vessel or lumen, ratio of volume of plaque to volume of vessel or lumen, and/or the like.

In some embodiments, the system can be configured to utilize one or more AI and/or ML algorithms to automatically and/or dynamically determine one or more plaque parameters and/or vessel parameters using image processing. For example, in some embodiments, the one or more AI and/or ML algorithms can be trained using a Convolutional Neural Network (CNN) on a set of medical images on which one or more plaque parameters and/or vessel parameters have been determined, thereby allowing the AI and/or ML algorithm to automatically determine one or more plaque parameters and/or vessel parameters directly from a medical image.

In some embodiments, at block 1418, the system can be configured to generate a hypothetical vessel volume without plaque. In particular, in some embodiments, the system can be configured to assume that one or more regions of plaque do not exist in an artery or vessel and determine what the vessel volume might have been without such one or more regions of plaque. In some embodiments, the system can be configured to determine the boundaries of one or more regions of plaque and interpolate the curvature of the vessel or artery based on the start and/or end points or boundary of the one or more regions of plaque. Boundaries of the one or more regions of plaque can include a posterior boundary and an anterior boundary opposite the posterior boundary. The posterior boundary and anterior boundary can be found, at least in part, by using the location and geometry of one or more regions of plaque that have been identified within the artery. For example, in some embodiments, the system can be configured to determine the geometry and/or location of a region of plaque and/or graphically remove the region of plaque from a vessel. In some embodiments, the system can be configured to interpolate what the curvature of the vessel would have been without the removed region of plaque. In some embodiments, the system can be configured to utilize one or more AI and/or ML algorithms to determine the hypothetical vessel volume and/or vessel curvature, for example by being trained on a plurality of vessel curvatures and/or volumes without plaque.

In some embodiments, at block 1419, the system can be configured to generate a hypothetical PAV based on the hypothetical vessel volume. For example, in some embodiments, the system can be configured to generate a hypothetical PAV by dividing plaque volume by the hypothetical vessel volume. In some embodiments, the system can be configured to generate a hypothetical PAV on a vessel-by-vessel basis. For example, in some embodiments, the system can be configured to generate a vessel-specific hypothetical PAV by determining the amount or volume of plaque (total, non-calcified, calcified, and/or low-attenuated non-calcified plaque) within a particular vessel and then dividing the same by the hypothetical vessel volume of that specific vessel. In some embodiments, the system can be configured to generate a weighted measure of one or more vessel-specific hypothetical PAV values. For example, in some embodiments, the system can be configured to weight a hypothetical PAV of a particular vessel more heavily compared to a hypothetical PAV of another vessel. In some embodiments, the system can be configured to generate a global or aggregate hypothetical PAV for the subject by determining the amount or volume of plaque (total, non-calcified, calcified, and/or low-attenuated non-calcified plaque) within a plurality of vessels and then dividing the same by the hypothetical vessel volume of those plurality of vessels.

In some embodiments, at block 1420, the system can be configured to analyze the hypothetical PAV based on one or more reference values of hypothetical PAV. Individual reference values of hypothetical PAV may be used from a dataset of reference hypothetical PAV values derived from a plurality of medical images of a population with varying states of cardiovascular disease. For example, in some embodiments, the system can be configured to access a reference values database 1421 that includes one or more hypothetical PAV values. The one or more hypothetical PAV values can be derived from other subjects with varying states or risks of cardiovascular disease, including for example normal values. In some embodiments, the one or more reference values can be obtained from one or more medical images using the same or similar imaging modalities as the medical image accessed at block 1413. In some embodiments, the one or more reference values can be obtained from analyzing one or more medical images to derive one or more hypothetical PAV values, for example using one or more processes described in relation to blocks 1413-1419. In some embodiments, the one or more reference hypothetical PAV values can be stored on a reference values database 1421, which can be locally accessible by the system and/or can be located remotely and accessible through a network connection.

In some embodiments, based on such analysis and/or comparison, the system, at block 1422, can be configured to generate a graphical representation of the analysis results. In some embodiments, the system can be configured to generate a graphical generation reporting the analysis results on a vessel-by-vessel basis and/or subject basis. For example, in some embodiments, the system can be configured to generate a graphical representation of one or more arteries or vessels, in which specific arteries and/or vessels can be color-coded or assigned some value or other indicator depending on the analysis results. As an illustrative example, in some embodiments, if the system determines that the hypothetical PAV of a particular vessel is high, the system can be configured to color code that vessel red in the graphical representation.

In some embodiments, based on such analysis and/or comparison of hypothetical PAV, the system, at block 1423, can be configured to determine a risk or state of cardiovascular disease or health of the subject. Further, in some embodiments, based on such analysis and/or comparison, the system, at block 1423, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1424, which can be locally accessible by the system and/or can be located remotely and accessible through a network connection. In some embodiments, the plaque risk/treatment database 1424 can include reference points or data that relate one or more treatment to cardiovascular disease risk or state determined based on one or more reference hypothetical PAV values.

In some embodiments, the system can be configured to repeat one or more processes described in relation to blocks 1413-1423, for example for one or more other vessels, segment, regions of plaque, different subjects, and/or for the same subject at a different time. As such, in some embodiments, the system can provide for longitudinal disease tracking and/or personalized treatment for a subject. In some embodiments, the system can track the efficacy of the treatment by determining assessment of the state of cardiovascular disease of the subject at a later point in time after the treatment.

Figure 14E:
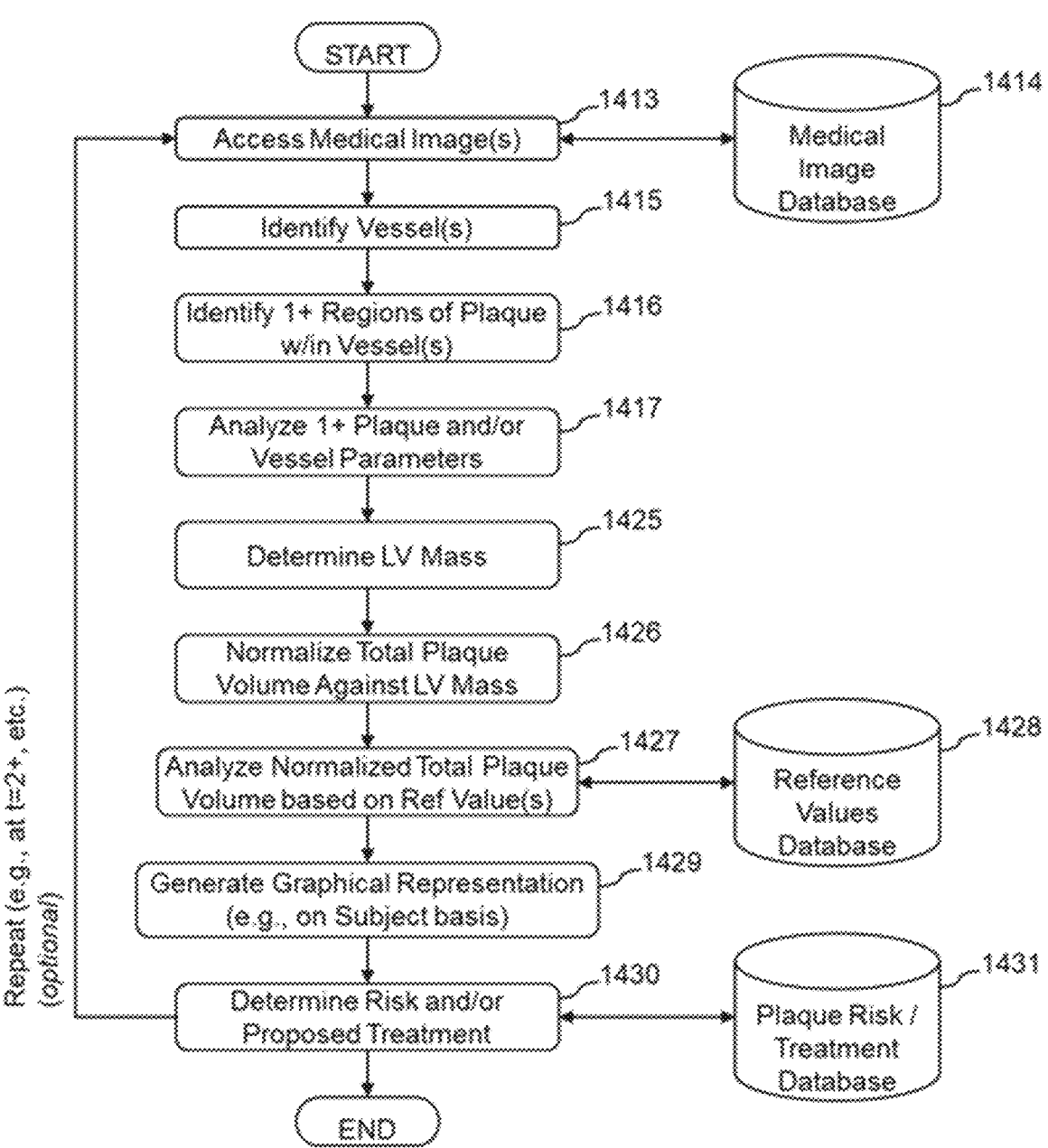

FIG. 14E is a flowchart illustrating example embodiment(s) of systems, devices, and methods for cardiovascular risk and/or disease state assessment using modified and/or normalized image analysis-based plaque parameters. The same reference numbers in FIGS. 14E and 14D represent similar features and can include any of the features described in reference to either figure.

As illustrated in FIG. 14E, in some embodiments, the system can be configured to normalize plaque volume against LV mass to account for other differences among subjects that may not necessarily be indicative of disease state or risk. As such, in some embodiments, the systems, methods, and devices described herein can provide a more accurate benchmark for comparison and/or analysis among different subjects.

In particular, as illustrated in FIG. 14E, in some embodiments, the system, at block 1425, can be configured to determine LV mass of the subject. For example, in some embodiments, the system can be configured to derive LV mass from the medical image using one or more image analysis techniques. In particular, in some embodiments, the system can be configured to derive LV volume based on the medical image and converting the same to LV mass. In some embodiments, the system can be configured to utilize one or more AI and/or ML algorithms to automatically and/or dynamically determine LV mass using image processing. For example, in some embodiments, the one or more AI and/or ML algorithms can be trained using a Convolutional Neural Network (CNN) on a set of medical images on which LV mass and/or volume have been derived, thereby allowing the AI and/or ML algorithm automatically derive LV mass and/or volume directly from a medical image.

In some embodiments, at block 1426, the system can be configured to normalize plaque volume by dividing the plaque volume by LV mass. In some embodiments, the system can be configured to divide one or more of the total plaque volume, total non-calcified plaque volume, total calcified plaque volume, and/or total low-attenuated, non-calcified plaque volume by LV mass.

In some embodiments, at block 1427, the system can be configured to analyze the normalized plaque volume based on one or more reference values of normalized plaque volume. For example, in some embodiments, the system can be configured to access a reference values database 1428 that includes one or more values of normalized plaque volume. The one or more values of normalized plaque volume can be derived from other subjects with varying states or risks of cardiovascular disease, including for example normal values. In some embodiments, the one or more reference values can be obtained from one or more medical images using the same or similar imaging modalities as the medical image accessed at block 1413. In some embodiments, the one or more reference values can be obtained from analyzing one or more medical images to derive one or more values of normalized plaque volume, for example using one or more processes described in relation to blocks 1413-1426. In some embodiments, the one or more reference values of normalized plaque volume can be stored on a reference values database 1428, which can be locally accessible by the system and/or can be located remotely and accessible through a network connection.

In some embodiments, based on such analysis and/or comparison, the system, at block 1429, can be configured to generate a graphical representation of the analysis results. In some embodiments, the system can be configured to generate a graphical generation reporting the analysis results on a subject basis.

In some embodiments, based on such analysis and/or comparison of normalized plaque volume, the system, at block 1430, can be configured to determine a risk or state of cardiovascular disease or health of the subject. Further, in some embodiments, based on such analysis and/or comparison, the system, at block 1430, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1431, which can be locally accessible by the system and/or can be located remotely and accessible through a network connection. In some embodiments, the plaque risk/treatment database 1431 can include reference points or data that relate one or more treatment to cardiovascular disease risk or state determined based on one or more reference values of plaque volume normalized to LV mass.

In some embodiments, the system can be configured to repeat one or more processes described in relation to blocks 1413-1430, for example for one or more different subjects and/or for the same subject at a different time. As such, in some embodiments, the system can provide for longitudinal disease tracking and/or personalized treatment for a subject.

Figure 14F:
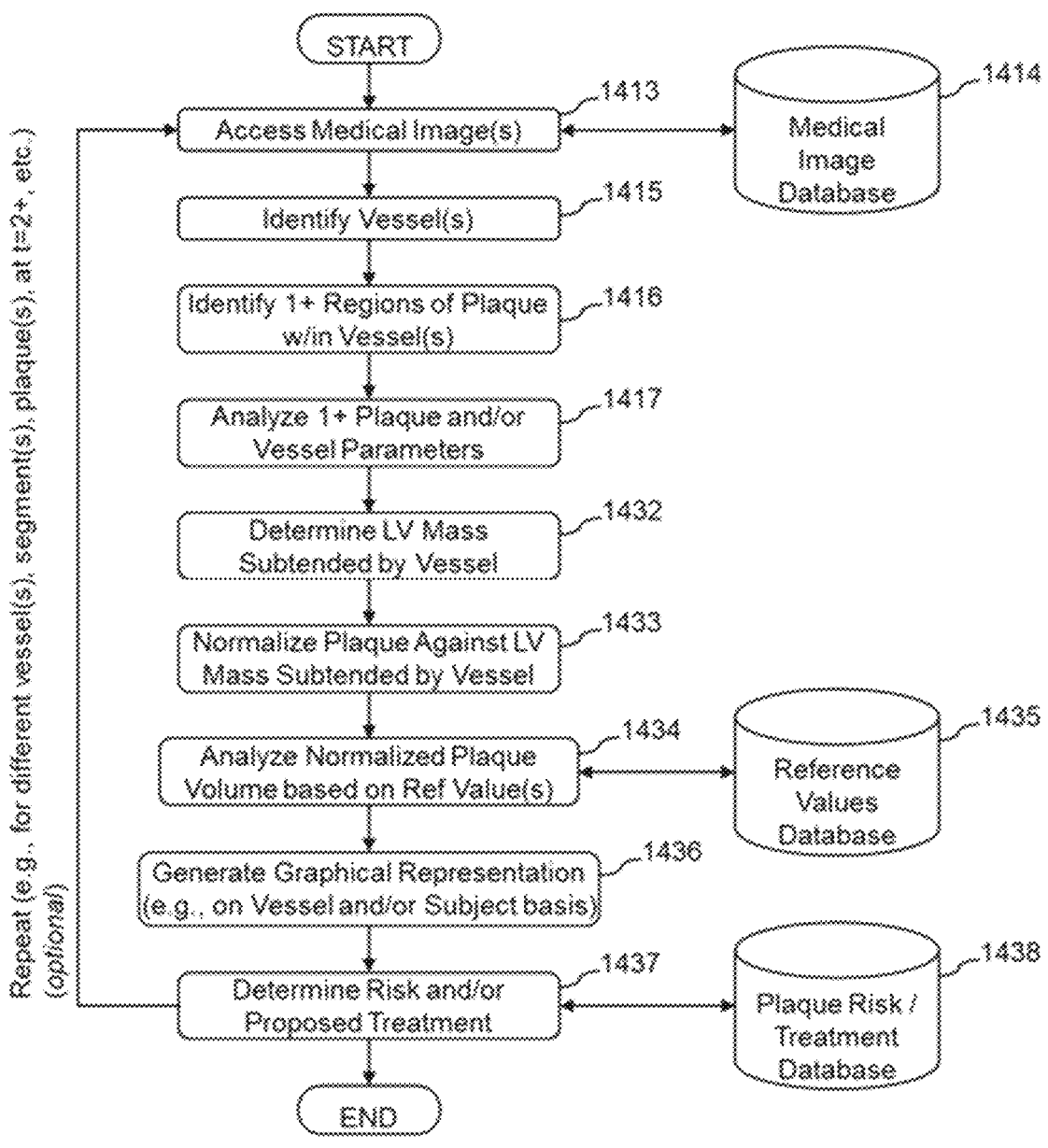

FIG. 14F is a flowchart illustrating example embodiment(s) of systems, devices, and methods for cardiovascular risk and/or disease state assessment using modified and/or normalized image analysis-based plaque parameters. The same reference numbers in FIGS. 14F, 14E, and 14D represent similar features and can include any of the features described in reference to any of these figures.

As illustrated in FIG. 14F, in some embodiments, the system can be configured to normalize plaque volume within a vessel against the amount of myocardium that vessel subtends to account for other differences among subjects that may not necessarily be indicative of disease state or risk. As such, in some embodiments, the systems, methods, and devices described herein can provide a more accurate benchmark for comparison and/or analysis among different subjects.

In particular, as illustrated in FIG. 14F, in some embodiments, the system, at block 1432, can be configured to determine myocardium or LV mass of the subject subtended by one or more vessels. For example, in some embodiments, the system can be configured to determine LV mass subtended by each or some of the vessels identified from the medical image at block 1415. In some embodiments, the system can be configured to derive LV mass subtended by one or more vessels from the medical image using one or more image analysis techniques. In particular, in some embodiments, the system can be configured to derive LV volume subtended by one or more vessels based on the medical image and converting the same to LV mass. In some embodiments, the system can be configured to utilize one or more AI and/or ML algorithms to automatically and/or dynamically determine LV mass subtended by one or more vessels using image processing. For example, in some embodiments, the one or more AI and/or ML algorithms can be trained using a Convolutional Neural Network (CNN) on a set of medical images on which LV mass and/or volume subtended by one or more vessels have been derived, thereby allowing the AI and/or ML algorithm automatically derive LV mass and/or volume subtended by one or more vessels directly from a medical image.

In some embodiments, at block 1433, the system can be configured to normalize the volume of plaque in a particular vessel by dividing the same by LV mass subtended by that particular vessel. In some embodiments, the system can be configured to divide one or more of the total plaque volume, total non-calcified plaque volume, total calcified plaque volume, and/or total low-attenuated, non-calcified plaque volume of one or more regions of plaque within a particular vessel by LV mass subtended by that vessel.

As described herein, in some embodiments, the system can be configured to normalize plaque volume on a vessel-by-vessel basis. In some embodiments, the system can be configured to generate a weighted measure of one or more plaque volumes normalized against LV mass subtended by each vessel. For example, in some embodiments, the system can be configured to weight a normalized volume of plaque within a particular vessel more heavily compared to a normalized volume of plaque within another vessel. In some embodiments, the system can be configured to generate a global or aggregate normalized plaque volume for the subject by adding and/or determining a weighted measure of a plurality of plaque volumes normalized by the LV mass subtended by the vessel in which the regions of plaque exist.

In some embodiments, at block 1434, the system can be configured to analyze the normalized plaque volume(s) based on one or more reference values of volumes of plaque normalized against LV mass subtended by a vessel comprising each volume or region of plaque. For example, in some embodiments, the system can be configured to access a reference values database 1435 that includes one or more plaque volumes normalized against LV mass subtended by a vessel in which the plaque exists. The one or more normalized plaque volumes can be derived from other subjects with varying states or risks of cardiovascular disease, including for example normal values. In some embodiments, the one or more reference values can be obtained from one or more medical images using the same or similar imaging modalities as the medical image accessed at block 1413. In some embodiments, the one or more reference values can be obtained from analyzing one or more medical images to derive one or more normalized plaque volumes, for example using one or more processes described in relation to blocks 1413-1433. In some embodiments, the one or more reference normalized plaque volumes can be stored on a reference values database 1435, which can be locally accessible by the system and/or can be located remotely and accessible through a network connection.

In some embodiments, based on such analysis and/or comparison, the system, at block 1436, can be configured to generate a graphical representation of the analysis results. In some embodiments, the system can be configured to generate a graphical generation reporting the analysis results on a vessel-by-vessel basis and/or subject basis. For example, in some embodiments, the system can be configured to generate a graphical representation of one or more arteries or vessels, in which specific arteries and/or vessels can be color-coded or assigned some value or other indicator depending on the analysis results. As an illustrative example, in some embodiments, if the system determines that the normalized plaque volume of a particular vessel is high, the system can be configured to color code that vessel red in the graphical representation.

In some embodiments, based on such analysis and/or comparison of normalized plaque volume, the system, at block 1437, can be configured to determine a risk or state of cardiovascular disease or health of the subject. Further, in some embodiments, based on such analysis and/or comparison, the system, at block 1437, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1438, which can be locally accessible by the system and/or can be located remotely and accessible through a network connection. In some embodiments, the plaque risk/treatment database 1438 can include reference points or data that relate one or more treatment to cardiovascular disease risk or state determined based on one or more reference values of plaque volumes normalized against LV mass subtended by a vessel in which the plaque appears.

In some embodiments, the system can be configured to repeat one or more processes described in relation to blocks 1413-1438, for example for one or more other vessels, segment, regions of plaque, different subjects, and/or for the same subject at a different time. As such, in some embodiments, the system can provide for longitudinal disease tracking and/or personalized treatment for a subject.

Figure 14G:
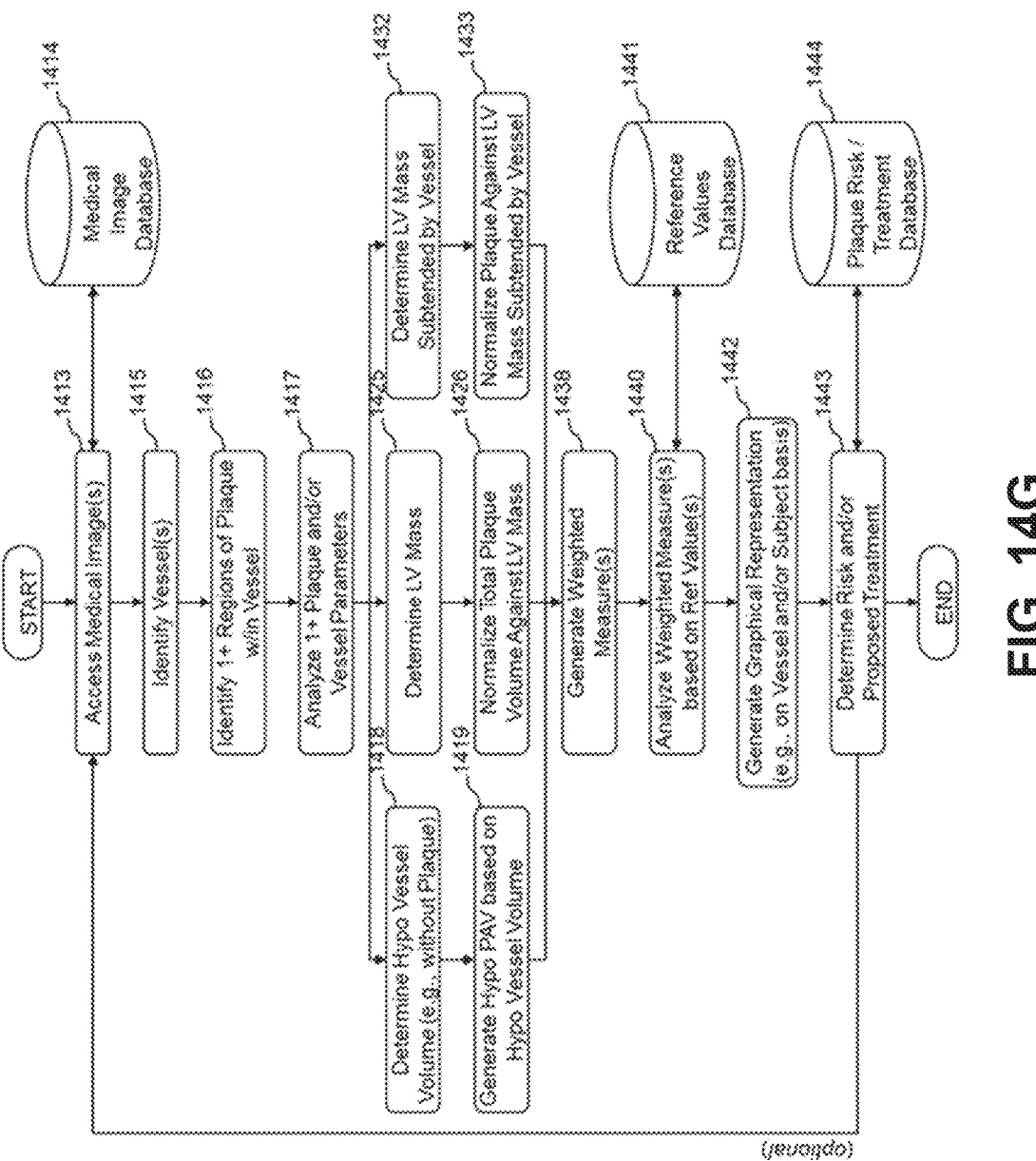

FIG. 14G is a flowchart illustrating example embodiment(s) of systems, devices, and methods for cardiovascular risk and/or disease state assessment using modified and/or normalized image analysis-based plaque parameters. The same reference numbers in FIGS. 14G, 14F, 14E, and 14D represent similar features and can include any of the features described in reference to any of these figures.

As illustrated in FIG. 14G, in some embodiments, the system can be configured to normalize plaque volume using a plurality of methods. In some embodiments, the system can be configured to generate a weighted measure of plaque volume normalized using a plurality of methods and use the weighted measure in assessing the risk and/or state of disease for the subject. As such, by utilizing a number of different normalization methods at once, in some embodiments, the systems, methods, and devices described herein can provide a more accurate benchmark for comparison and/or analysis among different subjects.

In particular, as illustrated in FIG. 14G, in some embodiments, at blocks 1418-1419, the system can be configured to normalize plaque volume against a hypothetical vessel volume and/or generate a hypothetical PAV. In some embodiments, the system, at blocks 1425-1426, can be configured to normalize total plaque volume against LV mass. In some embodiments, the system, at block 1432-1433, can be configured to normalize plaque volume against LV mass subtended by the vessel in which the plaque appears.

In some embodiments, at block 1439, the system can be configured to generate a weighted measure of the plaque volume normalized against different measures. In particular, in some embodiments, the system can be configured to generate a weighted measure of plaque volume normalized against a hypothetical vessel volume or hypothetical PAV, plaque volume normalized against LV mass, and plaque volume normalized against LV mass subtended by a vessel in which the plaque appears. In some embodiments, the system can be configured weight plaque normalized by a particular method more heavily than others. In some embodiments, one or more plaque normalization methods can be weighted 0 and/or 1, although other weighting factors can be used as well.

In some embodiments, at block 1440, the system can be configured to analyze the weighted measure of normalized plaque volumes based on one or more reference values of weighted measures of normalized plaque volumes. For example, in some embodiments, the system can be configured to access a reference values database 1441 that includes one or more weighted measures of normalized plaque volumes. The weighted measures of normalized plaque volumes can be derived from other subjects with varying states or risks of cardiovascular disease, including for example normal values. In some embodiments, the one or more reference values can be obtained from one or more medical images using the same or similar imaging modalities as the medical image accessed at block 1413. In some embodiments, the one or more reference values can be obtained from analyzing one or more medical images to derive one or more weighted measures of normalized plaque volumes, for example using one or more processes described in relation to blocks 1413-1439. In some embodiments, the one or more reference weighted measures of normalized plaque volumes can be stored on a reference values database 1441, which can be locally accessible by the system and/or can be located remotely and accessible through a network connection.

In some embodiments, based on such analysis and/or comparison, the system, at block 1442, can be configured to generate a graphical representation of the analysis results. In some embodiments, the system can be configured to generate a graphical generation reporting the analysis results on a vessel-by-vessel basis and/or subject basis. For example, in some embodiments, the system can be configured to generate a graphical representation of one or more arteries or vessels, in which specific arteries and/or vessels can be color-coded or assigned some value or other indicator depending on the analysis results. As an illustrative example, in some embodiments, if the system determines that the weighted normalized plaque volume of a particular vessel is high, the system can be configured to color code that vessel red in the graphical representation.

In some embodiments, based on such analysis and/or comparison of weighted measures of normalized plaque volumes, the system, at block 1443, can be configured to determine a risk or state of cardiovascular disease or health of the subject. Further, in some embodiments, based on such analysis and/or comparison, the system, at block 1443, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1444, which can be locally accessible by the system and/or can be located remotely and accessible through a network connection. In some embodiments, the plaque risk/treatment database 1444 can include reference points or data that relate one or more treatment to cardiovascular disease risk or state determined based on one or more reference values of weighted measures of normalized plaque volumes.

In some embodiments, the system can be configured to repeat one or more processes described in relation to blocks 1413-1444, for example for one or more other vessels, segment, regions of plaque, different subjects, and/or for the same subject at a different time. As such, in some embodiments, the system can provide for longitudinal disease tracking and/or personalized treatment for a subject.

Computer System

Figure 14H:
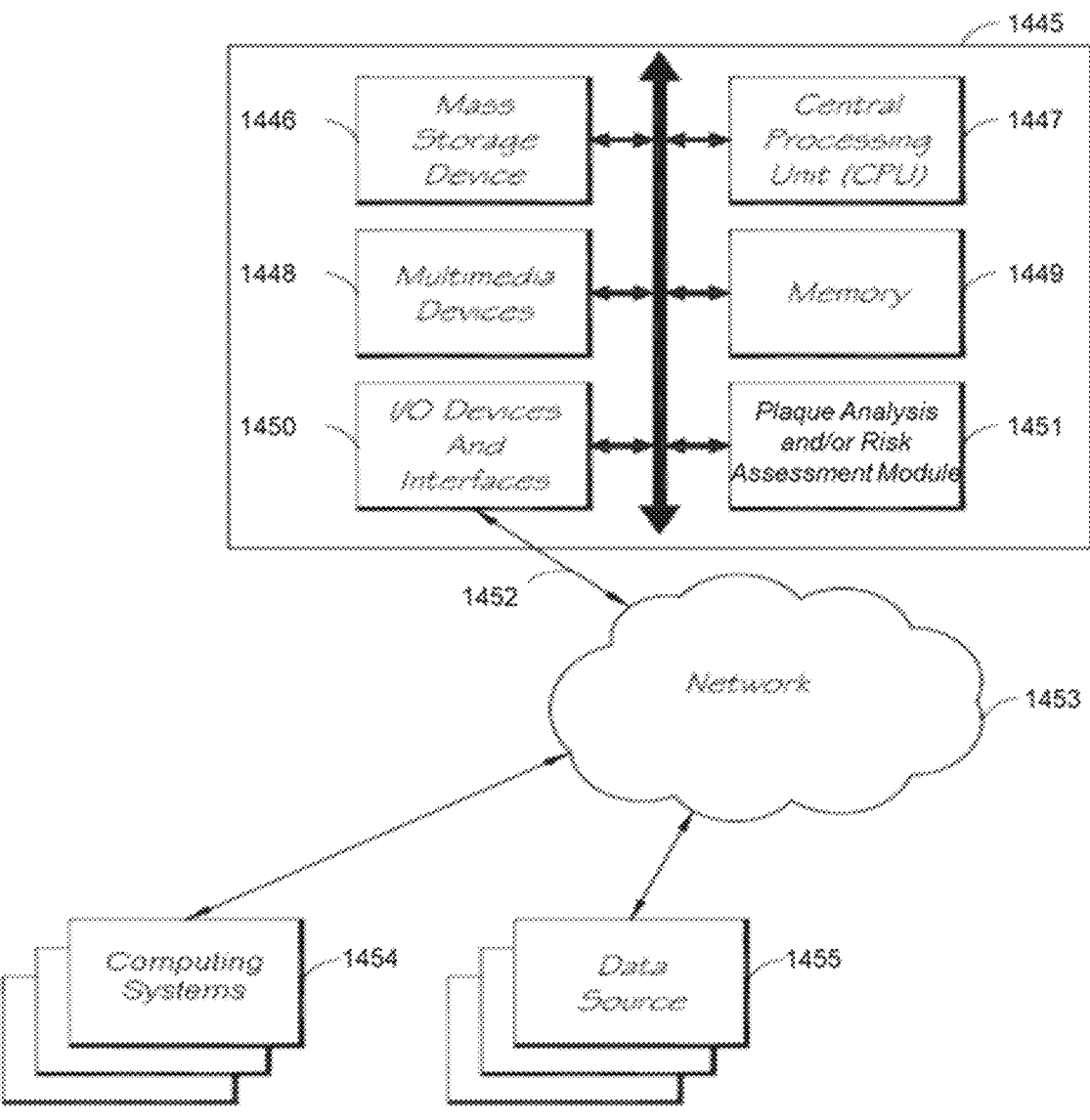
FIG. 14H is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 14H. The example computer system 1445 is in communication with one or more computing systems 1454 and/or one or more data sources 1455 via one or more networks 1453. While FIG. 14H illustrates an embodiment of a computing system 1445, it is recognized that the functionality provided for in the components and modules of computer system 1445 can be combined into fewer components and modules, or further separated into additional components and modules.

The computer system 1445 can comprise a Plaque Analysis and/or Risk Assessment Module 1451 that carries out the functions, methods, acts, and/or processes described herein. The Plaque Analysis and/or Risk Assessment Module 1451 executed on the computer system 1445 by a central processing unit 1447 discussed further below. Other features of the computer system 1445 can be similar to corresponding features of the computer system of FIG. 9G, described above.

Certain Examples of Embodiments of Normalized Plaque Parameters

The following are non-limiting examples of certain embodiments of systems and methods for normalized plaque parameters. Other embodiments may include one or more other features, or different features, that are discussed herein.

Embodiment 1: A computer-implemented method of assessing a state of cardiovascular disease of a subject based on one or more normalized plaque parameters derived from non-invasive medical image analysis, the method comprising: accessing, by a computer system, a medical image of a subject, wherein the medical image of the subject is obtained non-invasively; analyzing, by the computer system, the medical image of the subject to identify one or more arteries; determining, by the computer system, one or more vessel parameters associated with the identified one or more arteries, the one or more vessel parameters comprising vessel wall, volume, and curvature of the one or more identified arteries; analyzing, by the computer system, the medical image of the subject to identify one or more regions of plaque within the one or more arteries; determining, by the computer system, one or more plaque parameters associated with the identified one or more regions of plaque, the one or more plaque parameters comprising plaque volume, location, and geometry of the one or more identified regions of plaque; determining, by the computer system, a hypothetical vessel volume of the one or more identified arteries without the one or more regions of plaque, wherein the hypothetical vessel volume is determined by: identifying a posterior boundary and an anterior boundary of the one or more regions of plaque along the vessel wall of the one or more arteries based at least in part on the location and geometry of the one or more regions of plaque; graphically removing the one or more regions of plaque from the one or more arteries; interpolating a hypothetical curvature of the one or more arteries without the one or more regions of plaque based at least in part on the curvature of the one or more identified arteries and the identified posterior boundary and the anterior boundary of the one or more regions of plaque along the vessel wall of the one or more arteries after graphically removing the one or more regions of plaque; and determining the hypothetical vessel volume based at least in part on the volume of the one or more identified arteries and the interpolated hypothetical curvature of the one or more arteries without the one or more regions of plaque; normalizing, by the computer system, percent atheroma volume (PAV) by generating a hypothetical PAV value based at least in part on the volume of the one or more regions of plaque and the hypothetical vessel volume; analyzing, by the computer system, the hypothetical PAV value by comparison to a dataset of reference hypothetical PAV values derived from a plurality of medical images of a population with varying states of cardiovascular disease; and determining, by the computer system, an assessment of a state of cardiovascular disease of the subject based at least in part on analysis of the hypothetical PAV value, wherein the computer system comprises a computer processor and an electronic storage medium.

Embodiment 2: The computer-implemented method of Embodiment 1, wherein the hypothetical PAV value is determined on a vessel-by-vessel basis.

Embodiment 3: The computer-implemented method of Embodiment 2, further comprising: determining, by the computer system, hypothetical PAV values for a plurality of vessels; analyzing, by the computer system, the hypothetical PAV value for each of the plurality of vessels by comparison to the dataset of reference hypothetical PAV values; and determining, by the computer system, the assessment of the state of cardiovascular disease of the subject based at least in part on analysis of the hypothetical PAV value for each of the plurality of vessels.

Embodiment 4: The computer-implemented method of Embodiment 2, further comprising: determining, by the computer system, hypothetical PAV values for a plurality of vessels; generating, by the computer system, a weighted measure of the hypothetical PAV values for the plurality of vessels; and determining, by the computer system, the assessment of the state of cardiovascular disease of the subject based at least in part on the weighted measure of the hypothetical PAV values for the plurality of vessels.

Embodiment 5: The computer-implemented method of Embodiment 1, further comprising generating, by the computer system, a treatment for cardiovascular disease for the subject based at least in part on the determined assessment of the state of cardiovascular disease.

Embodiment 6: The computer-implemented method of Embodiment 5, wherein the treatment for cardiovascular disease comprises medical intervention, medical treatment, or lifestyle change.

Embodiment 7: The computer-implemented method of Embodiment 5, further comprising tracking, by the computer system, efficacy of the treatment by determining assessment of the state of cardiovascular disease of the subject at a later point in time after treatment.

Embodiment 8: The computer-implemented method of Embodiment 1, wherein the hypothetical PAV value is generated based at least in part on a total volume of the one or more regions of plaque and the hypothetical vessel volume.

Embodiment 9: The computer-implemented method of Embodiment 1, wherein the hypothetical PAV value is generated based at least in part on volume of non-calcified plaque of the one or more regions of plaque and the hypothetical vessel volume.

Embodiment 10: The computer-implemented method of Embodiment 1, wherein the hypothetical PAV value is generated based at least in part on volume of low density, non-calcified plaque of the one or more regions of plaque and the hypothetical vessel volume.

Embodiment 11: The computer-implemented method of Embodiment 1, wherein the medical image is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS).

Embodiment 12: A computer-implemented method of assessing a state of cardiovascular disease of a subject based on one or more normalized plaque parameters derived from non-invasive medical image analysis, the method comprising: accessing, by a computer system, a medical image of a subject, wherein the medical image of the subject is obtained non-invasively; analyzing, by the computer system, the medical image of the subject to identify one or more arteries; analyzing, by the computer system, the medical image of the subject to identify one or more regions of plaque within the one or more arteries; determining, by the computer system, one or more plaque parameters associated with the identified one or more regions of plaque, the one or more plaque parameters comprising plaque volume of the one or more identified regions of plaque; determining, by the computer system, left ventricular mass of the subject; normalizing, by the computer system, the plaque volume by dividing the plaque volume of the one or more regions of plaque by the determined left ventricular mass of the subject; analyzing, by the computer system, the normalized plaque volume by comparison to a dataset of reference normalized plaque volumes, the reference normalized plaque volumes generated by: accessing a database of a plurality of medical images obtained from a population with varying states of cardiovascular disease; determining, for each of the plurality of medical images, plaque volume and left ventricular mass; normalizing, for each of the plurality of medical images, plaque volume by dividing the plaque volume by the left ventricular mass; and generating the database of reference normalized plaque volumes by aggregating the normalized plaque volume derived from each of the plurality of medical images; and determining, by the computer system, an assessment of a state of cardiovascular disease of the subject based at least in part on analysis of the normalized plaque volume, wherein the computer system comprises a computer processor and an electronic storage medium.

Embodiment 13: The computer-implemented method of Embodiment 12, wherein the left ventricular mass of the subject is determined based at least in part on the medical image of the subject.

Embodiment 14: The computer-implemented method of Embodiment 12, wherein the plaque volume is determined on a vessel-by-vessel basis.

Embodiment 15: The computer-implemented method of Embodiment 14, further comprising: determining, by the computer system, the plaque volume for a plurality of vessels; normalizing, by the computer system, the plaque volume for each of the plurality of vessels by dividing the plaque volume for each of the plurality of vessels by the determined left ventricular mass of the subject; and determining, by the computer system, the assessment of the state of cardiovascular disease of the subject based at least in part on analysis of the normalized plaque volume for each of the plurality of vessels.

Embodiment 16: The computer-implemented method of Embodiment 12, further comprising: determining, by the computer system, the plaque volume for a plurality of vessels; generating, by the computer system, a weighted measure of the plaque volume for the plurality of vessels; and determining, by the computer system, the assessment of the state of cardiovascular disease of the subject based at least in part on the weighted measure of the plaque volume for the plurality of vessels.

Embodiment 17: The computer-implemented method of Embodiment 12, further comprising generating, by the computer system, a treatment for cardiovascular disease for the subject based at least in part on the determined assessment of the state of cardiovascular disease.

Embodiment 18: The computer-implemented method of Embodiment 17, wherein the treatment for cardiovascular disease comprises medical intervention, medical treatment, or lifestyle change.

Embodiment 19: The computer-implemented method of Embodiment 17, further comprising tracking, by the computer system, efficacy of the treatment by determining assessment of the state of cardiovascular disease of the subject at a later point in time after treatment.

Embodiment 20: The computer-implemented method of Embodiment 12, wherein the plaque volume comprises total plaque volume of the one or more regions of plaque.

Embodiment 21: The computer-implemented method of Embodiment 12, wherein the plaque volume comprises volume of non-calcified plaque of the one or more regions of plaque.

Embodiment 22: The computer-implemented method of Embodiment 12, wherein the plaque volume comprises volume of low density, non-calcified plaque of the one or more regions of plaque.

Embodiment 23: The computer-implemented method of Embodiment 12, wherein the medical image is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS).

Embodiment 24: A computer-implemented method of assessing a state of cardiovascular disease of a subject based on one or more normalized plaque parameters derived from non-invasive medical image analysis, the method comprising: accessing, by a computer system, a medical image of a subject, wherein the medical image of the subject is obtained non-invasively; analyzing, by the computer system, the medical image of the subject to identify one or more arteries; analyzing, by the computer system, the medical image of the subject to identify one or more regions of plaque within the one or more arteries; determining, by the computer system, one or more plaque parameters associated with the identified one or more regions of plaque, the one or more plaque parameters comprising plaque volume of the one or more identified regions of plaque; determining, by the computer system, left ventricular mass of the subject subtended by the one or more arteries; normalizing, by the computer system, the plaque volume by dividing the plaque volume of the one or more regions of plaque by the determined left ventricular mass of the subject subtended by the one or more arteries; analyzing, by the computer system, the normalized plaque volume by comparison to a dataset of reference normalized plaque volumes, the reference normalized plaque volumes generated by: accessing a database of a plurality of medical images obtained from a population with varying states of cardiovascular disease; determining, for each of the plurality of medical images, plaque volume in one or more arteries and left ventricular mass subtended by the one or more arteries; normalizing, for each of the plurality of medical images, plaque volume in the one or more arteries by dividing the plaque volume in the one or more arteries by the left ventricular mass subtended by the one or more arteries; and generating the database of reference normalized plaque volumes by aggregating the normalized plaque volume in the one or more arteries derived from each of the plurality of medical images; and determining, by the computer system, an assessment of a state of cardiovascular disease of the subject based at least in part on analysis of the normalized plaque volume, wherein the computer system comprises a computer processor and an electronic storage medium.

Embodiment 25: The computer-implemented method of Embodiment 24, wherein the left ventricular mass of the subject subtended by the one or more arteries is determined based at least in part on the medical image of the subject.

Embodiment 26: The computer-implemented method of Embodiment 24, wherein the plaque volume is determined on a vessel-by-vessel basis.

Embodiment 27: The computer-implemented method of Embodiment 26, further comprising: determining, by the computer system, the plaque volume for a plurality of vessels; determining, by the computer system, left ventricular mass of the subject subtended by each of the plurality of vessels; normalizing, by the computer system, the plaque volume for each of the plurality of vessels by dividing the plaque volume for each of the plurality of vessels by the determined left ventricular mass of the subject subtended by each of the plurality of vessels; and determining, by the computer system, the assessment of the state of cardiovascular disease of the subject based at least in part on analysis of the normalized plaque volume for each of the plurality of vessels.

Embodiment 28: The computer-implemented method of Embodiment 24, further comprising: determining, by the computer system, the plaque volume for a plurality of vessels; determining, by the computer system, left ventricular mass of the subject subtended by each of the plurality of vessels; normalizing, by the computer system, the plaque volume for each of the plurality of vessels by dividing the plaque volume for each of the plurality of vessels by the determined left ventricular mass of the subject subtended by each of the plurality of vessels; generating, by the computer system, a weighted measure of the normalized plaque volume for each of the plurality of vessels; and determining, by the computer system, the assessment of the state of cardiovascular disease of the subject based at least in part on the weighted measure of the normalized plaque volume for each of the plurality of vessels.

Embodiment 29: The computer-implemented method of Embodiment 24, further comprising generating, by the computer system, a treatment for cardiovascular disease for the subject based at least in part on the determined assessment of the state of cardiovascular disease.

Embodiment 30: The computer-implemented method of Embodiment 29, wherein the treatment for cardiovascular disease comprises medical intervention, medical treatment, or lifestyle change.

Embodiment 31: The computer-implemented method of Embodiment 29, further comprising tracking, by the computer system, efficacy of the treatment by determining assessment of the state of cardiovascular disease of the subject at a later point in time after treatment.

Embodiment 32: The computer-implemented method of Embodiment 24, wherein the plaque volume comprises total plaque volume of the one or more regions of plaque.

Embodiment 33: The computer-implemented method of Embodiment 24, wherein the plaque volume comprises volume of non-calcified plaque of the one or more regions of plaque.

Embodiment 34: The computer-implemented method of Embodiment 24, wherein the plaque volume comprises volume of low density, non-calcified plaque of the one or more regions of plaque.

Embodiment 35: The computer-implemented method of Embodiment 24, wherein the medical image is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS).

Embodiment 36: A computer-implemented method of assessing a state of cardiovascular disease of a subject based on one or more normalized plaque parameters derived from non-invasive medical image analysis, the method comprising: accessing, by a computer system, a medical image of a subject, wherein the medical image of the subject is obtained non-invasively; analyzing, by the computer system, the medical image of the subject to identify one or more arteries; analyzing, by the computer system, the medical image of the subject to identify one or more regions of plaque within the one or more arteries; determining, by the computer system, one or more plaque parameters associated with the identified one or more regions of plaque, the one or more plaque parameters comprising plaque volume of each of the one or more identified regions of plaque and total plaque volume of the one or more identified regions of plaque; determining, by the computer system, a hypothetical vessel volume of one of the one or more identified arteries without the one or more regions of plaque; normalizing, by the computer system, percent atheroma volume (PAV) of one of the one or more identified arteries by generating a hypothetical PAV value based at least in part on the plaque volume of one or more regions of plaque in the one of the one or more identified arteries and the hypothetical vessel volume of the one of the one or more identified arteries without the one or more regions of plaque; determining, by the computer system, left ventricular mass of the subject subtended by the one of the one or more arteries; normalizing, by the computer system, the plaque volume of the one or more regions of plaque in the one of the one or more identified arteries by dividing the plaque volume of the one or more regions of plaque in the one of the one or more identified arteries by the determined left ventricular mass of the subject subtended by the one of the one or more arteries; determining, by the computer system, total left ventricular mass of the subject; normalizing, by the computer system, total plaque volume of the one or more regions of plaque by dividing the total plaque volume of the one or more regions of plaque by the determined total left ventricular mass of the subject; generating, by the computer system, a weighted measure of the normalized PAV of the one of the one or more identified arteries, the normalized plaque volume of the one or more regions of plaque in the one of the one or more identified arteries, and the normalized total plaque volume of the one or more regions of plaque; analyzing, by the computer system, the weighted measure by comparison to a dataset of reference weighted measure values of normalized PAV, normalized individual plaque volumes, and normalized total plaque volumes derived from a plurality of medical images of a population with varying states of cardiovascular disease; and determining, by the computer system, an assessment of a state of cardiovascular disease of the subject based at least in part on analysis of the weighted measure, wherein the computer system comprises a computer processor and an electronic storage medium.

Embodiment 37: The computer-implemented method of Embodiment 36, further comprising generating, by the computer system, a treatment for cardiovascular disease for the subject based at least in part on the determined assessment of the state of cardiovascular disease.

Embodiment 38: The computer-implemented method of Embodiment 37, wherein the treatment for cardiovascular disease comprises medical intervention, medical treatment, or lifestyle change.

Embodiment 39: The computer-implemented method of Embodiment 38, further comprising tracking, by the computer system, efficacy of the treatment by determining assessment of the state of cardiovascular disease of the subject at a later point in time after treatment.

Embodiment 40: The computer-implemented method of Embodiment 37, wherein the medical image is obtained using an imaging technique comprising one or more of computed tomography (CT), x-ray, ultrasound, echocardiography, intravascular ultrasound (IVUS), magnetic resonance (MR) imaging, optical coherence tomography (OCT), nuclear medicine imaging, positron-emission tomography (PET), single photon emission computed tomography (SPECT), or near-field infrared spectroscopy (NIRS).

Non-Invasive FFR

Disclosed herein are systems, devices, and methods for non-invasive image-based determination of fractional flow reserve (FFR) and/or ischemia. In some embodiments, the systems, devices, and methods are related to FFR and/or ischemia analysis of arteries, such as coronary, aortic, and/or carotid arteries using one or more image analysis techniques. For example, in some embodiments, the systems, methods, and devices can be configured to derive one or more stenosis and/or normal measurements from a medical image, which can be obtained non-invasively, and use the same to derive an assessment of FFR and/or ischemia. In some embodiments, the systems, methods, and devices can be configured to apply one or more allometric scaling laws to one or more stenosis and/or normal measurements to derive and/or generate an assessment of FFR and/or ischemia.

Various systems, methods, and devices disclosed herein are directed to embodiments for addressing the foregoing issues. In particular, various embodiments described herein relate to systems, devices, and methods for non-invasive image-based determination of fractional flow reserve (FFR) and/or ischemia. In particular, in some embodiments, the systems, devices, and methods are related to FFR and/or ischemia analysis of coronary arteries using one or more image analysis techniques. For example, in some embodiments, the systems, methods, and devices can be configured to derive one or more stenosis and/or normal measurements from a medical image, which can be obtained non-invasively, and use the same to derive an assessment of FFR and/or ischemia. In some embodiments, the systems, methods, and devices can be configured to apply one or more allometric scaling laws to one or more stenosis and/or normal measurements to derive and/or generate an assessment of FFR and/or ischemia.

In some embodiments, the systems, devices, and methods described herein related to FFR and/or ischemia analysis are configured to utilize non-invasive medical imaging technologies, such as a CT image or CCTA for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

As will be discussed in further detail, the systems, devices, and methods described herein allow for automatic and/or dynamic quantified analysis of various parameters relating to plaque, cardiovascular arteries, and/or other structures. More specifically, in some embodiments described herein, a medical image of a patient, such as a coronary CT image or CCTA, can be taken at a medical facility. Rather than having a physician eyeball or make a general assessment of the patient, the medical image is transmitted to a backend main server in some embodiments that is configured to conduct one or more analyses thereof in a reproducible manner. As such, in some embodiments, the systems, methods, and devices described herein can provide a quantified measurement of one or more features of a coronary CT image using automated and/or dynamic processes. For example, in some embodiments, the main server system can be configured to identify one or more vessels, plaque, fat, and/or one or more measurements thereof from a medical image. Based on the identified features, in some embodiments, the system can be configured to generate one or more quantified measurements from a raw medical image, such as for example radiodensity of one or more regions of plaque, identification of stable plaque and/or unstable plaque, volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like. Based on the identified features and/or quantified measurements, in some embodiments, the system can be configured to generate a risk and/or disease state assessment and/or track the progression of a plaque-based disease or condition, such as for example atherosclerosis, stenosis, and/or ischemia, using raw medical images. Further, in some embodiments, the system can be configured to generate a visualization of a GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures.

As discussed herein, disclosed herein are systems, devices, and methods for non-invasive image-based determination of fractional flow reserve (FFR) and/or ischemia. In particular, in some embodiments, the systems, devices, and methods are related to FFR and/or ischemia analysis of arteries, such as coronary, aortic, and/or carotid arteries using one or more image analysis techniques. For example, in some embodiments, the systems, methods, and devices can be configured to derive one or more stenosis and/or normal measurements from a medical image, which can be obtained non-invasively, and use the same to derive an assessment of FFR and/or ischemia. In some embodiments, the systems, methods, and devices can be configured to apply one or more allometric scaling laws to one or more stenosis and/or normal measurements to derive and/or generate an assessment of FFR and/or ischemia.

In particular, in some embodiments, the systems, devices, and methods described herein can be configured to analyze one or more non-invasively obtained medical images of a subject, such as a CT image or CCTA, to non-invasively determine FFR and/or ischemia. Generally speaking, invasive fractional flow reserve or invasive FFR is widely used to assess for hemodynamically significant coronary artery stenosis. However, such techniques require patients to undergo costly and invasive coronary catheterization to measure invasive FFR and is therefore less than ideal. In some embodiments, computational fluid dynamics and coronary CT angiography (CCTA) can be used as an alternative to invasive measures to determine the hemodynamic significance of stenoses, for example via $FFR_{CT}$. However, $FFR_{CT}$ comes with many disadvantages. For example, $FFR_{CT}$ can typically require large computational time, such as several hours, as well as large computational power and resources to complete. $FFR_{CT}$ for physiologic assessment of CAD can typically require off-site processing that can take several hours to complete. Further, FFR$_{CT}$ can typically require high-quality images to be able to generate a reliable outcome. As such, FFR$_{CT}$ has many technical shortcomings that hinder its widespread use and adoption. The systems, methods, and devices described herein address such technical shortcomings of existing technologies.

In particular, in some embodiments, the systems, methods, and devices described herein are configured to utilize one or more stenosis and/or normal measurements derived from a medical image, such as a CT or CCTA image, to non-invasively determine FFR and/or ischemia. In some embodiments, the systems, methods, and devices herein can analyze a medical image and generate FFR and/or ischemia prediction and/or measurements within a much shorter period of time, such as for example in a matter of minutes, and/or require much less computational time and/or resources compared to FFR$_{CT}$. Further, in some embodiments, the systems, methods, and devices described herein can be configured to utilize less than ideal quality images while still producing reliable prediction and/or assessment of FFR and/or ischemia in cases where FFR$_{CT}$ would not be a viable option due to the image quality.

More specifically, in some embodiments, the systems, methods, and devices described herein can be configured to derive one or more stenosis and/or normal measurements from a medical image, such as for example the mass and/or volume of a subtended myocardium at-risk distal to a stenosis. In some embodiments, subtended myocardium at-risk distal to a stenosis can provide reliable value in predicting hemodynamically significant stenosis. In some embodiments, the mass and/or volume of subtended myocardium at-risk can be measured via CCTA. Further, in some embodiments, the mass and/or volume of subtended myocardium distal to a stenosis can be related to coronary flow and/or FFR by utilizing one or more allometric scaling principles.

As such, some of the systems, methods, and devices described herein related to non-invasive determination of FFR and/or ischemia based on one or more measurements derived from a non-invasive medical image can provide for drastically improved treatment of coronary artery disease (CAD) by stratifying patients based on the physiologic significance of CAD, while avoiding the added cost and invasive nature of traditional FFR as well as the large computational time and processing power required of FFR$_{CT}$.

More specifically, in some embodiments, the non-invasive FFR techniques described herein can allow for the physiologic assessment of a CAD lesion non-invasively, for example via CCTA. In addition, in some embodiments, the non-invasive FFR techniques described herein can provide a simplified and/or intuitive model for relating CCTA to invasive FFR. Further, in some embodiments, the non-invasive FFR techniques described herein can effectively calculate the equivalent of invasive FFR in seconds or minutes, as opposed to FFR$_{CT}$ which can require hours of processing time. For example, in some embodiments, the systems, methods, and devices described herein can generate the equivalent of invasive FFR within about 1 second, about 2 seconds, about 3 seconds, about 4 seconds, about 5 second, about 10 seconds, about 15 seconds, about 20 seconds, about 25 seconds, about 30 seconds, about 1 minute, about 2 minutes, about 3 minutes, about 4 minutes, about 5 minutes, about 10 minutes, about 20 minutes, about 30 minutes, and/or within a time period defined by two of the aforementioned values. Moreover, in some embodiments, the noninvasive FFR techniques described herein can provide a more robust yet simplified solution and thus can be less prone to image artifacts and/or noise as compared to FFR$_{CT}$.

As described herein, in some embodiments, the systems, methods, and devices can be configured to use allometric scaling laws to relate morphological measurements of coronary arteries to physiological measurements, such as coronary flow and/or the equivalent to invasive FFR, for example via a power scaling relationship. In some embodiments, morphological measurements can include, for example, coronary lumen area, mass or volume of myocardium subtended by a coronary stenosis, coronary lumen volume subtended by a coronary stenosis, coronary vessel length, and/or the like. In some embodiments, one or more or all morphological measurements can be obtained from analyzing a CT image and/or CCTA. In some embodiments, the systems, methods, and devices described herein can be configured to utilize a mathematical relationship between coronary lumen area, subtended myocardial mass, and/or invasive FFR, non-invasive, FFR, or equivalent thereof. In some embodiments, the systems, methods, and devices described herein can be configured to utilize one or more other morphological measurements, such as for example coronary lumen volume, coronary vessel length, and/or the like, as well as a mathematical relationship between the same and/or invasive FFR, non-invasive FFR, or equivalent thereof.

Relating Lumen Area and Myocardial Mass to FFR

Figure 15A:
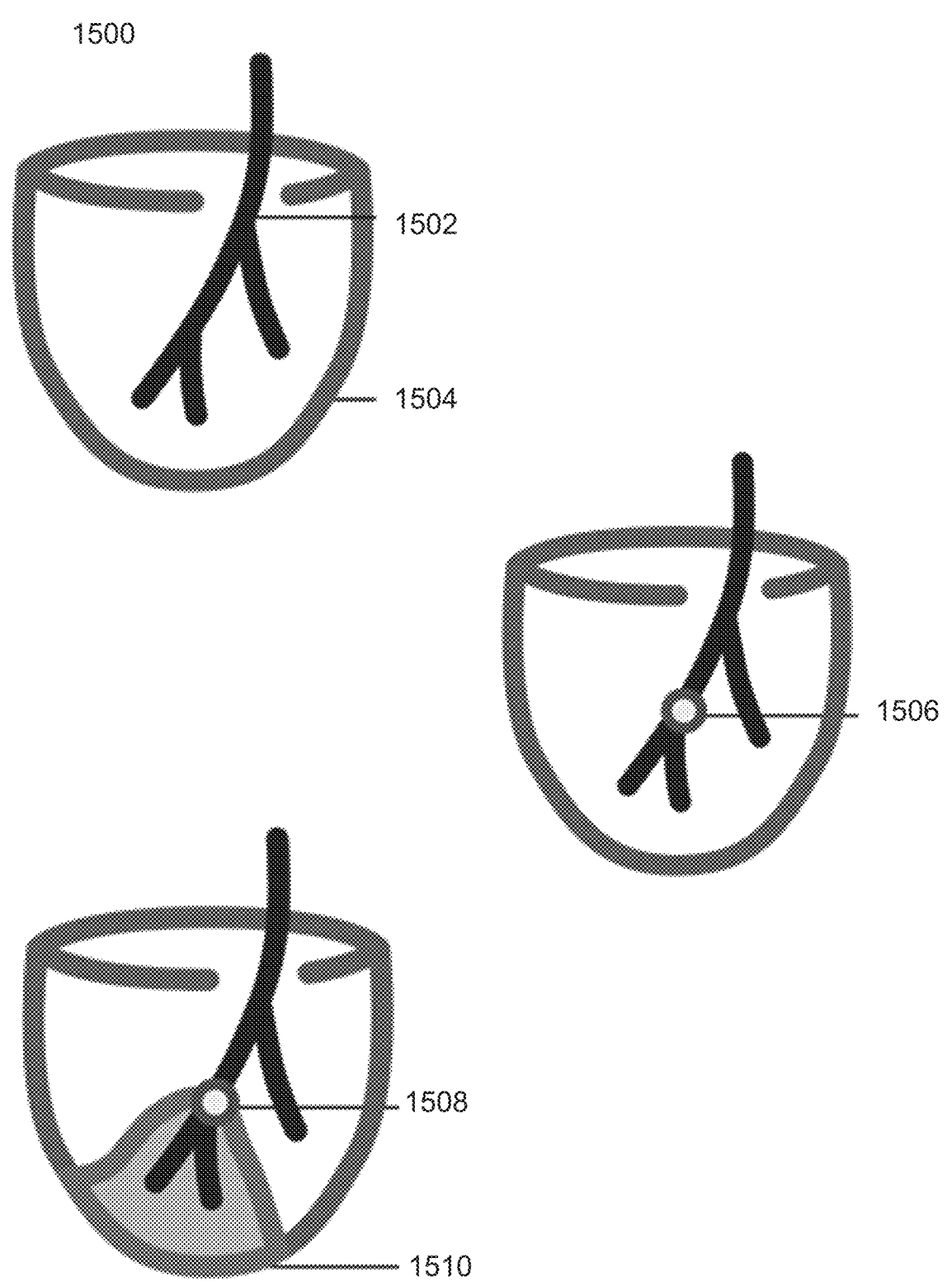
FIG. 15A is a schematic illustrating an example embodiment(s) of systems, devices, and methods for non-invasive image-based determination of fractional flow reserve (FFR) and/or ischemia.

For illustrative purposes, FIG. 15A provides a schematic illustrating an example embodiment(s) of systems, devices, and methods for non-invasive image-based determination of fractional flow reserve (FFR) and/or ischemia. As illustrated in FIG. 15A, in some embodiments, the systems, methods, and devices described herein can be configured to relate lumen area and myocardial mass to FFR and utilize the same for determining FFR and/or ischemia from analyzing a non-invasively obtained medical image. FIG. 15A depicts a left ventricle 1500 including a coronary artery center line 1502 and a left ventricle myocardium 1504. The left ventricle 1500 may, in some instances, include a lesion 1506 on the coronary artery centerline 1502. The lesion 1506 may affect a lumen with a lumen area 1508 that is useful in determining FFR. The left ventricle myocardium 1504 can, in some instances, become myocardial mass 1510 that is subtended by the lumen area 1508 at the lesion 1506. In some embodiments, measurements of the left ventricle 1500 can be used to predict FFR.

In particular, as illustrated in FIG. 15A, in some embodiments, allometric scaling laws can be used to relate coronary lumen area (A) and the myocardial mass 1510 subtended by a coronary lesion 1506(M) to predict FFR or invasive FFR by generating a non-invasive FFR, allometric FFR, or myocardium FFR. In some embodiments, based on allometric scaling laws, FFR or invasive FFR can be approximated by generating a non-invasive FFR, allometric FFR, or myocardium FFR via the Equation 1 below:

$$FFR_{non-invasive} = Y_0 * \frac{A^b A}{M^b M}$$

<div align="right">Equation 1</div>

In some embodiments, the exponential coefficients ($b_A$ and $b_M$) and/or the constant ($Y_0$) can be derived from the power relationship between lumen area, myocardial mass, and coronary flow. For example, in some embodiments, the system can be configured to derive the exponential coefficients ($b_A$ and $b_M$) and/or the constant ($Y_0$) from existing data comprising coronary lumen area (A), myocardial mass subtended by a coronary lesion (M), and invasive FFR. In some embodiments, using the determined exponential coefficients ($b_A$ and $b_M$) and/or the constant ($Y_0$), the system can be configured to apply the equation above to coronary lumen area (A) and myocardial mass subtended by a coronary lesion (M) derived from a prospective image to determine or estimate FFR non-invasively without using FFRCT. Further, in some embodiments, $Y_0$, $b_A$, and $b_M$ are derived from analysis of retrospective medical images and invasive FFR measurements ($FFR_{invasive}$).

Determining Coefficients to Relate Coronary Lumen Area and Myocardial Mass to FFR More specifically, in some embodiments, the system can be configured to determine exponential coefficients ($b_A$ and $b_M$) and/or the constant ($Y_0$) by utilizing the relationship between invasive FFR, lumen area, and myocardial mass. In particular, in some embodiments, the exponential coefficients ($b_A$ and $b_M$) and/or the constant ($Y_0$) can be calculated via multiple linear regression, following application of a logarithmic transformation. The derivation of a linear equation relating invasive FFR with lumen area and myocardial mass in some embodiments is provided below.

In some embodiments, in terms of coronary blood flow, invasive FFR ($FFR_{invasive}$) can be defined as the ratio of blood flow across a stenosis ($Q_{Stenosis}$) to the blood flow across the same coronary region in the absence of stenosis ($Q_{Normal}$) as set forth below in Equation 2.

$$FFR_{invasive} = \frac{Q_{Stenosis}}{Q_{Normal}} \qquad \text{Equation 2}$$

In some embodiments, blood across a stenosis ($Q_{Stenosis}$) can be related to the lumen area (A) at the point of the stenosis via allometric scaling using a power law as set forth below in Equation 3.

$$Q_{stenosis} = Y_A * A^{b_A} \qquad \text{Equation 3}$$

In some embodiments, blood flow in the absence of a stenosis (QNormal) can be related to the myocardial mass subtended by the stenosis (M) via allometric scaling using a power law as set forth below in Equation 4.

$$Q_{Normal} = Y_M * M^{b_M} \qquad \text{Equation 4}$$

In some embodiments, by substituting Equation 3 and 4 into Equation 1, lumen area (A) and subtended myocardial mass (M) can be related to invasive FFR as set forth below in Equation 5.

$$FFR_{invasive} = \frac{Y_A * A^{b_A}}{Y_M * M^{b_M}} \qquad \text{Equation 5}$$

In some embodiments, the power law constant for lumen area (YA) and subtended myocardial mass (YM) can be combined into a single constant (Y0) as set forth below in Equation 6.

$$FFR_{invasive} = Y_0 \frac{A^{b_A}}{M^{b_M}} \qquad \text{Equation 6}$$

In some embodiments, a log transform can be applied to Equation 6 as set forth below in Equation 7.

$$\log(FFR) = \log\left(Y_0 \frac{A^{b_A}}{M^{b_M}}\right) \qquad \text{Equation 7}$$

In some embodiments, following the log transform, Equation 7 can be expanded, providing a linear equation relating lumen area (A) and subtended myocardial mass (M) to invasive FFR as set forth below in Equation 8.

$$\log(FFR) = b_A * \log(A) - b_M * \log(M) + \log(Y_0) \qquad \text{Equation 8}$$

In some embodiments, utilizing one or more of Equations 2-8, the system can be configured to determine exponential coefficients ($b_A$ and $b_M$) and/or the constant ($Y_0$), for example by applying data sets with known invasive FFR, lumen area, and/or myocardial mass.

Validation

Figure 15B:
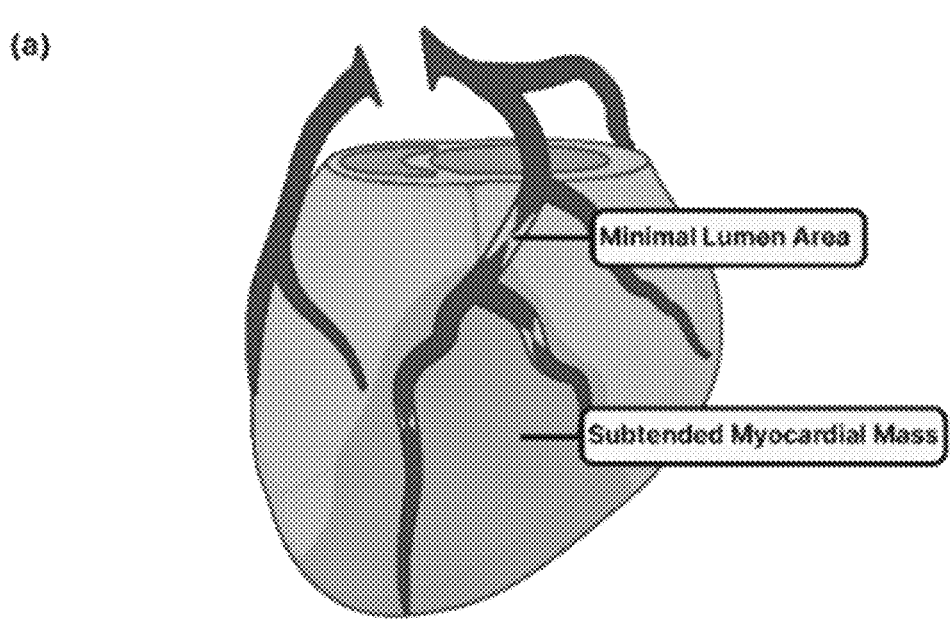
FIGS. 15B-15C are schematics illustrating results of a study utilizing an example embodiment(s) of systems, devices, and methods for non-invasive image-based determination of fractional flow reserve (FFR) and/or ischemia.
Figure 15C:
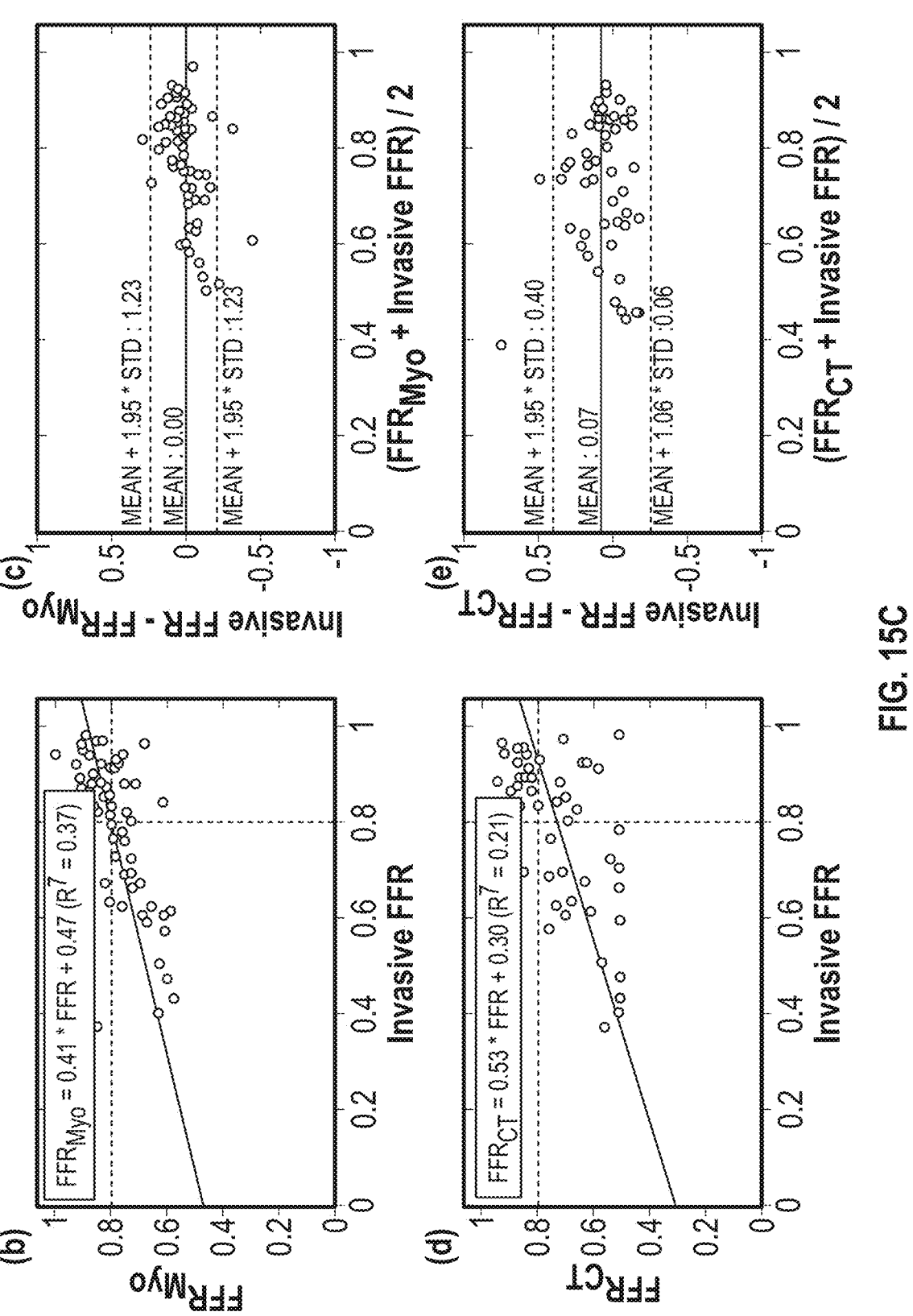
Figure 15C:
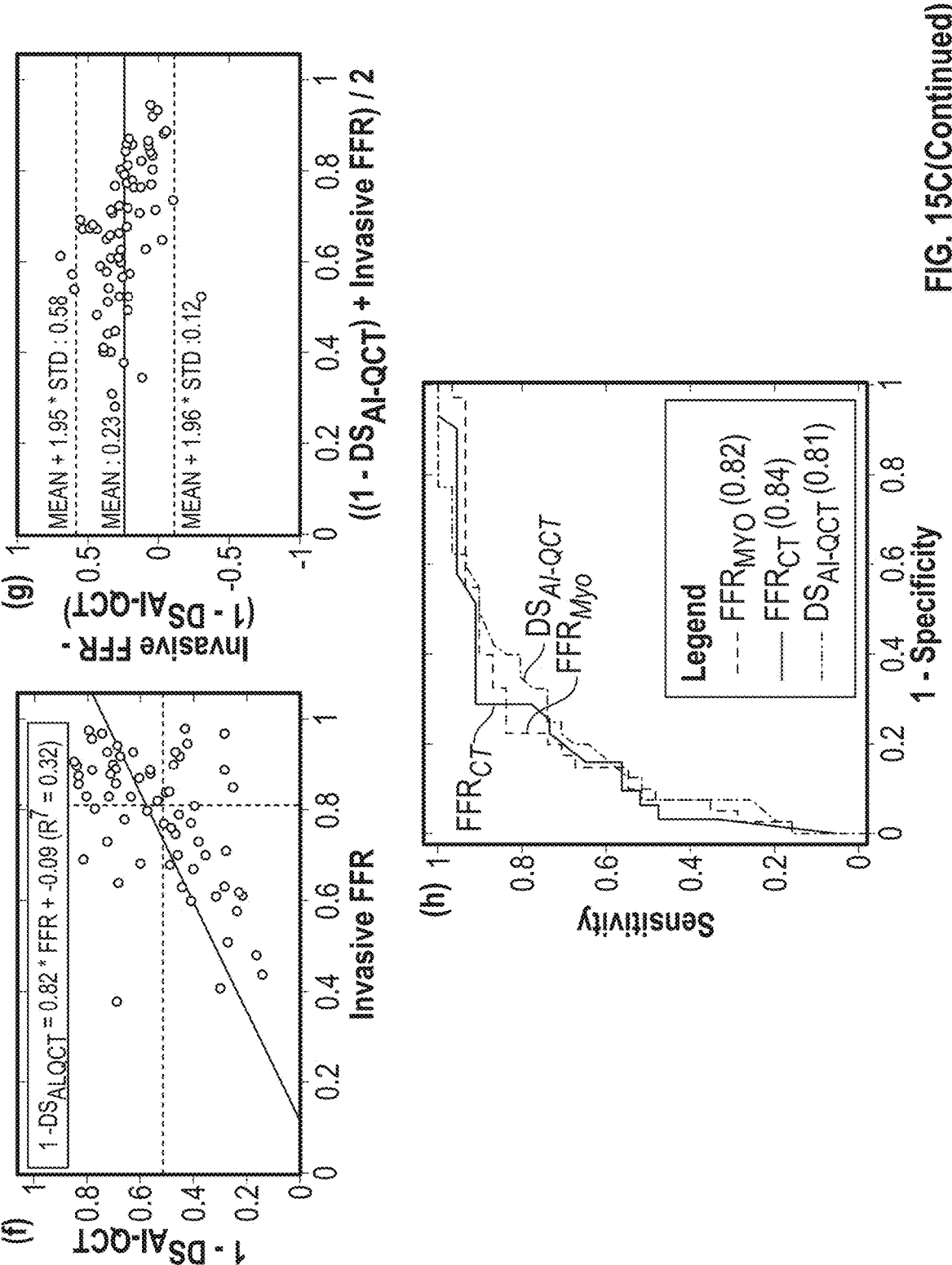

A non-limiting, illustrative study was performed to validate non-invasive FFR, allometric FFR, or myocardium FFR as described herein. In particular, as described herein, some embodiments of the systems, methods, and devices are configured to determine the equivalent to an "invasive" FFR using lumen area and subtended myocardial mass from CCTA. More specifically, in some embodiments, the systems, methods, and devices are configured to calculate an "invasive" FFR equivalent from CCTA using only subtended myocardial mass and minimal lumen area. FIGS. 15B-15C are schematics illustrating results of the study utilizing an example embodiment(s) of systems, devices, and methods for non-invasive image-based determination of fractional flow reserve (FFR) and/or ischemia.

In the study, a subset of 169 patients from a multicenter international study were selected for post-hoc analysis. In the study, all patients underwent CCTA and invasive coronary angiography with invasive FFR. In the study, 234 coronary territories were assessed with invasive FFR. Quantitative CT was performed by a validated software as a service.

In the study, territories were split into a training and testing cohort of 163 territories and 71 territories respectively. Invasive FFR was empirically related to the Lumen Area (b_Lumen) divided by Subtended Myocardial Mass (b_Myo). The training cohort was used to derive exponential coefficients b_Lumen and b_Myo using multiple linear regression, for example utilizing one or more of Equations 2-8 herein. The performance of the resulting non-invasive FFR, allometric FFR, or myocardial FFR based on the determined exponential coefficients and/or constant was assessed by prospectively applying b_Lumen and b_Myo to the testing cohort. The performance of the resulting non-invasive FFR, allometric FFR, or myocardial FFR to predict ischemia was directly compared with $FFR_{CT}$ and an AI-enabled CCTA diameter stenosis ($DS_{AI-QCT}$) measurement.

In the study, for all patients, the mean subtended myocardial mass distal from the minimal lumen area lesion for ischemic and non-ischemic territories was 35.85±20.85 g and 27.51±18.96 g (p-value <0.05). The minimal lumen area for ischemic and non-ischemic territories was 1.15±0.88 g and 2.52±1.51 g (p-value <0.05).

In the study, $FFR_{CT}$ failed in 17 test cohort cases due to inadequate image quality. The 17 territories wherein $FFR_{CT}$ failed were still included for evaluation of non-invasive FFR, allometric FFR, or myocardial FFR and $DS_{AI-QCT}$ b_Lumen and b_Myo were 0.11 (p-value <0.05) and 0.08 (p-value <0.05) respectively, with a constant Y of 0.96. In the study, using only the testing cohort non-invasive FFR, allometric FFR, or myocardial FFR ($FFR_{non-invasive}$) was related to invasive FFR by $FFR_{non-invasive}=0.41*FFR_{invasive}+0.47(R^2=0.37,$ RMSE=0.12). In the study, $FFR_{CT}$ was related to invasive FFR by $FFR_{CT}=0.53*FFR+0.30(R^2=0.23,$ RMSE=0.18). Further, in the study, $DS_{AI\text{-}QCT}$ was related to invasive FFR by $1-DS_{AI\_QCT}=0.82*FFR-0.09$ ($R^2=0.32$, RMSE=0.29). In the study, the area under the receiver operator characteristic curve to predict invasive FFR≤0.80 for $FFR_{non-invasive}$, $FFR_{CT}$, and $DS_{AI\text{-}QCT}$ was 0.82, 0.84, and 0.81 respectively.

As such, subtended myocardial mass may improve the non-invasive assessment of ischemia, as used in some embodiments of the systems, devices, and methods described herein. As shown in the study, in some embodiments, non-invasive FFR, allometric FFR, or myocardial FFR can provide a similar measurement of ischemia as $FFR_{CT}$ that is less susceptible to image quality.

Alternative Variables to Derive Non-Invasive FFR

In some embodiments, the systems, methods, and devices described herein can be configured to utilize one or more alternative measurements to derive non-invasive FFR using allometric laws. For example, in some embodiments, the system can be configured to utilize one or more other variables from CCTA imaging to determine non-invasive FFR. Figure is a schematic illustrating an example embodiment(s) of systems, devices, and methods for non-invasive image-based determination of fractional flow reserve (FFR) and/or ischemia.

Figure 15D:
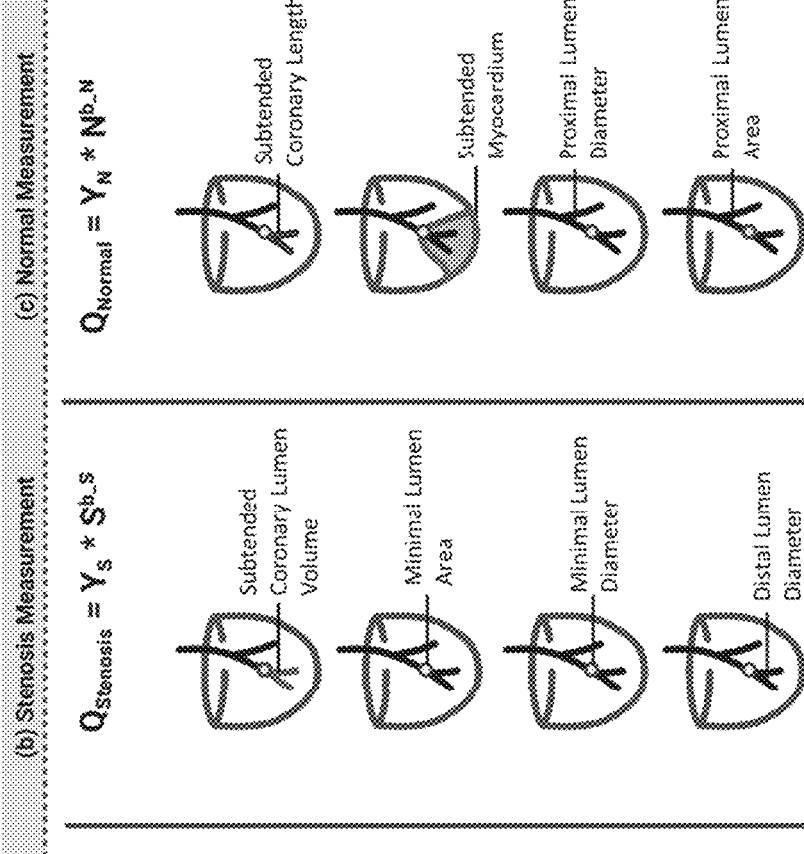
FIG. 15D is a schematic illustrating an example embodiment(s) of systems, devices, and methods for non-invasive image-based determination of fractional flow reserve (FFR) and/or ischemia.

As illustrated in FIG. 15D, in some embodiments, the systems, methods, and devices can be configured to utilize one or more variables from CCTA imaging to determine non-invasive FFR and/or allometric FFR, for example based on equations in column (a). In some embodiments, the systems, methods, and devices described herein can be configured to utilize one or more stenosis measurements, as depicted in column (b), and/or one or more normal measurements, as depicted in column (c).

In particular, in some embodiments, stenosis measurements can include one or more of subtended coronary lumen volume, minimal lumen area, minimal lumen diameter, distal lumen diameter, and/or the like. In some embodiments, distal lumen diameter can refer to the diameter beyond the coronary stenosis of interest. In some embodiments, one or more or all measurements noted in column (b) can be considered estimates of the extent of coronary obstruction. As such, in some embodiments, one or more or all measurements noted in column (b) may change in the presence of obstruction.

In some embodiments, normal measurements can include subtended coronary length, subtended myocardium, proximal lumen diameter, proximal lumen area, and/or the like. In some embodiments, subtended coronary length can refer to the length of the coronary tree distal to the coronary stenosis of interest. In some embodiments, proximal lumen diameter and/or area can be measured at any point along the coronary tree proximal to the coronary lesion of interest and/or within a portion of the coronary tree unaffected by the coronary stenosis of interest.

Non-Invasive FFR Example Systems, Methods, and Devices

Figure 15E:
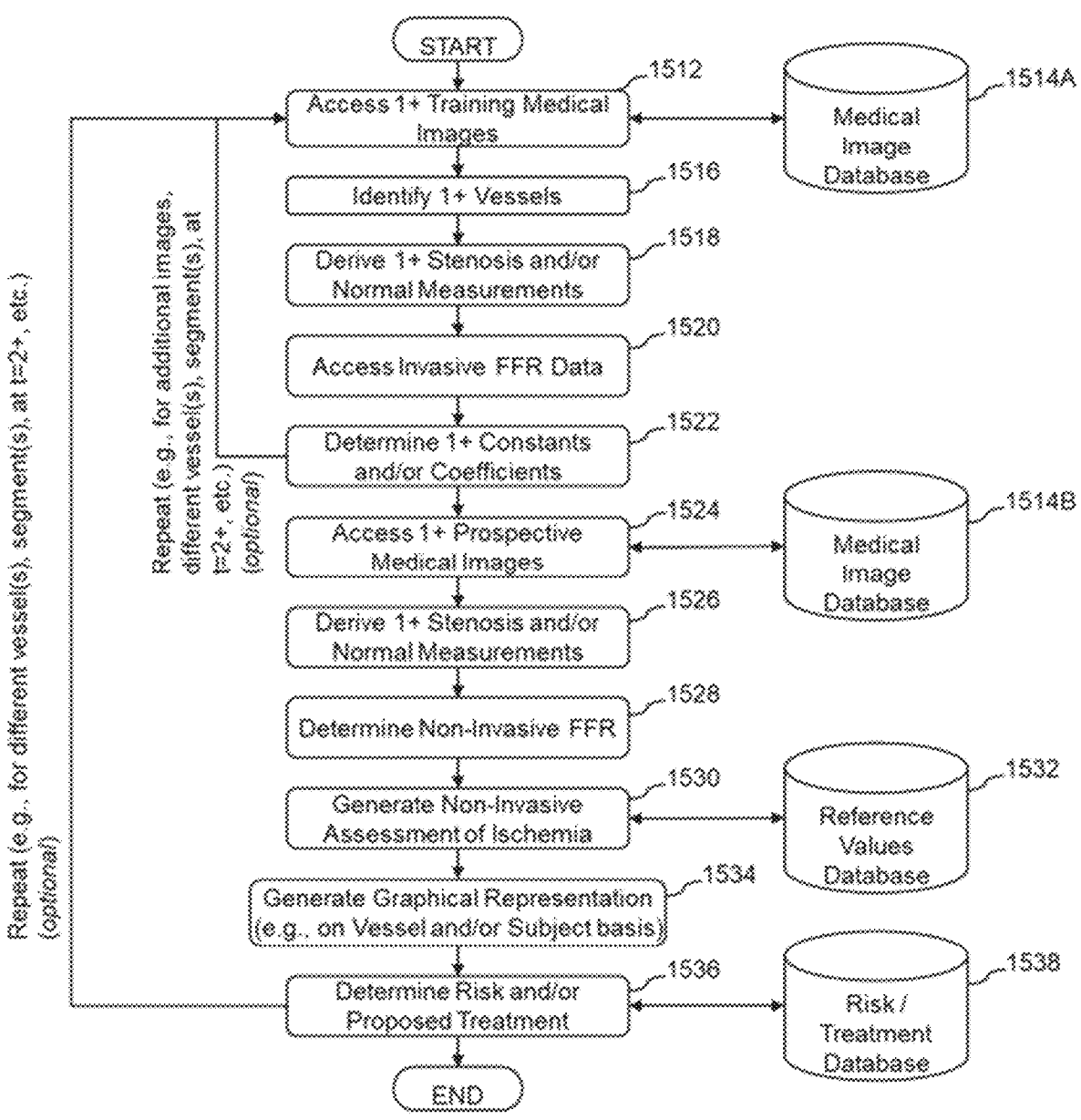
FIG. 15E is a flowchart illustrating an example embodiment(s) of systems, devices, and methods for non-invasive image-based determination of fractional flow reserve (FFR) and/or ischemia.

As discussed herein, in some embodiments, the systems, methods, and devices can be configured to determine non-invasive FFR or allometric FFR based on one or more stenosis and/or normal measurements derived from one or more medical images which can be obtained non-invasively. FIG. 15E is a flowchart illustrating an example embodiment(s) of systems, devices, and methods for non-invasive image-based determination of fractional flow reserve (FFR) and/or ischemia.

In particular, as illustrated in FIG. 15E, in some embodiments, the system can be configured to access one or more training medical images at block 1512. In some embodiments, the medical image can include one or more arteries, such as coronary, carotid, and/or other arteries of a subject. In some embodiments, the medical image can be stored in a medical image database 1514A. In some embodiments, the medical image database 1514A can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1516, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1518, the system can be configured to derive one or more stenosis and/or normal measurements from the identified vessels. For example, in some embodiments, the one or more stenosis measurements can include lumen area, subtended coronary lumen volume, minimal lumen area, minimal lumen diameter, distal lumen diameter, and/or the like. In some embodiments, the one or more normal measurements can include subtended coronary length, subtended myocardium mass and/or volume, proximal lumen diameter, proximal lumen area, and/or the like. In some embodiments, the system can be configured to utilize one or more AI and/or ML algorithms to automatically and/or dynamically derive one or more stenosis and/or normal measurements using image processing. For example, in some embodiments, the one or more AI and/or ML algorithms can be trained using a Convolutional Neural Network (CNN) on a set of medical images on which one or more stenosis and/or normal measurements have been derived, thereby allowing the AI and/or ML algorithm to automatically derive one or more stenosis and/or normal measurements directly from a medical image.

In some embodiments, at block 1520, the system can be configured to access invasive FFR data or measurements or otherwise obtained FFR measurements for the one or more training medical images. In some embodiments, based in part on the accessed FFR measurements, the system at block 1522 can be configured to derive and/or determine one or more constants and/or coefficients, for example of one or more mathematical equations describing the relationship between FFR and the one or more stenosis and/or normal measurements, thereby establishing a usable model to predict and/or determine FFR non-invasively based on the one or more stenosis and/or normal measurements of new cases. As an example, in some embodiments, the system can be configured to utilize a linear regression model to determine the one or more constants and/or coefficients.

In some embodiments, the system can be configured to repeat one or more processes described in relation to blocks 1512-1522 to improve accuracy of the model and/or determined constants and/or coefficients. For example, in some embodiments, the system can be configured to repeat one or more processes described in relation to blocks 1512-1522 for one or more additional images, vessels, segments, and/or at different times. As such, in some embodiments, the system can be configured to continuously improve accuracy of the model for determining FFR non-invasively using only one or more stenosis and/or normal measurements derived from a medical image.

In some embodiments, at block 5124, the system can be configured to access one or more prospective medical images. In some embodiments, the prospective medical image can include one or more arteries, such as coronary, carotid, and/or other arteries of a subject. In some embodiments, the prospective medical image can be stored in a medical image database 1514B, which can be the same and/or different database from the medical image database 1514A. In some embodiments, the medical image database 1514B can be locally accessible by the system and/or can be located remotely and accessible through a network connection. The prospective medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the prospective medical image comprises one or more of a contrast-enhanced CT image, non-contrast CT image, MR image, and/or an image obtained using any of the modalities described above.

In some embodiments, at block 1526, the system can be configured to derive one or more stenosis and/or normal measurements from one or more vessels identified on the prospective image. In some embodiments, one or more vessels can be identified on the prospective image using one or more techniques and/or features described above in relation to block 1516. In some embodiments, the one or more stenosis and/or normal measurements can be derived by the system using one or more techniques and/or features described above in relation to block 1518. For example, similar to the features described above in relation to block 1518, in some embodiments, the one or more stenosis measurements can include lumen area, subtended coronary lumen volume, minimal lumen area, minimal lumen diameter, distal lumen diameter, and/or the like. Similarly, in some embodiments, the one or more normal measurements can include subtended coronary length, subtended myocardium mass and/or volume, proximal lumen diameter, proximal lumen area, and/or the like.

In some embodiments, at block 1528, the system can be configured to determine non-invasive FFR based on the derived one or more stenosis and/or normal measurements. For example, in some embodiments, the system can be configured to apply the derived one or more stenosis and/or normal measurements to the mathematical model generated based on the one or more constants and/or coefficients determined in block 1522. As described herein, in some embodiments, the non-invasive FFR can be determined based on application of allometric scaling laws.

In some embodiments, at block 1530, the system can be configured to generate non-invasive assessment of ischemia based on the determined non-invasive FFR. For example, in some embodiments, the system can be configured to compare the determined non-invasive FFR to one or more reference values to generate assessment of ischemia based on benchmark values. In some embodiments, the reference values can be stored in a reference values database 1532, which can be locally accessible by the system and/or can be located remotely and accessible through a network connection. In some embodiments, the system can be configured to utilize one or more AI and/or ML algorithms to automatically and/or dynamically generate an assessment of ischemia based on benchmark reference values. In some embodiments, the one or more reference values can be derived from other subjects with varying states or risks of cardiovascular disease, including for example normal values. In some embodiments, the one or more reference values can be obtained from one or more medical images using the same or similar imaging modalities as the medical image accessed at block 1512. In some embodiments, the one or more reference values can be obtained from analyzing one or more medical images to generate one or more non-invasive FFR values, for example using one or more processes described in relation to blocks 1512-1528.

In some embodiments, based on such assessment of ischemia and/or non-invasive FFR, the system, at block 1534, can be configured to generate a graphical representation of the analysis results. In some embodiments, the system can be configured to generate a graphical generation reporting the analysis results on a vessel-by-vessel basis and/or subject basis. For example, in some embodiments, the system can be configured to generate a graphical representation of one or more arteries or vessels, in which specific arteries and/or vessels can be color-coded or assigned some value or other indicator depending on the analysis results. As an illustrative example, in some embodiments, if the system determines that ischemia or non-invasive FFR of a particular vessel is high, the system can be configured to color code that vessel red in the graphical representation. In some embodiments, the assessment of ischemia is generated based at least in part on comparison to one or more reference values of non-invasive FFR.

In some embodiments, based on such assessment of ischemia and/or non-invasive FFR, the system, at block 1536, can be configured to determine a risk or state of cardiovascular disease or health of the subject. Further, in some embodiments, based on such analysis, the system, at block 1536, can be configured to determine a proposed treatment for the subject. The treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a risk/treatment database 1538, which can be locally accessible by the system and/or can be located remotely and accessible through a network connection. In some embodiments, the risk/treatment database 1538 can include reference points or data that relate one or more treatment to cardiovascular disease risk or state determined based on one or more reference non-invasive FFR and/or ischemia values.

In some embodiments, the system can be configured to repeat one or more processes described in relation to blocks 1512-1536, for example for one or more other vessels, segment, regions of plaque, different subjects, and/or for the same subject at a different time. As such, in some embodiments, the system can provide for longitudinal disease tracking and/or personalized treatment for a subject.

Computer System

Figure 15F:
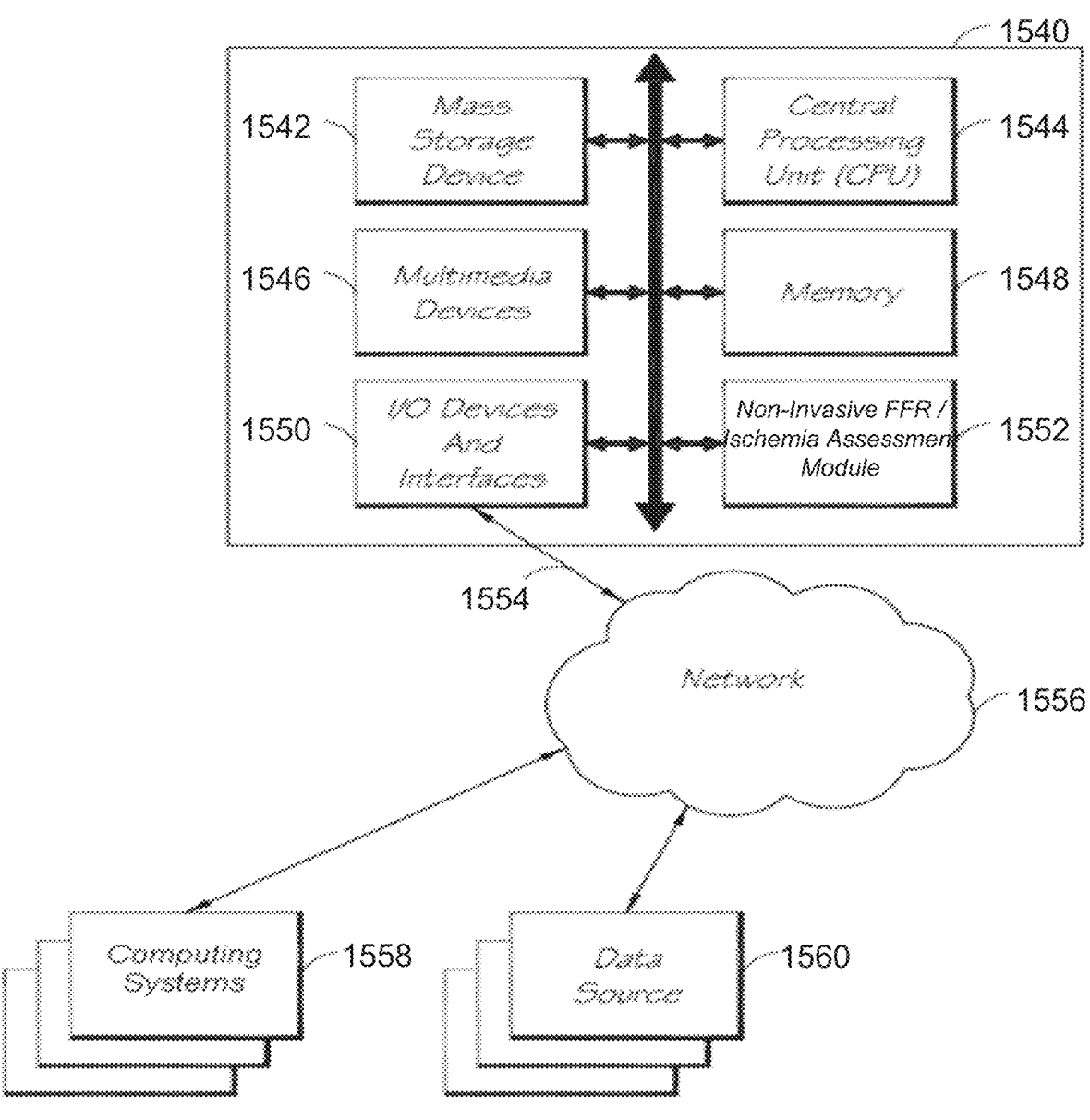
FIG. 15F is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 15F. The example computer system 1540 is in communication with one or more computing systems 1558 and/or one or more data sources 1560 via one or more networks 1556. While FIG. 15F illustrates an embodiment of a computing system 1540, it is recognized that the functionality provided for in the components and modules of computer system 1540 can be combined into fewer components and modules, or further separated into additional components and modules.

The computer system 1540 can comprise a Non-Invasive FFR/Ischemia Assessment Module 1552 that carries out the functions, methods, acts, and/or processes described herein. The Non-Invasive FFR/Ischemia Assessment Module 1552 executed on the computer system 1540 by a central processing unit 1544 discussed further below. Other features of the computer system 1540 can be similar to corresponding features of the computer system of FIG. 9G, described above.

Certain Examples of Embodiments of Non-Invasive FFR

The following are non-limiting examples of certain embodiments of systems and methods of non-invasive FFR introduction. Other embodiments may include one or more other features, or different features, that are discussed herein.

Embodiment 1: A computer-implemented method of determination of fractional flow reserve and assessment of ischemia based at least in part on one or more measurements derived from non-invasive medical image analysis, the computer-implemented method comprising: accessing, by a computer system, a medical image of a subject, wherein the medical image of the subject is obtained non-invasively; analyzing, by the computer system, the medical image of the subject to identify one or more coronary arteries; determining, by the computer system, one or more stenosis measurements based on analysis of the identified one or more coronary arteries in the medical image of the subject, the one or more stenosis measurements comprising coronary lumen area (A) and subtended myocardial mass (M); determining, by the computer system, non-invasive fractional flow reserve ($FFR_{non-invasive}$) for the identified one or more coronary arteries based at least in part by applying the one or more stenosis measurements to $$FFR_{non-invasive} = Y_0 * \frac{A^b A}{M^b M},$$

wherein $Y_0$ comprises a constant, and wherein $b_A$ and $b_M$ comprise exponential coefficients; and generating, by the computer system, an assessment of ischemia based at least in part on the determined non-invasive fractional flow reserve for the identified one or more coronary arteries, wherein the computer system comprises a computer processor and an electronic storage medium.

Embodiment 2: The computer-implemented method of Embodiment 1, wherein the determined non-invasive fractional flow reserve is determined using allometric scaling.

Embodiment 3: The computer-implemented method of Embodiment 1, wherein $Y_0$, $b_A$, and $b_M$ are derived from analysis of retrospective medical images and invasive FFR measurements ($FFR_{invasive}$).

Embodiment 4: The computer-implemented method of Embodiment 1, wherein $Y_0$, $b_A$, and $b_M$ are derived using an equation relating coronary lumen area (A) and subtended myocardial mass (M) to $FFR_{invasive}$.

Embodiment 5: The computer-implemented method of Embodiment 4, wherein the equation comprises $$FFR_{invasive} = Y_0 * \frac{A^b A}{M^b M}.$$

Embodiment 6: The computer-implemented method of Embodiment 4, wherein the equation comprises log ($FFR_{invasive}$)=$b_A$*log (A)−$b_M$*log(M)+log ($Y_0$).

Embodiment 7: The computer-implemented method of Embodiment 1, wherein the coronary lumen area comprises minimal lumen area.

Embodiment 8: The computer-implemented method of Embodiment 1, wherein the generated assessment of ischemia is generated based at least in part on comparison to one or more reference values of the determined non-invasive fractional flow reserve.

Embodiment 9: The computer-implemented method of Embodiment 1, further comprising generating, by the computer system, a graphical representation of the generated assessment of ischemia for the identified one or more coronary arteries.

Embodiment 10: The computer-implemented method of Embodiment 1, further comprising generating, by the computer system, a recommended treatment for the subject based at least in part on the generated assessment of ischemia for the one or more coronary arteries.

Embodiment 11: A computer-implemented method of determination of fractional flow reserve and assessment of ischemia based at least in part on one or more measurements derived from non-invasive medical image analysis, the computer-implemented method comprising: accessing, by a computer system, a medical image of a subject, wherein the medical image of the subject is obtained non-invasively; analyzing, by the computer system, the medical image of the subject to identify one or more coronary arteries; determining, by the computer system, one or more stenosis measurements (S) based on analysis of the identified one or more coronary arteries in the medical image of the subject, the one or more stenosis measurements (S) comprising one or more of subtended coronary lumen volume, minimal lumen area, minimal lumen diameter, or distal lumen diameter; determining, by the computer system, one or more normal measurements (N) based on analysis of the identified one or more coronary arteries in the medical image of the subject, the one or more normal measurements (N) comprising one or more of subtended coronary length, subtended myocardium, proximal lumen diameter, or proximal lumen area; determining, by the computer system, non-invasive fractional flow reserve ($FFR_{non-invasive}$) for the identified one or more coronary arteries based at least in part by applying the one or more stenosis measurements (S) and the one or more normal measurements (N) to $$FFR_{non-invasive} = \frac{Y_S * S^{b\_S}}{Y_N * N^{b\_N}},$$

wherein $Y_S$ comprises a constant, and wherein b_S and b_N comprise exponential coefficients; and generating, by the computer system, an assessment of ischemia based at least in part on the determined non-invasive fractional flow reserve for the identified one or more coronary arteries, wherein the computer system comprises a computer processor and an electronic storage medium.

Embodiment 12: The computer-implemented method of Embodiment 11, wherein the determined non-invasive fractional flow reserve is determined using allometric scaling.

Embodiment 13: The computer-implemented method of Embodiment 11, wherein $Y_S$, b_s, and b_N are derived from analysis of retrospective medical images and invasive FFR measurements ($FFR_{invasive}$).

Embodiment 14: The computer-implemented method of Embodiment 13, wherein $Y_S$, b_s, and b_N are derived from using $$FFR_{invasive} = \frac{Y_S * S^{b\_S}}{Y_N * N^{b\_N}}.$$

Embodiment 15: The computer-implemented method of Embodiment 11, wherein the distal lumen diameter comprises a diameter beyond an area of coronary stenosis of interest in the identified one or more coronary arteries.

Embodiment 16: The computer-implemented method of Embodiment 11, wherein the proximal lumen diameter and proximal lumen area are measured at a point along a coronary tree proximal to a coronary lesion of interest, wherein the point along the coronary tree is unaffected by coronary stenosis of interest.

Embodiment 17: The computer-implemented method of Embodiment 11, wherein the generated assessment of ischemia is generated based at least in part on comparison to one or more reference values of the determined non-invasive fractional flow reserve.

Embodiment 18: The computer-implemented method of Embodiment 11, further comprising generating, by the computer system, a graphical representation of the generated assessment of ischemia for the identified one or more coronary arteries.

Embodiment 19: The computer-implemented method of Embodiment 11, further comprising generating, by the computer system, a recommended treatment for the subject based at least in part on the generated assessment of ischemia for the identified one or more coronary arteries.

Embodiment 20: The computer-implemented method of Embodiment 11, wherein the medical image is obtained using an imaging technique comprising one or more of computed tomography (CT), x-ray, ultrasound, echocardiography, magnetic resonance (MR) imaging, optical coherence tomography (OCT), nuclear medicine imaging, positron-emission tomography (PET), single photon emission computed tomography (SPECT), or near-field infrared spectroscopy (NIRS).

Embodiment 21: A system for determining fractional flow reserve and assessment of ischemia based at least in part on one or more measurements derived from non-invasive medical image analysis, the system comprising: one or more computer readable storage devices configured to store a plurality of computer executable instructions; and one or more hardware computer processors in communication with the one or more computer readable storage devices and configured to execute the plurality of computer executable instructions in order to cause the system to: access a medical image of a subject, wherein the medical image of the subject is obtained non-invasively; analyze the medical image of the subject to identify one or more coronary arteries; determine one or more stenosis measurements based on analysis of the identified one or more coronary arteries in the medical image of the subject, the one or more stenosis measurements comprising coronary lumen area (A) and subtended myocardial mass (M); determine non-invasive fractional flow reserve ($FFR_{non-invasive}$) for the identified one or more coronary arteries based at least in part by applying the one or more stenosis measurements to $$FFR_{non-invasive} = Y_0 * \frac{A^b A}{M^b M},$$

wherein $Y_0$ comprises a constant, and wherein $b_A$ and $b_M$ comprise exponential coefficients; and generate an assessment of ischemia based at least in part on the determined non-invasive fractional flow reserve for the identified one or more coronary arteries.

Embodiment 22: The system of Embodiment 21, wherein the determined non-invasive fractional flow reserve is determined using allometric scaling.

Embodiment 23: The system of Embodiment 21, wherein $Y_0$, $b_A$, and $b_M$ are derived from analysis of retrospective medical images and invasive FFR measurements ($FFR_{invasive}$).

Embodiment 24: The system of Embodiment 21, wherein $Y_0$, $b_A$, and $b_M$ are derived using an equation relating coronary lumen area (A) and subtended myocardial mass (M) to $FFR_{invasive}$.

Embodiment 25: The system of Embodiment 24, wherein the equation comprises $$FFR_{invasive} = Y_0 * \frac{A^b A}{M^b M}.$$

Embodiment 26: The system of Embodiment 24, wherein the equation comprises $log(FFR_{invasive})=b_A*log(A)-b_M*log(M)+log(Y_0)$.

Embodiment 27: The system of Embodiment 21, wherein the coronary lumen area comprises minimal lumen area.

Embodiment 28: The system of Embodiment 21, wherein the generated assessment of ischemia is generated based at least in part on comparison to one or more reference values of the determined non-invasive fractional flow reserve.

Embodiment 29: The system of Embodiment 21, wherein the system is further caused to generate a graphical representation of the generated assessment of ischemia for the identified one or more coronary arteries.

Embodiment 30: The system of Embodiment 21, wherein the system is further caused to generate a recommended treatment for the subject based at least in part on the generated assessment of ischemia for the identified one or more coronary arteries.

Embodiment 31: A computer-implemented method of determination of fractional flow reserve and assessment of ischemia based at least in part on one or more measurements derived from non-invasive medical image analysis, the computer-implemented method comprising: accessing, by a computer system, a medical image of a subject, wherein the medical image of the subject is obtained non-invasively; analyzing, by the computer system, the medical image of the subject to identify one or more coronary arteries; determining, by the computer system, one or more measurements (n) based on analysis of the identified one or more coronary arteries in the medical image of the subject, the one or more measurements (n) comprising one or more of coronary artery disease (CAD) variables, lumen area, subtended lumen volume, subtended myocardium, minimal lumen area, minimal lumen diameter, distal lumen diameter, subtended coronary length, proximal lumen diameter, or proximal lumen area; determining, by the computer system, non-invasive fractional flow reserve (FFR$_{non-invasive}$) for the identified one or more coronary arteries based at least in part by applying the one or more measurements (n) to $$FFR_{non-invasive} = \prod_n^{CAD\ vars.} Y_n * n^{b_n},$$

wherein Y$_n$ comprises a constant, and wherein b$_n$ comprises an exponential coefficient; and generating, by the computer system, an assessment of ischemia based at least in part on the determined non-invasive fractional flow reserve for the identified one or more coronary arteries, wherein the computer system comprises a computer processor and an electronic storage medium.

Embodiment 32: The computer-implemented method of Embodiment 31, wherein the determined non-invasive fractional flow reserve is determined using allometric scaling.

Embodiment 33: The computer-implemented method of Embodiment 31, wherein Y$_n$, and b$_n$ are derived from analysis of retrospective medical images and invasive FFR measurements (FFR$_{invasive}$).

Embodiment 34: The computer-implemented method of Embodiment 31, wherein the distal lumen diameter comprises a diameter beyond an area of coronary stenosis of interest in the identified one or more coronary arteries.

Embodiment 35: The computer-implemented method of Embodiment 31, wherein the proximal lumen diameter and proximal lumen area are measured at a point along a coronary tree proximal to a coronary lesion of interest, wherein the point along the coronary tree is unaffected by coronary stenosis of interest.

Embodiment 36: The computer-implemented method of Embodiment 31, wherein the generated assessment of ischemia is generated based at least in part on comparison to one or more reference values of the determined non-invasive fractional flow reserve.

Embodiment 37: The computer-implemented method of Embodiment 31, further comprising generating, by the computer system, a graphical representation of the generated assessment of ischemia for the one or more coronary arteries.

Embodiment 38: The computer-implemented method of Embodiment 31, further comprising generating, by the computer system, a recommended treatment for the subject based at least in part on the generated assessment of ischemia for the identified one or more coronary arteries.

Embodiment 39: The computer-implemented method of Embodiment 31, wherein the medical image is obtained using an imaging technique comprising one or more of computed tomography (CT), x-ray, ultrasound, echocardiography, magnetic resonance (MR) imaging, optical coherence tomography (OCT), nuclear medicine imaging, positron-emission tomography (PET), single photon emission computed tomography (SPECT), or near-field infrared spectroscopy (NIRS).

Other Embodiment(s)

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm" Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

The invention claimed is:

1. A computer-implemented method of assessing a state of cardiovascular disease for a subject based on multi-dimensional information derived from non-invasive medical image analysis, the method comprising:

accessing, by a computer system, a medical image of a subject, wherein the medical image of the subject is obtained non-invasively;

analyzing, by the computer system, the medical image of the subject to identify one or more arteries, wherein the one or more arteries comprise one or more regions of plaque;

identifying, by the computer system, a hypothetical cut line along the one or more arteries, wherein the hypothetical cut line is substantially parallel to a longitudinal axis of the one or more arteries;

computationally unfolding, by the computer system, the one or more arteries along the hypothetical cut line;

identifying, by the computer system, one or more regions of plaque on the computationally unfolded one or more arteries;

identifying, by the computer system, one or more regions of exposed plaque among the one or more regions of plaque on the computationally unfolded one or more arteries;

analyzing, by the computer system, the one or more regions of exposed plaque to determine one or more plaque parameters and one or more vessel parameters, wherein the one or more plaque parameters comprises one or more of surface area of plaque, thickness of plaque, composition of plaque, heterogeneity of plaque, or depth to a plaque component, and wherein the one or more vessel parameters comprises one or more of surface area of vessel wall, thickness of vessel wall, stenosis of vessel lumen, remodeling index, surface irregularity, surface asymmetry, or surface ulceration;

mapping, by the computer system, the one or more regions of exposed plaque and the computationally unfolded one or more arteries to a coordinate system;

analyzing, by the computer system, a position of the one or more regions of exposed plaque based at least in part on the mapping of the one or more regions of exposed plaque and the computationally unfolded one or more arteries to a coordinate system; and generating, by the computer system, an assessment of a cardiovascular disease state of the one or more regions of exposed plaque based at least in part on the determined one or more plaque parameters, one or more vessel parameters, and analyzed position of the one or more regions of exposed plaque, wherein the computer system comprises a computer processor and an electronic storage medium.

2. The computer-implemented method of claim 1, wherein the medical image is obtained using an imaging technique comprising one or more of computed tomography (CT), x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

3. The computer-implemented method of claim 1, wherein the hypothetical cut line is identified on a straightened view of the one or more arteries.

4. The computer-implemented method of claim 1, wherein the one or more regions of plaque comprise the one or more regions of exposed plaque and one or more regions of unexposed plaque.

5. The computer-implemented method of claim 1, wherein the coordinate system comprises one or more of a cartesian coordinate system, polar coordinate system, cylindrical coordinate system, spherical coordinate system, homogeneous coordinate system, curvilinear coordinate system, log-polar coordinate system, Plücker coordinate system, generalized coordinate system, canonical coordinate system, barycentric coordinate system, or trilinear coordinate system.

6. The computer-implemented method of claim 1, further comprising:

determining, by the computer system, one or more plaque to vessel parameters, the one or more plaque to vessel parameters comprising one or more of a ratio of surface area of plaque to surface area of vessel or a ratio of thickness of plaque to thickness of vessel; and generating, by the computer system, the cardiovascular risk assessment of the subject further based at least in part on the determined one or more plaque to vessel parameters.

7. The computer-implemented method of claim 1, wherein the heterogeneity of plaque is determined by identifying one or more components of plaque within a region of plaque, wherein the one or more components of plaque comprise one or more of low density non-calcified plaque, calcified plaque, or non-calcified plaque.

8. The computer-implemented method of claim 1, wherein the plaque component comprises one or more of low density non-calcified plaque, calcified plaque, or non-calcified plaque.

9. The computer-implemented method of claim 1, wherein the position of the one or more regions of exposed plaque is determined as a Euclidian distance from one or more locations of interest.

10. The computer-implemented method of claim 1, wherein the position of the one or more regions of exposed plaque is determined in relation to one or more of one or more regions of fat, one or more other regions of plaque, vessel lumen, myocardium, myocardial side the of vessel, pericardium, pericardial side of the vessel, epicardial fat, epicardial fat side of the vessel, branch point, bifurcation, trifurcation, or distance from vessel ostium.

11. The computer-implemented method of claim 10, wherein a higher risk is assessed for one or more regions of exposed plaque that is adjacent to the epicardial side of the vessel compared to one or more regions of exposed plaque that is adjacent to the myocardial side of the vessel.

12. The computer-implemented method of claim 1, further comprising generating a graphical representation of the one or more regions of exposed plaque based on the generated cardiovascular disease risk assessment of the one or more regions of exposed plaque.

13. The computer-implemented method of claim 1, wherein generating the graphical representation comprises assigning one or more of color, shading, translucency, three-dimensional annotation, or partial translucency.

14. The computer-implemented method of claim 1, further comprising generating a graphical representation of one or more components within the one or more regions of exposed plaque based on the generated cardiovascular disease risk assessment of the one or more regions of exposed plaque.

15. The computer-implemented method of claim 1, wherein the cardiovascular disease risk assessment of the one or more regions of exposed plaque is generated by utilizing an artificial intelligence or machine learning algorithm based on prior subject image analysis data.

16. The computer-implemented method of claim 1, further comprising generating, by the computer system, cardiovascular disease risk assessment of all regions of exposed plaque within a vessel segment.

17. The computer-implemented method of claim 16, further comprising generating a cardiovascular disease risk assessment of the subject by combining the generated cardiovascular disease risk assessment of all regions of exposed plaque within the vessel segment.

18. The computer-implemented method of claim 17, wherein the cardiovascular disease risk assessment of the subject is generated based at least in part on comparison to a database of previously generated cardiovascular disease risk assessments of other subjects.

19. The computer-implemented method of claim 16, further comprising generating a proposed treatment for the subject by combining the generated cardiovascular disease risk assessment of all regions of exposed plaque within the vessel segment.

20. The computer-implemented method of claim 19, wherein the proposed treatment for the subject is generated based at least in part on comparison to a database of previously proposed treatments of other subjects.

* * * * *